(12) United States Patent
Curran et al.

(10) Patent No.: US 7,122,686 B2
(45) Date of Patent: Oct. 17, 2006

(54) ANALOGS OF DISCODERMOLIDE AND DICTYOSTATIN-1, INTERMEDIATES THEREFOR AND METHODS OF SYNTHESIS THEREOF

(75) Inventors: Dennis P. Curran, Pittsburgh, PA (US); Youseung Shin, Pittsburgh, PA (US); Nakyen Choy, Belle Mead, NJ (US); Billy W. Day, Pittsburgh, PA (US); Raghavan Balachandran, Wexford, PA (US); Charitha Madiraju, Pittsburgh, PA (US); Tiffany Turner, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 127 days.

(21) Appl. No.: 10/655,916

(22) Filed: Sep. 5, 2003

(65) Prior Publication Data

US 2004/0186165 A1    Sep. 23, 2004

Related U.S. Application Data

(60) Provisional application No. 60/437,736, filed on Jan. 2, 2003, provisional application No. 60/408,503, filed on Sep. 6, 2002.

(51) Int. Cl.
*C07D 313/00* (2006.01)
(52) U.S. Cl. .......................................... 549/266; 560/1
(58) Field of Classification Search ................ 549/271, 549/266
See application file for complete search history.

(56) References Cited

U.S. PATENT DOCUMENTS 5,430,053 A * 7/1995 Pettit et al. .................. 514/450

FOREIGN PATENT DOCUMENTS

| EP | 0 680 958 | 11/1995 |
|---|---|---|
| WO | WO 01/62239 | 8/2001 |
| WO | WO 02/12220 | 2/2002 |
| WO | WO 02/057251 | 7/2002 |
| WO | WO 2004/022552 | 9/2003 |

OTHER PUBLICATIONS

Shin et al, Organic Letters, vol. 4(25), pp. 4443-4446, 2002.*
Querolle et al., Synthesis of Novel Macrocyclic Docetaxel Analogues. Influence of Their Macrocylic Ring Size on Tubulin Activity, J. Med. Chem., 46:3623-3630 (2003).*
Nerenberg, J. B. et.al. Total synthesis of the immunosuppressive agent (-)- discodermolide. J. Am. Chem. Soc. 1993, 115, 12621-12622.
Smith, A. B. et.al.;Total Synthesis of (-)- Discodermolide. J. Am. Chem. Soc. 1995, 117, 12011-12012.
Marshall, J. A. et.al.; Total synthesis of (+)-discodermolide. J. Org. Chem. 1998, 63, 7885-7892.
Paterson, I.et.al; Total synthesis of the antimicrotubule agent (+)-discodermolide using boron mediated aldol reactions of chiral ketones. Angew. Chem., Int. Ed. Eng. 2000, 39, 377-380.
Paterson, I.et.al.; Synthesis of (+)-discodermolide and analogues by control of asymmetric induction in aldol reactions of gamma-chiral (Z)-enals. Tetrahedron Lett. 2000, 41, 6935-6939.

(Continued)

*Primary Examiner*—Cecilia Tsang
*Assistant Examiner*—James Balls
(74) *Attorney, Agent, or Firm*—Barton & Hare, LLP

(57) ABSTRACT

A compound of the following structure:

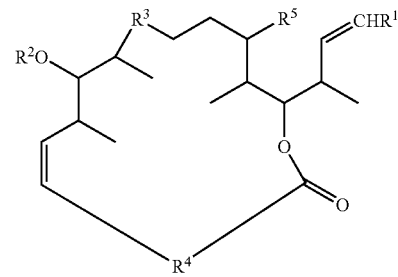

wherein $R^1$ is H, an alkyl group, an aryl group, an alkenyl group, an alkynyl group, or a halogen atom;

$R^2$ is H, an alkyl group, an aryl group, a benzyl group, a trityl group, $-SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, $-R^iSiR^aR^bR^c$ or a benzyl group, wherein $R^i$ is an alkylene group;

$R^e$ is an alkyl group, an allyl group, a benzyl group, an aryl group, an alkoxy group, or $-NR^gR^h$, wherein $R^g$ and $R^h$ are independently H, an alkyl group or an aryl group;

$R^3$ is $(CH_2)_n$ where n is and integer in the range of 0 to 5, $-CH_2CH(CH_3)-$, $-CH=CH-$, $-CH=C(CH_3)-$, or $-C\equiv C-$;

$R^4$ is $(CH_2)_p$ where p is an integer in the range of 4 to 12, $-(CHR^{k1})_{y1}(CHR^{k2})_{y2}(CHR^{k3})_{y3}(CHR^{k4})_{y4}(CHR^{k5})_{y5}$ $C(R^{s1})=C(R^{s2})C(R^{s3})=C(R^{s4})-$, $-(CHR^{k1})_{y1}$ $(CHR^{k2})_{y2}(CHR^{k3})_{y3}(CHR^{k4})_{y4}(CHR^{k5})_{y5}CH(R^{s1})$ $CH(R^{s2})C(R^{s3})=C(R^{s4})-$, $-(CHR^{k1})_{y1}(CHR^{k2})_{y2}$ $(CHR^{k3})_{y3}(CHR^{k4})_{y4}(CHR^{k5})_{y5}C(R^{s1})=C(R^{s2})CH$ $(R^{s3})CH(R^{s4})-$, $-(CHR^{k1})_{y1}(CHR^{k2})_{y2}(CHR^{k3})_{y3}$ $(CHR^{k4})_{y4}(CHR^{k5})_{y5}CH(R^{s1})$ $CH(R^{s2})CH(R^{s3})CH$ $(R^{s4})-$, wherein y1 and y2 are 1 and y3, y4 and y5 are independently 0 or 1, $R^{k1}$, $R^{k2}$, $R^{k3}$, $R^{k4}$ and $R^{k5}$ are independently H, $CH_3$, or $OR^{2a}$, and $R^{s1}$, $R^{s2}$, $R^{s3}$, and $R^{s4}$ are independently H or $CH_3$, wherein $R^{2a}$ is H, an alkyl group, an aryl group, a benzyl group, a trityl group, $-SiR^aR^bR^c$, $CH_2OR^d$, or $COR^e$; and $R^5$ is H or $OR^{2b}$, wherein $R^{2b}$ is H, an alkyl group, an aryl group, an aryl group, a benzyl group, a trityl group, $-SiR^aR^bR^c$, $CH_2OR^d$, or $COR^e$; provided that the compound is not dictyostatin 1.

10 Claims, 19 Drawing Sheets

OTHER PUBLICATIONS

Roush, W. R.et.al.; Asymmetric synthesis using tartrate modified allyl boronates. 2. Single and double asymmetric reactions with alkoxy-substituted aldehydes, J. Org. Chem. 1990, 55, 4117-4126.

Paterson, I.et.al.; A practical synthesis of (+)-discodermolide and analogues: Fragment union by complex aldol reactions. J. Am. Chem. Soc. 2001, 123, 9535-9544.

Martello, L. A. et al. The relationship between taxol and (+)-discodermolide: synthetic analogs and modeling studies. Chemistry Biol. 2001, 8, 843-855.

Harried, S. et.al. Total Synthesis of (-)-Discodermolide: An Application of a Chelation-Controlled Alkylation Reaction. J. Org. Chem. 1997, 62, 6098-6099.

Evans, D. A.et.al . . . Diastereoselective magnesium halide-catalyzed anti-aldol reactions of chiral N-acyloxazolidinones. J. Am. Chem. Soc. 2002, 124, 392-393.

Pettit, G. R. et. al; Isolation and structure of the cancer cell growth inhibitor dictyostatin 1. J. Chem. Soc., Chem. Commun. 1994, 1111-1112.

CAS Online, STN, Columbus, Ohio, USA, 135: 371269, RN 374568-47-5.

Day, B. W., et.al;. Convenient synthesis of (2R,3S,4R)-3-(tert-butyldimethylsilanyloxy)-2,4-dimethyl-5-oxopentanoic acid methoxymethyl-amide from methacrolein. Preparation of C1-C7 and C17-C24 fragments of (+)-discodermolide. Tetrahedron Asymmetry 2002, 13, 1161-1165.

Clark, D. L. et. al.; Studies on the alkylation of chiral enolates: application toward the total synthesis of discodermolide. J. Org. Chem. 1993, 58 5878-5879.

Smith, A. B . . . et al. Evolution of a gram-scale synthesis of (+)-discodermolide. J. Am. Chem. Soc. 2000, 122, 8654-8664.

Heathcock, C. H.et.al.;. Acyclic stereoselection-13; Aryl esters: reagents for threo-aldolization. Tetrahedron 1981, 37, 4087-4095.

Paterson, I.et.al.; A. Studies towards the total synthesis of the marine-derived immunosuppresant discodermolide: stereoselective synthesis of a C9-C24 subunit. Synlett. 1995, 498-500.

Kocovsky, P. Carbamates: a method of synthesis and some synthetic applications. Tetrahedron Lett. 1986, 27 5521-5524.

Fujiwara et. al. Synthesis of the Tetrahydropyran Part of a Marine Toxin Polycavernoside-A. Chemistry Letters. 1994, pp. 2147-2150.

CAS Online, STN, Columbus, Ohio, USA, 124: 86679, RN 172269-30-6P.

CAS Online, STN, Columbus, Ohio, USA, 66: 94583, RN 16078-24-3P.

* cited by examiner

PMB is para-methoxybenzyl
MOM is methoxymethyl

Figure 3.
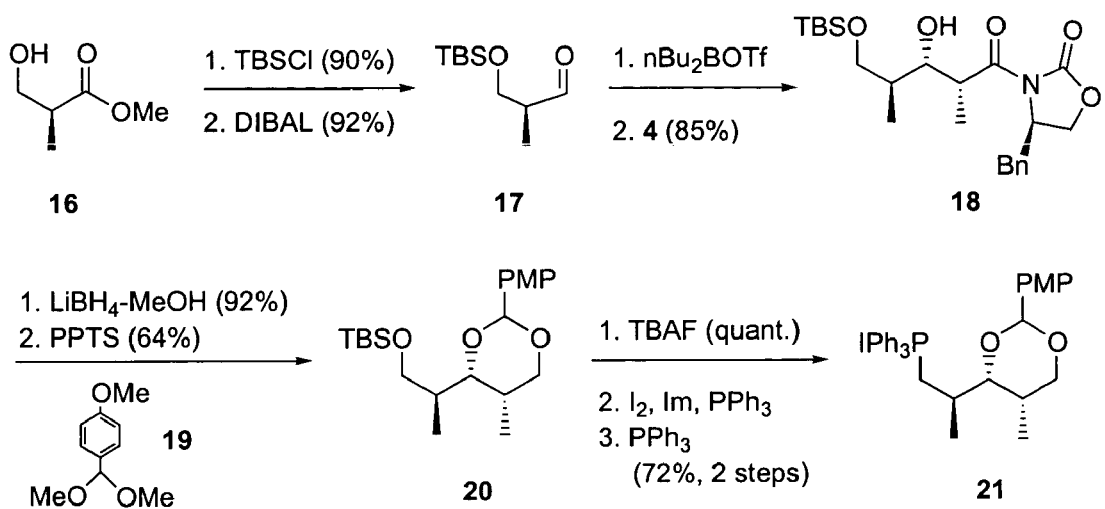
Other Phosphonium Salts
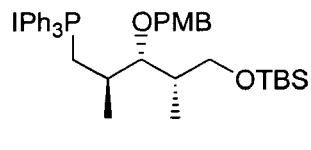
22
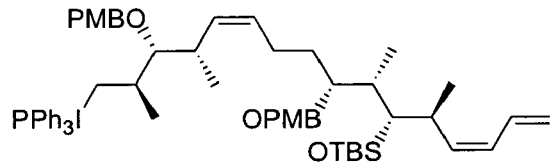
23
PMP is para-methyoxyphenyl Figure 4.
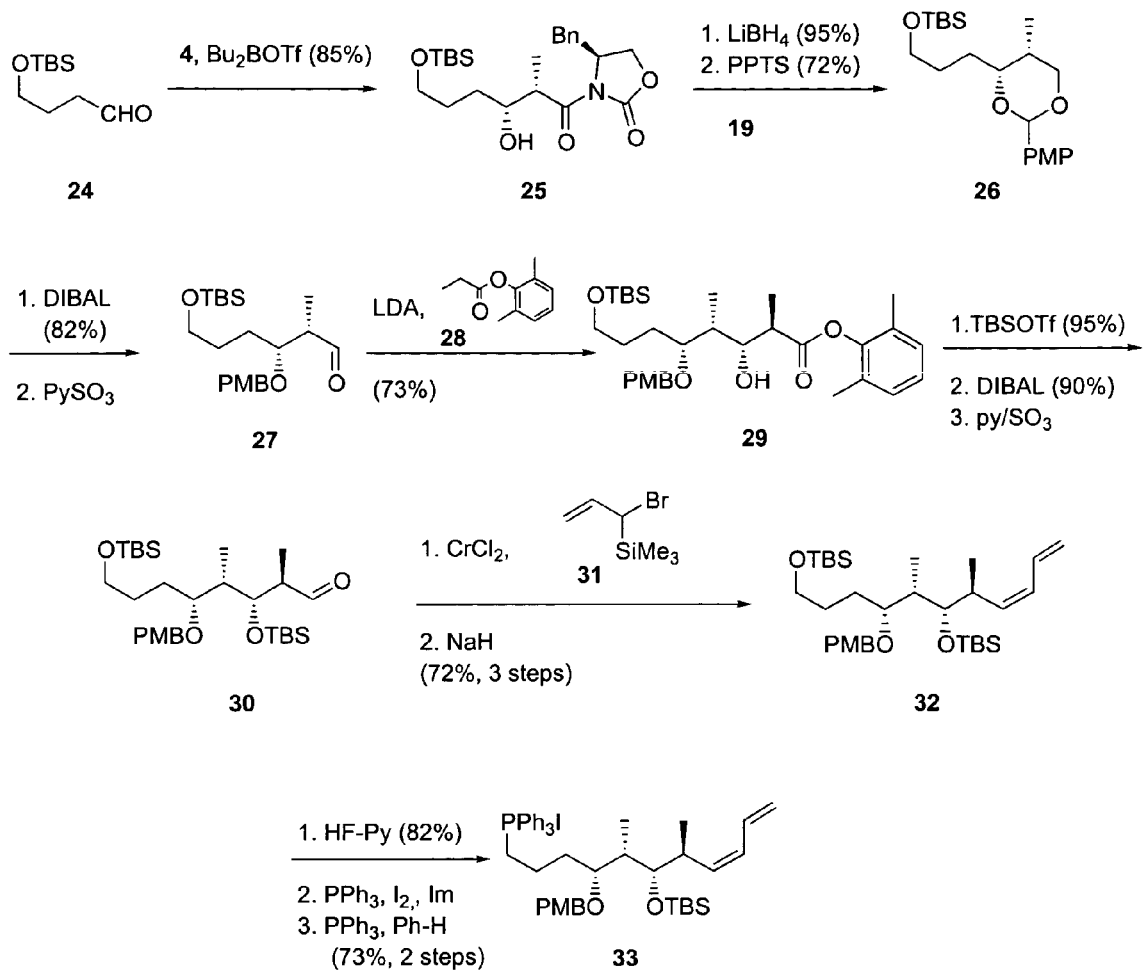
Assignment of configuration
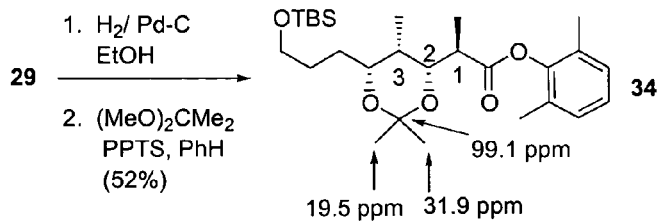

Figures 6A-D. Tubulin polymerization-inducing properties of discodermolide (A), 40 (B), 41 (C) and 42 (D) in comparison to 10 μM paclitaxel (PTX).
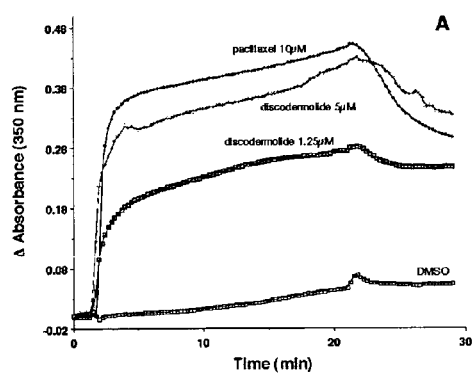
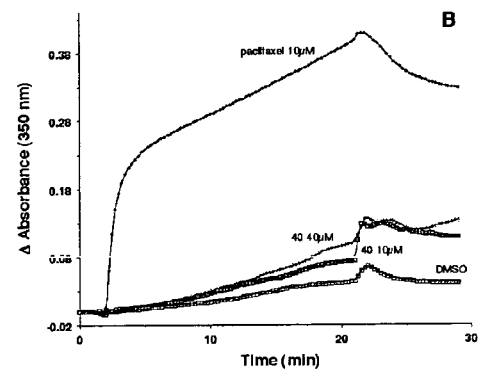
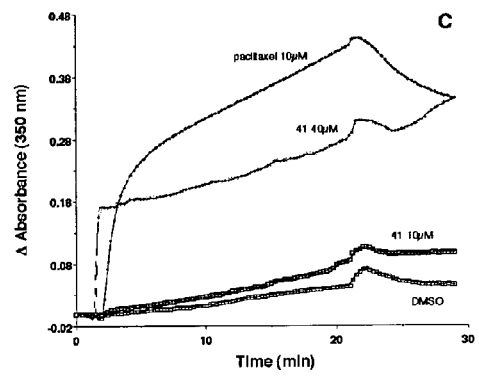
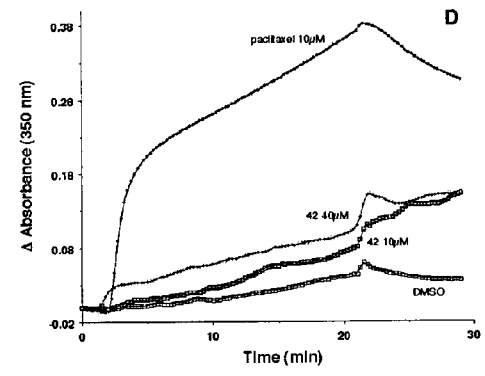

Figure 7. Retrosynthetic analysis of hybrid 3
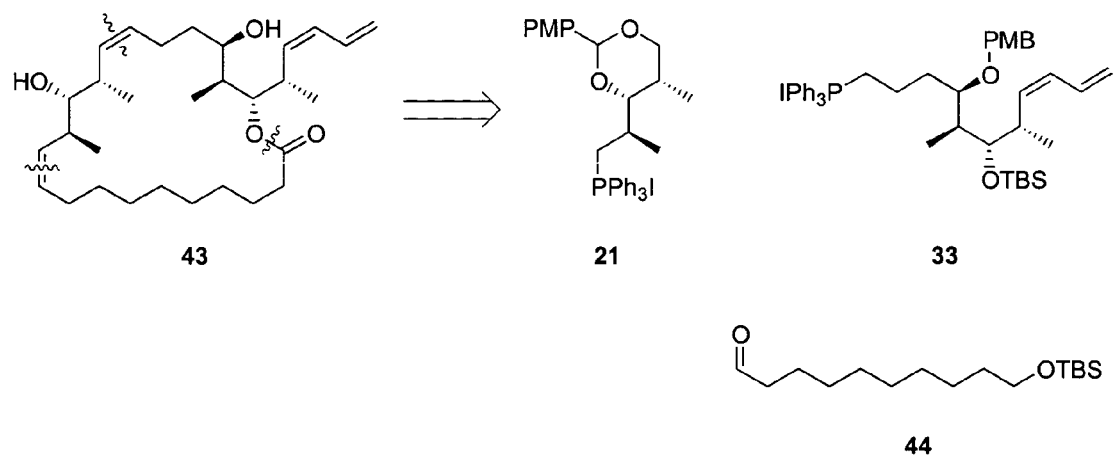

Figure 9. Acyclic Compounds for Biological Testing

47  R = CH₂OH
48  R = CO₂Me
49  R = CO₂H configuration at C16 controlled by chiral auxilliary
configuration at C19 controlled by reduction
configurations of other stereocenters originate from
readily available precursors, so the plan allows access
to substantially all stereoisomers

ANALOGS OF DISCODERMOLIDE AND DICTYOSTATIN-1, INTERMEDIATES THEREFOR AND METHODS OF SYNTHESIS THEREOF

CROSS-REFERENCE TO RELATED APPLICATIONS

The present application claims the benefit of U.S. Provisional Patent Application Ser. No. 60/408,503, filed Sep. 6, 2002 and U.S. Provisional Patent Application Ser. No. 60/437,736 filed Jan. 2, 2003, the disclosures of which are incorporated herein by reference.

GOVERNMENT INTEREST

This invention was made with government support under grant CA 78039 awarded by the National Institutes of Health. The government has certain rights in this invention.

BACKGROUND OF THE INVENTION

The present invention relates to analogs of discodermolide and dictyostatin-1, intermediates for the synthesis of such analogs and methods of synthesis of such intermediates and analogs.

Discodermolide has been shown to have a mechanism of action similar to Taxol but it is active against Taxol-resistant cell lines and it is more water soluble than Taxol. Accordingly, it may have a different and/or broader spectrum of action than Taxol and be easier to formulate and administer. Like Taxol, discodermolide is difficult to synthesize. Some syntheses of discodermolide are described in the following papers: Nerenberg, J. B.; Hung, D. T.; Somers, P. K.; Schreiber, S. L. Total synthesis of the immunosuppressive agent (−)-discodermolide. *J. Am. Chem. Soc.* 1993, 115, 12621–12622; Smith, A. B., III; Qiu, Y.; Jones, D. R.; Kobayashi, K. Total Synthesis of (−)-Discodermolide. *J. Am. Chem. Soc.* 1995, 117, 12011–12012; Marshall, J. A.; Johns, B. A. Total synthesis of (+)-discodermolide. *J. Org. Chem.* 1998, 63, 7885–7892; Paterson, I.; Florence, G. J.; Gerlach, K.; Scott, J. P. Total synthesis of the antimicrotubule agent (+)-discodermolide using boron-mediated aldol reactions of chiral ketones. *Angew. Chem., Int. Ed. Eng.* 2000, 39, 377–380; Paterson, I.; Florence, G. J. Synthesis of (+)-discodermolide and analogues by control of asymmetric induction in aldol reactions of gamma-chiral (Z)-enals. *Tetrahedron Lett.* 2000, 41, 6935–6939; Smith, A. B.; Beauchamp, T. J.; LaMarche, M. J.; Kaufman, M. D.; Qiu, Y. P. et al. Evolution of a gram-scale synthesis of (+)-discodermolide. *J. Am. Chem. Soc.* 2000, 122, 8654–8664.

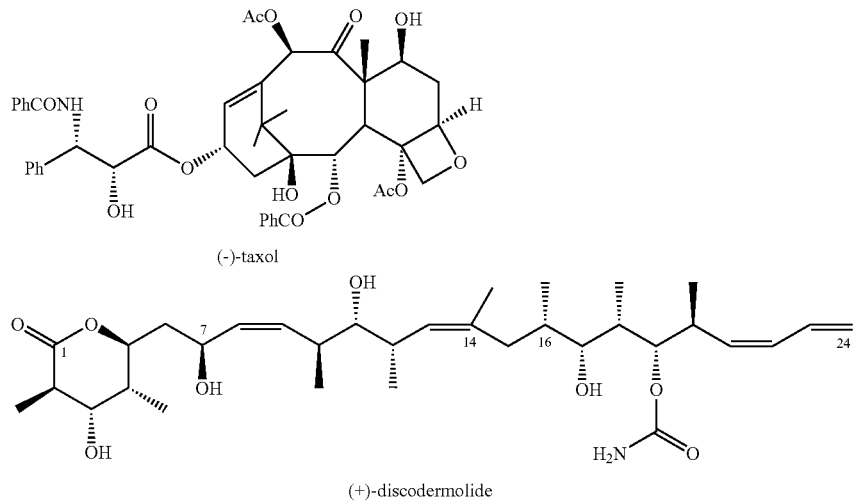

(−)-taxol (+)-discodermolide

References set forth herein may facilitate understanding of the present invention or the background of the present invention. Inclusion of a reference herein, however, is not intended to and does not constitute an admission that the reference is available as prior art with respect to the present invention.

The discovery and development of new chemotherapeutic agents for the treatment of cancer is currently of high importance. Some of the best currently available chemotherapeutic agents are natural products or natural product analogs. For example, Taxol (paclitaxel) is a natural product that is currently being used to treat patients with breast and ovarian cancer among others. A number of analogs of Taxol, including Taxotere (docetaxel), are also powerful anticancer agents.

Recently, the natural product (+)-discodermolide and its analogs have shown great promise as anticancer agents.

Analogs of discodermolide have also been made and tested for activity. For example, see the above references and Paterson, I.; Florence, G. J.; Gerlach, K.; Scott, J. P.; Sereinig, N. A practical synthesis of (+)-discodermolide and analogues: Fragment union by complex aldol reactions. *J. Am. Chem. Soc.* 2001, 123, 9535–9544; Martello, L. A.; LaMarche, M. J.; He, L.; Beauchamp, T. J.; Smith, A. B. et al. The relationship between taxol and (+)-discodermolide: synthetic analogs and modeling studies. *Chemistry Biol.* 2001, 8, 843–855; Harried, S. S.; Yang, G.; Strawn, M. A.; Myles, D. C. Total Synthesis of (−)-Discodermolide: An Application of a Chelation-Controlled Alkylation Reaction. *J. Org. Chem.* 1997, 62, 6098–6099; Paterson, I.; Florence, G. J. Synthesis of (+)-discodermolide and analogues by control of asymmetric induction in aldol reactions of gamma-chiral (Z)-enals. *Tetrahedron Lett.* 2000, 41, 6935–6939.

Unlike Taxol, discodermolide is not readily available in large quantities from natural sources. Accordingly, assuring a sufficient supply of discodermolide is problematic. Simplified analogs that retain high anti-cancer activity but are easier to make are in urgent need.

Very recently, an unusual macrolactone natural product dictyostatin 1 has been isolated from two different sponges and a partial structure has been assigned as shown below. See Pettit, G. R.; Cichacz, Z. A. Isolation and structure of dictyostatin 1. In U.S. Pat. No. 5,430,053; 1995; Pettit, G. R.; Cichacz, Z. A.; Gao, F.; Boyd, M. R.; Schmidt, J. M. Isolation and structure of the cancer cell growth inhibitor dictyostatin 1. *J. Chem. Soc., Chem. Commun.* 1994, 1111–1112. The configurations at C16 and C19 have not yet been assigned in the natural product and the absolute configuration is not known. Dictyostatin shows extremely high potencies against and array of cancer cell lines.

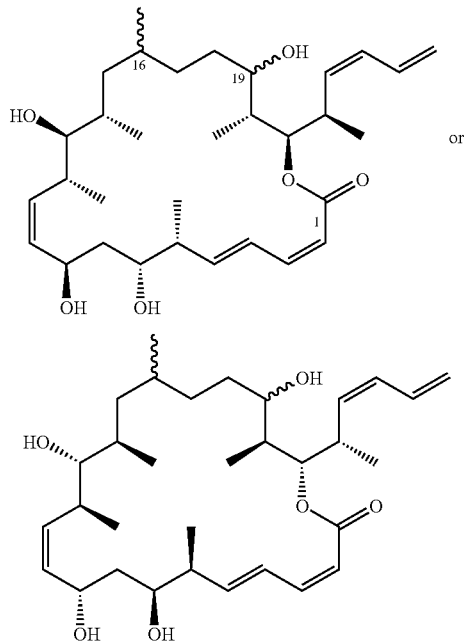

dictyostatin 1 absolute configuration unknown, configurations at C16 and C19 unknown Recently, dictyostatin has also been shown to stabilize microtubules, like discodermolide and Taxol. See Wright, A. E.; Cummins, J. L.; Pomponi, S. A.; Longley, R. E.; Isbrucker, R. A. Dictyostatin compounds for stabilization of microtubules. In PCT Int. Appl.; WO62239, 2001. Accordingly, dictyostatin 1 and its analogs show great promise as new anticancer agents. There is an urgent need for a synthetic route to make dictyostatin 1 and its analogs in order to fully assign the structure of dictyostatin 1, to produce analogs to study the structure/activity relationship and to identify and produce the best possible drugs in this family.

The inventors of the present invention, as one aspect of the present invention, herein set forth a number of analogs of discodermolide, as well as methods and intermediates for the synthesis thereof. The inventors of the present invention, as another aspect, herein set forth a family of both closed and open analogs of dictyostatin 1 with methods and intermediates for the synthesis of this family.

SUMMARY OF THE INVENTION

In one aspect, the present invention provides a compound of the following structure:

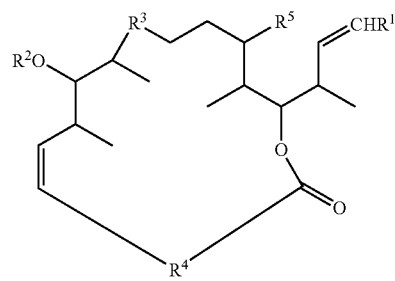

wherein $R^1$ is H, an alkyl group, an aryl group, an alkenyl group, an alkynyl group, or a halogen atom;

$R^2$ is H, an alkyl group, an aryl group, a benzyl group, a trityl group, —$SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —$CH=CH$—, —$CH=C(CH_3)$—, or —$C\equiv C$—;

$R^4$ is $(CH_2)_p$ where p is an integer in the range of 4 to 12, —$(CHR^{k1})_{y1}(CHR^{k2})_{y2}(CHR^{k3})_{y3}(CHR^{k4})_{y4}(CHR^{k5})_{y5}C(R^{s1})=C(R^{s2})C(R^{s3})=C(R^{s4})$—, —$(CHR^{k1})_{y1}(CHR^{k2})_{y2}(CHR^{k3})_{y3}(CHR^{k4})_{y4}(CHR^{k5})_{y5}CH(R^{s1})$  $CH(R^{s2})C(R^{s3})=C(R^{s4})$—, —$(CHR^{k1})_{y1}(CHR^{k2})_{y2}(CHR^{k3})_{y3}(CHR^{k4})_{y4}(CHR^{k5})_{y5}C(R^{s1})=C(R^{s2})CH(R^{s3})CH(R^{s4})$—, —$(CHR^{k1})_{y1}(CHR^{k2})_{y2}(CHR^{k3})_{y3}(CHR^{k4})_{y4}(CHR^{k5})_{y5}CH(R^{s1})CH(R^{s2})CH(R^{s3})CH(R^{s4})$—, wherein y1 and y2 are 1 and y3, y4 and y5 are independently 0 or 1, $R^{k1}$, $R^{k2}$, $R^{k3}$, $R^{k4}$ and $R^{k5}$ are independently H, $CH_3$, or $OR^{2a}$, and $R^{s1}$, $R^{s2}$, $R^{s3}$, and $R^{s4}$ are independently H or $CH_3$, wherein $R^{2a}$ is H, an alkyl group, an aryl group, a benzyl group, a trityl group, —$SiR^aR^bR^c$, $CH_2OR^d$, or $COR^e$; and $R^5$ is H or $OR^{2b}$, wherein $R^{2b}$ is H, an alkyl group, an aryl group, an aryl group, a benzyl group, a trityl group, —$SiR^aR^bR^c$, $CH_2OR^d$, or $COR^e$; provided that the compound is not dictyostatin 1.

When groups including, but not limited to, —$SiR^aR^bR^c$, $CH_2OR^d$, and/or $COR^e$ are set forth as a substituent for more than one group in compounds of the claims and the specification of the present invention (for example, as a substituent of $R^2$, $R^{2a}$, $R^{s1}$, $R^{s2}$, $R^{s3}$, $R^{s4}$ and $R^5$ above), it is to be understood that the groups of those substituents ($R^a$, $R^b$, $R^c$, $R^d$, and $R^e$ in this example), are independently, the same of different within each group and among the groups.

In one embodiment, the compound has the following stereostructure, or its enantiomer:

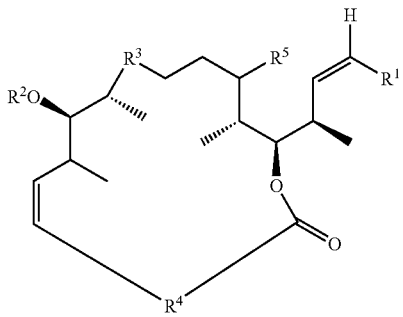

wherein $R^1$ is alkenyl; $R^2$ is H; $R^3$ is —$CH_2CH(CH_3)$ or —CH=$C(CH_3)$; and $R^4$ is —$(CHR^{k1})_{y1}(CHR^{k2})_{y2}$ $(CHR^{k3})_{y3}(CHR^{k4})_{y4}(CHR^{k5})_{y5}C(R^{s1})$=C $(R^{s2})C(R^{s3})$=C $(R^{s4})$— wherein y1–y4 are 1, y5 is 0, $R^{k1}$ and $R^{k3}$ are OH, $R^{k2}$ is H, $R^{k4}$ is $CH_3$, $R^{s1}$, $R^{s2}$, $R^{s3}$ and $R^{s4}$ are H, and $R^5$ is OH.

In one embodiment, $R^1$ is —CH=$CH_2$ and $R^4$ is

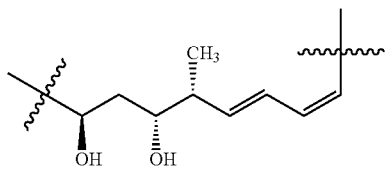

In another aspect, the present invention provides a compound of the following structure:

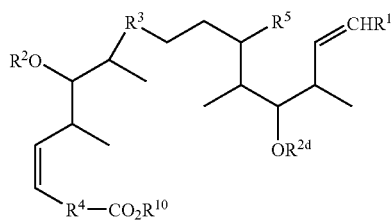

wherein $R^1$ is H, an alkyl group, an aryl group, an alkenyl group, an alkynyl group, or a halogen atom;
$R^2$ and $R^{2d}$ are independently H, an alkyl group, an aryl group, a benzyl group, a trityl group, —$SiR^aR^bR^c$, $CH_2OR^d$, or $COR^e$;
$R^a$, $R^b$ and $R^c$ are independently an alkyl group or an aryl group;
$R^d$ is an alkyl group, an aryl group, an alkoxylalkyl group, —$R^iSiR^aR^bR^c$ or a benzyl group, wherein $R^i$ is an alkylene group;
$R^e$ is an alkyl group, an allyl group, a benzyl group, an aryl group, an alkoxy group, or —$NR^gR^h$, wherein $R^g$ and $R^h$ are independently H, an alkyl group or an aryl group;
$R^3$ is $(CH_2)_n$ where n is and integer in the range of 0 to 5, —$CH_2CH(CH_3)$—, —CH=CH—, —CH=$C(CH_3)$—, or —C≡C—;
$R^4$ is $(CH_2)_p$ where p is an integer in the range of 4 to 12, —$(CHR^{k1})_{y1}(CHR^{k2})_{y2}(CHR^{k3})_{y3}(CHR^{k4})_{y4}(CHR^{k5})_{y5}$ $C(R^{s1})$=C $(R^{s2})C(R^{s3})$=$C(R^{s4})$—, —$(CHR^{k1})_{y1}$ $(CHR^{k2})_{y2}(CHR^{k3})_{y3}(CHR^{k4})_{y4}(CHR^{k5})_{y5}CH(R^{s1})CH$ $(R^{s2})C(R^{s3})$=$C(R^{s4})$—, —$(CHR^{k1})_{y1}(CHR^{k2})_{y2}$ $(CHR^{k3})_{y3}(CHR^{k4})_{y4}(CHR^{k5})_{y5}C(R^{s1})$=C $(R^{s2})CH(R^{s3})$ $CH(R^{s4})$—, —$(CHR^{k1})_{y1}(CHR^{k2})_{y2}(CHR^{k3})_{y3}(CHR^{k4})_{y4}$ $(CHR^{k5})_{y5}CH(R^{s1})CH$ $(R^{s2})CH(R^{s3})CH(R^{s4})$—, wherein y1 and y2 are 1 and y3, y4 and y5 are independently 0 or 1, $R^{k1}$, $R^{k2}$, $R^{k3}$, $R^{k4}$ and $R^{k5}$ are independently H, —$CH_3$, or $OR^{2a}$, and $R^{s1}$, $R^{s2}$, $R^{s3}$, and $R^{s4}$ are independently H or $CH_3$, wherein $R^{2a}$ is H, an alkyl group, an aryl group, a benzyl group, a trityl group, —$SiR^aR^bR^c$, $CH_2OR^d$, or $COR^e$; and
$R^5$ is H or $OR^{2b}$, wherein $R^{2b}$ is H, an alkyl group, an aryl group, a benzyl group, a trityl group, —$SiR^aR^bR^c$, $CH_2OR^d$, or $COR^e$; and
$R^{10}$ is H or alkyl.

In one embodiment, the compound has the following stereostructure, or its enantiomer

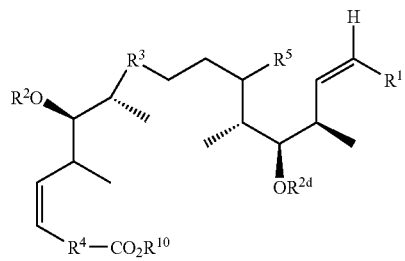

wherein $R^1$ is alkenyl; $R^2$ is H; $R^{2d}$ is H, $OC(O)CH_3$ or $OC(O)NR^gR^h$ wherein $R^g$ and $R^h$ are independently H, an alkyl group or an aryl group; $R^3$ is $CH_2CH(CH_3)$ or CH=$C(CH_3)$; and $R^4$ is —$(CHR^{k1})_{y1}(CHR^{k2})_{y2}(CHR^{k3})_{y3}$ $(CHR^{k4})_{y4}(CHR^{k5})_{y5}C(R^{s1})$=C $(R^{s2})C(R^{s3})$=$C(R^{s4})$— wherein y1–y4 are 1, y5 is 0, $R^{k1}$ and $R^{k3}$ are OH, $R^{k2}$ is H, $R^{k4}$ is $CH_3$, $R^{s1}$, $R^{s2}$, $R^{s3}$ and $R^{s4}$ are H, $R^5$ is OH; and $R^{10}$ is H or alkyl.

In another embodiment, $R^1$ is —CH=$CH_2$, and $R^{2d}$ is H, $OC(O)CH_3$ or $OC(O)NH_2$.

In a further aspect, the present invention provides a compound of the following structure:

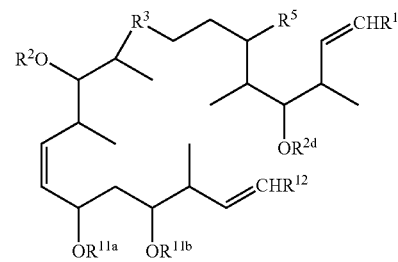

wherein $R^1$ is H, an alkyl group, an aryl group, an alkenyl group, an alkynyl group, or a halogen atom;
$R^2$ and $R^{2d}$ are independently H, an alkyl group, an aryl group, a benzyl group, a trityl group, —$SiR^aR^bR^c$, $CH_2OR^d$, or $COR^e$;
$R^a$, $R^b$ and $R^c$ are independently an alkyl group or an aryl group;
$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —CH=CH—, —CH=C(CH_3)—, or —C≡C—;

$R^5$ is H or $OR^{2b}$, wherein $R^{2b}$ is H, an alkyl group, an aryl group, a benzyl group, a trityl group, —$SiR^aR^bR^c$, $CH_2OR^d$, or $COR^e$;

$R^{11a}$ and $R^{11b}$ are independently H, an alkyl group, an aryl group, a benzyl group, a trityl group, —$SiR^aR^bR^c$, $CH_2OR^d$, $COR^e$, or $R^{11a}$ and $R^{11b}$ together form a portion of six-membered acetal ring incorporating $CR^tR^u$;

$R^t$ and $R^u$ are independently H, an alkyl group, an aryl group or an alkoxyarly group; and $R^{12}$ is a halogen atom, $CH_2OR^{2c}$, CHO, $CO_2R^{10}$, CH=CHCH_2OR^{2c}, CH=CHCHO, wherein $R^{2c}$ is H, an alkyl group, an aryl group, a benzyl group, a trityl group, —$SiR^aR^bR^c$, $CH_2OR^d$, or $COR^e$, and $R^{10}$ is H or alkyl.

In one embodiment, the compound has the following stereostructure, or its enantiomer

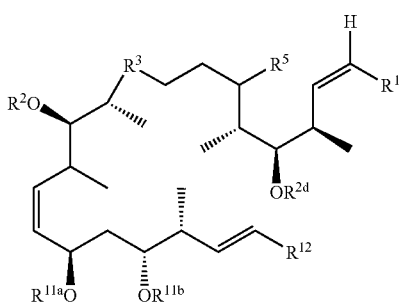

wherein $R^1$ is alkenyl; $R^{2d}$ is H, OC(O)CH_3 or OC(O)NR^gR^h wherein $R^g$ and $R^h$ are independently H, an alkyl group or an aryl group; $R^3$ is $CH_2CH(CH_3)$ or CH=C(CH_3); $R^{11a}$ and $R^{11b}$ are H or together form a portion of a six-membered acetal ring containing $C(H)(p-C_6H_4OCH_3)$ or $C(CH_3)_2$; $R^{12}$ is a halogen atom, $CH_2OR^{2c}$, CHO, $CO_2R^{10}$, CH=CHCH_2OR^{2c}, CH=CHCHO, wherein $R^{2c}$ is H, an alkyl group, an aryl group, a benzyl group, a trityl group, —$SiR^aR^bR^c$, $CH_2OR^d$, or $COR^e$, and $R^{10}$ is H or alkyl.

In another embodiment, $R^1$ is —CH=CH_2, $R^{2d}$ is H, —OC(O)CH_3 or —OC(O)NH_2, and $R^{12}$ is —CH_2OH, —CHO or —CO_2R^{10}.

In another aspect, the present invention provides a compound having the following structure:

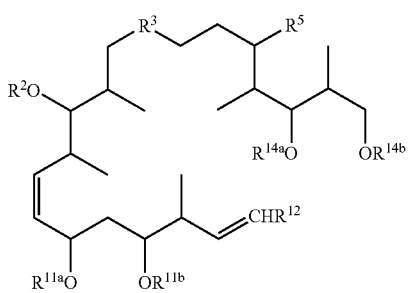

wherein $R^2$ is H, an alkyl group, an aryl group, a benzyl group, a trityl group, —$SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —CH=CH—, —CH=C(CH_3)—, or —C≡C—;

$R^5$ is H or $OR^{2b}$, wherein $R^{2b}$ is H, an alkyl group, an aryl group, a benzyl group, a trityl group, —$SiR^aR^bR^c$, $CH_2OR^d$, or $COR^e$;

$R^{11a}$ and $R^{11b}$ are independently H, an alkyl group, an aryl group, a benzyl group, a trityl group, —$SiR^aR^bR^c$, $CH_2OR^d$, $COR^e$, or $R^{11a}$ and $R^{11b}$ together form a portion of six-membered acetal ring containing $CR^tR^u$;

$R^t$ and $R^u$ are independently H, an alkyl group, an aryl group or an alkoxy aryl group;

$R^{12}$ is a halogen atom, $CH_2OR^{2c}$, CHO, $CO_2R^{10}$, CH=CHCH_2OR^{2c} or CH=CHCHO, CH=CHCO_2R^{10}, wherein $R^{2c}$ is H, an alkyl group, a benzyl group, a trityl group, —$SiR^aR^bR^c$, $CH_2OR^d$, or $COR^e$, and $R^{10}$ is H or alkyl; and $R^{14a}$ and $R^{14b}$ are independently H, an alkyl group, an aryl group, a benzyl group, a trityl group, —$SiR^aR^bR^c$, $CH_2OR^d$, $COR^e$, or $R^{14a}$ and $R^{14b}$ together form a six-membered ring containing $CR^vR^w$, wherein $R^v$ and $R^w$ are independently H, an alkyl group, an aryl group or an alkoxyaryl group.

In one embodiment, the compound has the following stereostructure, or its enantiomer

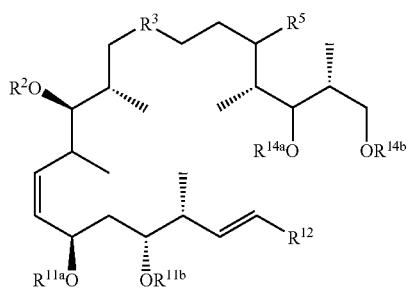

$R^2$ is H; $R^{2d}$ is H, OC(O)CH_3 or OC(O)NR^gR^h wherein $R^g$ and $R^h$ are independently H, an alkyl group or an aryl group; $R^3$ is $CH_2CH(CH_3)$ or CH=C(CH_3); $R^{11a}$ and $R^{11b}$ are H or together form a portion of a six-membered acetal ring containing $C(H)(p-C_6H_4OCH_3)$ or $C(CH_3)_2$; $R^{12}$ is a halogen atom, $CH_2OR^{2c}$, CHO, $CO_2R^{10}$, CH=CHCH_2OR^{2c}, CH=CHCHO or CH=CHCO_2R^{10}, wherein $R^{2c}$ is H, an alkyl group, an aryl group, a benzyl group, a trityl group, —$SiR^aR^bR^c$, $CH_2OR^d$, or $COR^e$, and $R^{10}$ is H or alkyl; and $R^{14a}$ and $R^{14b}$ are H or together form a portion of a six-membered acetal ring containing $C(H)(p-C_6H_4OCH_3)$ or $C(CH_3)_2$.

In another aspect, the present invention provides a compound having the following formula

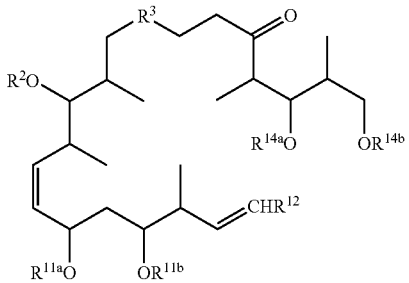

wherein $R^1$ is H, an alkyl group, an aryl group, an alkenyl group, an alkynyl group, or a halogen atom;

$R^2$ is H, an alkyl group, an aryl group, a benzyl group, a trityl group, —$SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —$CH=CH$—, —$CH=C(CH_3)$—, or —$C\equiv C$—;

$R^{11a}$ and $R^{11b}$ are independently H, an alkyl group, an aryl group, a benzyl group, a trityl group, —$SiR^aR^bR^c$, $CH_2OR^d$, $COR^e$, or $R^{11a}$ and $R^{11b}$ together form a portion of six-membered acetal ring containing $CR^tR^u$;

$R^t$ and $R^u$ are independently H, an alkyl group, an aryl group or an alkoxyarly group;

$R^{12}$ is a halogen atom, $CH_2OR^{2c}$, CHO, $CO_2R^{10}$, $CH=CHCH_2OR^{2c}$, $CH=CHCHO$ or $CH=CHCO_2R^{10}$, wherein $R^{2c}$ is H, an alkyl group, an aryl group; a benzyl group, a trityl group, —$SiR^aR^bR^c$, $CH_2OR^d$, or $COR^e$, and $R^{10}$ is H or alkyl; and $R^{14a}$ and $R^{14b}$ are independently H, an alkyl group, and aryl group, a benzyl group, a trityl group, —$SiR^aR^bR^c$, $CH_2OR^d$, $COR^e$, or $R^{14a}$ and $R^{14b}$ together form a six-membered ring containing $CR^vR^w$, wherein $R^v$ and $R^w$ are independently H, an alkyl group, an aryl group or an alkoxyaryl group.

In one embodiment, the compound has the following stereostructure, or its enantiomer

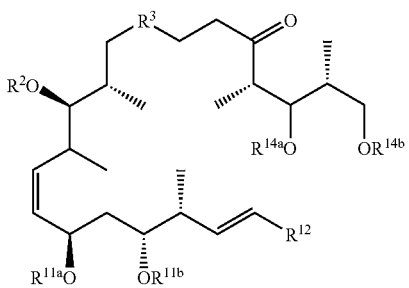

wherein $R^3$ is $CH_2CH(CH_3)$ or $CH=C(CH_3)$; $R^{11a}$ and $R^{11b}$ are H or together form a portion of a six-membered acetal ring containing $C(H)(p-C_6H_4OCH_3)$ or $C(CH_3)_2$; $R^{12}$ is a halogen atom, $CH_2OR^{2c}$, CHO, $CO_2R^{10}$, $CH=CHCH_2OR^{2c}$, $CH=CHCHO$ or $CH=CHCO_2R^{10}$, wherein $R^{2c}$ is H, an alkyl group, an aryl group, a benzyl group, a trityl group, —$SiR^aR^bR^c$, $CH_2OR^d$, or $COR^e$, and $R^{10}$ is H or alkyl; and $R^{14a}$ and $R^{14b}$ are H or together form a portion of a six-membered acetal ring containing C(H) (p-$C_6H_4OCH_3$) or $C(CH_3)_2$.

In a further aspect, the present invention provides a compound having the following formula

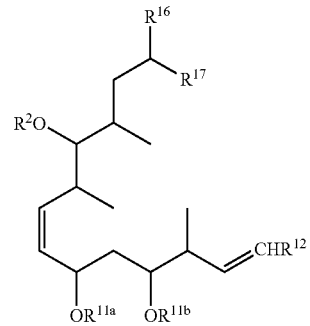

wherein $R^2$ is H, an alkyl group, an aryl group, a benzyl group, a trityl group, —$SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^{11a}$ and $R^{11b}$ are independently H, an alkyl group, and aryl group, a benzyl group, a trityl group, —$SiR^aR^bR^c$, $CH_2OR^d$, $COR^e$, or $R^{11a}$ and $R^{11b}$ together form a portion of six-membered acetal ring containing $CR^tR^u$;

$R^t$ and $R^u$ are independently H, an alkyl group, an aryl group or an alkoxyarly group;

$R^{12}$ is a halogen atom, $CH_2OR^{2c}$, CHO, $CO_2R^{10}$, $CH=CHCH_2OR^{2c}$, $CH=CHCHO$ or $CH=CHCO_2R^{10}$, wherein $R^{2c}$ is H, an alkyl group, an aryl group, a benzyl group, a trityl group, —$SiR^aR^bR^c$, $CH_2OR^d$, or $COR^e$, and $R^{10}$ is H or alkyl;

$R^{16}$ is H or alkyl; and $R^{17}$ is $CH_2OR^{2f}$, CHO, $CO_2R^{10}$, wherein $R^{2f}$ is H, an alkyl group, a benzyl group, a trityl group, —$SiR^aR^bR^c$, $CH_2OR^d$, or $COR^e$.

In one embodiment, the compound has the following stereostructure, or its enantiomer

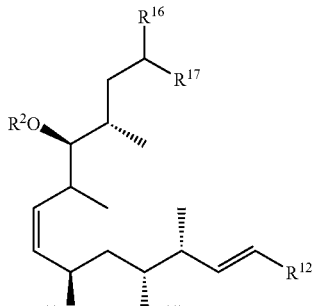

wherein $R^2$ is H, an alkyl group, a benzyl group, a trityl group, —$SiR^aR^bR^c$, $CH_2OR^d$, or $COR^e$; $R^{11a}$ and $R^{11b}$ are H or together form a portion of a six-membered acetal ring containing $C(H)(p-C_6H_4OCH_3)$ or $C(CH_3)_2$; and $R^{16}$ is H or alkyl.

In still a further aspect, the present invention provides a compound having the following formula

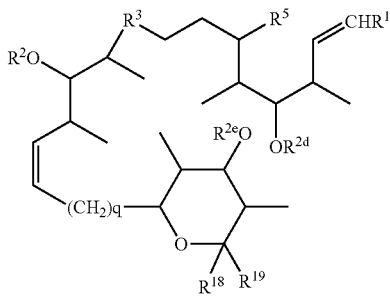

wherein $R^1$ is H, an alkyl group, an aryl group, an alkenyl group, an alkynyl group, or a halogen atom;

$R^2$, $R^{2d}$ and $R^{2e}$ are independently H, an alkyl group, an aryl group, a benzyl group, a trityl group, —$SiR^aR^bR^c$, $CH_2OR^d$, or $COR^e$;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —CH=CH—, —CH=C($CH_3$)—, or —C≡C—;

$R^5$ is H or $OR^{2b}$, wherein $R^{2b}$ is H, an alkyl group, an aryl group, a benzyl group, a trityl group, —$SiR^aR^bR^c$, $CH_2OR^d$, or $COR^e$; q is an integer in the range of 2 to 5;

$R^{18}$ is H, and $R^{19}$ is hydroxy, alkoxy or —$SR^z$, wherein $R^z$ is an alkyl group or an aryl group, or $R^{18}$ and $R^{19}$ taken together are =O.

In one embodiment, the compound has the following stereostructure, or its enantiomer

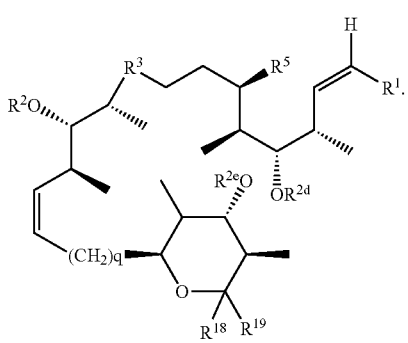

In one embodiment of the compound, $R^1$ is a CH=$CH_2$ and $R^3$ is (Z)—CH=CH—, or —$CH_2CH_2$—.

In a further aspect, the present invention provides a compound having the following structure

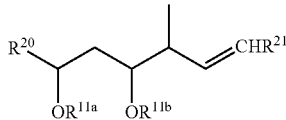

$R^{11a}$ and $R^{11b}$ are independently H, an alkyl group, an aryl group, a benzyl group, a trityl group, —$SiR^aR^bR^c$, $CH_2OR^d$, $COR^e$, or $R^{11a}$ and $R^{11b}$ together form a portion of six-membered acetal ring containing $CR^tR^u$;

$R^t$ and $R^u$ are independently H, an alkyl group, an aryl group or an alkoxyarly group;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^{20}$ is $CH_2OR^{2g}$, CHO, $CO_2R^{10}$; wherein $R^{2g}$ is H, an alkyl group, an aryl group, a benzyl group, a trityl group, —$SiR^aR^bR^c$, $CH_2OR^d$, or $COR^e$, and wherein $R^{10}$ is H or alkyl; and $R^{21}$ is a halogen atom, $CH_2OR^{2c}$, CHO, $CO_2R^{10a}$, CH=CH$CH_2OR^{2c}$, CH=CHCHO or CH=CH$CO_2R^{10}$, wherein $R^{2c}$ is H, an alkyl group, an aryl group, a benzyl group, a trityl group, —$SiR^aR^bR^c$, $CH_2OR^d$, or $COR^e$, and wherein $R^{10a}$ is H or alkyl.

In one embodiment, the compound has the following stereostructure, or its enantiomer

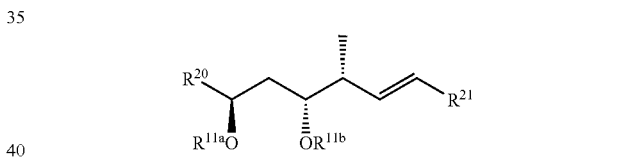

wherein $R^{11a}$ and $R^{11b}$ are independently H, an alkyl group, and aryl group, a benzyl group, a trityl group, —$SiR^aR^bR^c$, $CH_2OR^d$, $COR^e$, or $R^{11a}$ and $R^{11b}$ together form a portion of six-membered acetal ring incorporating $CR^tR^u$;

$R^t$ and $R^u$ are independently H, an alkyl, an aryl group or an alkoxyarly group;

$R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^{20}$ is $CH_2OR^{2g}$, CHO, $CO_2R^{10}$; wherein $R^{2g}$ is H, an alkyl group, a benzyl group, a trityl group, —$SiR^aR^bR^c$, $CH_2OR^d$, or $COR^e$, and wherein $R^{10}$ is H or alkyl; and $R^{21}$ is a halogen atom, $CH_2OR^{2c}$, CHO, $CO_2R^{10a}$, CH=CH$CH_2OR^{2c}$, CH=CHCHO, CH=CH$CO_2R^{10}$ wherein $R^{2c}$ is H, an alkyl group, a benzyl group, a trityl group, —$SiR^aR^bR^c$, $CH_2OR^d$, or $COR^e$, and wherein $R^{10a}$ is H or alkyl.

In one embodiment, $R^{11a}$ and $R^{11b}$ are H or together form a portion of a six-membered acetal ring containing $C(H)(p-C_6H_4OCH_3)$ or $C(CH_3)_2$; $R^{21}$ is a halogen atom, $CH_2OR^{2c}$, CHO, $CO_2R^{10}$, $CH=CHCH_2OR^{2c}$, $CH=CHCHO$, wherein $R^{2c}$ is H, an alkyl group, an aryl group, a benzyl group, a trityl group, $-SiR^aR^bR^c$, $CH_2OR^d$, or $COR^e$, and $R^{10}$ is H or alkyl.

In another embodiment, $R^1$ is $CH=CH_2$, and $R^{21}$ is $CH_2OH$, CHO or $CO_2R^{10}$.

In still another aspect, the present invention provides a compound having the following formula

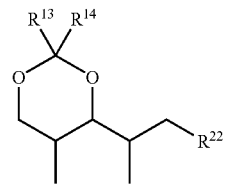

wherein $R^{13}$ is H or an alkyl group, $R^{14}$ is H, an aryl group, an alkoxyaryl group or an alkyl group, and $R^{22}$ is a halogen atom or $-P(Ar)_3X$, wherein X is a counteranion selected from the groups halide, tetrafluoroborate, hexafluorophosphate and sulfonate, provided that when $R^{13}$ and $R^{14}$ are methyl groups, X is not I. In one embodiment, when $R^{13}$ and $R^{14}$ are alkyl groups, X is not halogen.

In another embodiment, the compound has the following stereostructure, or its enantiomer

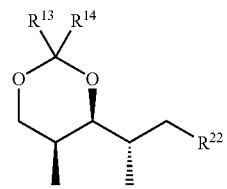

wherein $R^{13}$ is H or an alkyl group, and $R^{14}$ is H, an aryl group, an alkoxyaryl group, or an alkyl group, an aryl group or an alkoxyarly group, $R^{22}$ is a halogen atom or $-P(Ar)_3X$, wherein X is a counteranion selected from the groups halide, tetrafluoroborate, hexafluorophosphate and sulfonate, provided that when $R^{13}$ and $R^{14}$ are methyl groups, X is not I.

In one embodiment, $R^{13}$ is H, $R^{14}$ is aryl, and $R^{22}$ is $P(C_6H_5)_3X$. In another embodiment, $R^{14}$ is $C_6H_4\text{-p-OCH}_3$.

In still a further aspect, the present invention provides a process for conversion of a first compound with the formula

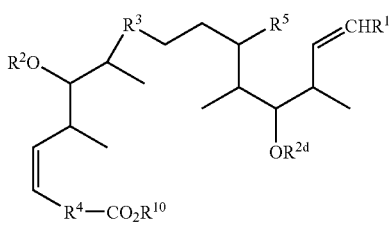

wherein $R^1$ is H, an alkyl group, an aryl group, an alkenyl group, an alkynyl group, or a halogen atom;
$R^2$ is H, an alkyl group, an aryl group, a benzyl group, a trityl group, $-SiR^aR^bR^c$, $CH_2OR^d$, or $COR^e$;
$R^{2d}$ is H $R^a$, $R^b$ and $R^c$ are independently an alkyl group or an aryl group;
$R^d$ is an alkyl group, an aryl group, an alkoxylalkyl group, $-R^iSiR^aR^bR^c$ or a benzyl group, wherein $R^i$ is an alkylene group;
$R^e$ is an alkyl group, an allyl group, a benzyl group, an aryl group, an alkoxy group, or $-NR^gR^h$, wherein $R^g$ and $R^h$ are independently H, an alkyl group or an aryl group;
$R^3$ is $(CH_2)_n$ where n is and integer in the range of 0 to 5, $-CH_2CH(CH_3)-$, $-CH=CH-$, $-CH=C(CH_3)-$, or $-C\equiv C-$;
$R^4$ is $(CH_2)_p$ where p is an integer in the range of 4 to 12, $-(CHR^{k1})_{y1}(CHR^{k2})_{y2}(CHR^{k3})_{y3}(CHR^{k4})_{y4}(CHR^{k5})_{y5}C(R^{s1})=C(R^{s2})C(R^{s3})=C(R^{s4})-$, $-(CHR^{k1})_{y1}(CHR^{k2})_{y2}(CHR^{k3})_{y3}(CHR^{k4})_{y4}(CHR^{k5})_{y5}CH(R^{s1})CH(R^{s2})C(R^{s3})=C(R^{s4})-$, $-(CHR^{k1})_{y1}(CHR^{k2})_{y2}(CHR^{k3})_{y3}(CHR^{k4})_{y4}(CHR^{k5})_{y5}C(R^{s1})=C(R^{s2})CH(R^{s3})CH(R^{s4})-$, $-(CHR^{k1})_{y1}(CHR^{k2})_{y2}(CHR^{k3})_{y3}(CHR^{k4})_{y4}(CHR^{k5})_{y5}CH(R^{s1})CH(R^{s2})CH(R^{s3})CH(R^{s4})-$, wherein y1 and y2 are 1 and y3, y4 and y5 are independently 0 or 1, $R^{k1}$, $R^{k2}$, $R^{k3}$, $R^{k4}$ and $R^{k5}$ are independently H, $CH_3$, or $OR^{2a}$, and $R^{s1}$, $R^{s2}$, $R^{s3}$, and $R^{s4}$ are independently H or $CH_3$, wherein $R^{2a}$ is H, an alkyl group, an aryl group, a benzyl group, a trityl group, $-SiR^aR^bR^c$, $CH_2OR^d$, or $COR^e$; and
$R^5$ is H or $OR^{2b}$, wherein $R^{2b}$ is H, an alkyl group, an aryl group, a benzyl group, a trityl group, $-SiR^aR^bR^c$, $CH_2OR^d$, or $COR^e$; and
$R^{10}$ is H;

to a second compound with the formula

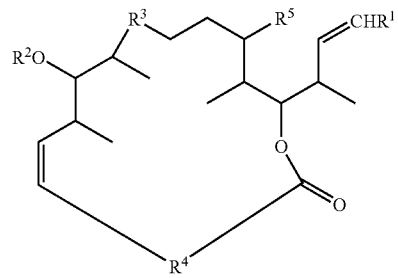

comprising the step of reacting the first compound under conditions suitable to effect macrolactonization.

In one embodiment, the process is for conversion of a compound with the following stereostructure or its enantiomer

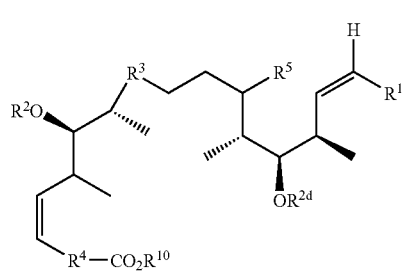

wherein $R^1$ is H, an alkyl group, an alkenyl group, an alkynyl group, or a halogen atom;

$R^2$ is H, an alkyl group, an aryl group, a benzyl group, a trityl group, —SiR$^a$R$^b$R$^c$, CH$_2$OR$^d$, or COR$^e$;

$R^{2d}$ is H $R^a$, $R^b$ and $R^c$ are independently an alkyl group or an aryl group;

$R^d$ is an alkyl group, an aryl group, an alkoxylalkyl group, —R$^i$SiR$^a$R$^b$R$^c$ or a benzyl group, wherein R$^i$ is an alkylene group;

$R^e$ is an alkyl group, an allyl group, a benzyl group, an aryl group, an alkoxy group, or —NR$^g$R$^h$, wherein R$^g$ and R$^h$ are independently H, an alkyl group or an aryl group;

$R^3$ is (CH$_2$)$_n$ where n is and integer in the range of 0 to 5, —CH$_2$CH(CH$_3$)—, —CH=CH—, —CH=C(CH$_3$)—, or —C≡C—;

$R^4$ is (CH$_2$)$_p$ where p is an integer in the range of 4 to 12, —(CHR$^{k1}$)$_{y1}$(CHR$^{k2}$)$_{y2}$(CHR$^{k3}$)$_{y3}$(CHR$^{k4}$)$_{y4}$(CHR$^{k5}$)$_{y5}$C(R$^{s1}$)=C (R$^{s2}$)C(R$^{s3}$)=C(R$^{s4}$)—, —(CHR$^{k1}$)$_{y1}$(CHR$^{k2}$)$_{y2}$(CHR$^{k3}$)$_{y3}$(CHR$^{k4}$)$_{y4}$(CHR$^{k5}$)$_{y5}$CH(R$^{s1}$)CH(R$^{s2}$)C(R$^{s3}$)=C(R$^{s4}$)—, —(CHR$^{k1}$)$_{y1}$(CHR$^{k2}$)$_{y2}$(CHR$^{k3}$)$_{y3}$(CHR$^{k4}$)$_{y4}$(CHR$^{k5}$)$_{y5}$C(R$^{s1}$)=C (R$^{s2}$)CH(R$^{s3}$)CH(R$^{s4}$)—, —(CHR$^{k1}$)$_{y1}$(CHR$^{k2}$)$_{y2}$(CHR$^{k3}$)$_{y3}$(CHR$^{k4}$)$_{y4}$(CHR$^{k5}$)$_{y5}$CH(R$^{s1}$)CH (R$^{s2}$)CH(R$^{s3}$)CH(R$^{s4}$)—, wherein y1 and y2 are 1 and y3, y4 and y5 are independently 0 or 1, R$^{k1}$, R$^{k2}$, R$^{k3}$, R$^{k4}$ and R$^{k5}$ are independently H, —CH$_3$, or OR$^{2a}$, and R$^{s1}$, R$^{s2}$, R$^{s3}$, and R$^{s4}$ are independently H or CH$_3$, wherein R$^{2a}$ is H, an alkyl group, an aryl group, a benzyl group, a trityl group, —SiR$^a$R$^b$R$^c$, CH$_2$OR$^d$, or COR$^e$;

$R^5$ is H or OR$^{2b}$, wherein R$^{2b}$ is H, an alkyl group, an aryl group, a benzyl group, a trityl group, —SiR$^a$R$^b$R$^c$, CH$_2$OR$^d$, or COR$^e$; and $R^{10}$ is H to a second compound with the formula

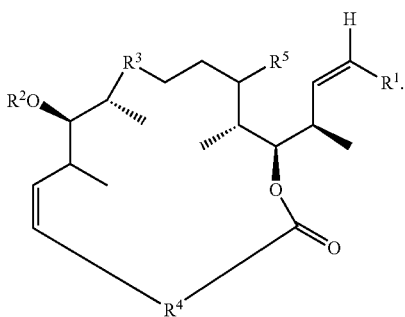

In one embodiment of the process, $R^1$ is alkenyl; $R^3$ is CH$_2$CH(CH$_3$) or CH=C(CH$_3$); and $R^4$ is —(CHR$^{k1}$)$_{y1}$(CHR$^{k2}$)$_{y2}$(CHR$^{k3}$)$_{y3}$(CHR$^{k4}$)$_{y4}$(CHR$^{k5}$)$_{y5}$C(R$^{s1}$)=C (R$^{s2}$)C(R$^{s3}$)=C(R$^{s4}$)— wherein y1–y4 are 1, y5 is 0, R$^{k1}$ and R$^{k3}$ are R$^{2a}$, R$^{k2}$ is H, R$^{k4}$ is CH$_3$, R$^{s1}$–R$^{s4}$ are H, and R$^5$ is OR$^{2b}$.

In another embodiment of the process, $R^1$ is CH=CH$_2$ and $R^4$ is

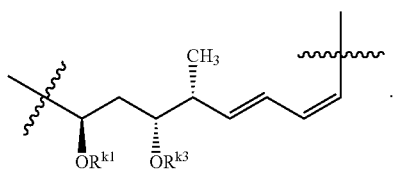

In one embodiment of the process, the first compound is converted by reacting the first compound with 2,4,6-trichlorobenzoylchloride.

The above general structures for the compounds of the present invention include all stereoisomers thereof (other than the natural compound dictyostatin 1). Moreover, the structures of the compounds of the present invention include the compounds in racemic form, enantiomerically enriched form or enantiomerically pure form.

The terms "alkyl", "aryl" and other groups refer generally to both unsubstituted and substituted groups unless specified to the contrary. In that regard, the groups set forth above can be substituted with a wide variety of substituents to synthesize analogs retaining biological activity. Unless otherwise specified, alkyl groups are hydrocarbon groups and are preferably C$_1$–C$_{15}$ (that is, having 1 to 15 carbon atoms) alkyl groups, and more preferably C$_1$–C$_{10}$ alkyl groups, and can be branched or unbranched, acyclic or cyclic. The above definition of an alkyl group and other definitions apply also when the group is a substituent on another group (for example, an alkyl group as a substituent of an alkylamino group or a dialkylamino group). The term "aryl" refers to phenyl or naphthyl. As used herein, the terms "halogen" or "halo" refer to fluoro, chloro, bromo and iodo.

The term "alkoxy" refers to —OR, wherein R is an alkyl group. The term "alkenyl" refers to a straight or branched chain hydrocarbon group with at least one double bond, preferably with 2–15 carbon atoms, and more preferably with 2–10 carbon atoms (for example, —CH=CHR or —CH$_2$CH=CHR; wherein R can be a group including, but not limited to, an alkyl group, an alkoxyalkyl group, an amino alkyl group, an aryl group, or a benzyl group). The term "alkynyl" refers to a straight or branched chain hydrocarbon group with at least one triple bond, preferably with 2–15 carbon atoms, and more preferably with 2–10 carbon atoms (for example, —C≡CR or —CH$_2$—C≡CR; wherein R can be a group including, but not limited to, an alkyl group, an alkoxyalkyl group, an amino alkyl group, an aryl group, or a benzyl group). The terms "alkylene," "alkenylene" and "alkynylene" refer to bivalent forms of alkyl, alkenyl and alkynyl groups, respectively.

The term "trityl" refers to a triphenyl methyl group or —C(Ph)$_3$.

Certain groups such as amino and hydroxy groups may include protective groups as known in the art. Preferred protective groups for amino groups include tert-butyloxycarbonyl, formyl, acetyl, benzyl, p-methoxybenzyloxycarbonyl, trityl. Other suitable protecting groups as known to those skilled in the art are disclosed in Greene, T., Wuts, P. G. M., *Protective Groups in Organic Synthesis*, Wiley (1991), the disclosure of which is incorporated herein by reference.

Other aspects of the present invention include the synthesis of the compounds of the present invention as well as the biological assaying of such compound and the biological activity of such compounds against, for example, cancer (such as breast, prostate cancer and ovarial cancer). For example, in another aspect, the present invention provides a method of treating a patient for cancer, including the step of administering a pharmaceutically effective amount of a biologically active compound of the present invention or a pharmaceutically acceptable salt thereof.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 2 illustrates one embodiment of the syntheses of an intermediate for the center part of the configuration of (+)-discodermolide.

FIG. 4 illustrates one embodiment of the construction of the right fragment or part of the molecule.

FIGS. 6A through D illustrate the tubulin polymerization-inducing properties of discodermolide (Figure A), as well as discodermolide analog compounds 40 (Figure B), 41 (Figure C) and 42 (Figure D) of the present invention in comparison to 10 μM paclitaxel (PTX).

FIG. 7 illustrates a retrosynthetic analysis of a dictyostatin analog of the present invention.

DETAILED DESCRIPTION OF THE INVENTION

Synthesis of Simplified Analogs of Discodermolide: The inventors of the present invention hypothesized that active analogs of discodermolide would result after removal of the C14 and C16 methyl groups and the C7 hydroxy group. These deletions greatly simplify the synthesis by allowing the two cis-disubstituted alkenes of analogs 1 and 2 to be made by Wittig-type reactions. A family of simple analogs 1 were shown to have moderate activity. However, by incorporating a lactone in place of the simple ester side chains of 1, the inventors of the present invention have discovered anti-cancer agents of increased activity that are still significantly simpler to make than discodermolide.

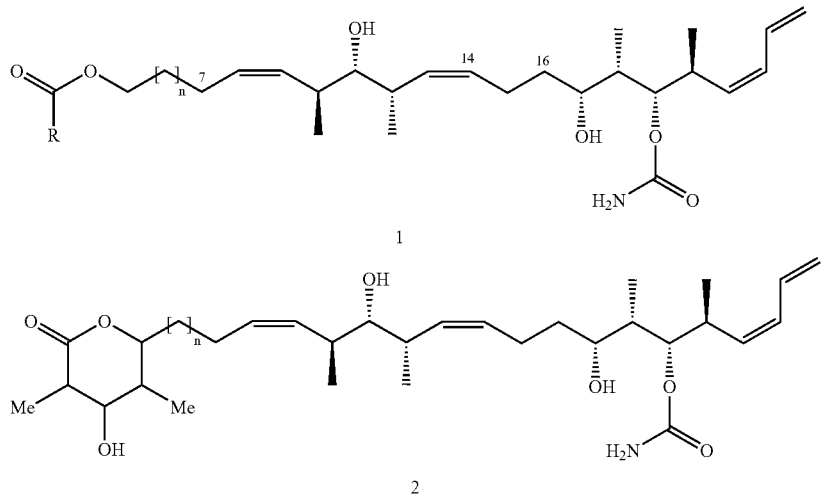

Figure 1:
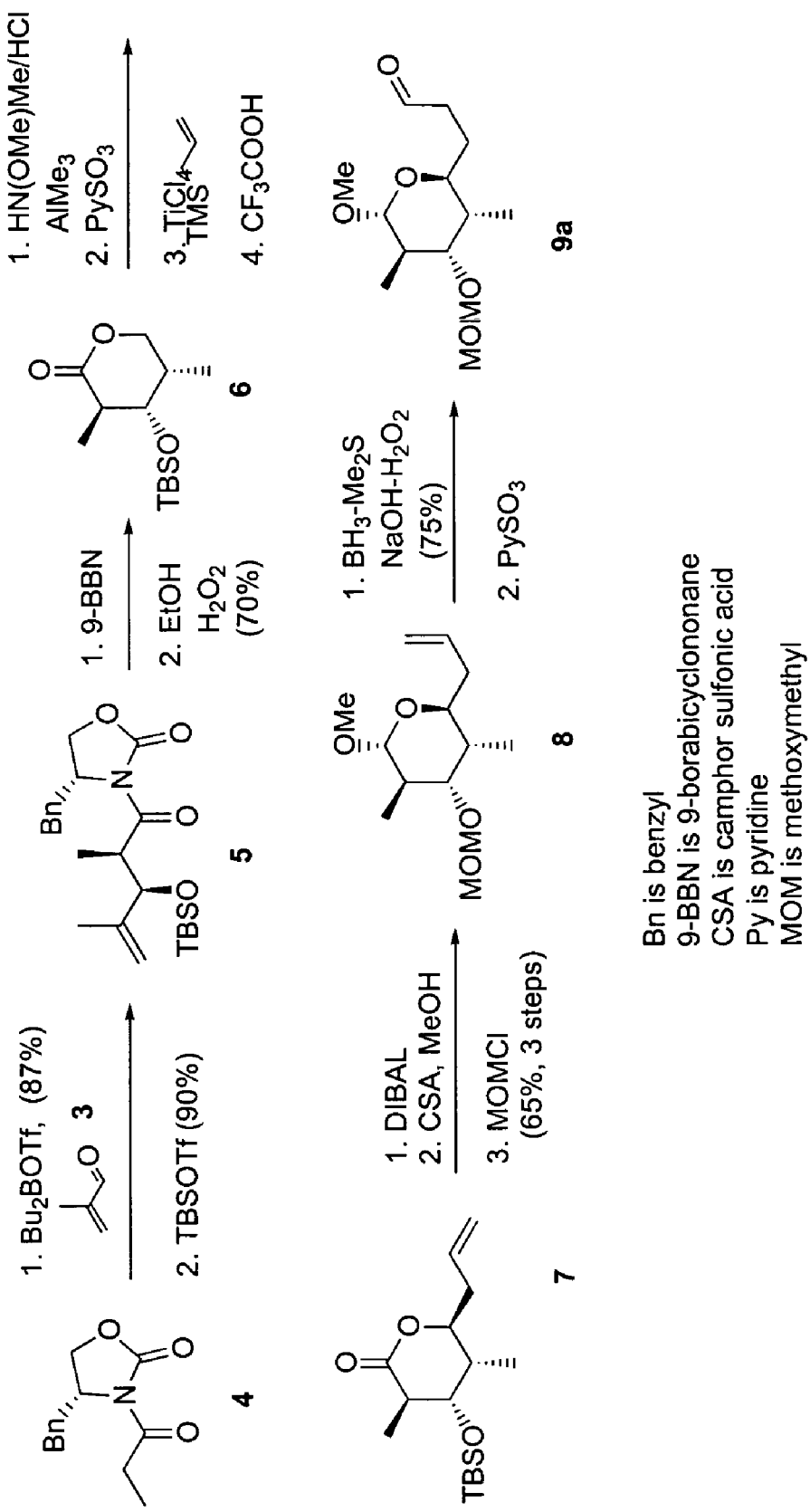
FIG. 1 illustrates one embodiment of the syntheses of a representative isomeric aldehyde for incorporation of the left part of the configuration of (+)-discodermolide.
Figure 2:
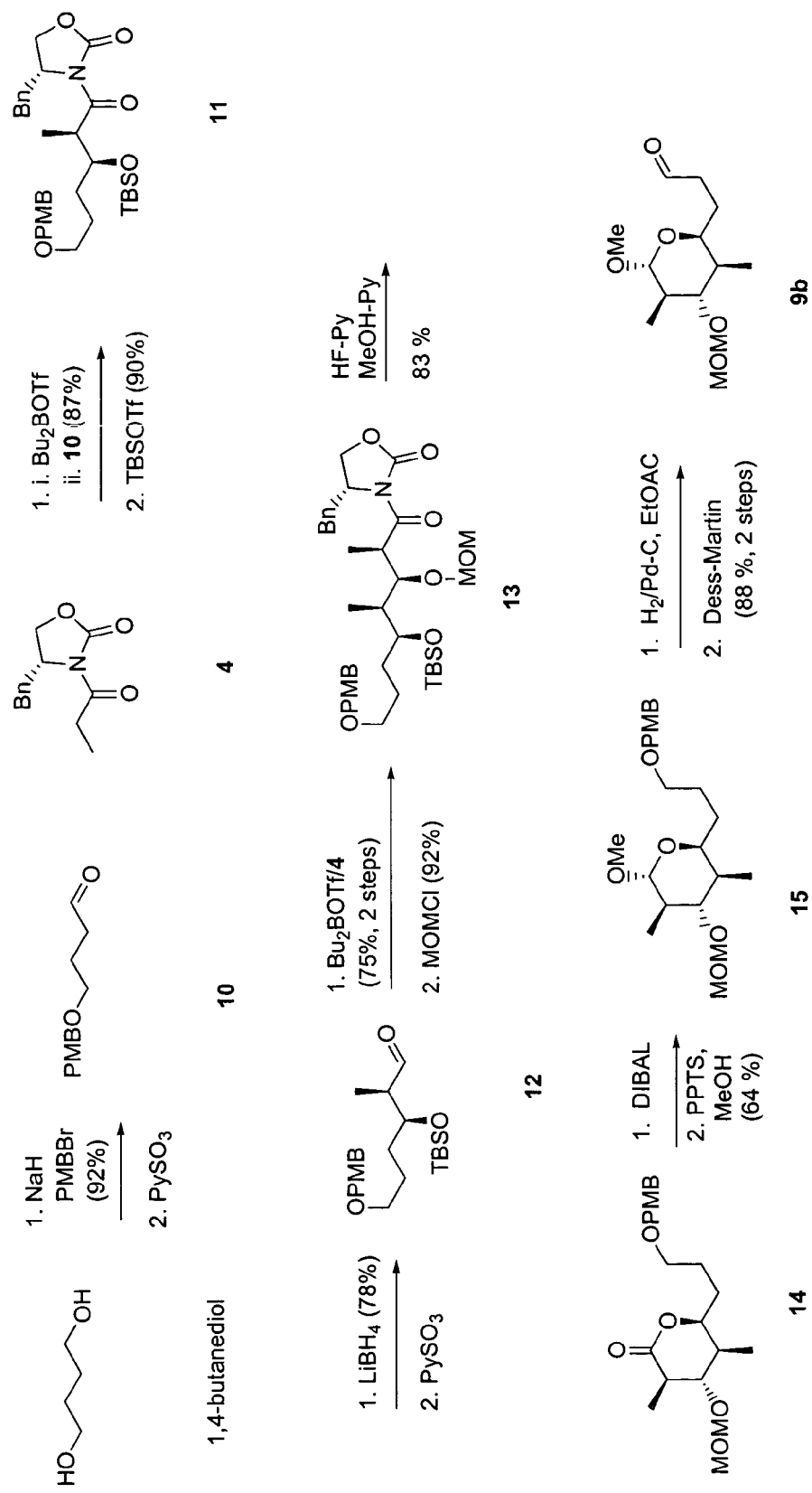
FIG. 2 illustrates one embodiment of the syntheses of another representative isomeric aldehyde for incorporation of the left part of the configuration of (+)-discodermolide.

The syntheses of two representative isomeric aldehydes 9a and 9b for incorporation of the left part of these molecules are shown in FIGS. 1 and 2. he synthesis of the left display bearing the configuration of (+)-discodermolide started with the commercially available methacrolein 3 (FIG. 1). Reaction of 3 with the boron enolate of Evans oxazolidinone 4 gave the corresponding alcohol, which was silylated to give compound 5 in 90% yield. Lactonization followed by the introduction of allyl group was performed by the previously reported method to give 6 in good yield. See Day, B. W.; Kangani, C. O.; Avor, K. S. Convenient syntheses of (2R,3S,4R)-3-(tert-butyldimethylsilanyloxy)-2,4-dimethyl-5-oxopentanoic acid methoxymethyl-amide from methacrolein. Preparation of C1–C7 and C17–C24 fragments of (+)-discodermolide. *Tetrahedron Asymmetry* 2002, 13, 1161–1165. Lactone opening, oxidation and allylation gave 7. Conversion to the methyl acetal was accomplished by DIBAL (diisobutylaluminum hydride) reduction to the corresponding lactol followed by treatment with camphorsulfonic acid (CSA) in methanol to give a desilylated intermediate, which was protected with methoxymethyl chloride (MOMCl) to give a mixture of anomers 8 (β:α=1:1). These were separable by silica gel flash chromatography. The final left fragment 9a was obtained by hydroboration of the α-anomer 8 with BH$_3$-DMS (borane-dimethysulfide) followed by oxidation with SO$_3$-pyridine.

The synthesis of the C4-epi lactone left display 9b started from 1,4-butanediol (FIG. 2). Monoprotection with PMB bromide (PMB is p-methoxybenzyl) was performed with NaH in DMF. After oxidation, reaction of the crude aldehyde 10 with the boron enolate of Evans oxazolidinone 4 gave the corresponding syn-alcohol, which was silylated to give compound 11 in 90% yield. Lithium borohydride reduction followed by oxidation gave the aldehyde 12. A second syn-aldol addition was performed with same Evans oxazolidinone 4 to give the corresponding alcohol, which was protected with MOM chloride to give compound 13. Desilylation of 13 with HF gave the cyclized product 14 in high yield. Conversion to the methyl acetal was easily accomplished by DIBAL reduction to the corresponding lactol followed by treatment with PPTS (pyridinium p-toluene sulfonate) in methanol to give 15 as a 2.5:1 (α:β) mixture of anomers from which the major anomer (α) was isolated by silica gel flash chromatography. The final left fragment 9b was obtained by hydrogenolysis of the PMB protecting group followed by Dess-Martin oxidation.

These synthetic routes are flexible and substantially any stereoisomer of the lactone 9 can be made with the appropriate chiral auxiliary and reaction conditions.

Center intermediate 21 was prepared as shown in FIG. 3. Oxazolidinone 18 was prepared from (S)-3-hydroxy-2-methylpropionic methyl ester 16 by the known procedure for the preparation of ent-18. See Clark, D. L.; Heathcock, C. H. Studies on the alkylation of chiral enolates: application toward the total synthesis of discodermolide. *J. Org. Chem.* 1993, 58 5878–5879. Reduction of 18 with lithium borohydride gave the diol, which was protected by anisaldehyde dimethyl acetal 19 to give the acetal 20. Deprotection of the primary TBS group with tetrabutylammonium fluoride (TBAF), iodination, and treatment with triphenylphosphine afforded the phosphonium salt 21 in 72% yield. Phosphonium salts 22 and 23 were also used for Wittig olefination, but the results were unsatisfactory. Smith also encountered difficulties with related Wittig reagents in discodermolide synthesis. See: Smith, A. B.; Beauchamp, T. J.; LaMarche, M. J.; Kaufman, M. D.; Qiu, Y. P. et al. Evolution of a gram-scale synthesis of (+)-discodermolide. *J. Am. Chem. Soc.* 2000, 122, 8654–8664. These difficulties may result, at least in part, from the hygroscopic nature of the phosphonium salts. In contrast, compound 21 is a white, non-hygroscopic solid and its Wittig reactions were reliable even though no special care was taken with its storage (for example, salt 21 was useful for reactions even after it was stored at room temperature for several months).

As shown in FIG. 4, the construction of the right fragment 34 featured aldol reactions. Syn-Aldol reaction of aldehyde 24 with 4 provided 25, which was reduced to a diol and protected with anisaldehyde dimethyl acetal 19 to give 26. Selective opening of the benzylidine ring of 26 with DIBAL gave a primary alcohol, which was oxidized to aldehyde 27. The subsequent anti-aldol condensation using Heathcock's aldol reaction with dimethylphenyl propionate 28 furnished compound 29 as the major product in 73% yield. See Heathcock, C. H.; Pirrung, M. C.; Montgomery, S. H.; Lampe, J. Acyclic stereoselection-13; Aryl esters: reagents for threo-aldolization. *Tetrahedron* 1981, 37, 4087–4095.

The relative configuration of intermediate 29 was confirmed by $^{13}$C and $^1$H NMR analyses of the corresponding acetonide 34. Silylation of the newly formed hydroxyl group of 29, reduction of the aryl ester with DIBAL and Dess-Martin oxidation of the resultant primary alcohol afforded aldehyde 30. The Z-diene moiety was introduced by a two-step procedure developed by Paterson and coworkers using a Nozaki-Hiyama reaction. See Paterson, I.; Schlapbach, A. Studies towards the total synthesis of the marine-derived immunosuppresant discodermolide: stereoselective synthesis of a C9–C24 subunit. *Synlett.* 1995, 498–500. Addition of the aldehyde 30 and allyl bromide 31 to a suspension of CrCl$_2$ in THF produced an intermediate β-hydroxy silane (not shown), which upon treatment with NaH underwent syn elimination to generate the required Z-diene 32. Selective deprotection of the primary TBS group, iodination, and then treatment with triphenylphosphine gave the phosphonium salt 33 in good yield.

Figure 5:
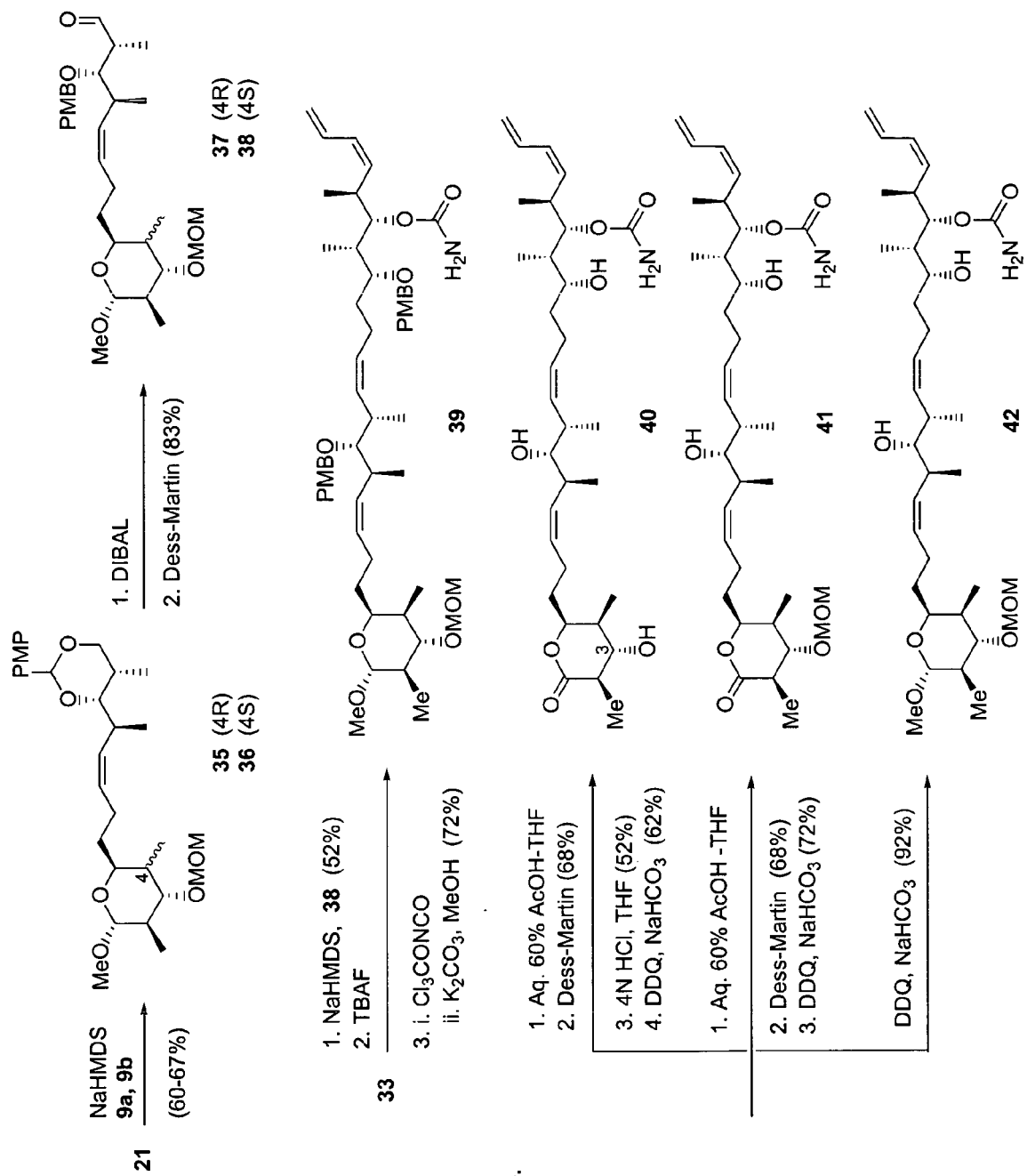
FIG. 5 illustrates an embodiment of the synthesis of several discodermolide analogs of the present invention.

The first Wittig reaction of 9a with 21 provided 35 (see FIG. 5). DIBAL reductive cleavage of the acetal followed by Dess-Martin oxidation gave aldehyde 37. Likewise, aldehyde 38 was made from 9b via 36. The second Wittig olefination was accomplished with 38 as an example and phosphonium salt 33 (FIG. 5). Tetrabutylammonium fluoride deprotection followed by carbamoylation using Koçovsky's method (See Koçovsky, P. Carbamates: a method of synthesis and some synthetic applications. *Tetrahedron Lett.* 1986, 27 5521–5524) afforded the C19 carbamate-containing compound 39. The lactone was built from the methyl acetal in the left fragment by using aqueous 60% acetic acid in THF followed by Dess-Martin oxidation. Deprotected analog 40 containing a free C3 hydroxy group on the lactone was obtained by the removal of MOM group with 4N HCl followed by removal of the PMB protecting groups with DDQ oxidation. Two additional example compounds, 41 and 42, were prepared from the intermediate 39 by using appropriate conditions. All three of these analogs exhibited significant activity, as shown in FIGS. 6A–D and Table 1. Surprisingly, the C3-MOM-protected analogs 41 and 42 showed better microtubule hypernucleation activities than the analog 40 with a free C3-hydroxy group. As can be seen in FIG. 6A, discodermolide is superior to paclitaxel (taxol) in that it causes equivalent microtubule assembly at both lower concentrations and temperatures (the increase in absorbance caused by discodermolide occurs at a time point earlier than that caused by paclitaxel). Additionally, the polymer induced to form by discodermolide is more resistant to cold-induced disassembly than is the paclitaxel-induced polymer. Both analogs 41 (FIG. 6C) and 42 (FIG. 6D) showed these more rapid polymer-inducing and cold-resistant properties, albeit at somewhat lower potencies (for example, higher concentrations of the analogs were necessary for these effects to be detected) than discodermolide. MOM ether lactone 41 was the most potent among these analogs.

Table 1 shows microtubule stabilizing, antiproliferative, and paclitaxel-displacing properties of 40–42. Again, the lactone, MOM ether 41 was more potent than the lactol 42 or free hydroxy 40 relatives. The cellular activity of 41 was good, showing a submicromolar 50% growth inhibitory (GI$_{50}$) concentration. This compound also showed considerable affinity for the paclitaxel binding site on tubulin. A 2-fold molar excess of 41 displaced [$^3$H]paclitaxel from microtubules better than paclitaxel and at almost the same potency as discodermolide.

TABLE 1

Microtubule stabilizing, antiproliferative and paclitaxel-displacing properties of compounds 40–42 in comparison to (+)-discodermolide (1) and paclitaxel.

| Compound | MT stabilizing activity (%)[a] | $GI_{50}$ (μM)[b] | | | Displacement of [³H]paclitaxel (%)[c] |
| --- | --- | --- | --- | --- | --- |
| | | MDA-MB231 (breast) | PC3 (prostate) | 2008 (ovarian) | |
| discodermolide | >100 | 0.016 ± 0.003 | 0.067 ± 0.004 | 0.072 ± 0.005 | 64 ± 2 |
| paclitaxel | 100 | 0.0024 ± 0.0016 | 0.015 ± 0.002 | 0.0092 ± 0.0016 | 37 ± 1 |
| 40 | 11 | 2.1 ± 1.8 | 7.5 ± 2.0 | 5.2 ± 1.0 | 21 ± 1 |
| 41 | 27 | 0.87 ± 0.21 | 1.8 ± 0.9 | 0.65 ± 0.25 | 57 ± 2 |
| 42 | 11 | 3.4 ± 0.8 | 15 ± 3 | 4.7 ± 0.6 | 19 ± 2 |

[a]Percent tubulin assembly induced by test agent at 10 μM vs. that caused by 10 μM paclitaxel (100%); single determinations at 30° C.
[b]Concentration at which test agent caused 50% inhibition of cell growth; means (N = 4 over 10 concentrations) ± SD after 72 h of continuous exposure to the agent.
[c]Percent displacement by 4 μM test agent of 2 μM [³H]paclitaxel bound to microtubules formed from 2 μM tubulin and 20 μM dideoxyGTP.

Macrocycle 43 is a representative example of a dictyostatin analog with an alkyl chain bridging the lactone carbonyl group and the C10/C11 alkene and with two Z-double bonds in the macrocycle. It can also be considered as a macrocyclic analog of discodermolide. This can be synthesized convergently from three components—33, 21 and 44—via sequential Wittig couplings and a macrocyclization (FIG. 7). This design allows the synthesis of substantially any stereoisomer by employing the desired isomer of the relevant precursor—21 or 33.

Fragment 45 was synthesized from 1,10-decanediol (not shown) by mono-TBS protection (NaH/TBSCl, 42%) followed by Dess-Martin oxidation (80%). Fragment 21 was prepared as shown in FIG. 3. Fragment 33 was prepared as shown in FIG. 4.

Figure 8:
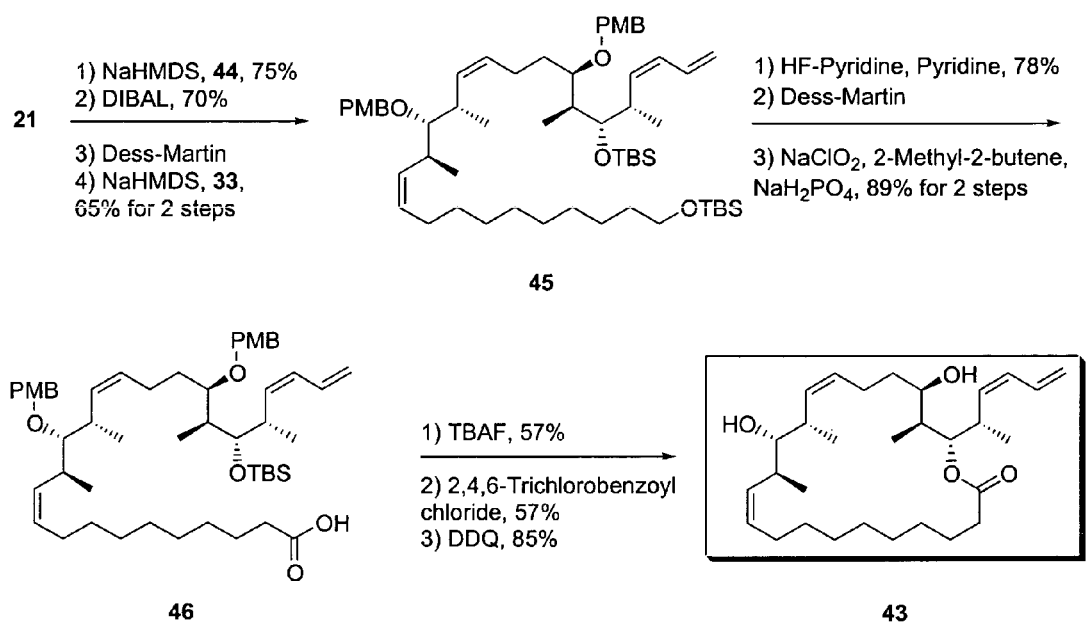
FIG. 8 illustrates an embodiment of the coupling of three fragments of a dictyostatin analog of the present invention.

The coupling of the three fragments is summarized in FIG. 8. Generation of the ylide from phosphonium salt 21 and NaHDMS followed by addition of aldehyde 44 gave the Wittig product in good yield (75%) provided that the reaction was conducted at high concentration (1M in 21). The formation of the Z-alkene was confirmed by the 10 Hz coupling constant between the vinyl protons. Selective opening of the PMB acetal was accomplished by addition of 3 equiv of DIBAL to give a primary alcohol. This was oxidized to an aldehyde under Dess-Martin conditions. Wittig conditions similar to those above were then deployed to prepare 45 from this aldehyde and phosphonium salt 33.

Selective deprotection of 45 was achieved using HF-pyridine and the resulting primary alcohol was oxidized to acid 46. The other TBS group was then removed with TBAF. Using the Yamaguchi protocol, the macrolactone ring was then constructed. PMB deprotection using DDQ provided target product 43, whose protons and carbons were assigned by COSY and HMQC NMR experiments. The location of the macrolactone ring was confirmed by HMBC NMR experiments.

Figure 9:
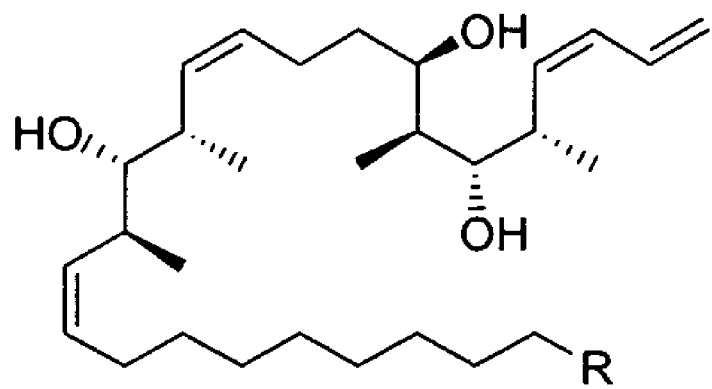
FIG. 9 illustrates the structures of several acyclic compounds of the present invention that were tested for biological activity.

Acyclic compounds 47, 48 and 49 were readily made from appropriate synthetic intermediates (45 or 46) in reasonable yields (FIG. 9).

These analogs were tested for antiproliferative activity in vitro against two human cancer cell lines (Table 2). Macrolactone 43 and non-cyclized alcohol 47 and ester 48 exhibited similar 50% growth inhibitory concentrations, in the 15–30 μM range. Carboxylic acid 49 was inactive (>50 μM) possibly due to poor cell membrane penetration. The modest activity of these compounds is encouraging given the simplicity and flexibility of their lower chain.

Figure 10:
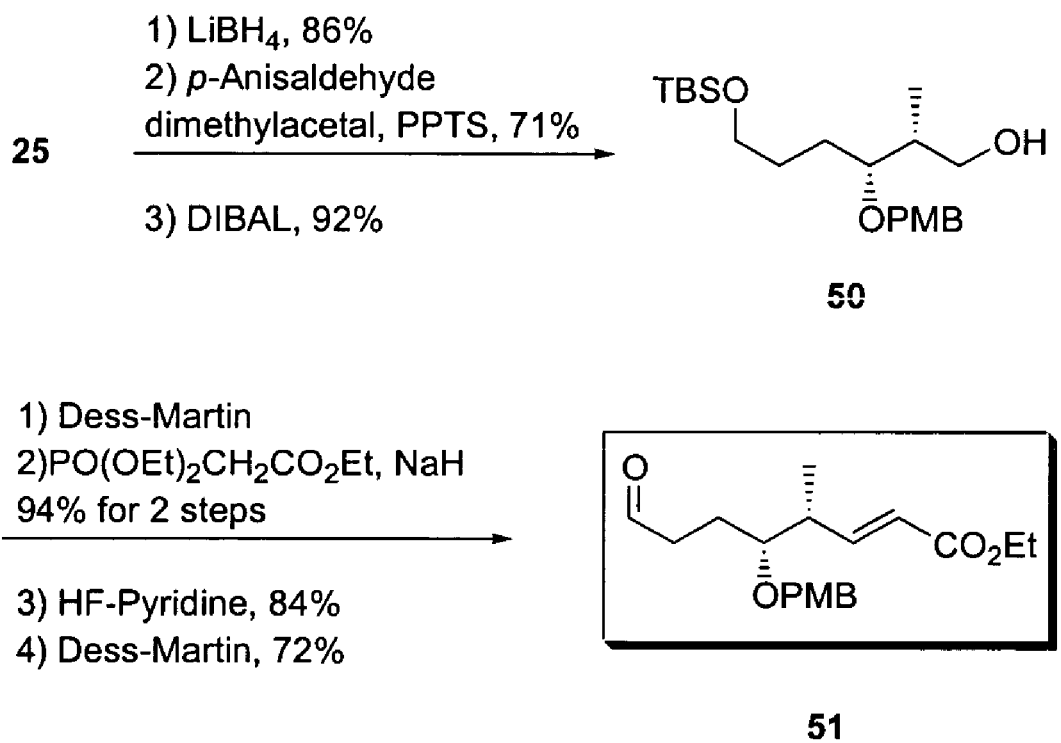
FIG. 10 illustrates an embodiment of the synthesis of a lower fragment of a dictyostatin analog of the present invention.

We therefore decided to introduce the more complex bottom part of dictyostatin-1 lacking only the C9'-OH group. The synthesis of a lower fragment more closely related to dictyostatin is shown in FIG. 10. Synthesis of the needed aldehyde 51 (FIG. 10) started from the intermediate 25, which was reduced to an alcohol with LiBH₄, followed by PMB acetal protection as in FIG. 4. Selective acetal opening produced alcohol 50, which was subjected to Dess-Martin oxidation to give aldehyde 27 (see FIG. 4). Wittig-Horner reaction, and removal of the TBS group with HF-pyridine gave a primary alcohol, which was oxidized to aldehyde 51.

Figure 11:
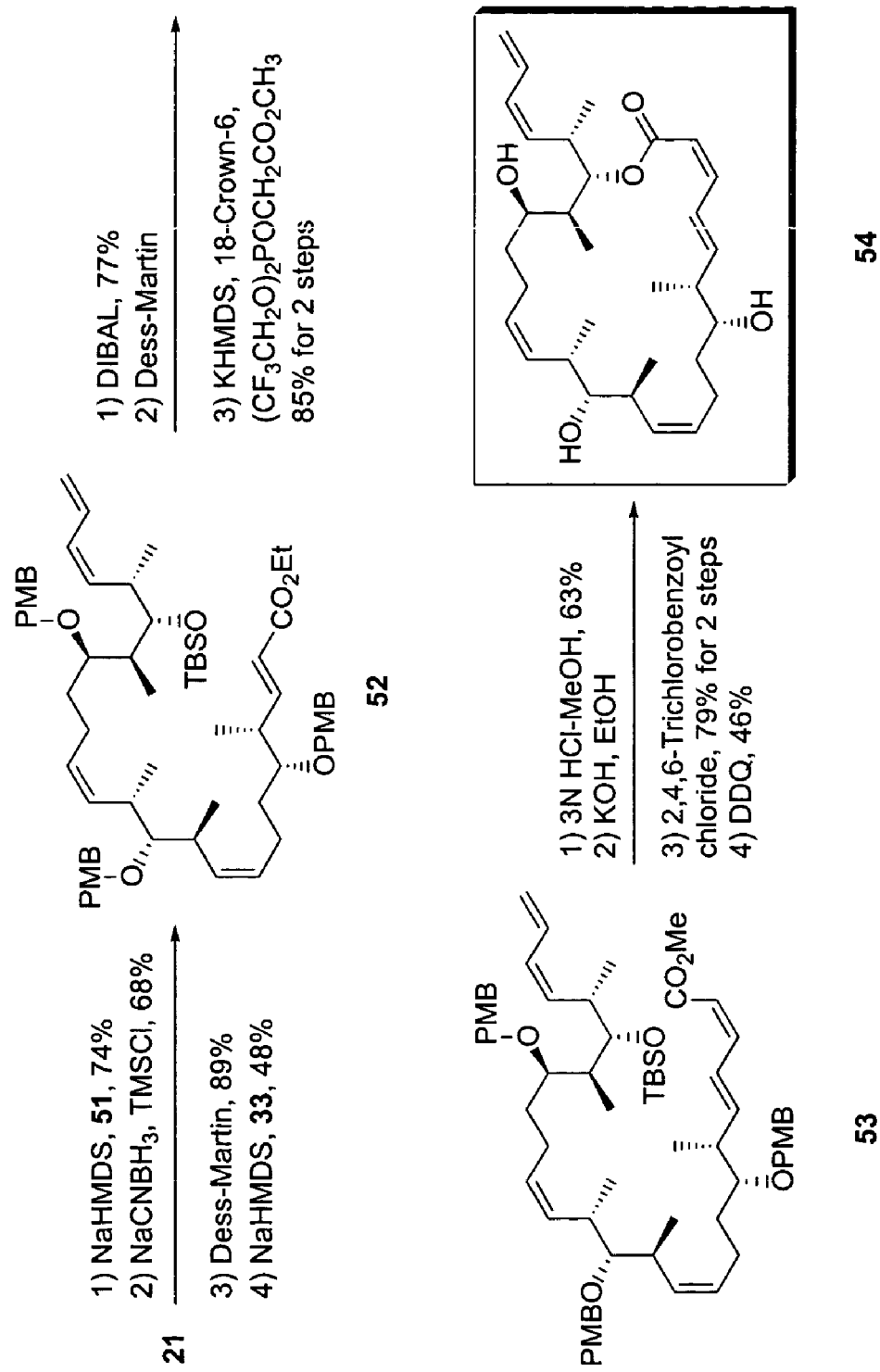
FIG. 11 illustrates an embodiment of the synthesis of a macrolactone of the present invention.

Center part Wittig salt 21 (FIG. 3) was reacted with aldehyde 51 to give the (Z)-olefin (FIG. 11). This was followed by selective PMP acetal opening with NaCNBH₃-TMSCl to yield a primary alcohol. The aldehyde obtained after Dess-Martin oxidation was again subjected to Wittig reaction with 33 to generate 52. Ester 52 was reduced to the alcohol with DIBAL, followed by Dess-Martin oxidation and application of the Still (Z)-variant of the Wittig reaction to afford (E,Z) doubly unsaturated ester 53. Selective removal of the TBS groups was accomplished by exposure to 3N HCl-MeOH in THF (1:1). The resulting ester was hydrolyzed by using 1N KOH in refluxing in EtOH. Finally, the Yamaguchi lactonization protocol followed by DDQ deprotection gave macrolactone 54, whose structure was confirmed by HMBC and other NMR experiments. No isomerization of either of the dienes or the isolated cis-alkenes was detected.

Compound 54 proved to be quite potent in terms of antiproliferative activity against human carcinoma cells (Table 2) showing a 50% growth inhibitory concentration against breast and ovarian cancer cells of about 1 μM. Furthermore compound 54 displaced [³H]paclitaxel stoichiometrically bound to microtubules at about ⅓rd the potency of discodermolide.

TABLE 2

Human Cancer Cell Growth Inhibitory and Paclitaxel Displacing Properties of Macrolactone Discodermolide Analogs

| | GI$_{50}$(μM)[a] | | Displacement of |
|---|---|---|---|
| | MDA-MB-231 (breast) | 2008 (ovary) | [$^3$H]paclitaxel (%)[c] |
| 43 | 27 ± 1 | 16 ± 1 | 18 ± 5 |
| 47 | 18 ± 1 | 22 ± 5 | 21 ± 2 |
| 48 | 26 ± 3 | 19 ± 2 | 17 ± 1 |
| 49 | >50 | >50 | 16 ± 3 |
| 54 | 1.4 ± 0.1[b] | 1.0 ± 0.1[b] | 27 ± 8 |
| discodermolide | 0.016 ± 0.003[b] | 0.072 ± 0.005[b] | 64 ± 2 |

[a]Fifty percent growth inhibitory concentration after 48 or 72
[b]hours of continuous exposure (mean ± standard deviation; N = 4).
[c]Percent displacement by 4 μM test agent of 2 μM [$^3$H]paclitaxel bound to microtubules formed from 2 μM tubulin and 20 μM dideoxyGTP (N = 6, means ± SD).

Figure 12:
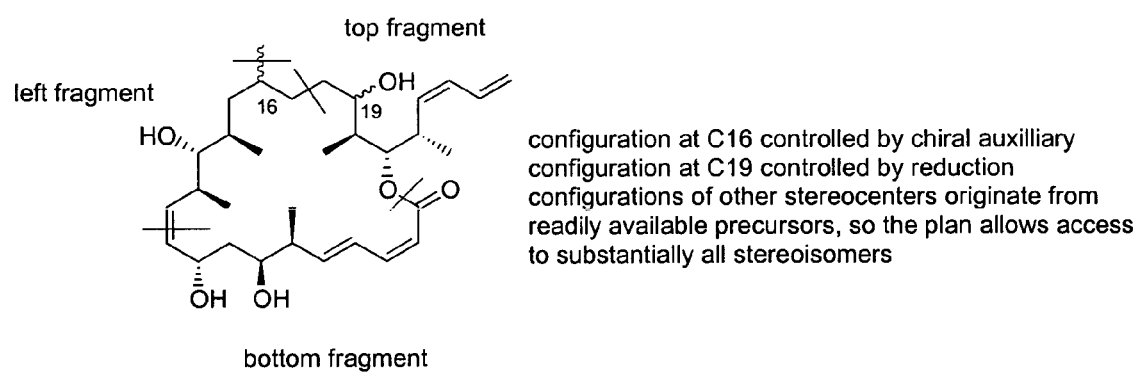
FIG. 12 illustrates a second representative general scheme for synthesis of stereoisomers and analogs of dictyostatin.

A second representative general strategy for the synthesis of stereoisomers and close analogs of dictyostatin is shown in FIG. 12. Again the molecule is dissected such that every stereocenter can be controlled and modified either by starting with an appropriate precursor or through an asymmetric reaction allowing access to both possible isomers.

Figure 13:
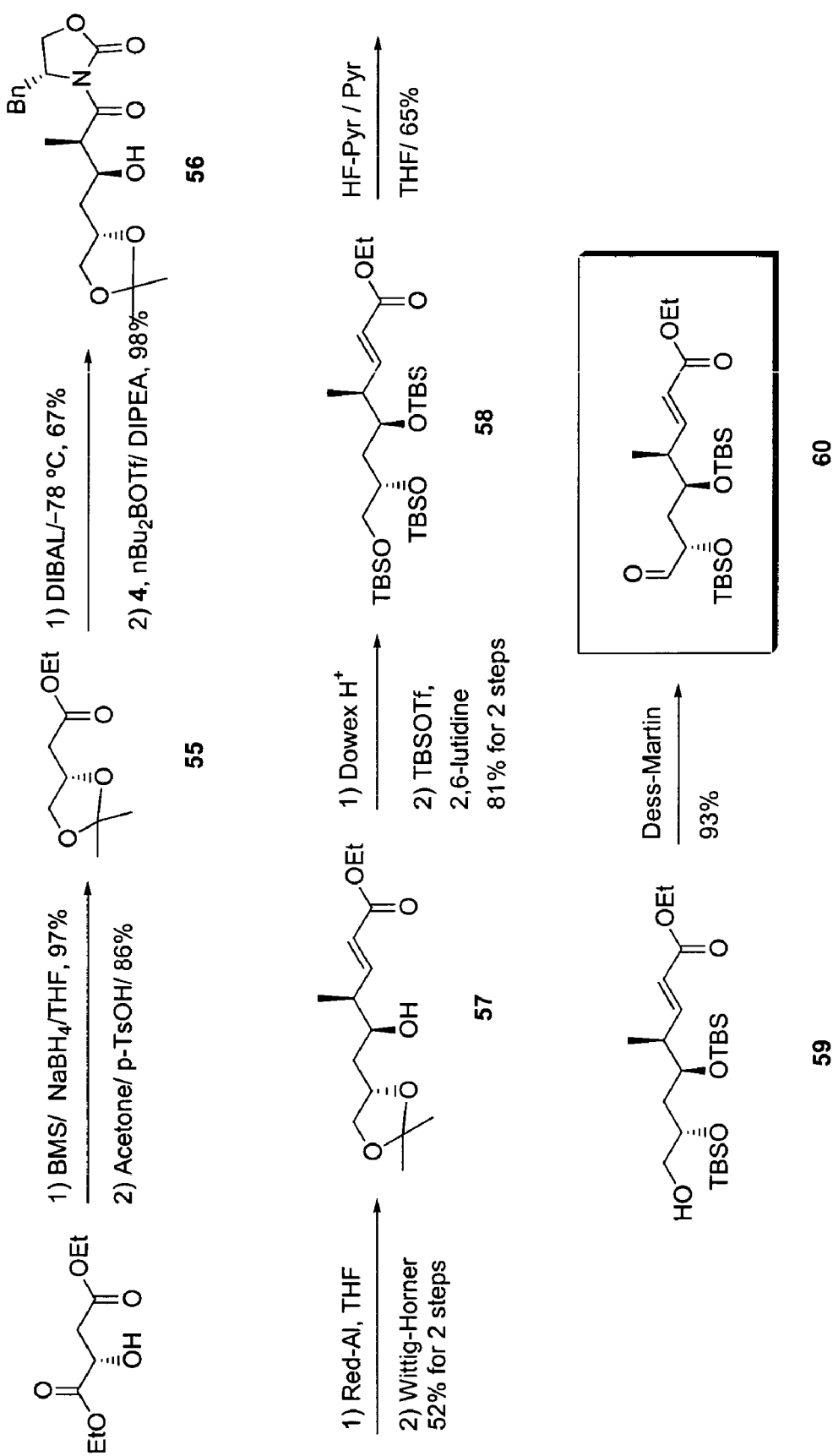
FIG. 13 illustrates a summary of an embodiment of the synthesis of the bottom fragment of dictyostatin analogs of the present invention.

FIG. 13 summarizes the synthesis of the bottom fragment. (S)-Diethyl maleate was reduced and the resulting diol was converted to acetonide 55. Reduction to the aldehyde and standard Evans aldol reaction gave 56. Reduction of this to the aldehyde and Wittig-Homer Emmons reaction gave 57. Removal of the acetonide and silyation gave 58, which was mono-desilylated to 59 and oxidized to aldehyde 60.

Figure 14:
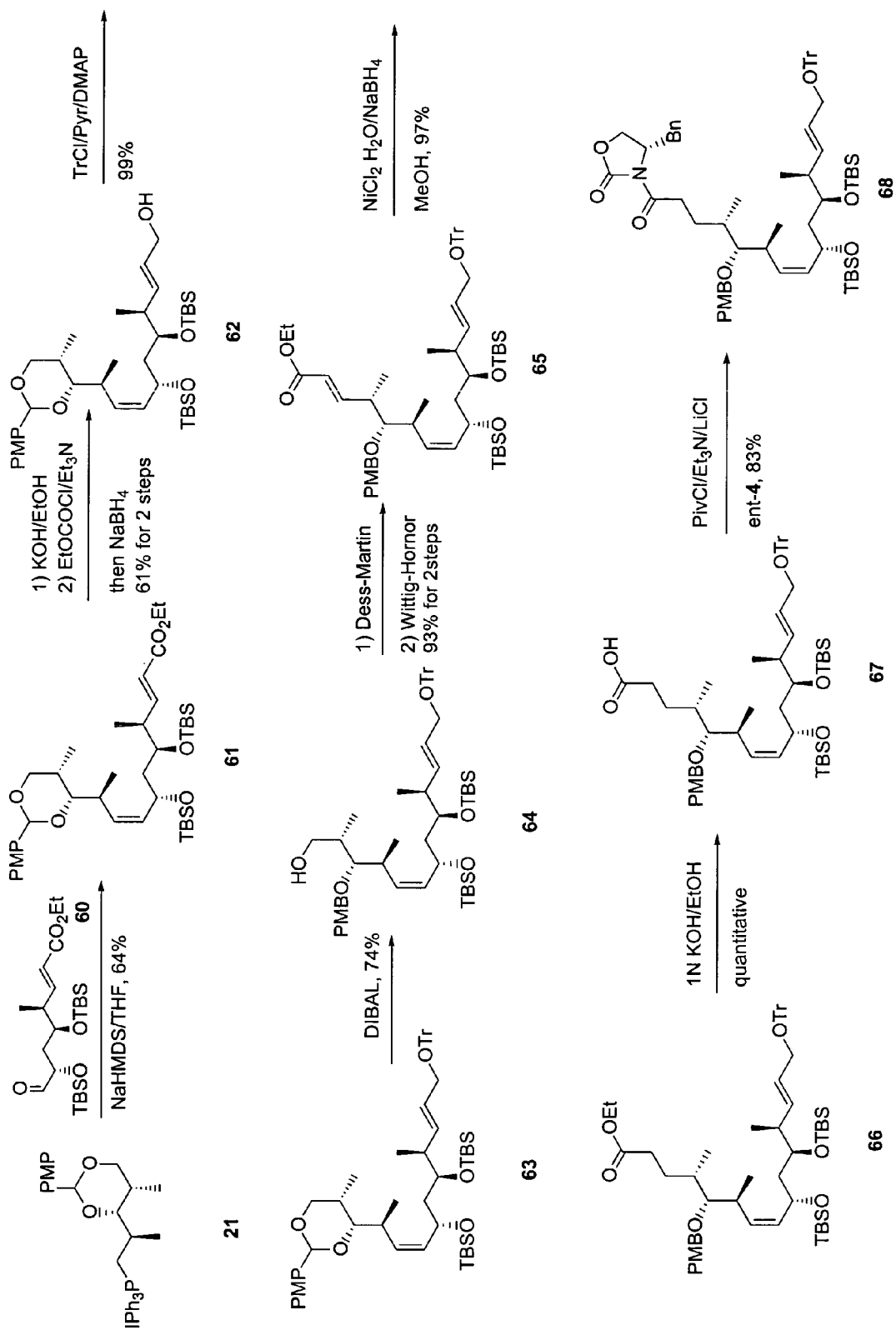
FIG. 14 illustrates an embodiment of the coupling of the bottom fragment of FIG. 13 with the center fragment of the dictyostatin analogs of the present invention.

Coupling of the bottom fragment with the center fragment and elaboration are shown in FIG. 14. Wittig reaction of 21 (FIG. 3) and 60 proceeded smoothly to form 61, which was hydrolyzed and reduced to give 62. After tritylation to 63, DIBAL reduction gave 64. Oxidation and Wittig-Homer reaction produced 65, which was reduced to give 66 and hydrolyzed to acid 67. Activation of 67 as the mixed anhydride preceded conversion to the oxazolidinone 68.

Figure 15:
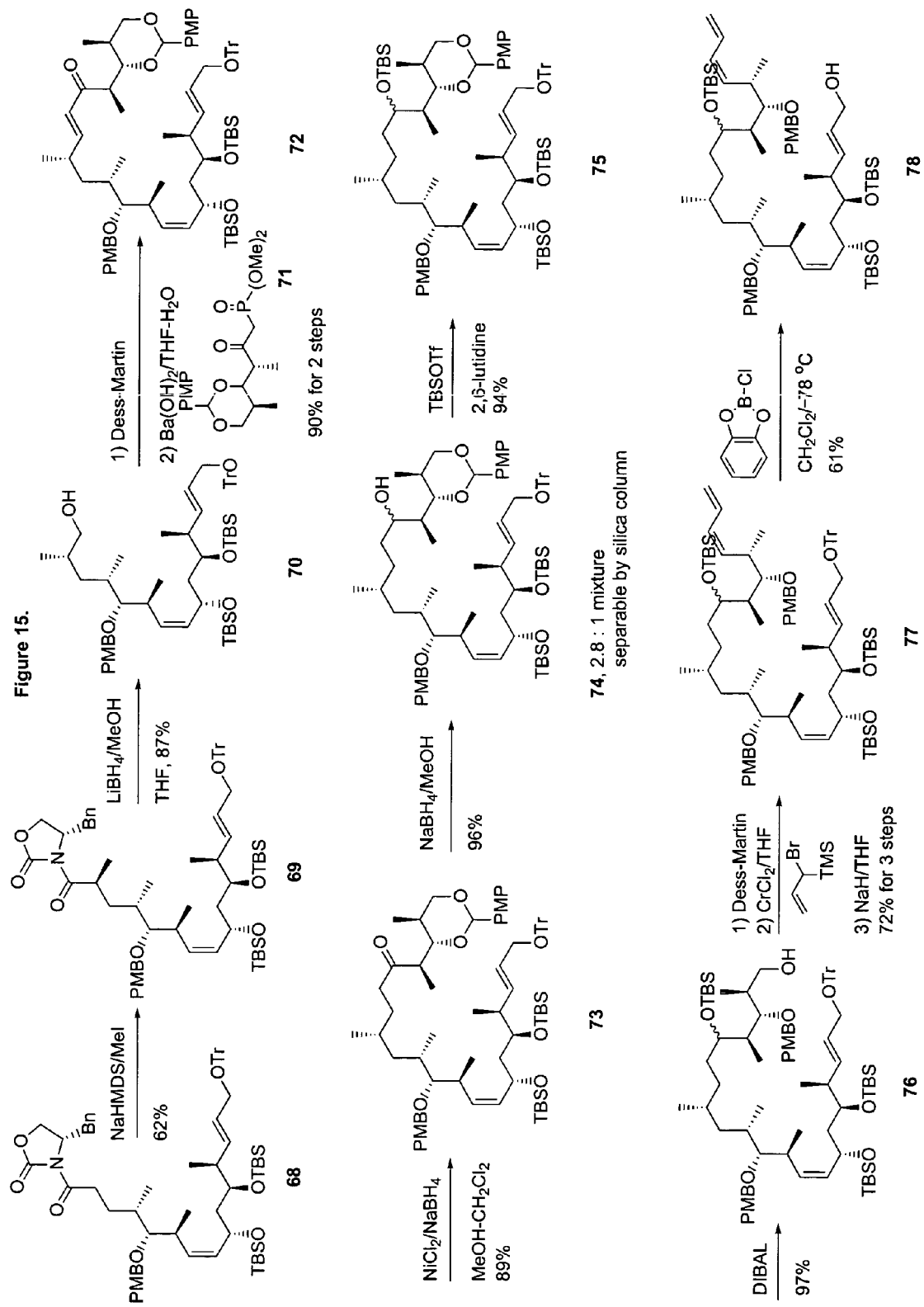
FIG. 15 illustrates an embodiment of the introduction of the C16 stereocenter and introduction of the top fragment of the dictyostatin analog of the present invention.

Introduction of the C16 stereocenter and introduction of the top fragment are shown in FIG. 15. Evans asymmetric alkylation to 69 followed by removal of the chiral auxiliary by reduction gave 70. Separately, reagent 71 was made from the Evans oxazolindinone by displacement with LiCH$_2$P(O)(OMe)$_2$. Dess-Martin oxidation and Horner-Emmons olefination with 71 then gave 72, which was reduced with NiCl$_2$/NaBH$_4$ to 73. Now reduction with sodium borohydride gave a 2.8/1 mixture of stereoisomers, which could be separated and converted to the final products independently. Silylation to 75 followed by DIBAL reduction gave 76, which was converted to diene 77 as described above. Detriylation then gave 78.

Figure 16:
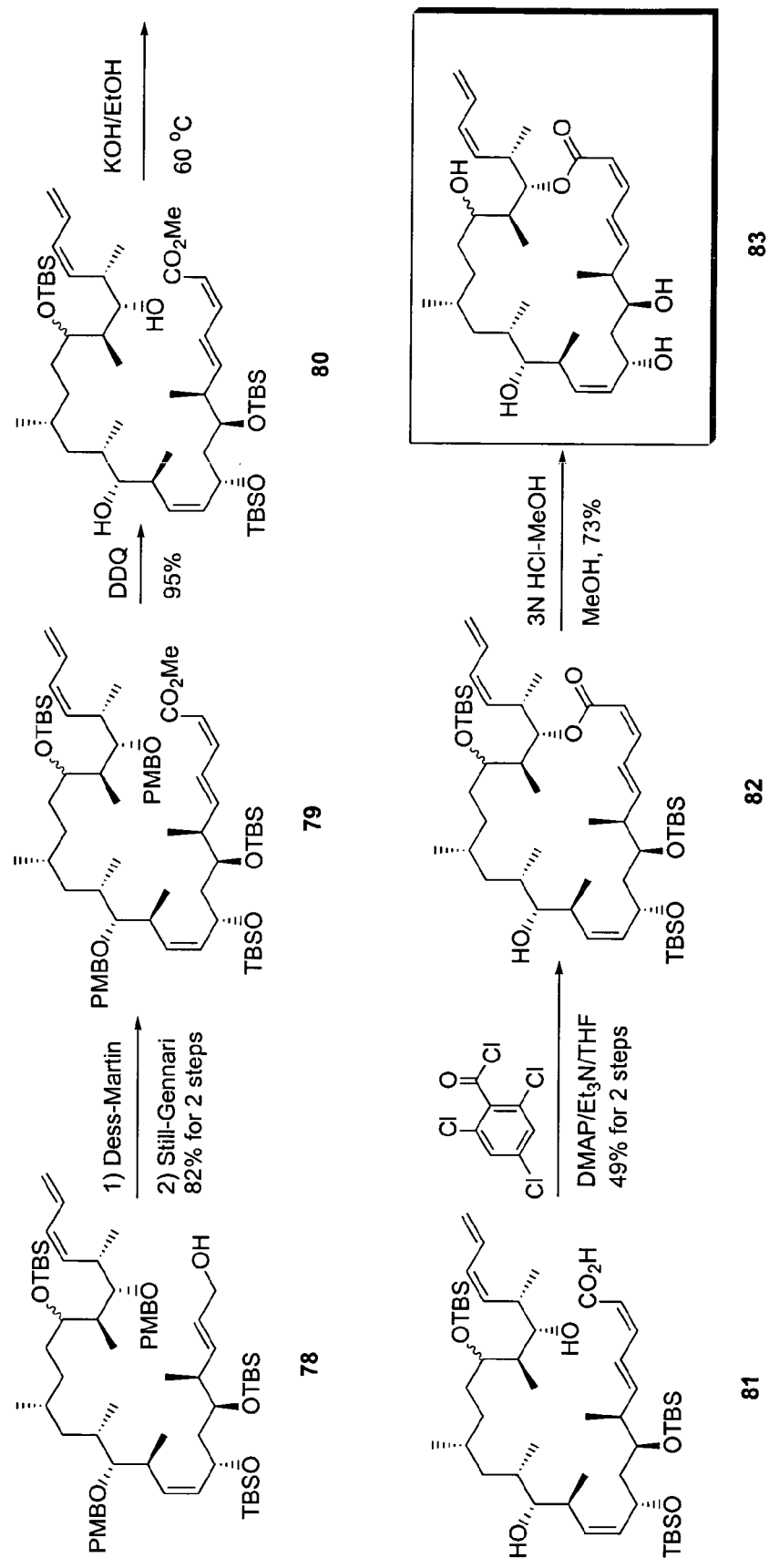
FIG. 16 illustrates an embodiment of the completion of the synthesis of the dictyostatin analog of the present invention.

Completion of the synthesis is shown in FIG. 16. Dess-Martin oxidation and Still-Gennari olefination gave 79 which was deprotected with DDQ to 80. Saponification then gave the hydroxy acid 81 ready for macrocyclization. Treatment of 81 under the Yamaguchi protocol gave 82, which was finally deprotected to give the target product 83, an isomer of dictyostatin 1 called dictyostatin 5.

Figure 17:
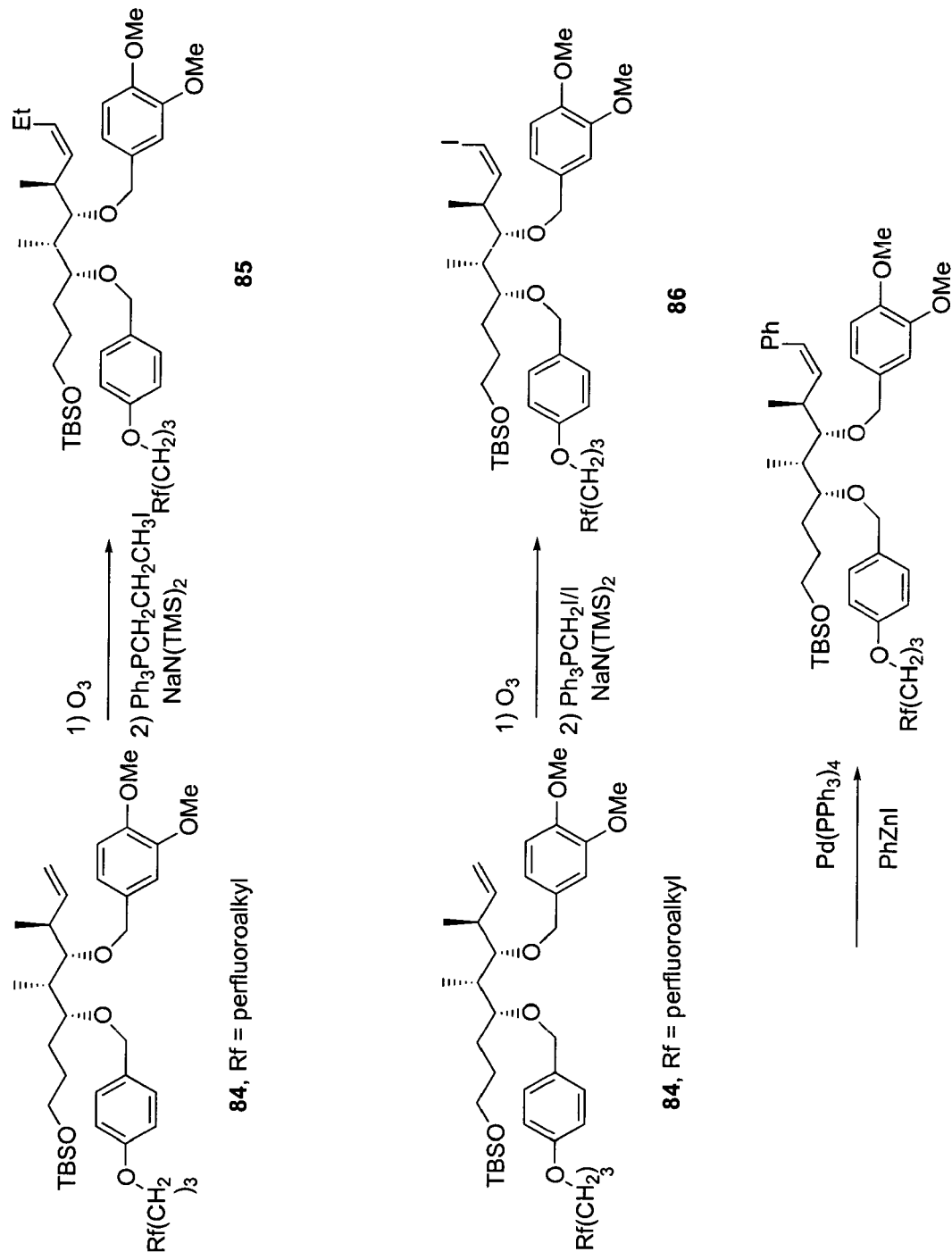
FIG. 17 illustrates embodiments of representative methods to make analogs of the terminal diene fragment of the dictyostatin analog of the present invention.

Representative methods to make analogs of the terminal diene fragment are shown in FIG. 17. Alkene 84 was ozonized to give the aldehyde, which was subjected to a Wittig reaction to give analogs like 85. Alternatively, 84 can be converted to the Z-vinyl iodide 86, which can in turn be coupled with organometallic reagents like phenyl zinc iodide to give 87. This combination of olefination and organometallic and related coupling methods allows access to a wide variety of groups in this position.

Figure 18:
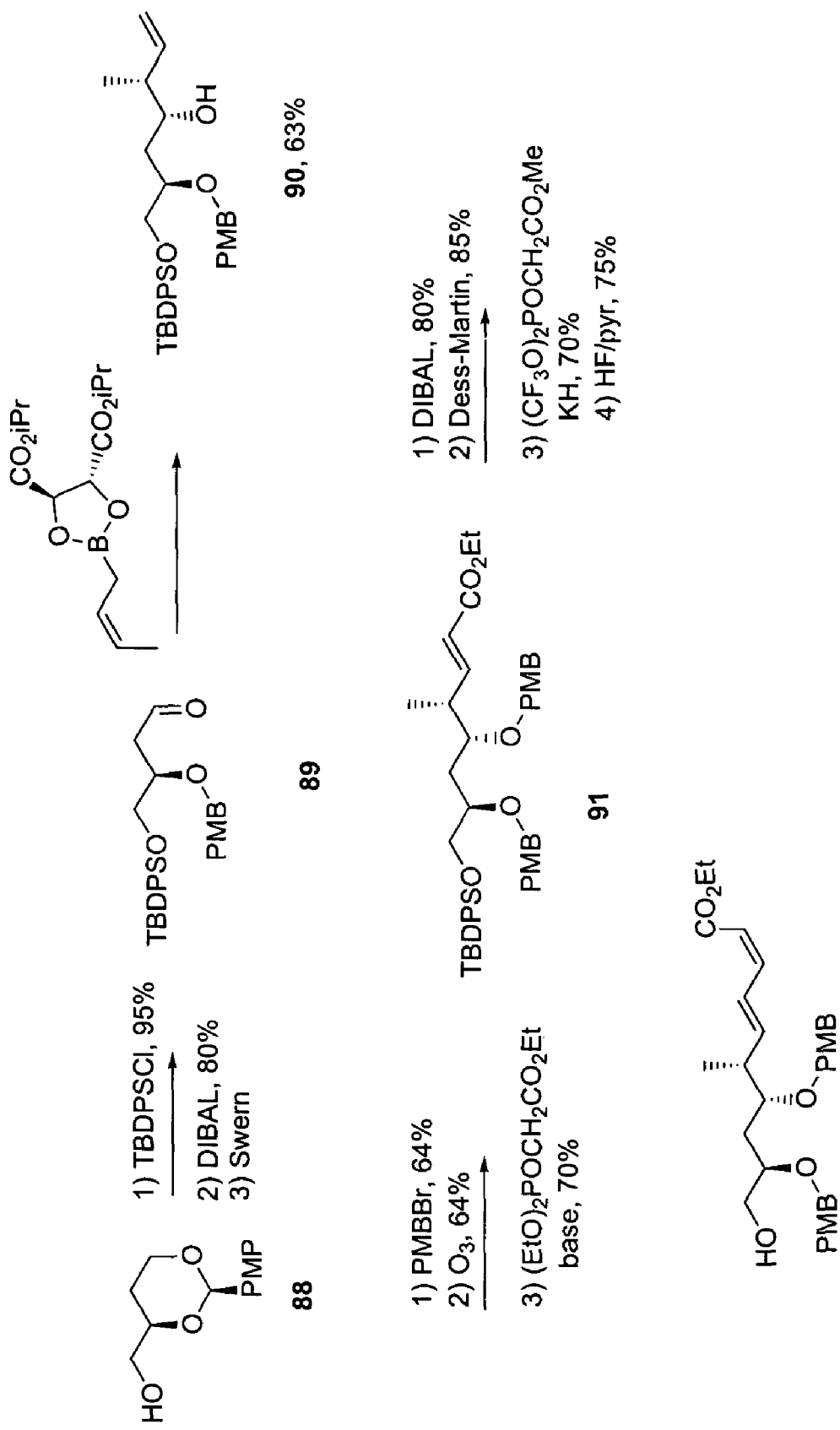
FIG. 18 illustrates a summary of an embodiment of the synthesis of the bottom fragment of the dictyostatin analog of the present invention.

The versatility of the synthesis is illustrated by the preparations of representative additional fragments that can be used to make dictyostatin, its isomers and its analogs. FIG. 18 summarizes the synthesis of a fully elaborated bottom fragment 92. Acetal 88, readily prepared from (D)-malic acid, was silylated with t-butyldiphenylsilyl chloride (TB-DPSCl). Reductive cleavage of the acetal with DIBAL followed by Swern oxidation provided aldehyde 89. Reaction of 89 with the indicated Z-crotyl boronate according to Roush (See: Roush, W. R.; Hoong, L. K.; Palmer, M. A. J.; Straub, J. A.; Palkowitz, A. D. Asymmetric synthesis using tartrate modified allyl boronates. 2. Single and double asymmetric reactions with alkoxy-substituted aldehydes, *J. Org. Chem.* 1990, 55, 4117–4126) provided 90 in 63% isolated yield. PMB protection, ozonolysis and Wittig-Horner olefination then gave 91. This was converted to the E/Z diene 92 by DIBAL reduction, Dess-Martin oxidation, Still-Gennari olefination and desilylation with HF/pyridine.

Figure 19:
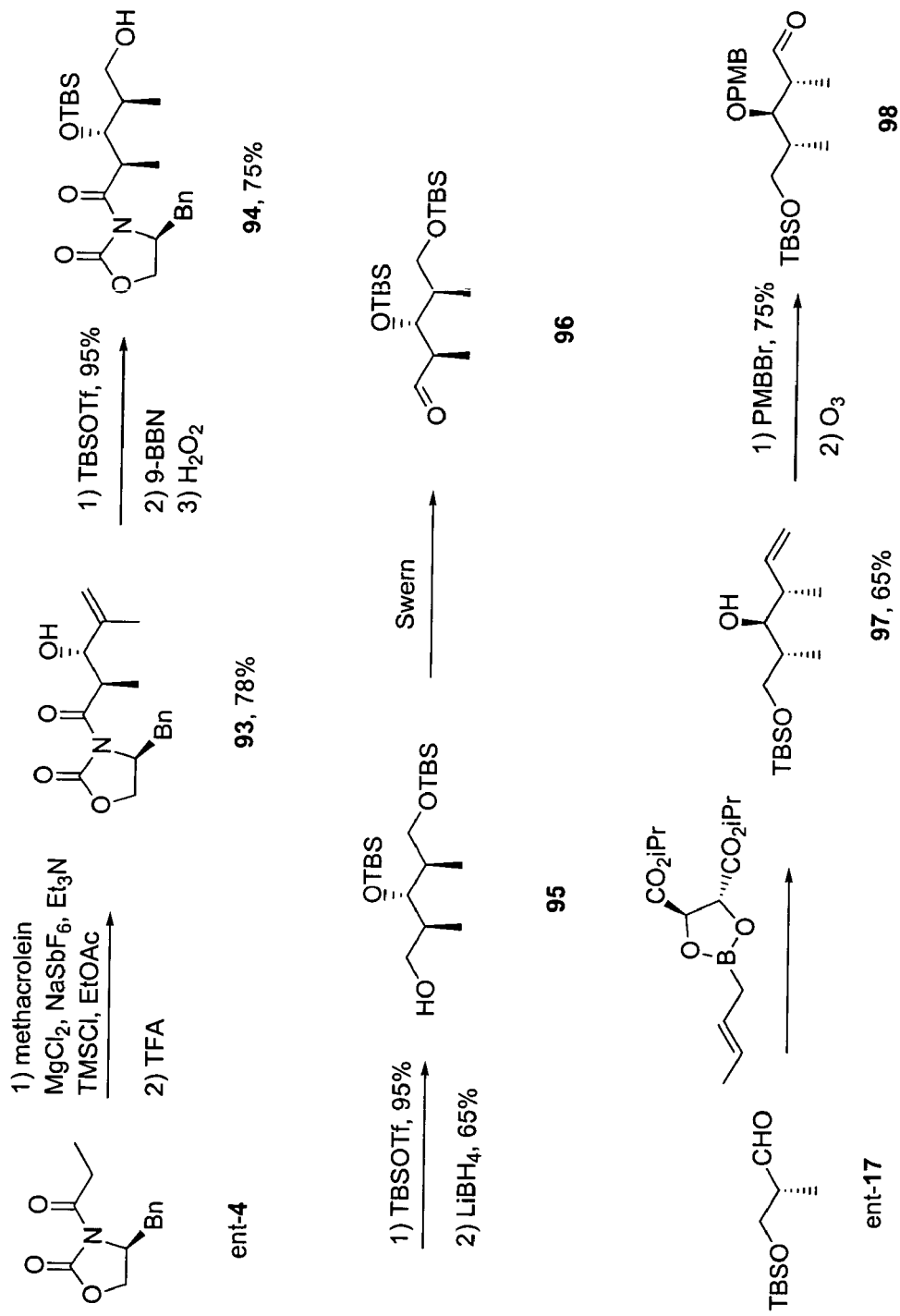
FIG. 19 illustrates an embodiment of the synthesis of two fragments with anti/anti configurations as assigned to dictyostatin 1 at C13–C15.

FIG. 19 shows the synthesis of two fragments with anti/anti configurations as assigned to dictyostatin 1 at C13–C15. Evan anti-aldol reaction of ent-4 and methacrolein (See: Evans, D. A.; Tedrow, J. S.; Shaw, J. T.; Downey, C. W. Diastereoselective magnesium halide-catalyzed anti-aldol reactions of chiral N-acyloxazolidinones. *J. Am. Chem. Soc.* 2002, 124, 392–393) followed by TFA treatment gave 93 in 78% yield. A minor diastereomer of 93 (about 16/1 ratio) was separated by chromatography. Silylation of 93 followed by hydroboration and oxidation provided alcohol 94 in 75% yield alongside the lactone resulting from cyclization of the terminal hydroxyl group with displacement of the chiral auxiliary (not shown, 10% yield). Silylation of 94 and reductive cleavage of the auxiliary provided 95, which was oxidized to 96 by the Swern method. Related aldehyde 98 was made by Roush allylboration of ent-17 (see 17 in FIG. 3) with the indicated E-crotylborate (mismatched case, 4/1 selectivity) to give 97, followed by reaction with PMBBr and ozonolysis.

EXAMPLES (4R)-4-Benzyl-3-[(2R,3R)-3-(tert-butyldimethylsilanyloxy)-2,4-dimethylpent-4-enoyl]oxazolidin-2-one (5). TBDMSOTf (3.44 mL, 15 mmol) was added to a stirred solution of aldol product (3.03 g, 10 mmol) and 1,6-lutidine (2.32 mL, 20 mmol) in CH$_2$Cl$_2$ (20 mL) at −78° C. and the mixture was stirred for 2 h at ambient temperature. The reaction was quenched by the addition of aqueous HCl (0.5 N, 50 mL). The resulting mixture was extracted with CH$_2$Cl$_2$ and dried over MgSO$_4$ followed by the evaporation of solvent under reduced pressure. The product was purified by short column chromatography (hexane/EtOAc 9:1). Crude 5 was used without purification.

(2S,3R,4S,5R)-2-Allyl-6-methoxy-4-methoxymethoxy-3,5-dimethyltetrahydropyran (8). Diisobutylaluminum hydride (1.0 M in THF, 3.3 mL, 3.3 mmol) was added dropwise to a stirred solution of 7 (894 mg, 3 mmol) in anhydrous CH$_2$Cl$_2$ (30 mL) under an atmosphere of N$_2$ at −78° C. and the resulting mixture was stirred for an additional 1 h at −78° C. The reaction was quenched by the careful addition of saturated aqueous potassium sodium tartrate (50 mL) and stirred for 3 h at room temperature. Once the organic and aqueous layers had separated, the aqueous layer was extracted with CH$_2$Cl$_2$. The combined organic layer was washed with brine and dried over MgSO$_4$ followed by the evaporation of the solvent under reduced pressure. The crude lactol was used for the next reaction without further purification.

A solution of the lactol and CSA (0.3 mmol) in MeOH was stirred for 24 h at room temperature. The reaction mixture was diluted with EtOAc (100 mL) and washed with saturated NaHCO$_3$ (50 mL). The aqueous layer was extracted with EtOAc (50 mL). The combined organic layer was dried over MgSO$_4$. The solvent was removed under reduced pressure and the crude product was used for the next reaction.

N,N-Diisopropylethylamine (7.5 mL) and chloromethyl methyl ether (1.13 mL, 15 mmol) were added to a solution of the alcohol in CH$_2$Cl$_2$ (15 mL). The reaction mixture was heated to reflux and stirred overnight. The reaction was quenched with aqueous saturated NaHCO$_3$ (50 mL) followed by washing with brine. The aqueous layer was extracted with CH$_2$Cl$_2$ (2×50 mL). The combined organic layer was dried over MgSO$_4$. The solvent was removed under reduced pressure and the crude product was purified by column chromatography (hexane/EtOAc 7:3) to provide the pure anomers of 8 (β, 33%; α, 32%). β8: IR (CHCl$_3$) 3053, 2985, 2305, 1422, 1264 cm$^{-1}$; $^1$H NMR (300 MHz, CDCl$_3$) δ 6.04 (m, 1H), 5.20–5.10 (m, 2H), 4.81 (d, 1H, J=6.9 Hz), 4.73 (d, 1H, J=2.37 Hz), 4.67 (d, 1H, J=6.8 Hz), 3.62 (m, 2H), 3.55 (s, 3H), 2.47 (m, 1H), 2.30 (m, 1H), 2.16 (m, 1H), 1.85 (m, 1H), 1.03 (d, 3H, J=7.1 Hz), 0.97 (d, 3H, J=6.8 Hz); $^{13}$C NMR (75 MHz, CDCl$_3$) 135.1, 116.4, 101.3, 95.9, 81.9, 75.8, 56.4, 55.7, 37.5, 37.3, 33.6, 13.2, 9.9; HRMS (EI) calcd for C$_{13}$H$_{24}$O$_4$ 244.1596, found 244.1592. α8: $^1$H NMR (300 MHz, CDCl$_3$) δ 6.00 (m, 1H), 5.22–5.12 (m, 2H), 4.83 (d, 1H, J=6.9 Hz), 4.69 (d, 1H, J=7.2 Hz), 4.49 (d, 1H, J=1.8 Hz), 3.88 (dt, 1H, J=3.6, 8.8 Hz), 3.53 (t, 2H, J=3.6 Hz), 3.48 (s, 3H), 2.45 (m, 1H), 2.28–2.11 (m, 3H), 1.94 (m, 1H), 1.12 (d, 3H, J=7.3 Hz), 1.00 (d, 3H, J=6.9 Hz); $^{13}$C NMR (75 MHz, CDCl$_3$) 135.2, 116.7, 103.4, 95.6, 78.7, 69.6, 55.7, 37.2, 35.8, 33.6, 15.9, 13.5.

(2S,3R,4S,5R,6R)-3-(6-Methoxy-4-methoxymethoxy-3,5-dimethyltetrahydropyran-2-yl)propionaldehyde (9a). BH$_3$.Me$_2$S (1 M in THF, 3 mL, 3 mmol) was added to a solution of 8 (488 mg, 2 mmol) in THF (10 mL) at 0° C. with stirring. The mixture was allowed to warm to room temperature and stirred for 3 h. The reaction was quenched with 2N aqueous NaOH (10 mL) followed by H$_2$O$_2$ (30%, 3 mL). After 1 h, the mixture was extracted with CH$_2$Cl$_2$ (3×20 mL). The combined organic layers were dried over anhydrous MgSO$_4$, evaporated and chromatographed (hexane/EtOAc 7:3) to yield 392 mg (75%) of alcohol as a colorless oil: IR (CHCl$_3$) 3103, 2982, 1375, 1240 cm$^{-1}$; $^1$H NMR (300 MHz, CDCl$_3$) δ 4.83 (d, 1H, J=6.9 Hz), 4.76 (d, 1H, J=2.4 Hz), 4.69 (d, 1H, J=6.9 Hz), 3.75 (t, 2H, J=5.4 Hz), 3.61 (t, 1H, J=2.7 Hz), 3.57 (s, 3H), 2.58 (br s, 1H), 2.17 (m, 1H), 1.90–1.80 (m, 4H), 1.04 (d, 3H, J=7.1 Hz), 0.97 (d, 3H, J=6.8 Hz); $^{13}$C NMR (75 MHz, CDCl$_3$) 101.5, 96.0, 82.0, 75.9, 62.8, 56.6, 55.8, 37.6, 34.0, 29.4, 28.6, 13.4, 9.8; HRMS (EI) calcd for C$_{13}$H$_{26}$O$_5$ 262.1780, found 262.1792.

Pyridinium sulfurtrioxide (477 mg, 3 mmol) was added to a stirred solution of alcohol (262 mg, 1 mmol) and N,N-diisopropylethylamine (0.52 mL, 3 mmol) in anhydrous CH$_2$Cl$_2$ (6 mL) and DMSO (12 mL) at 0° C. The reaction mixture was stirred at the ambient temperature for 1 h. The mixture was diluted with ethyl ether (50 mL) and washed with aqueous HCl (0.5 N, 50 mL) and brine (10 ml). The organic layer was dried over MgSO$_4$, filtered and concentrated under vacuum. Flash silica gel column chromatography filtration (hexane/EtOAc 4:1) to remove SO$_3$-pyridine residue provided the crude aldehyde 9a as a colorless oil which was used without further purification.

(4R)-4-Benzyl-3-[(2R,3S)-3-(tert-butyldimethylsilyloxy)-6-(4-methoxybenzyloxy)-2-methylhexanoyl]oxazolidin-2-one (11). Pyridinium sulfur trioxide (7.15 g, 45 mmol) was added to a stirred solution of the mono-PMB-protected alcohol 10 (3.15 g, 15 mmol) and N,N-diisopropylethylamine (8.0 mL, 45 mmol) in anhydrous CH$_2$Cl$_2$ (15 mL) and DMSO (30 mL) at 0° C. The mixture was stirred at ambient temperature for 1 h, diluted with ethyl ether (300 mL) and washed with aqueous HCl (0.5 N, 200 mL), and brine. The separated organic layer was dried over MgSO$_4$. Filtration and concentration provided the crude aldehyde 10 as a colorless oil which was used for the next reaction without further purification.

N,N-Diisopropylethylamine (1.9 mL, 11 mmol) was added to a solution of propionyloxazolidinone (2.33 g, 10 mmol) in anhydrous CH$_2$Cl$_2$ (110 mL) at 0° C., followed by dropwise addition of Bu$_2$BOTf (1.0 M in CH$_2$Cl$_2$, 11 mL, 11 mmol). The solution was stirred for 0.5 h at 0° C. Crude 10 in anhydrous CH$_2$Cl$_2$ (30 mL) was added at −78° C. The mixture was stirred for 10 min at −78° C. followed by an additional 2 h at 0° C. The reaction was quenched by addition of phosphate buffer, pH 7.0 (50 mL). A solution of hydrogen peroxide (30%, 10 mL) in methanol (20 mL) was added and the mixture was allowed to stir for 1 h at 0° C. After separation of organic and aqueous layers, the aqueous layer was extracted with CH$_2$Cl$_2$. The combined organic layers were dried over anhydrous MgSO$_4$, evaporated and chromatographed (hexane/EtOAc 4:1) to yield the aldol adduct (3.83 g, 87%) as a colorless oil: IR (CHCl$_3$) 3472, 2954, 2860, 2252, 1778, 1691, 1383 cm$^{-1}$; $^1$H NMR (300 MHz, CDCl$_3$) δ 7.48–7.36 (m, 7H), 7.01 (d, 2H, J=8.7 Hz), 4.58 (m, 1H), 4.33 (s, 2H), 4.18 (br s, 1H), 3.94 (s, 3H), 3.91 (m, 1H), 3.63 (t, 2H, J=6.0 Hz), 3.40 (dd, 1H, J=3.2, 13.3 Hz), 3.37 (br s, 1H), 2.90 (dd, 1H, J=3.8, 13.3 Hz), 1.97–1.59 (m, 5H), 1.40 (d, 3H, J=7.2 Hz); $^{13}$C NMR (75 MHz, CDCl$_3$) 177.3, 159.2, 153.1, 135.3, 130.6, 129.5, 129.3, 129.0, 127.4, 113.8, 72.5, 71.5, 69.9, 66.2, 55.2, 42.7, 37.7, 31.3, 26.4, 14.3, 11.1; HRMS (EI) calcd for C$_{25}$H$_{31}$NO$_6$ 441.2151, found 441.2162.

TBDMSOTf (1.7 mL, 7.5 mmol) was added to a stirred solution of the above alcohol (2.20 g, 5 mmol) and 2,6-lutidine (1.2 mL, 10 mmol) in CH$_2$Cl$_2$ (50 mL) at −78° C. and the mixture was stirred for 2 h at ambient temperature. The reaction was quenched by addition of aqueous HCl (0.5 N, 100 mL). The reaction mixture was extracted with CH$_2$Cl$_2$ and dried over MgSO$_4$ followed by the evaporation of the solvent under reduced pressure. The product was purified by column chromatography (hexane/EtOAc 9:1) to yield 11: IR (CHCl$_3$) 3020, 2955, 2858, 1779, 1362, 1211 cm$^{-1}$; $^1$H NMR (300 MHz, CDCl$_3$) δ 7.45–7.36 (m, 7H), 7.00 (d, 2H, J=8.7 Hz), 4.70 (m, 1H), 4.56 (s, 2H), 4.27–4.15 (m, 3H), 4.04 (dd, 1H, J=5.4, 6.8), 3.91 (s, 3H), 3.60 (m, 3H), 3.40 (dd, 1H, J=3.0, 13.2 Hz), 2.90 (dd, 1H, J=9.5, 13.2 Hz), 1.80 (br m, 4H), 1.38 (d, 3H, J=6.8 Hz), 1.05 (s, 9H), 0.21 (s, 3H), 0.17 (s, 3H); $^{13}$C NMR (75 MHz, CDCl$_3$) 175.4, 159.2, 153.2, 135.5, 130.9, 129.6, 129.3, 129.0, 127.4, 113.8, 72.9, 72.5, 70.2, 66.1, 55.9, 55.3, 42.8, 37.7, 32.1, 26.0, 25.2, 18.2, 12.2, −3.92, −4.65; LRMS (ESI) 578.3 (M+Na).

(2S,3S)-3-(tert-Butyldimethylsilanyloxy)-6-(4-methoxybenzyloxy)-2-methylhexan-1-ol. Lithium borohydride (2.0 M in THF, 5 mL, 10 mmol) was added dropwise to a stirred solution of 11 (2.77 g, 5 mmol) and methanol (0.4 mL, 10 mmol) in anhydrous THF (20 mL) under an atmosphere of N$_2$ at 0° C. The mixture was stirred for 20 min at 0° C. and then warmed to ambient temperature. After 3 h at room temperature, the reaction was quenched with aqueous NH$_4$Cl (100 mL) and extracted with CH$_2$Cl$_2$ (3×20 mL). The combined organic layers were dried over anhydrous MgSO$_4$, evaporated and chromatographed (hexane/EtOAc 7:3) to yield the alcohol (1.48 g, 78%) as a colorless oil: IR (CHCl$_3$) 2948, 2856, 2302, 1612, 1265 cm$^{-1}$; $^1$H NMR (300 MHz, CDCl$_3$) δ 7.27 (d, 2H, J=8.5 Hz), 7.00 (d, 2H, J=8.5 Hz), 4.43 (s, 2H), 3.78 (s, 3H), 3.67 (dd, 1H, J=8.6, 10.5 Hz), 3.51–3.41 (m, 3H), 2.78 (br s, 1H), 1.94 (m, 1H), 1.72–1.49 (m, 4H), 0.90 (s, 9H), 0.81 (d, 3H, J=7.0 Hz), 0.09 (s, 3H), 0.08 (s, 3H); $^{13}$C NMR (75 MHz, CDCl$_3$) 159.2, 130.6, 129.3, 113.8, 75.4, 72.6, 70.1, 65.8, 55.9, 55.3, 39.7, 29.1, 26.6, 25.9, 18.0, 12.1, −4.28, −4.38; LRMS (ESI) 405.2 (M+Na).

(4R)-4-Benzyl-3-[(2R,3S,4R,5S)-5-(tert-butyldimethylsilanyloxy)-3-hydroxy-8-(4-methoxybenzyloxy)-2,4-dimethyloctanoyl]oxazolidin-2-one (12). Pyridinium sulfur trioxide (2.38 g, 15 mmol) was added to a stirred solution of the above TBS-protected alcohol (1.91 g, 5 mmol) and N,N-diisopropylethylamine (2.65 mL, 15 mmol) in anhydrous CH$_2$Cl$_2$ (5 mL) and DMSO (10 mL) at 0° C. The mixture was stirred at the ambient temperature for 1 h, diluted with ethyl ether (100 mL), washed with aqueous HCl (0.5 N, 100 mL) and brine, then dried over MgSO$_4$. Filtration and concentration provided the crude aldehyde as a colorless oil which was used without further purification.

N,N-Diisopropylethylamine (0.97 mL, 5.5 mmol) was added to a solution of propionyloxazolidinone (1.16 g, 5 mmol) in anhydrous CH$_2$Cl$_2$ (11 mL) at 0° C., followed by dropwise addition of Bu$_2$BOTf (1.0 M in CH$_2$Cl$_2$, 5.5 mL, 5.5 mmol). The solution was stirred for 0.5 h at 0° C. A solution of crude aldehyde 12 from above in anhydrous CH$_2$Cl$_2$ (10 mL) was added at −78° C. The reaction mixture was stirred for 10 min at −78° C. then for 2 h at 0° C. The reaction mixture was quenched with phosphate buffer, pH 7.0 (50 mL). A solution of hydrogen peroxide (30%, 10 mL) in methanol (20 mL) was slowly added and the mixture was stirred for 1 h. After the separation of organic and aqueous layers, the aqueous layer was extracted with CH$_2$Cl$_2$. The combined organic layers were dried over anhydrous MgSO$_4$, evaporated and chromatographed (hexane/EtOAc 4:1) to yield desired compound (2.29 g, 75%) as a colorless oil: IR (CHCl$_3$) 2949, 2855, 2253, 1779, 1692, 1463 cm$^{-1}$; $^1$H NMR (300 MHz, CDCl$_3$) δ 7.33–7.19 (m, 7H), 7.01 (d, 2H, J=8.1 Hz), 4.42 (m, 1H), 4.44 (s, 2H), 4.16 (d, 1H, J=5.1 Hz), 4.01 (m, 1H), 3.95 (t, 1H, J=6.3 Hz), 3.85 (m, 1H), 3.79 (s, 3H), 3.43 (br s, 2H), 3.24 (br s, 1H), 3.20 (dd, 1H, J=2.4, 13.5 Hz), 2.77 (dd, 1H, J=9.6, 13.2 Hz), 1.56–1.31 (m, 5H), 1.32 (d, 3H, J=6.9 Hz), 0.95 (d, 3H, J=6.9 Hz), 0.89 (s, 9H), 0.08 (s, 6H); $^{13}$C NMR (75 MHz, CDCl$_3$) 177.2, 159.2, 152.7, 135.1, 130.6, 129.5, 129.3, 129.0, 127.5, 113.8, 76.8, 74.2, 72.6, 70.0, 66.1, 55.3, 55.0, 40.6, 38.1, 37.8, 31.3, 25.9, 18.1, 13.2, 7.4, −3.5, −4.6; HRMS (EI) calcd for C$_{34}$H$_{51}$NO$_7$Si 613.3435, found 613.3427.

(4R)-4-Benzyl-3-[(2R,3S,4R,5S)-5-(tert-butyldimethylsilanyloxy)-8-(4-methoxybenzyloxy)-3-methoxymethoxy-2,4-dimethyloctanoyl]oxazolidin-2-one (13). N,N-Diisopropylethylamine (7.5 mL) and chloromethyl methyl ether (mL, 9 mmol) were added to a solution of the alcohol from above (1.83 g, 3 mmol) in CH$_2$Cl$_2$ (15 mL). The mixture was stirred at reflux overnight. The reaction was quenched with aqueous sat'd NaHCO$_3$ (50 mL) and washed with brine. The aqueous layer was extracted with CH$_2$Cl$_2$ (2×50 mL). The combined organic layer was dried over MgSO$_4$. The solvent was removed under reduced pressure and the crude product was purified by column chromatography (hexane/EtOAc 4:1) to provide the pure product in 92% yield: IR (CHCl$_3$) 3020, 2862, 1781, 1215 cm$^{-1}$; $^1$H NMR (300 MHz, CDCl$_3$) δ 7.36–7.27 (m, 7H), 6.94 (d, 2H, J=8.7 Hz), 4.75 (s, 2H), 4.69 (m, 1H), 4.53 (s, 2H), 4.19 (dd, 1H, J=10.2, 15.0 Hz), 3.97 (dd, 1H, J=3.0, 6.6 Hz), 3.84 (br s, 4H), 3.43 (br t, 2H), 3,45 (s, 3H), 3.30 (dd, 1H, J=3.0, 13.2 Hz), 2.77 (dd, 1H, J=9.3, 13.5 Hz), 1.81–1.75 (m, 5H), 1.36 (d, 3H, J=6.9 Hz), 1.02 (d, 3H, J=6.9 Hz), 0.98 (s, 9H), 0.16 (s, 3H), 0.15 (s, 3H); $^{13}$C NMR (75 MHz, CDCl$_3$) 175.5, 159.1, 153.0, 135.4, 131.0, 129.5, 129.2, 129.0, 127.4, 113.7, 98.3, 80.3, 76.9, 73.2, 72.3, 70.5, 66.0, 56.3, 55.6, 55.2, 41.7, 40.8, 37.6, 30.6, 26.1, 24.2, 18.3, 14.0, 10.5, −3.9, −4.3; HRMS (EI) calcd for C$_{34}$H$_{50}$NO$_7$Si (M−CH$_2$OCH$_3$) 612.3356, found 612.3367 (M−CH$_2$OCH$_3$).

6-[(3R,4S,5S,6S)-3-(4-Methoxybenzyloxy)propyl]-4-methoxymethoxy-3,5-dimethyltetrahydropyran-2-one (14). HF-pyridine (6 mL) was added to a solution of 13 (1.31 g, 2 mmol) in MeOH (20 mL) and pyridine (10 mL) at 0° C. The mixture was stirred at room temperature for 48 h, diluted with EtOAc (100 mL), washed with aqueous HCl (0.5 N, 2×50 mL) and with brine. The aqueous layer was extracted with EtOAc (50 mL). The combined organic layer was dried over anhydrous Na$_2$SO$_4$. The solvent was removed under reduced pressure, and the crude product was purified by column chromatography (hexane/EtOAc 4:1) to provide the pure product in 83% yield: IR (CHCl$_3$) 3020, 2952, 1730, 1513, 1216 cm$^{-1}$; $^1$H NMR (300 MHz, CDCl$_3$) δ 7.24 (d, 2H, J=8.7 Hz), 6.87 (d, 2H, J=8.7 Hz), 4.72 (d, 1H, J=7.2 Hz), 4.60 (d, 1H, J=7.2 Hz), 4.48 (m, 1H), 4.43 (s, 2H), 3.80 (s, 3H), 3.50–3.39 (m, 2H), 3.39 (s, 3H), 3.26 (dd, 1H, J=1.1, 7.0 Hz), 2.58 (t, 1H, J=6.9 Hz), 2.03 (d, 1H, J=7.5 Hz), 1.81–1.63 (m, 4H), 1.31 (d, 3H, J=6.7 Hz), 0.91 (d, 3H, J=7.3 Hz); $^{13}$C NMR (75 MHz, CDCl$_3$) 174.1, 159.2, 130.5, 129.3, 113.8, 95.5, 82.6, 76.7, 72.6, 69.4, 55.9, 55.3, 40.5, 38.4, 28.6, 26.0, 14.4, 11.9, −3.9; HRMS (EI) calcd for C$_{20}$H$_{30}$O$_6$ 366.2042, found 366.2050.

2-Methoxy-6-[(3R,4S,5S,6S)-3-(4-methoxybenzyloxy)propyl]4-methoxymethoxy-3,5-dimethyltetrahydropyran (15). Diisobutylaluminum hydride (1.0 M in THF, 2.2 mL, 2.2 mmol) was added dropwise to a stirred solution of 14 (732 mg, 2 mmol) in anhydrous CH$_2$Cl$_2$ (20 mL) under an atmosphere of N$_2$ at −78° C. and the mixture was stirred for 1 h at −78° C. The reaction was quenched by the careful addition of aqueous sat'd potassium sodium tartrate (50 mL) and stirring for 3 h at room temperature. Once the organic and aqueous layers separated, the aqueous layer was extracted with CH$_2$Cl$_2$. The combined organic layer was washed with brine and dried over MgSO$_4$ followed by the evaporation of solvent under reduced pressure. The crude lactol obtained was used without further purification.

A solution of the lactol and PPTS (0.2 mmol) in MeOH was stirred for 15 h at room temperature. The reaction mixture was diluted with EtOAc (100 mL) and washed with sat'd aqueous NaHCO$_3$ (50 mL). The aqueous layer was extracted with EtOAc (50 mL). The combined organic layer was dried over MgSO$_4$. The solvent was removed under reduced pressure, and the crude product was purified by column chromatography (hexane/EtOAc 7:3) to provide the pure product each anomer 15 (p, 64%; a, 26%). β-15: IR (CHCl$_3$) 3020, 2858, 2299, 1514, 1216 cm$^{-1}$; $^1$H NMR (300 MHz, CDCl$_3$) δ 7.35 (d, 2H, J=8.7 Hz), 6.95 (d, 2H, J=8.7 Hz), 4.76 (d, 2H, J=3.0 Hz), 4.52 (s, 2H), 4.37 (d, 1H, J=4.6 Hz), 4.09 (m, 1H), 3.89 (s, 2H), 3.57 (m, 2H), 3.47 (s, 3H), 3.32 (t, 1H, J=5.7 Hz), 1.89–1.71 (m, 6H), 1.16 (d, 3H, J=7.2 Hz), 1.07 (d, 3H, J=7.9 Hz); $^{13}$C NMR (75 MHz, CDCl$_3$) 159.2, 130.7, 129.3, 113.8, 103.2, 96.3, 82.0, 72.6, 69.9, 69.3, 55.7, 55.3, 39.1, 38.0, 27.1, 26.5, 16.0, 13.1; HRMS (EI) calcd for $C_{21}H_{34}O_6$ 382.2353, found 382.2355. α-15: $^1$H NMR (300 MHz, CDCl$_3$) δ 7.34 (d, 2H, J=8.7 Hz), 6.95 (d, 2H, J=8.7 Hz), 4.72 (s, 2H), 4.70 (d, 1H, J=2.8 Hz), 4.52 (s, 2H), 4.09 (br m, 4H), 3.67 (br s, 1H), 3.56 (m, 5H), 3.44 (s, 3H), 2.08–1.54 (m, 6H), 1.11 (d, 3H, J=3.0 Hz), 1.08 (d, 3H, J=2.9 Hz).

(2S,3S,4S,5R,6R)-3-(6-Methoxy-4-methoxymethoxy-3,5-dimethyltetrahydropyran-2-yl)propionaldehyde (9b). A mixture of PMB ether 15 (458 mg, 1.2 mmol) and palladium (10% Pd/C, 5 mg) was stirred in EtOAc (12 mL) for 3 h at room temperature under an H$_2$ atmosphere (balloon), filtered and concentrated to yield the debenzylated alcohol which was used without further purification.

The crude alcohol in CH$_2$Cl$_2$ (12 mL) was treated with Dess-Martin periodinane (636 mg, 1.5 mmol) at room temperature. The reaction was quenched with saturated aqueous NaHCO$_3$ (20 mL). The aqueous layer was extracted with CH$_2$Cl$_2$ (10 mL×2) and the combined extracts were dried over anhydrous MgSO$_4$. Filtration and concentration followed by short flash column chromatography (hexane/EtOAc 4:1) provided 274 mg (88%) of the crude aldehyde as a colorless oil which was used without further purification: $^1$H NMR (500 MHz, CDCl$_3$) δ 9.80 (s, 1H), 4.67 (dd, 2H, J=7.0, 12.5 Hz), 4.27 (d, 1H, J=4.5 Hz), 3.99 (dd, 1H, J=3.5, 4.0 Hz), 3.36 (s, 6H), 3.24 (t, 1H, J=6.0 Hz), 2.61 (m, 1H), 2.52 (m, 1H), 1.83 (m, 3H), 1.68 (m, 1H), 1.05 (d, 3H, J=7.0 Hz), 1.01 (d, 3H, J=7.5 Hz).

(2S,3R,4S)-5-(tert-Butyldimethylsilanyloxy)-2,4-dimethylpentane-1,3-diol. MeOH (0.51 mL) and LiBH$_4$ (2.0 M in THF, 6.2 mL, 12.4 mmol) were added dropwise to a stirred solution of aldol product 18 [22] (5.38 g, 12.3 mmol) in THF (50 mL) at 0° C. After stirring for 1 h at 0° C., saturated aqueous sodium potassium tartrate (70 mL) was added. The mixture was allowed to warm room temperature and extracted with CH$_2$Cl$_2$ (2×50 mL). The combined organic layer was washed with brine (40 mL), dried over anhydrous MgSO$_4$, concentrated and flash column chromatographed (hexane/EtOAc 4:1) to yield 2.99 g (92%) of the desired product as a colorless oil: IR (CHCl$_3$) 3409, 2958, 2927, 2853, 2878, 1469, 1385, 1361, 1252, 1082, 838, 773 cm$^{-1}$; $^1$H NMR (300 MHz, CDCl$_3$) δ 4.45 (br s, 1H), 3.54 (br s, 1H), 1.92 (m, 1H), 1.83 (m, 1H), 1.06 (d, 3H, J=6.98 Hz), 1.00 (s, 9H), 0.84 (d, 3H, J=6.88 Hz), 0.19 (s, 6H); $^{13}$C NMR (75 MHz, CDCl$_3$) 79.3, 69.7, 67.5, 37.4, 36.6, 25.9, 18.1, 12.8, 8.9, −5.5, −5.6; LRMS (EI) 263 (M+H); HRMS (EI) calcd for $C_{13}H_{30}O_3Si$ 263.2042, found 263.2042; $[α]^{20}_D$ +35.5 (c 0.85, CHCl$_3$).

(2S)-tert-Butyl-{(4R,5S)-2-[2-(4-methoxyphenyl)-5-methyl[1,3]dioxan-4-yl]propoxy}dimethylsilane (20). A solution of the above diol (2.8 g, 10.7 mmol), p-anisaldehyde dimethylacetal (2.0 mL, 11.7 mmol) and PPTS (0.27 g, 1.1 mmol) in benzene was heated to reflux for 3 h. The solvent was evaporated under reduced pressure and the residue was purified by column chromatography (hexane/EtOAc 9:1) to give 20 (2.6 g, 6.8 mmol) in 64% yield: IR (CHCl$_3$) 2955, 2927, 2853, 1617, 1518, 1459, 1382, 1157, 1101, 1033, 826 cm$^{-1}$; $^1$H NMR (300 MHz, CDCl$_3$) δ 7.49 (m, 2H), 6.98 (m, 2H), 5.50 (m, 2H), 3.89 (s, 3H), 3.82 (dd, 1H, J=10.9, 4.9 Hz), 3.76 (dd, 2H, J=8.1, 2.8 Hz), 1.87 (m, 1H), 1.71 (m, 1H), 1.23 (d, 3H, J=7.6 Hz), 1.00 (d, 3H, J=6.5 Hz); $^{13}$C NMR (75 MHz, CDCl$_3$) 160.1, 132.1, 127.6, 113.8, 113.7, 101.9, 80.1, 74.3, 65.2, 64.3, 55.5, 37.4, 30.0, 26.3, 26.2, 18.7, 12.4, 11.3, −5.0, −5.1; LRMS (EI) 323, 207, 187, 157, 145, 121, 75; HRMS (EI) calcd for $C_{21}H_{36}O_4Si_1$ 323.1678 (M−$^t$Bu), found 323.1694 (M−$^t$Bu); $[α]^{20}_D$ −33.6 (c 1.24, CHCl$_3$).

(2S)-2-[(4R,5S)-2-(4-Methoxyphenyl)-5-methyl[1,3]dioxan-4-yl]propan-1-ol. TBAF (1.0M in THF, 22 mL, 22 mmol) was added to a solution of 20 (2.8 g, 7.3 mmol) in THF (70 mL) at room temperature and the mixture was stirred for 2 h. The mixture was diluted with ethyl ether (100 mL) and brine. The organic layer was dried over MgSO$_4$. Filtration and concentration followed by flash column chromatography (hexane/EtOAc 7:3) provided alcohol (1.95 g, 7.2 mmol) as a yellow oil: IR (CHCl$_3$) 3428, 2964, 2930, 2835, 1614, 1512, 1463, 1391, 1249, 1098, 1027 cm$^{-1}$; $^1$H NMR (300 MHz, CDCl$_3$) δ 7.38 (m 2H), 6.87 (m, 2H), 5.48 (s, 1H), 4.11 (dd, 2H, J=4.6, 4.5 Hz), 3.75 (s, 3H), 3.73 (m, 2H), 3.52 (apparent t, 1H, J=11.1 Hz), 2.08 (m, 1H), 2.00 (m, 1H), 1.04 (d, 3H, J=7.1 Hz), 0.77 (d, 3H, J=6.7 Hz); $^{13}$C NMR (75 MHz, CDCl$_3$) 160.0, 131.5, 127.4, 113.6, 101.6, 83.4, 73.9, 66.3, 55.2, 36.8, 30.4, 11.9, 9.9; LRMS (EI) 266, 207, 177, 153, 135, 77; HRMS (EI) calcd for $C_{15}H_{22}O_4$ 266.1518, found 266.1517; $[α]^{20}_D$ −4.8 (c 0.67, CHCl$_3$).

(2S)-{2-[(4R,5S)-2-(4-Methoxyphenyl)-5-methyl[1,3]dioxan-4-yl]propyl}triphenyl-□5-phosphane iodide (21). I$_2$ (4.48 g, 17.6 mmol) was added at 0° C. to a solution of the alcohol from above (2.35 g, 8.82 mmol) in CH$_2$Cl$_2$ (110 mL) containing imidazole (1.32 g, 19.4 mmol) and triphenylphosphine (4.63 g, 17.6 mmol). The resulting slurry was stirred for 1 h and quenched with saturated aqueous Na$_2$S$_2$O$_3$ (10 mL). The organic layer was separated and washed with water (20 mL), brine and dried over anhydrous MgSO$_4$. The solvent was evaporated under reduced pressure and the residue was purified by column chromatography (hexane/EtOAc 9:1) to give the pure iodide.

The iodide was quickly dissolved in benzene (44 mL), PPh$_3$ was added (11.5 g, 44.1 mmol) and the mixture heated to reflux for 36 h. The reaction mixture was cooled to room temperature and anhydrous ethyl ether (50 mL) was added, whereupon a white solid precipitated. Filtration followed by washing of the solid with ethyl ether (10 mL) provided the phosphonium salt (4.5 g) as a white foam: IR (CHCl$_3$) 3054, 2961, 2909, 1611, 1515, 1435, 1246, 1107, 993, 752 cm$^{-1}$; $^1$H NMR (300 MHz, CDCl$_3$) δ 7.55 (m, 9H), 7.37 (m, 6H), 7.21 (m, 2H), 6.65 (m, 1H), 5.41 (s, 1H), 3.95 (d, 1H, J=10.2 Hz), 3.68 (d, 2H, J=12.3 Hz), 3.54 (s, 3H), 3.26 (m, 1H), 1.85 (m, 1H), 1.46 (apparent d, 1H, J=6.5 Hz), 0.78 (d, 3H, J=6.8 Hz), 0.44 (d, 3H, J=6.6 Hz); $^{13}$C NMR (75 MHz, CDCl$_3$) 160.0, 135.2, 135.1, 133.7, 133.5, 131.1, 130.5, 130.4, 127.9, 119.0, 117.9, 113.5, 101.9, 82.3, 82.1, 73.2, 55.5, 30.7, 29.2, 25.3, 15.7, 10.4 HRMS (EI) calcd for $C_{33}H_{36}O_3P$ 511.2402, found 511.2428; $[α]^{20}_D$ +31.9 (c 0.78, CHCl$_3$).

(4R,5R)-tert-Butyl-{3-[2-(4-methoxyphenyl)-5-methyl[1,3]dioxan-4-yl]propoxy}dimethylsilane (26). Lithium borohydride (2.0 M in THF, 25 mL, 50 mmol) was added dropwise to a stirred solution of 25 (8.70 g, 20 mmol) and MeOH (1.61 mL, 40 mmol) in anhydrous THF (100 mL) under an atmosphere of N$_2$ at 0° C. The mixture was stirred for 20 min at 0° C. and then warmed to ambient temperature. After 2 h at room temperature, the reaction was quenched with aqueous NH$_4$Cl (100 mL) and extracted with CH$_2$Cl$_2$ (3×10 mL). The combined organic layers were dried over anhydrous MgSO$_4$, evaporated and chromatographed (hexane/EtOAc 7:3) to yield 4.97 g (95%) of the diol as a colorless oil.

A solution of the diol (2.62 g, 10 mmol), anisaldehyde dimethyl acetal (2.00 g, 11.0 mmol), and PPTS (0.1 equiv) in benzene was stirred for 15 h at reflux. The reaction mixture was quenched with aqueous sat'd NaHCO$_3$ (50 mL) followed by washing with water. The aqueous layer was extracted with ethyl ether (2×50 mL). The combined organic layer was dried over MgSO$_4$. The solvent was removed under reduced pressure and the residue was purified by column chromatography (hexane/EtOAc 7:3) to provide the pure 26 in 72% yield: IR (CHCl$_3$) 2992, 1742, 1373, 1240 cm$^{-1}$; $^1$H NMR (500 MHz, CDCl$_3$) δ 7.43 (d, 2H, J=8.4 Hz), 6.88 (d, 2H, J=8.4 Hz), 5.45 (s, 1H), 4.08 (dd, 2H, J=10.5, 29.9 Hz), 3.90 (br s, 1H), 3.80 (s, 3H), 3.67 (m, 2H), 1.67–1.50 (m, 5H), 1.17 (d, 3H, J=7.0 Hz), 0.90 (s, 9H), 0.06 (s, 6H); $^{13}$C NMR (75 MHz, CDCl$_3$) 159.9, 131.6, 127.4, 113.6, 101.7, 79.7, 73.9, 63.1, 55.3, 31.8, 29.3, 28.7, 26.0, 18.4, 11.1, −5.1; LRMS (ESI) 402.68 (M+Na).

(4R,5S)-4-{(1S,2Z)-5-[(2S,3R,4S,5R,6R)-6-Methoxy-4-methoxymethoxy-3,5-dimethyltetrahydropyran-2-yl]-1-methylpent-2-enyl}-2-(4-methoxyphenyl)-5-methyl[1,3]dioxane (35). NaHMDS (1.0 M in THF, 1.1 mL, 1.1 mmol) was slowly added to a solution of the salt 21 (701 mg, 1.1 mmol) in dry THF (2.2 mL) at 0° C. The resulting red solution was stirred at room temperature for 20 min. The mixture was cooled to −78° C. and a solution of the aldehyde 9a (260 mg, 1 mmol) in THF (1 mL×2) was added dropwise. The mixture was stirred for 20 min at −78° C. and then warmed to room temperature. After 4 h at room temperature, the mixture was quenched with saturated NH$_4$Cl (10 mL) and extracted with CH$_2$Cl$_2$ (3×10 mL). The combined organic layers were dried over anhydrous MgSO$_4$, evaporated and chromatographed (hexane/ether 9:1) to yield 329 mg (67%) of 35 as a colorless oil: IR (CHCl$_3$) 2922, 2866, 2628, 2350, 1740, 1516 cm$^{-1}$; $^1$H NMR (300 MHz, CDCl$_3$) δ 7.45 (d, 2H, J=8.4 Hz), 6.88 (d, 2H, J=8.4 Hz), 5.46 (m, 2H), 5.30 (t, 1H, J=9.9 Hz), 4.77 (d, 1H, J=6.9 Hz), 4.70 (d, 1H, J=1.8 Hz), 4.63 (d, 1H, J=6.9 Hz), 4.06 (br d, 1H, J=2.1 Hz), 3.80 (s, 3H), 3.54 (m, 3H), 3.43 (s, 3H), 3.32 (s, 3H), 2.77 (m, 1H), 2.31 (dd, 2H, J=7.5, 14.7 Hz), 1.79–1.55 (m, 4H), 1.22 (d, 3H, J=6.6 Hz), 1.02 (d, 3H, J=7.2 Hz), 0.96 (d, 3H, J=6.9 Hz), 0.86 (d, 3H, J=6.9 Hz); $^{13}$C NMR (75 MHz, CDCl$_3$) δ 159.7, 133.4, 131.8, 130.1, 127.3, 113.3, 101.5, 101.3, 95.9, 83.5, 82.0, 75.2, 73.9, 56.4, 55.7, 55.2, 37.6, 34.2, 33.6, 33.0, 30.0, 23.4, 16.1, 13.3, 11.2, 9.9; HRMS (EI) calcd for C$_{27}$H$_{40}$O$_6$ 460.2824, found 460.2846.

(4R,5S)-4-{(1S,2Z)-5-[(2S,3S,4S,5R,6R)-6-Methoxy-4-methoxymethoxy-3,5-dimethyltetrahydropyran-2-yl]-1-methylpent-2-enyl}-2-(4-methoxyphenyl)-5-methyl[1,3]dioxane (36). NaHMDS (1.0 M in THF, 1.1 mL, 1.1 mmol) was slowly added to a solution of the salt 21 (0.70 g, 1.1 mmol) in dry THF (2 mL) at 0° C. The resulting red solution was stirred at room temperature for 20 min. The mixture was cooled to −78° C. and a solution of the aldehyde 9b (260 mg, 1 mmol) in THF (1 mL) was added dropwise. The mixture was stirred for 20 min at −78° C. and then warmed to room temperature. After 4 h at room temperature, the reaction was quenched with saturated NH$_4$Cl (10 mL) and extracted with CH$_2$Cl$_2$ (3×10 mL). The combined organic layers were dried over anhydrous MgSO$_4$, evaporated and chromatographed (hexane/ether 9:1) to yield 329 mg (67%) of 36 as a colorless oil: IR (CHCl$_3$) 2922, 2866, 2628, 2350, 1740, 1516 cm$^{-1}$; $^1$H NMR (300 MHz, CDCl$_3$) δ 7.48 (d, 2H, J=9.0 Hz), 6.91 (d, 2H, J=9.0 Hz), 5.46 (m, 2H), 5.32 (t, 1H, J=9.6 Hz), 4.73 (s, 2H), 4.31 (d, 1H, J=5.4 Hz), 4.07 (br s, 2H), 3.81 (s, 1H), 3.57 (dd, 1H, J=1.8, 9.6 Hz), 3.45 (s, 3H), 3.43 (s, 3H), 3.20 (t, 1H, J=6.6 Hz), 2.77 (m, 1H), 2.31–2.17 (m, 2H), 1.90–1.62 (m, 4H), 1.24–0.98 (m, 12H); $^{13}$C NMR (75 MHz, CDCl$_3$) δ 159.7, 133.7, 131.7, 129.4, 127.2, 113.4, 102.8, 101.5, 96.6, 83.5, 82.2, 73.9, 70.0, 55.7, 55.2, 39.8, 38.4, 33.6, 30.0, 29.9, 24.3, 15.9, 15.5, 13.2, 11.1; HRMS (EI) calcd for C$_{27}$H$_{40}$O$_6$ (M−HOCH$_3$) 460.2824, found 460.2846.

(2R,3S,4S,5Z)-3-(4-Methoxybenzyloxy)-8-[(2S,3R,4S,5R,6R)-6-methoxy-4-methoxymethoxy-3,5-dimethyltetrahydropyran-2-yl]-2,4-dimethyloct-5-enal (37). DIBAL (1.0 M in hexane, 2.1 mL, 2.1 mmol) was added dropwise to a solution of the acetal 35 (329 mg, 0.67 mmol) in dry CH$_2$Cl$_2$ (6.7 mL) at 0° C. After stirring for 2 h, the reaction was quenched with saturated aqueous sodium tartrate (20 mL) followed by vigorously stirring for several hours. The aqueous phase was extracted with CH$_2$Cl$_2$ (3×10 mL) and the combined organic layers were washed with brine (10 mL). The residue obtained after drying over MgSO$_4$ and evaporation under vacuum was dissolved in anhydrous CH$_2$Cl$_2$ (6 mL) and DMSO (12 mL), treated with N,N-diisopropylethylamine (0.52 mL, 3 mmol), cooled to 0° C. and treated with pyridinium sulfur trioxide (477 mg, 3 mmol). The reaction mixture was stirred at ambient temperature for 1 h, diluted with ethyl ether (50 mL) and washed with aqueous HCl (0.5 N, 50 mL) and brine (10 ml). The separated organic layer was dried over MgSO$_4$. Filtration and concentration followed by short flash column chromatography (hexane/EtOAc 4:1) provided the crude aldehyde 37 (270 mg, 0.55 mmol) as a colorless oil which was used without further purification.

(2R,3S,4S,5Z)-3-(4-Methoxybenzyloxy)-8-[(2S,3S,4S,5R,6R)-6-methoxy-4-methoxymethoxy-3,5-dimethyltetrahydropyran-2-yl]-2,4-dimethyloct-5-enal (38). DIBAL (1.0 M in hexane, 2.1 mL, 2.1 mmol) was added dropwise to a solution of the acetal 36 (329 mg, 0.67 mmol) in dry CH$_2$Cl$_2$ (6.7 mL) at 0° C. After the mixture was stirred for 2 h, the reaction was quenched with saturated aqueous sodium tartrate (20 mL) followed by vigorous stirring for several hours. The aqueous phase was extracted with CH$_2$Cl$_2$ (3×10 mL) and the combined organic layers were washed with brine (10 mL). After drying over MgSO$_4$ and evaporation under vacuum, the residue was used for the next reaction without further purification. The crude alcohol in CH$_2$Cl$_2$ (13 mL) was treated with Dess-Martin periodinane (340.8 mg, 0.80 mmol). After the reaction was complete, the mixture was quenched with saturated NaHCO$_3$ (20 mL). The aqueous layer was extracted with CH$_2$Cl$_2$ (2×10 mL) and the combined extracts were dried over anhydrous MgSO$_4$. Filtration and concentration followed by short flash column chromatography filtration (hexane/EtOAc 9:1) provided crude aldehyde 38 (267 mg, 81%) as a colorless oil which was used without further purification.

(2S,3R)-6-(tert-Butyldimethylsilanyloxy)-3-(4-methoxybenzyloxy)-2-methylhexanal (27). DIBAL (1.0 M in THF, 15 mL, 15 mmol) was added dropwise to a stirred solution of 26 (1.90 g, 5 mmol) in anhydrous CH$_2$Cl$_2$ (50 mL) under an atmosphere of N$_2$ at 0° C. and the mixture was stirred for 1 h at 0° C. The reaction was quenched by the careful addition of aqueous sat'd potassium sodium tartrate (100 mL) and stirring for 3 h at room temperature. Once the aqueous and organic layers separated, the aqueous layer was extracted with CH$_2$Cl$_2$. The combined organic layer was washed with brine and dried over MgSO$_4$ followed by the evaporation of the solvent under reduced pressure. The crude alcohol (1.56 g, 4.1 mmol) was used without further purification.

Pyridinium sulfur trioxide (2.38 g, 15 mmol) was added to a stirred solution of the crude alcohol from above and diisopropylethylamine (2.6 mL, 15 mmol) in anhydrous CH$_2$Cl$_2$ (10 mL) and DMSO (20 mL) at 0° C. The mixture was stirred at ambient temperature for 1 h. After the reaction was complete, the mixture was diluted with ethyl ether (100 mL) and washed with aqueous HCl (0.5 N, 100 mL) and brine (100 ml). The separated organic layer was dried over MgSO$_4$. Filtration and concentration followed by short flash column chromatography filtration (hexane/EtOAc 4:1) to remove SO$_3$-pyridine provided the crude aldehyde 27 as a colorless oil which was used without further purification.

(2R,3R,4R,5R)-8-(tert-Butyldimethylsilanyloxy)-3-hydroxy-5-(4-methoxybenzyloxy) -2,4-dimethyloctanoic acid, 2,6-dimethylphenyl ester (29). LDA (2M in THF, 3.1 mL, 6.2 mmol) was added to a solution of 2,6-dimethylphenoxy propionate (1.10 g, 6.2 mmol) in anhydrous THF (12.4 mL) at −78° C., followed by stirring for 1 h at −78° C. The crude aldehyde 27 (4.1 mmol) from above dissolved in anhydrous THF (10 mL) was added slowly at −78° C. After 2 h at room temperature, the mixture was quenched with saturated aqueous NH$_4$Cl (10 mL) and extracted with CH$_2$Cl$_2$ (3×10 mL). The combined organic layer was dried over anhydrous MgSO$_4$, evaporated and chromatographed (hexane/EtOAc 4:1) to yield 29 (1.67 g, 2.99 mmol) as a colorless oil: IR (CHCl$_3$) 3120, 2857, 1744, 1514, 1216, 1099 cm$^{-1}$; $^1$H NMR (300 MHz, CDCl$_3$) δ 7.26 (d, 2H, J=8.4 Hz), 6.87 (d, 2H, J=8.4 Hz), 4.62 (d, 1H, J=11.1 Hz), 4.40 (d, 1H, J=11.1 Hz), 4.06 (d, 1H, J=6.8 Hz), 3.79 (s, 3H), 3.66–3.61 (m, 3H), 2.89 (m, 1H), 2.19 (s, 6H), 1.86 (m, 2H), 1.55 (m, 3H); 1.27 (d, 3H, J=6.8 Hz), 1.01 (d, 3H, J=6.9 Hz), 0.93 (s, 9H), 0.07 (s, 6H); $^{13}$C NMR (75 MHz, CDCl$_3$) δ 173.5, 159.2, 148.0, 130.0, 129.9, 129.4, 128.4, 125.6, 113.8, 83.5, 70.7, 62.9, 55.1, 44.0, 35.6, 28.7, 26.6, 25.8, 18.2, 16.3, 14.2, 5.7, −5.3; HRMS (EI) calcd for C$_{32}$H$_{50}$O$_6$Si 558.3377, found 558.3392.

(2S,3S,4R,5R)-3,8-Bis-(tert-butyldimethylsilanyloxy)-5-(4-methoxybenzyloxy) -2,4-dimethyloctan-1-ol. TBDMSOTf (0.68 mL, 3 mmol) was added to a stirred solution of 29 (1.11 g, 2 mmol) and 2,6-lutidine (0.69 mL, 6 mmol) in CH$_2$Cl$_2$ (20 mL) at −78° C. The mixture was stirred for 2 h at ambient temperature. The reaction was quenched by the addition of aqueous HCl (0.5 N, 50 mL). The reaction mixture was extracted with CH$_2$Cl$_2$, dried over MgSO$_4$ and the solvent was removed under reduced pressure. Short column chromatography (hexane/EtOAc 4:1) provided the crude product.

DIBAL (1.0 M in THF, 6 mL, 6 mmol) was added dropwise to a stirred solution of the TBS-protected aryl ester (1.90 g, 2 mmol) from above in anhydrous CH$_2$Cl$_2$ (20 mL) under an atmosphere of N$_2$ at 0° C. and the mixture was stirred for additional 1 h at 0° C. The reaction was quenched by the careful addition of aqueous sat'd potassium sodium tartrate (50 mL). The mixture was stirred for 3 h at room temperature. Once the aqueous and organic layers had separated, the aqueous layer was extracted with CH$_2$Cl$_2$ (20 mL). The combined organic layer was washed with brine and dried over MgSO$_4$ followed by the evaporation of the solvent under reduced pressure. The residue was purified by column chromatography (EtOAc/hexane/EtOAc 3:7) to give pure (997 mg, 1.8 mmol): IR (CHCl$_3$) 3125, 1544, 1289, 1065 cm$^{-1}$, $^1$H NMR (300 MHz, CDCl$_3$) δ 7.28 (d, 2H, J=8.7 Hz), 6.89 (d, 2H, J=8.7 Hz), 4.51 (d, 1H, J=11.1), 4.41 (d, 1H, J=10.8 Hz), 3.83 (d, 3H), 3.79 (m, 1H), 3.64 (m, 4H), 3.36 (m, 1H), 2.45 (br s, 1H), 1.93 (m, 2H), 1.63 (m, 4H), 1.00 (d, 2H, J=7.0 Hz), 0.92 (s, 24H), 0.14 (s, 6H), 0.13 (s, 6H); $^{13}$C NMR (75 MHz, CDCl$_3$) δ 159.1, 130.6, 129.4, 113.6, 80.3, 76.0, 71.2, 65.2, 63.0, 55.1, 39.1, 39.0, 29.0, 27.1, 26.1, 25.9, 11.6, −3.6, −3.9, −5.3; LRMS (ESI) 576.8 (M+Na).

(2R,3S,4R,5R)-3,8-Bis-(tert-butyldimethylsilanyloxy)-5-(4-methoxybenzyloxy) -2,4-dimethyloctanal (30). Pyridinium sulfurtrioxide (858 mg, 5.4 mmol) was added to a stirred solution of alcohol (997 mg, 1.8 mmol) from above and diisopropylethylamine (0.94 mL, 5.4 mmol) in anhydrous CH$_2$Cl$_2$ (3.6 mL) and DMSO (7.2 mL) at 0° C. The mixture was stirred at ambient temperature for 1 h. After the reaction was complete, the mixture was diluted with ethyl ether (50 mL) and washed with aqueous HCl (0.5N, 50 mL) and brine (10 ml). The organic layer was dried over MgSO$_4$. Filtration and concentration followed by short flash column chromatography filtration (hexane/EtOAc 4:1) to remove SO$_3$-pyridine provided the crude aldehyde 30 as a colorless oil which was used without further purification: $^1$H NMR (300 MHz, CDCl$_3$) δ 9.69 (s, 1H), 7.22 (d, 2H, J=8.6 Hz), 6.85 (d, 2H, J=8.6 Hz), 4.45 (d, 1H, J=11.1 Hz), 4.28 (d, 1H, J=11.1 Hz), 3.94 (dd, 1H, J=5.5, 4.0 Hz), 3.79 (s, 3H), 3.60 (t, 2H, J=6.0 Hz), 3.40–3.34 (m, 1H), 2.66–2.58 (m, 1H), 1.92–1.84 (m, 1H), 1.67–1.59 (m, 2H), 1.55–1.45 (m, 2H), 1.02 (d, 3H, J=7.0 Hz), 0.98 (d, 3H, J=7.0 Hz), 0.89 (s, 9H), 0.86 (s, 9H), 0.05 (s, 3H), 0.04 (s, 9H).

(1R,2R,3S,4S,5Z)-1-{3-(tert-Butyldimethylsilanyloxy)-1-[3-(tert-butyldimethylsilanyloxy)propyl]-2,4-dimethylocta-5,7-dienyloxymethyl}-4-methoxybenzene (32). CrCl$_2$ (1.09 g, 9.0 mmol) was added to a stirred solution of the crude aldehyde (1.8 mmol) from above and 1-bromoallyl trimethylsilane 31 (578 mg, 5.4 mmol) in anhydrous THF (18 mL) under an atmosphere of N$_2$ at room temperature. The mixture was stirred for 14 h at ambient temperature, then diluted with ethyl ether followed by filtration through Celite. After the evaporation of the solvent under reduced pressure, the residue was purified by short silica gel column chromatography (CH$_2$Cl$_2$). The resulting residue was used without further purification.

The above product in THF (50 mL) was cooled to 0° C. and NaI (95% w/w, 207 mg, 9.0 mmol) was added in one portion. The ice bath was removed after 15 min and the mixture was stirred for 2 h at ambient temperature. The reaction mixture was cooled to 0° C., quenched with H$_2$O (10 mL) and extracted with ethyl ether (2×50 mL). The combined organic layer was washed with brine and dried over MgSO$_4$ followed by the evaporation of the solvent under reduced pressure. The residue was purified by column chromatography (hexane/EtOAc 4:1) to give pure 32 (622 mg, 1.2 mmol): IR (CHCl$_3$) 2954, 2931, 2857, 1608, 1513, 1463, 1251, 1098, 1047 cm$^{-1}$; $^1$H NMR (300 MHz, CDCl$_3$) δ 7.35 (d, 2H, J=8.6 Hz), 6.96 (d, 2H, J=8.6 Hz), 6.41 (ddd, 1H, J=16.7, 11.0, 10.1 Hz), 6.04 (dd, 1H, J=11.1, 11.0 Hz), 5.57 (dd, 1H, J=10.1, 16.8 Hz), 5.20 (d, 1H, J=16.7 Hz), 5.06 (d, 1H, J=10.1 Hz), 4.51 (d, 1H, J=11.3 Hz), 4.35 (d, 1H, J=11.3 Hz), 3.81 (s, 3H), 3.63–3.57 (m, 3H), 3.28 (dt, 1H, J=5.5, 5.5 Hz), 2.70 (ddq, 1H, J=10.3, 6.9, 3.2 Hz), 1.73–1.58 (m, 3H), 1.50–1.44 (m, 2H), 0.94 (d, 3H, J=6.9 Hz), 0.93–0.91 (m, 21H), 0.06 (s, 6H), 0.05 (s, 6H); $^{13}$C NMR (75 MHz, CDCl$_3$) 159.1, 134.8, 132.5, 131.0, 129.5, 128.9, 117.1, 113.7, 78.9, 76.6, 70.7, 63.2, 55.2, 40.0, 36.4, 31.6, 28.7, 26.2, 26.0, 18.9, 18.5, 18.3, 10.9, −3.3, −3.4, −5.3; LRMS (EI) 576, 519, 467, 387, 357, 293, 225, 121; HRMS (EI) calcd for C$_{29}$H$_{51}$O$_4$Si$_2$ 519.3326, found 519.3332; [α]$^{20}_D$ −18.8° (c 0.75, CHCl$_3$).

(2R)-2-{(4R,5S,6R)-6-[3-(tert-Butyldimethylsilanyloxy) propyl]-2,2,5-trimethyl[1,3]dioxan-4-yl}-propionic acid, 2,6-dimethylphenyl ester (34). A mixture of PMB ether 29 (55.8 mg, 0.1 mmol) and palladium (10% Pd/C, 5 mg) in EtOAc (10 mL) was stirred at room temperature under an H$_2$ atmosphere (balloon) for 3 h. The mixture was filtered and concentrated to yield the diol which was used without further purification. A solution of the crude diol, dimethyl dimethyl acetal (12.4 mg, 0.12 mmol) and PPTS (0.1 equiv.) in benzene was stirred for 5 h at 65° C. The reaction was quenched with aqueous sat'd NaHCO$_3$ (50 mL) followed by washing with water. The aqueous layer was extracted with ethyl ether (2×50 mL). The combined organic layer was dried over MgSO$_4$. The solvent was removed under reduced pressure and the crude product was purified by column chromatography (hexane/EtOAc 9:1) to provide the pure 34 in 52% yield: IR (CHCl$_3$) 2855, 1742, 1510, 1091 cm$^{-1}$; $^1$H NMR (500 MHz, CDCl$_3$) δ 7.03 (br s, 3H), 4.20 (dd, 1H, J=1.7, 10.2 Hz), 3.91 (m, 1H), 3.64 (m, 2H), 2.91 (dq, 1H, J=10.2, 6.9 Hz), 2.16 (s, 6H), 1.59–1.32 (m, 6H), 1.41 (s, 3H), 1.39 (s, 3H), 1.24 (d, 3H, J=4.2 Hz), 0.92 (br s, 12H), 0.06 (s, 6H); $^{13}$C NMR (75 MHz, CDCl$_3$) 173.7, 148.2, 130.3, 128.5, 125.8, 99.1, 75.2, 73.0, 63.1, 42.3, 31.8, 29.9, 29.3, 28.8, 26.0, 19.5, 18.4, 16.4, 12.9, 4.54, −5.19; HRMS (EI) calcd for C$_{27}$H$_{46}$O$_5$Si 478.3115, found 463.2889 (M−CH$_3$).

(1S,2S,3R,6Z,8S,9S,10S,11Z)-13,9-Bis-(4-methoxybenzyloxy)-14-[(2S,3S,4S,5R,6R)-6-methoxy-4-methoxymethoxy-3,5-dimethyltetrahydropyran-2-yl]-2,8,10-trimethyl-1-[(1S,2Z)-1-methylpenta-2,4-dienyl)tetradeca-6,11-dienyloxy]-tert-butyldimethylsilane. NaHMDS (1.0 M in THF, 0.54 mL, 0.54 mmol) was added slowly to a solution of the salt 33 (475.9 mg, 0.54 mmol) in dry THF (1.08 mL) at 0° C. The mixture was cooled to −78° C. and a solution of the aldehyde 38 (267 mg, 0.54 mmol) in THF (0.54 mL×2) was added dropwise. The mixture was stirred for 20 min at −78° C. and then warmed to room temperature. After 4 h at room temperature the mixture was quenched with saturated aqueous NH$_4$Cl (10 mL) and extracted with CH$_2$Cl$_2$ (3×10 mL). The combined organic layer was dried over anhydrous MgSO$_4$, evaporated and chromatographed (hexane/EtOAc 9:1) to yield the desired compound (257 mg, 0.28 mmol) as a colorless oil: IR (CHCl$_3$) 2920, 2861, 2620, 1740, 1520 cm$^{-1}$, $^1$H NMR (300 MHz, CDCl$_3$) 7.38 (m, 4H), 6.96 (m, 4H), 6.47 (ddd, 1H, J=16.8, 11.0, 10.1 Hz), 6.04 (t, 1H, J=11.1 Hz), 5.57 (t, 1H, J=10.5 Hz), 5.49–5.12 (m, 6H), 4.75 (d, 2H, J=2.1 Hz), 4.67–4.33 (m, 5H), 4.07 (m, 1H), 3.65 (dd, 1H, J=3.3, 6.0 Hz), 3.47 (br s, 7H), 3.35 (dd, 1H, J=4.5, 4.7 Hz), 3.27 (t, 1H, J=6.6 Hz), 3.15 (dd, 1H, J=4.5, 6.9 Hz), 2.77 (m, 3H), 2.18 (m, 2H), 1.91 (m, 2H), 1.74–1.62 (m, 4H), 1.11–0.99 (m, 18H), 0.12 (s, 6H); $^{13}$C NMR (75 MHz, CDCl$_3$) 159.2, 159.0, 134.7, 133.7, 132.9, 132.5, 131.4, 131.0, 129.6, 129.1, 128.9, 128.6, 117.3, 113.8, 113.7, 103.0, 96.5, 88.0, 82.1, 78.8, 74.9, 70.8, 69.7, 55.8, 55.3, 40.0, 39.5, 38.3, 35.6, 35.4, 31.3, 30.3, 26.4, 24.2, 23.7, 19.0, 18.8, 18.6, 17.3, 15.7, 13.2, 11.0, −3.1, −3.2; LRMS (ESI) 942.5 (M+Na).

Carbamic acid, (1S,2S,3R,6Z,8S,9S,10S,11Z)-3,9-bis-(4-methoxybenzyloxy)-14-[(2S,3S,4S,5R,6R)-6-methoxy-4-methoxymethoxy-3,5-dimethyltetrahydropyran-2-yl]-2,8,10-trimethyl-1-[(1S,2Z)-1-methylpenta-2,4-dienyl] tetradeca-6,11-dienyl ester (39). The above compound (128.5 mg, 0.14 mmol) in THF (4 mL) was treated with TBAF (1.0 M in THF, 0.40 mL, 0.40 mmol) and the mixture was stirred at room temperature for 48 h. The mixture was diluted with ethyl ether (30 mL) and washed with water (10 mL). After drying over MgSO$_4$ and evaporation under vacuum, the resulting alcohol was used without further purification.

A solution of the alcohol in CH$_2$Cl$_2$ (8 mL) at 0° C. was treated with trichloroacetylisocyanate (0.05 mL, 0.42 mmol) and stirred at room temperature. After 30 min, the solution was concentrated under reduced pressure and the residue was taken up in MeOH (4 mL). K$_2$CO$_3$ (50 mg) was added to this solution and the mixture was stirred at room temperature for 3 h at room temperature. The mixture was diluted with EtOAc (30 mL). The organic layer was washed with brine. The aqueous layer was extracted with EtOAc, and the combined extracts were dried over anhydrous Na$_2$SO$_4$. Filtration and concentration followed by flash column chromatography (hexane/EtOAc 3:2) provided carbamate 39 (84.9 mg, 72%) as a yellow oil: IR (CHCl$_3$) 3100, 3019, 2430, 2286, 1720, 1524 cm$^{-1}$; $^1$H NMR (300 MHz, CDCl$_3$) 7.41 (m, 4H), 7.01 (m, 4H), 6.46 (ddd, 1H, J=16.8, 11.0, 10.1 Hz), 6.11 (t, 1H, J=10.8 Hz), 5.62 (t, 1H, J=10.5 Hz), 5.53–5.18 (m, 6H), 4.94 (t, 1H, J=6.0 Hz), 4.84 (br s, 2H), 4.81 (d, 2H, J=2.1 Hz), 4.71–4.45 (m, 4H), 4.39 (d, 1H, J=5.1 Hz), 4.12 (m, 1H), 3.37 (m, 2H), 3.19 (dd, 1H, J=4.5, 6.9 Hz), 2.90 (m, 3H), 2.27 (m, 2H), 1.91 (m, 2H), 1.74–1.61 (m, 4H), 1.11–0.99 (m, 18H); $^{13}$C NMR (75 MHz, CDCl$_3$) 159.2, 159.0, 157.1, 133.7, 133.3, 132.8, 132.2, 131.4, 130.9, 129.8, 129.6, 129.1, 128.5, 117.8, 113.8, 113.7, 102.9, 96.5, 88.0, 82.1, 78.4, 78.1, 74.9, 70.5, 69.8, 55.8, 55.7, 55.3, 39.5, 38.2, 37.7, 35.8, 35.4, 34.3, 30.6, 30.3, 24.2, 23.6, 18.9, 17.8, 17.4, 15.7, 13.2, 9.8; LRMS (ESI) 888.4 (M+K).

Carbamic acid, (1S,2S,3R,6Z,8S,9S,10S,11Z)-3,9-bis-(4-methoxybenzyloxy)-14-[(2S,3S,4S,5R)-4-methoxymethoxy-3,5-dimethyl-6-oxotetrahydropyran-2-yl]-2,8,10-trimethyl-1-[(1S,2Z)-1-methylpenta-2,4-dienyl] tetradeca-6,11-dienyl ester. A solution of 39 (42.4 mg, 0.05 mmol) in THF (0.5 mL) and 60% aqueous acetic acid (2.5 mL) was stirred at 70° C. for 4 h. After the reaction was complete by TLC, the mixture was neutralized slowly with saturated aqueous K$_2$CO$_3$ and diluted with EtOAc (20 mL). The aqueous phase was extracted with EtOAc (2×10 mL). The combined organic layers were dried over MgSO$_4$ and evaporated under reduced pressure. The crude lactol was used for the next reaction without further purification.

Dess-Martin periodinane reagent (31.8 mg, 0.075 mmol) was added to a solution of the lactol in CH$_2$Cl$_2$ (5 mL). The resultant solution was stirred for 1 h and quenched by the simultaneous addition of saturated aqueous Na$_2$S$_2$O$_3$ (5 mL) and saturated aqueous NaHCO$_3$. The aqueous layer was extracted with CH$_2$Cl$_2$ (2×10 mL) and the combined extracts were dried over anhydrous MgSO$_4$. Filtration and concentration followed by flash column chromatography (hexane/EtOAc 8:2) provided 28.3 mg (68%) of the lactone as a colorless oil: IR (CHCl$_3$) 2992, 2361, 2332, 1742, 1374, 1242, 1047 cm$^{-1}$; $^1$H NMR (300 MHz, CDCl$_3$) 7.40 (m, 4H), 7.03 (m, 4H), 6.51 (ddd, 1H, J=16.8, 11.1, 10.0 Hz), 6.11 (t, 1H, J=11.1 Hz), 5.67 (t, 1H, J=10.8 Hz), 5.52–5.18 (m, 7H), 4.94 (t, 1H, J=6.0 Hz), 4.87–4.47 (m, 9H), 3.94 (br s, 4H), 3.93 (s, 3H), 3.54 (s, 3H), 3.40 (m, 2H), 3.19 (dd, 1H, J=4.5, 6.9 Hz), 2.87 (m, 2H), 2.72 (m, 2H), 2.32–1.89 (m, 7H), 1.45 (d, 3H, J=6.6 Hz), 1.15–01.02 (m, 15H); $^{13}$C NMR (75 MHz, CDCl$_3$) 174.2, 159.2, 159.0, 156.9, 133.6, 133.5, 133.4, 132.2, 131.3, 130.9, 129.8, 129.6, 129.5, 129.2, 128.7, 127.8, 113.8, 113.7, 95.4, 88.0, 82.7, 79.9, 78.4, 76.5, 75.0, 55.9, 55.7, 55.3, 40.5, 38.6, 37.7, 36.0, 35.4, 34.3, 31.3, 30.6, 23.9, 23.6, 23.5, 19.0, 17.8, 14.4, 12.1, 9.8; LRMS (ESI) 872.4 (M+K).

Carbamic acid, (1S,2S,3R,6Z,8S,9S,10S,11Z)-3,9-dihydroxy-14-[(2S,3S,4S,5R)-4-hydroxy-3,5-dimethyl-6-oxotetrahydropyran-2-yl]-2,8,10-trimethyl-1-[(1S,2Z)-1-methylpenta-2,4-dienyl]tetradeca-6,11-dienyl ester (40). A solution of the above lactone (2.83 mg, 0.005 mmol) in THF (2 mL) was treated with aqueous 4N HCl (1 mL). The flask was fitted with a glass stopper and the resulting solution was stirred at room temperature for 48 h. Saturated aqueous K$_2$CO$_3$ was added dropwise followed by EtOAc. The aqueous layer was extracted with EtOAc and the combined extracts were dried over MgSO$_4$. Filtration and concentration followed by simple short flash column chromatography (EtOAc/hexane/ether 3:2) provided the crude MOM-deprotected compound. A solution of PMB ether in CH$_2$Cl$_2$ (2 mL) at 0° C. was treated with NaHCO$_3$ (4.2 mg, 0.5 mmol).

After 1 h, the mixture was diluted with $CH_2Cl_2$ and washed with water. The aqueous layer was extracted with $CH_2Cl_2$ and the combined extracts were dried over anhydrous $MgSO_4$. Filtration and concentration followed by flash column chromatography (EtOAc/hexane 3:2) provided carbamate 40 (1.1 mg, 0.002 mmol) as a colorless oil: IR ($CHCl_3$) 2995, 2937, 2323, 1755, 1449, 1374, 1242, 1049 $cm^{-1}$; $^1H$ NMR (500 MHz, $CDCl_3$) 6.63 (ddd, 1H, J=16.8, 11.0, 10.1 Hz), 6.06 (t, 1H, J=11.0 Hz), 5.46–5.32 (m, 5H), 5.25 (d, 1H, J=17 Hz), 5.14 (d, 1H, J=10.0 Hz), 4.94 (t, 1H, J=6.0 Hz), 4.74 9m, 1H), 4.60 (br s, 1H), 4.54 (m, 1H), 3.65 (m, 1H), 3.38 (d, 1H, J=5.0 Hz), 3.27 (t, 1H, J=6.0 Hz), 3.00 (m, 1H), 2.78 (m, 1H), 2.63 (m, 2H), 2.18 (m, 1H), 2.01 (m, 1H), 1.83 (m, 1H), 1.77 (m, 1H), 1.35 (d, 3H, J=7.0), 1.01–0.93 (m, 15H); $^{13}C$ NMR (125 MHz, $CDCl_3$) 174.2, 157.3, 133.6, 132.9, 129.6, 128.9, 125.0, 121.4, 118.0, 95.5, 82.6, 79.7, 79.2, 72.8, 55.9, 40.5, 39.9, 38.6, 35.4, 34.7, 31.6, 23.8, 19.2, 18.2, 17.7, 15.7, 14.8, 12.0; LRMS (ESI) 571.4 (M+Ka); HRMS (ESI) calcd for $C_{31}H_{51}NO_7Na$ 588.3303, found 588.3336 (M+K); $[\alpha]^{20}_D$ +34.0 (c 0.05, $CHCl_3$).

Carbamic acid, (1S,2S,3R,6Z,8S,9S,10S,11Z)-3,9-dihydroxy-14-[(2S,3S,4S,5R)-4-methoxymethoxy-3,5-dimethyl-6-oxotetrahydropyran-2-yl]-2,8,10-trimethyl-1-[(1S,2Z)-1-methylpenta-2,4-dienyl]tetradeca-6,11-dienyl ester (41). Carbamate 39 (8.49 mg, 0.01 mmol) was subjected to the lactonization procedure described above. The removal of the PMB protecting group was accomplished by treating with $NaHCO_3$ and DDQ. Flash chromatography (EtOAc/hexane 3:2) provided 41 (2.9 mg, 49% overall 3 steps) as a colorless oil: IR ($CHCl_3$) 3404, 2362, 1749, 1373, 1241, 1049 $cm^{-1}$; $^1H$ NMR (500 MHz, $CDCl_3$) 6.62 (ddd, 1H, J=16.8, 11.0, 10.1 Hz), 6.04 (t, 1H, J=11.0 Hz), 5.48–5.33 (m, 5H), 5.24 (d, 1H, J=17 Hz), 5.13 (d, 1H, J=10.0 Hz), 4.77–4.60 (br m, 5H), 4.48 (m, 1H), 3.65 (m, 1H), 3.41 (s, 3H), 3.28 (d, 1H, J=7.0 Hz), 3.23 (t, 1H, J=5.5 Hz), 3.02 (m, 1H), 2.62 (m, 2H), 2.25–2.18 (m, 3H), 2.04 (m, 2H), 1.90 (m, 1H), 1.88 (m, 1H), 1.83 (m, 1H), 1.77–1.67 (m, 2H), 1.51 (m, 2H), 1.34 (d, 3H, J=7.0), 1.02–0.92 (m, 15H); $^{13}C$ NMR (125 MHz, $CDCl_3$) 174.1, 157.3, 133.6, 132.9, 132.2, 129.6, 128.9, 125.0, 121.4, 118.0, 95.5, 82.6, 79.7, 79.2, 72.8, 55.9, 40.5, 39.8, 38.6, 35.4, 34.9, 34.7, 31.6, 23.8, 19.2, 18.2, 17.2, 15.7, 14.8, 12.0; LRMS (ESI) 616.3 (M+Na); HRMS (ESI) calcd for $C_{33}H_{55}NO_8Na$ 616.3825, found 616.3829 (M+Na); $[\alpha]^{20}_D$ +59.0 (c 0.1, $CHCl_3$).

Carbamic acid, (1S,2S,3R,6Z,8S,9S,10S,11Z)-3,9-dihydroxy-14-[(2S,3S,4S,5R,6R)-6-methoxy-4-methoxymethoxy-3,5-dimethyltetrahydropyran-2-yl]-2,8,10-trimethyl-1-[(1S,2Z)-1-methylpenta-2,4-dienyl]tetradeca-6,11-dienyl ester (42). Carbamate 39 (4.25 mg, 0.005 mmol) was subjected to the deprotection procedure of PMB described in the preparation of 40. Flash chromatography (EtOAc/hexane 3:2) of the crude product provided 42 (2.8 mg, 92%) as a colorless oil: IR ($CHCl_3$) 3115, 2749, 2328, 1676, 1508, 1215 $cm^{-1}$; $^1H$ NMR (300 MHz, $CDCl_3$) 6.76 (ddd, 1H, J=16.8, 11.0, 10.1 Hz), 6.18 (t, 1H, J=10.8 Hz), 5.70–5.46 (m, 5H), 5.35 (d, 1H, J=16.8 Hz), 4.49 (dd, 1H, J=4.5, 6.6 Hz), 4.82 (d, 2H, J=2.4 Hz), 4.73 (br s, 2H), 4.43 (d, 1H, J=5.1 Hz), 4.15, (m, 1H), 3.78 (m, 1H), 3.56 (s, 3H), 3.54 (s, 3H), 3.36 (t, 2H, J=6.9 Hz), 3.14 (m, 1H), 2.76 (m, 2H), 2.35–2.18 (m, 6H), 2.00–1.60 (m, 7H), 1.22 (d, 3H, J=7.2 Hz), 1.16–1.12 (m, 12H), 1.07 (d, 3H, J=7.2 Hz); $^{13}C$ NMR (125 MHz, $CDCl_3$) 157.3, 133.7, 133.5, 132.2, 132.0, 130.0, 128.7, 118.0, 109.6, 103.0, 96.5, 82.1, 79.7, 79.1, 72.7, 55.8, 39.9, 39.5, 38.3, 35.5, 35.0, 34.8, 34.6, 30.2, 29.8, 24.3, 18.1, 17.7, 15.7, 15.4, 14.2, 13.2, 8.1; LRMS (ESI) 632.4 (M+Na); HRMS (ESI) calcd for $C_{33}H_{55}NO_8Na$ 632.4138, found 632.4139; $[\alpha]^{20}_D$ +21.6 (c 0.25, $CHCl_3$).

(12S,13S,14S,19R,20R,21R,22S)-21-(tert-Butyldimethylsilanyloxy)-13,19-bis-(4-methoxybenzyloxy)-12,14,20,22-tetramethylhexacosa-10,15,23,25-tetraen-1-(tert-Butyldimethylsilanyl)-ol (45). NaHMDS (1.0 M in THF, 0.45 mL, 0.45 mmol) was slowly added to a solution of the salt 21 (322 mg, 1.1 mmol) in dry THF (0.3 mL) at 0° C. The resulting red solution was stirred at room temperature for 20 min. The mixture was cooled to −78° C. and a solution of the aldehyde 44 (120 mg, 0.42 mmol) in THF (0.1 mL×2) was added dropwise. The mixture was stirred for 20 min at −78° C. and then warmed to room temperature. After 4 h, the mixture was quenched with saturated $NH_4Cl$ (5 mL) and extracted with ethyl ether (3×10 mL). The combined organic layers were dried over anhydrous $MgSO_4$, evaporated and the residue was column chromatographed (hexane/ether 9:1) to yield 163 mg (75%) as a colorless oil: IR ($CHCl_3$) 2928, 2854, 1617, 1517, 1462, 1390, 1249, 1114, 1035, 833, 726 $cm^{-1}$; $^1H$ NMR (300 MHz, $CDCl_3$) δ 7.44–7.38 (m, 2H), 6.90–6.85 (m, 2H), 5.42 (s, 1H), 5.39 (ddd, J=11.7, 10.2, 7.2 Hz, 1H), 5.24 (apparent t, J=10.2 Hz, 1H), 4.08–4.00 (m, 2H), 3.79 (s, 3H), 3.61 (t, J=6.5 Hz, 2H), 3.54 (dd, J=10.5, 1.9 Hz, 1H), 2.69 (dd, J=16.1, 9.2 Hz, 1H), 2.04 (apparent d, J=6.6 Hz, 2H), 1.71–1.68 (m, 1H), 1.54–1.50 (m, 3H), 1.27 (br, 1H), 1.20 (d, J=6.9 Hz, 3H), 0.91 (s, 9H), 0.06 (s, 6H); $^{13}C$ NMR (75 MHz, $CDCl_3$) δ 160.0, 133.3, 132.6, 132.5, 132.1, 130.7, 128.9, 128.7, 127.6, 113.7, 101.8, 83.9, 74.2, 63.6, 55.5, 33.9, 33.3, 30.4, 30.1, 30.0, 29.9, 29.8, 29.7, 28.0, 26.3, 26.2, 18.7, 16.3, 11.5, −4.9; LRMS (API-ES) 541 (M+Na)$^+$, 493, 431, 365, 295, 251; $[\alpha]^{20}_D$ +26.0 (c 0.90, $CHCl_3$).

To a solution of 164 mg (0.32 mmol) of the above acetal in dry $CH_2Cl_2$ (2.0 mL) DIBAL (1.0 M in hexane, 0.95 mL, 0.96 mmol) at 0° C. was added dropwise. After 2 h, the mixture was quenched with saturated sodium potassium tartrate solution (20 mL) followed by vigorously stirring for 4 h. The aqueous phase was extracted with $CH_2Cl_2$ (3×10 mL) and the combined organic layers were washed with brine (10 mL). After drying over $MgSO_4$ and evaporation under vacuum, flash column chromatography (hexane/ether 9:1) provided 115 mg (70%) of alcohol as a colorless oil: IR ($CHCl_3$) 3430, 2928, 2855, 1613, 1514, 1463, 1249, 1098, 1038, 835, 776 $cm^{-1}$; $^1H$ NMR (300 MHz, $CDCl_3$) δ 7.28–7.25 (m, 2H), 6.88–6.85 (m, 2H), 4.59 (d, J=10.8 Hz, 1H), 4.47 (d, J=10.8 Hz, 1H), 3.80 (s, 3H), 3.65–3.50 (m, 4H), 3.36 (dd, J=5.9, 3.9 Hz, 1H), 2.86–2.78 (m, 1H), 2.11–2.01 (m, 2H), 1.98–1.95 (m, 1H), 1.77 (br, 1H), 1.50 (br, 3H), 1.27 (br, 1H), 0.97 (apparent t, J=7.1 Hz, 6H), 0.90 (s, 9H), 0.05 (s, 6H); $^{13}C$ NMR (75 MHz, $CDCl_3$) δ 159.2, 132.8, 131.1, 130.0, 129.5, 113.8, 84.5, 73.7, 66.4, 63.5, 55.3, 37.6, 34.6, 33.0, 29.8, 29.7, 29.64, 29.61, 29.5, 27.7, 26.1, 25.9, 18.8, 18.4, 11.7, −5.1; LRMS (EI) 541 (M+Na)$^+$, 462, 375, 325, 255, 207, 122; HRMS (EI) calcd for $C_{27}H_{47}O_4Si_1$ 463.3254 (M−$^t$Bu)$^+$, found 463.3254; $[\alpha]^{20}_D$ +25.9 (c 0.48, $CHCl_3$).

The above alcohol (94 mg, 0.18 mmol) in $CH_2Cl_2$ (2 mL) was treated with Dess-Martin periodinane (120 mg, 0.27 mmol). After 2 h, the mixture was quenched with saturated $NaHCO_3$ (20 mL). The aqueous layer was extracted with ethyl ether (10 mL×2) and the combined extracts were dried over anhydrous $MgSO_4$. Filtration and concentration followed by short flash column chromatography (hexane/EtOAc 9:1) to remove the residue from Dess-Martin reagent provided 78 mg (83%) of the crude aldehyde as a colorless oil which was used for the next reaction without further purification. NaHMDS (1.0 M in THF, 0.15 mL, 0.15 mmol) was slowly added to a solution of the salt 33 (140 mg, 0.17 mmol) in dry THF (0.15 mL) at 0° C. The resulting red solution was stirred at room temperature for 20 min. The mixture was cooled to −78° C. and a solution of the aldehyde above (69 mg, 0.13 mmol) in THF (0.05 mL×2) was added dropwise. The mixture was stirred for 20 min at −78° C. and then warmed to room temperature. After 4 h at room temperature, the mixture was quenched with saturated $NH_4Cl$ (2 mL) and extracted with ethyl ether (3×5 mL). The combined organic layers were dried over anhydrous $MgSO_4$, evaporated and the residue was purified by column chromatography (hexane/ether 9:1) to yield 45 (111 mg, 65% for 2 steps) as a colorless oil: IR ($CHCl_3$) 2926, 1612, 1513, 1462, 1361, 1250, 1173, 1098, 836, 774 $cm^{-1}$; $^1H$ NMR (300 MHz, $CDCl_3$) δ 7.40–7.33 (m, 4H), 6.99–6.93 (m, 4H), 6.49 (ddd, J=16.8, 10.8, 10.7 Hz, 1H), 6.06 (apparent t, J=11.0 Hz, 1H), 5.59 (d, J=10.5 Hz, 1H), 5.51 (d, J=9.8 Hz, 1H), 5.44–5.31 (m, 3H), 5.23 (d, J=16.8 Hz, 1H), 5.13 (d, J=10.1 Hz, 1H), 4.68–4.57 (m, 3H), 4.42 (d, J=11.3 Hz, 1H), 3.90 (s, 6H), 3.69 (t, J=6.5 Hz, 2H), 3.37–3.36 (m, 1H), 3.14 (q, J=3.7 Hz, 1H), 2.82–2.71 (m, 2H), 2.08–2.00 (m, 4H), 1.78–1.77 (m, 2H), 1.71–1.58 (m, 6H), 1.36 (br, 11H), 1.11 (d, J=6.7 Hz, 6H), 1.04–1.00 (m, 24H), 0.15 (s, 12H); $^{13}C$ NMR (75 MHz, $CDCl_3$) δ 159.3, 159.1, 134.8, 133.8, 132.5, 132.0, 131.5, 131.1, 129.9, 129.7, 129.2, 129.1, 128.6, 117.3, 113.8, 113.7, 88.1, 79.1, 74.8, 71.0, 63.4, 55.4, 40.1, 36.6, 35.8, 35.3, 33.0, 31.5, 30.0, 29.8, 29.7, 29.6, 27.7, 26.4, 26.1, 23.8, 19.0, 18.9, 18.5, 17.6, 11.1, −3.2, −3.3, −5.1; LRMS (EI) 890(M–$^t$Bu)$^+$, 866; HRMS (EI) calcd for $C_{54}H_{89}O_6Si_2$ 865.5258(M–$^t$Bu)$^+$, found 865.5225; $[α]^{20}_D$ +20.5 (c 0.60, $CHCl_3$).

(12S,13S,14S,19R,20R,21R,22S)-21-(tert-Butyldimethylsilanyloxy)-13,19-bis-(4-methoxybenzyloxy)-12,14,20,22-tetramethylhexacosa-10,15,23,25-tetraenoic acid (46). To a solution of TBS ether 45 (93 mg, 0.098 mmol) in THF (2 ml) was slowly added HF-pyridine in pyridine (4 ml, prepared by slow addition of 1.2 ml pyridine to 0.3 ml HF-pyridine complex followed by dilution with 3 ml THF). The mixture was stirred overnight at room temperature and quenched with sat'd $NaHCO_3$ (20 ml). The aqueous layer was separated and extracted with $CH_2Cl_2$ (3×10 ml). The combined organic layer was washed with sat'd $CuSO_4$ (3×20 ml), dried over $MgSO_4$, and concentrated. Flash column chromatography (EtOAc/Hexane 1:4) afforded 64 mg (78%) of the alcohol: IR ($CHCl_3$) 3429, 2928, 2855, 1694, 1612, 1513, 1462, 1250, 1173, 1038, 836, 773 $cm^{-1}$; $^1H$ NMR (300 MHz, $CDCl_3$) δ 7.40–7.33 (m, 4H), 6.99–6.95 (m, 4H), 6.49 (ddd, J=16.8, 10.6, 10.5 Hz, 1H), 6.05 (apparent t, J=11.0 Hz, 1H), 5.58 (d, J=10.9 Hz, 1H), 5.52 (d, J=9.7 Hz, 1H), 5.46–5.34 (m, 2H), 5.23 (d, J=16.8 Hz, 1H), 5.14 (d, J=10.1 Hz, 1H), 4.68–4.57 (m, 3H), 4.45–4.41 (m, 1H), 3.89 (s, 3H), 3.88 (s, 3H), 3.72–3.67 (m, 2H), 3.37–3.36 (m, 2H), 3.14 (q, J=3.6 Hz, 1H), 2.80–2.70 (m, 2H), 2.08–1.99 (m, 4H), 1.78–1.77 (m, 2H), 1.71–1.58 (m, 6H), 1.36 (br, 1H), 1.10 (d, J=6.6 Hz, 6H), 1.02 (d, J=2.6 Hz, 6H), 1.00 (s, 9H), 0.15 (s, 6H); $^{13}C$ NMR (75 MHz, $CDCl_3$) δ 159.3, 159.1, 134.8, 134.8, 133.8, 132.5, 132.1, 131.5, 131.1, 129.9, 129.7, 129.2, 129.1, 128.6, 117.3, 113.8, 113.7, 88.1, 79.0, 76.7, 74.8, 71.0, 63.1, 55.4, 40.1, 36.6, 35.8, 35.4, 32.9, 31.4, 30.0, 29.7, 29.63, 29.56, 27.6, 26.4, 25.9, 23.8, 19.0, 18.9, 18.6, 17.6, 11.1, −3.2, −3.3; LRMS (API-ES) 871 (M+K)$^+$, 445, 364, 338; $[α]^{20}_D$ +27.0 (c 0.24, $CHCl_3$).

The above alcohol (0.213 g, 0.26 mmol) in $CH_2Cl_2$ (10 mL) was treated with Dess-Martin periodinane (160 mg, 0.38 mmol). After 2 h, the mixture was quenched with saturated $NaHCO_3$ (10 mL). The aqueous layer was extracted with ethyl ether (10 mL×2) and the combined extracts were dried over anhydrous $MgSO_4$. Filtration and concentration followed by short flash column chromatography (hexane/EtOAc 8:2) to remove the residue from Dess-Martin reagent provided the aldehyde as a colorless oil which was used for the next reaction without further purification. A solution of the above aldehyde in 1 ml of THF and 0.5 ml of $H_2O$ was treated with 0.74 ml (1.48 mmol) of a 2M solution of 2-methyl-2-butene in THF, 0.11 g (0.77 mmol) of $NaH_2PO_4.H_2O$ and 0.087 g (0.77 mmol) of $NaClO_2$. The reaction mixture was stirred for 2 h, diluted with 20 ml of 1N HCl and extracted with $CH_2Cl_2$ (2×20 ml). The combined organic layers were dried over $MgSO_4$, concentrated in vacuo and the residue was chromatographed on $SiO_2$ (EtOAc/hexane 1:3) to yield 192 mg (89% for 2 steps) of the acid 46 as a viscous oil: IR ($CHCl_3$) 3398, 2929, 2855, 1710, 1612, 1513, 1249, 1040 $cm^{-1}$; $^1H$ NMR (300 MHz, $CDCl_3$) δ 7.46–7.40 (m, 4H), 7.05–6.99 (m, 4H), 6.55 (ddd, J=16.8, 10.6, 10.3 Hz, 1H), 6.12 (apparent t, J=11.0 Hz, 1H), 5.66 (d; J=10.6 Hz, 1H), 5.58 (d, J=11.0 Hz, 1H), 5.52–5.37 (m, 3H), 5.30 (d, J=16.8 Hz, 1H), 5.21 (d, J=10.0 Hz, 1H), 4.74–4.64 (m, 3H), 4.52–4.48 (m, 1H), 3.95 (s, 6H), 3.72 (dd, J=6.2, 3.3 Hz, 1H), 3.43 (dd, J=10.5, 5.9 Hz, 1H), 3.21 (q, J=3.8 Hz, 1H), 2.87–2.77 (m, 3H), 2.49 (t, J=7.4 Hz, 2H), 2.15–2.09 (m, 4H), 1.87–1.70 (m, 5H), 1.43 (br, 1H), 1.17 (d, J=6.8 Hz, 6H), 1.10 (d, J=3.0 Hz, 6H), 1.07 (s, 9H), 0.22 (s, 6H); $^{13}C$ NMR (75 MHz, $CDCl_3$) δ 180.06 159.3, 159.1, 134.8, 133.8, 132.5, 132.1, 131.5, 131.1, 129.8, 129.7, 129.2, 129.1, 128.6, 117.3, 113.8, 113.7, 88.1, 79.0, 76.7, 74.8, 70.9, 55.4, 40.1, 36.6, 35.8, 35.4, 34.2, 31.4, 29.9, 29.5, 29.3, 29.2, 27.6, 26.4, 24.8, 23.8, 19.0, 18.9, 18.6, 17.6, 11.1, −3.2, −3.3; LRMS (API-ES) 846 (M)$^−$, 845 (M−H)$^−$; $[α]^{20}_D$ +24.5 (c 0.38, $CHCl_3$).

(1S,13S,14S,15S,20R,21R,22R)-14,20-Dihydroxy-13,15,21-trimethyl-22-(1-methylpenta-2,4-dienyl)-oxacyclodocosa-11,16-dien-2-one (43). To 46 (146 mg, 0.17 mmol) in THF (2 mL) was added TBAF (1.0 M in THF, 1.72 mL, 1.72 mmol) and the mixture was stirred at room temperature for 48 h. The reaction mixture was diluted with ethyl ether (30 mL) and was washed with water (10 mL). After drying over $MgSO_4$ and evaporation under vacuum, the crude was chromatographed on $SiO_2$ (EtOAc/hexane 1:4) to yield 72 mg (57%) of the acid as a colorless oil: IR ($CHCl_3$) 3467, 2927, 2854, 1710, 1612, 1513, 1460, 1248, 1174, 1036 $cm^{-1}$; $^1H$ NMR (300 MHz, $CDCl_3$) δ 7.39–7.32 (m, 4H), 6.98–6.93 (m, 4H), 6.69 (ddd, J=16.7, 10.7, 10.6 Hz, 1H), 6.18 (apparent t, J=10.9 Hz, 1H), 5.57 (d, J=10.4 Hz, 1H), 5.50 (d, J=10.9 Hz, 1H), 5.46–5.37 (m, 3H), 5.30 (d, J=17.2 Hz, 1H), 5.19 (d, J=10.1 Hz, 1H), 4.69–4.58 (m, 3H), 4.47–4.44 (m, 1H), 3.89 (s, 3H), 3.87 (s, 3H), 3.58–3.56 (m, 2H), 3.16 (q, J=3.5 Hz, 1H), 2.86–2.79 (m, 2H), 2.73–2.70 (m, 1H), 2.42 (t, J=7.3 Hz, 2H), 2.14–2.02 (m, 4H), 1.91–1.89 (m, 1H), 1.81–1.71 (m, 4H), 1.37 (br, 1H), 1.12 (d, J=6.6 Hz, 6H), 1.07 (d, J=6.9 Hz, 3H), 1.01 (d, J=6.6 Hz, 3H); $^{13}C$ NMR (75 MHz, $CDCl_3$) δ 179.6 159.3, 159.1, 135.6, 134.1, 132.4, 132.0, 131.4, 130.4, 130.1, 129.9, 129.6, 129.3, 128.3, 117.9, 113.9, 113.8, 88.1, 83.0, 78.2, 74.9, 71.0, 55.4, 36.7, 36.2, 36.1, 35.4, 34.1, 30.6, 29.9, 29.8, 29.5, 29.3, 29.2, 27.6, 24.8, 23.7, 19.0, 17.7, 17.5, 6.9; LRMS (API-ES) 755.5 (M+Na)$^+$, 866; $[α]^{20}_D$ +31.3 (c 0.64, $CHCl_3$).

A solution of above hydroxy acid (60 mg, 0.081 mmol) in THF (1 ml) was treated at 0° C. with $Et_3N$ (0.068 ml, 0.49 mmol) and 2,4,6-trichlorobenzoyl chloride (0.064 ml, 0.41 mmol). The reaction mixture was stirred at 0° C. for 30 min and then added to a 4-DMAP (41 ml, 0.81 mmol, 0.02 M solution in toluene) at 25° C. and stirred for overnight. The reaction mixture was concentrated, EtOAc (10 mL) was added and the crude was washed with 1N HCl (2×10 ml), dried over $MgSO_4$. Purification by flash column chromatography (EtOAc/hexane 1:9) furnished macrolactone (33 mg, 57%) as a colorless oil: IR (CHCl$_3$) 2926, 2855, 1730, 1612, 1513, 1459, 1248, 1174, 1109 cm$^{-1}$; $^1$H NMR (300 MHz, CDCl$_3$) δ 7.41–7.35 (m, 4H), 6.98–6.94 (m, 4H), 6.55 (ddd, J=16.5, 10.9, 10.6 Hz, 1H), 6.06 (apparent t, J=10.8 Hz, 1H), 5.66 (apparent t, J=10.0 Hz, 1H), 5.48–5.29 (m, 4H), 5.24 (d, J=6.9 Hz, 1H), 5.16 (d, J=10.3 Hz, 1H), 5.01 (dd, J=7.5, 3.5 Hz, 1H), 4.66–4.53 (m, 3H), 4.43 (d, J=10.6 Hz, 1H), 3.89 (s, 3H), 3.85 (s, 3H), 3.20–3.18 (m, 1H), 3.13 (d, J=9.6 Hz, 1H), 2.97–2.89 (m, 1H), 2.76–2.64 (m, 2H), 2.37–2.19 (m, 3H), 2.04–1.98 (m, 4H), 1.78–1.57 (m, 4H), 1.38 (br, 1H), 1.16–1.10 (m, 9H), 0.99 (d, J=6.6 Hz, 3H); $^{13}$C NMR (75 MHz, CDCl$_3$) δ 173.4 159.6, 159.3, 134.4, 133.7, 132.5, 131.8, 131.4, 131.0, 130.2, 130.0, 129.9, 129.4, 129.3, 118.0, 114.2, 114.0, 89.0, 80.6, 76.6, 75.7, 72.0, 55.6, 38.3, 37.5, 36.1, 34.9, 34.7, 31.7, 30.0, 29.6, 29.0, 28.8, 28.7, 27.2, 25.1, 24.5, 20.0, 18.8, 17.4, 10.4; HRMS (EI) calcd for C$_{46}$H$_{66}$O$_6$ 714.4859, found 714.4848; [α]$^{20}_D$ +5.8 (c 0.39, CHCl$_3$).

The above macrolactone (12 mg, 16. μmol) was dissolved in CH$_2$Cl$_2$ (2 ml)—H$_2$O (0.2 ml) and DDQ (12 mg, 53 μmol) was added at 0° C. After 1 h of stirring at 0° C., the reaction mixture was quenched by adding sat'd NaHCO$_3$ (5 ml). The organic phase was washed by sat'd NaHCO$_3$ solution (3×20 ml) and brine, dried over MgSO$_4$ and concentrated. Purification by flash column chromatography (EtOAc/hexane 1:4) furnished macrolactone (6.8 mg, 85%) as a colorless oil: IR (CHCl$_3$) 3434, 2926, 2854, 2359, 2341, 1731, 1651, 1505, 1456, 1377, 1261, 1107, 965, 905, 803 cm$^{-1}$; $^1$H NMR (300 MHz, CDCl$_3$) δ 6.75 (dt, J=16.8, 10.9 Hz, 1H), 6.13 (t, J=10.9 Hz, 1H), 5.60–5.56 (m, 1H), 5.54–5.46 (m, 2H), 5.42–5.30 (m, 3H), 5.25 (d, J=10.1 Hz, 1H), 5.08 (dd, J=8.9, 2.6 Hz, 1H), 3.49 (ddd, J=9.5, 7.4, 2.8 Hz, 1H), 3.37 (dd, J=7.3, 4.3 Hz, 1H), 3.18–3.05 (m, 1H), 2.86–2.74 (m, 2H), 2.43–2.30 (m, 3H), 2.23–2.05 (m, 2H), 1.84 (br, 9H), 1.42 (br, 9H), 1.23 (d, J=6.8 Hz, 3H), 1.19 (d, J=6.9 Hz, 3H), 1.17 (d, J=6.9 Hz, 3H), 1.11 (d, J=6.7 Hz, 3H); $^{13}$C NMR (75 MHz, CDCl$_3$) δ 173.4, 134.6, 132.4, 131.9, 130.5, 129.9, 129.8, 129.1, 117.9, 80.1, 76.4, 72.9, 40.0, 36.9, 35.4, 34.8, 34.6, 34.5, 29.0, 28.6, 28.4, 28.3, 28.1, 26.9, 24.8, 24.2, 18.9, 18.8, 17.1, 9.6; HRMS (EI) calcd for C$_{30}$H$_{49}$O$_3$ 456.3603 (M−OH)$^+$, found 456.3622; [α]$^{20}_D$ +29.0 (c 0.10, CHCl$_3$).

(12S,13S,14S,19R,20R,21R,22S)-12,14,20,22-Tetramethylhexacosa-10,15,23,25-tetraene-1,13,19,21-tetraol (47). The protected alcohol 45 (54 mg, 57 μmol) was dissolved in CH$_2$Cl$_2$ (3 ml)—H$_2$O (0.3 ml) and DDQ (39 mg, 0.17 mmol) was added at 0° C. After 1 h of stirring at 0° C., the reaction mixture was quenched by adding sat'd NaHCO$_3$ (10 ml). The organic phase was washed by sat'd NaHCO$_3$ solution (3×20 ml) and brine, dried over MgSO$_4$ and concentrated. Purification by flash column chromatography (EtOAc/hexane 1:9) furnished the diol (20 mg, 53%) as a colorless oil: IR (CHCl$_3$) 3434, 2958, 2924, 2853, 2362, 1463, 1382, 1246, 1095, 1021, 832, 773 cm$^{-1}$; $^1$H NMR (300 MHz, CDCl$_3$) δ 6.58 (ddd, J=16.7, 10.7, 10.6 Hz, 1H), 6.05 (apparent t, J=11.0 Hz, 1H), 5.62 (t, J=10.3 Hz, 1H), 5.55–5.45 (m, 1H), 5.41–5.27 (m, 3H), 5.21 (d, J=7.6 Hz, 1H), 5.14 (d, J=10.2 Hz, 1H), 3.74–3.72 (m, 1H), 3.65–3.63 (m, 1H), 3.60 (t, J=6.6 Hz, 2H), 3.20 (dd, J=6.1, 5.4 Hz, 1H), 2.96–2.91 (m, 1H), 2.69–2.56 (m, 2H), 2.17–1.95 (m, 4H), 1.60–1.51 (m, 8H), 1.27 (br, 111H), 1.03 (d, J=7.0 Hz, 3H), 0.98 (d, J=6.7 Hz, 3H), 0.97 (d, J=6.7 Hz, 3H), 0.92 (s, 11H), 0.90 (s, 10H), 0.10 (s, 3H), 0.08 (s, 3H), 0.06 (s, 6H); LRMS (API-ES) 729.5 (M+Na)$^+$, 557.5, 413, 243; [α]$^{20}_D$ +48.0 (c 0.025, CHCl$_3$).

To an above solution (20 mg, 28 μmol) in THF (1 mL) was added TBAF (1.0 M in THF, 0.28 mL, 0.28 mmol) and the mixture was stirred at room temperature for 2 h. The reaction mixture was diluted with EtOAc (10 mL) and was washed with water (10 mL). After drying over MgSO$_4$ and evaporation under vacuum, the crude was chromatographed on SiO$_2$ (EtOAc/hexane 1:3) to yield 11 mg (83%) of the alcohol 47 as a colorless oil: IR (CHCl$_3$) 3378, 2925, 2853, 2359, 1651, 1455, 1377, 1056, 971, 903 cm$^{-1}$; $^1$H NMR (300 MHz, CDCl$_3$) δ □□□. ddd, J=16.8, 10.6, 10.5 Hz, 1H), 6.21 (apparent t, J=11.0 Hz, 1H), 5.54–5.46 (m, 1H), 5.43–5.36 (m, 2H), 5.31–5.18 (m, 4H), 3.84 (dd, J=7.3, 4.6 Hz, 1H), 3.65 (apparent t, J=6.6 Hz, 2H), 3.46 (d, J=9.3 Hz, 1H), 3.22 (t, J=5.6 Hz, 1H), 2.86–2.78 (m, 1H), 2.72–2.59 (m, 2H), 2.23–2.02 (m, 4H), 1.71–1.53 (m, 8H), 1.29–1.26 (m, 13H), 1.01–0.91 (m, 12H); $^{13}$C NMR (75 MHz, CDCl$_3$) δ 134.5, 133.8, 132.2, 132.1, 131.9, 131.3, 128.9, 119.1, 80.6, 79.1, 76.1, 63.2, 53.6, 37.6, 36.4, 35.5, 35.1, 34.5, 32.9, 29.8, 29.6, 29.5, 29.4, 27.7, 25.8, 24.2, 18.1, 16.7, 15.3, 4.5; LRMS (API-ES) 517 (M+K)$^+$, 501 (M+Na)$^+$, 479 (M+H)$^+$, 461 (M+H−H$_2$O)$^+$, 443; [α]$^{20}_D$ +43.3 (c 0.18, CHCl$_3$).

(12S,13S,14S,19R,20R,21R,22S)-13,19,21-Trihydroxy-12,14,20,22-tetramethylhexacosa-10,15,23,25-tetraenoic acid methyl ester (48). To an acid 46 (34 mg, 40 μmol) in DMF (3 ml) K$_2$CO$_3$ (0.017 g, 0.12 mmol) and MeI (0.009 ml, 0.06 mmol) were added and stirred for 1 h at room temperature. The reaction mixture was quenched by H$_2$O (1 ml) and extracted with EtOAc (3×5 ml) and washed with brine (5 ml). The organic phase was dried over MgSO$_4$ and evaporated and the residue was used as crude without no further purification (36 mg, 85%): IR (CHCl$_3$) 2928, 2855, 1740, 1613, 1513, 1462, 1301, 1248, 1172, 1038, 836, 773 cm$^{-1}$; $^1$H NMR (300 MHz, CDCl$_3$) δ 7.30–7.24 (m, 4H), 6.90–6.86 (m, 4H), 6.39 (ddd, J=16.9, 10.7, 10.6 Hz, 1H), 5.96 (apparent t, J=11.0 Hz, 1H), 5.50 (d, J=10.3 Hz, 1H), 5.42 (d, J=10.7 Hz, 1H), 5.36–5.21 (m, 3H), 5.14 (d, J=16.8 Hz, 1H), 5.04 (d, J=9.9 Hz, 1H), 4.59–4.47 (m, 3H), 4.39–4.31 (m, 1H), 3.81 (s, 3H), 3.80 (s, 3H), 3.67 (s, 3H), 3.57 (dd, J=5.9, 3.3 Hz, 1H), 3.28–3.26 (m, 1H), 3.05 (q, J=3.7 Hz, 1H), 2.71–2.61 (m, 3H), 2.30 (t, J=7.5 Hz, 2H), 1.99–1.90 (m, 4H), 1.68–1.59 (m, 5H), 1.26 (br, 11H), 1.01 (d, J=6.6 Hz, 6H), 0.91 (br, 15H), 0.05 (s, 6H); $^{13}$C NMR (75 MHz, CDCl$_3$) δ 177.4, 159.3, 159.1, 134.8, 133.8, 132.5, 132.1, 131.5, 131.1, 129.8, 129.7, 129.2, 129.1, 128.6, 117.3, 113.8, 113.7, 88.1, 79.0, 55.4, 51.6, 40.0, 36.5, 35.8, 35.4, 34.2, 31.4, 29.9, 29.8, 29.5, 29.4, 29.3, 27.6, 26.4, 25.1, 23.7, 19.0, 18.6, 17.6, 11.1, −3.2, −3.3; LRMS (API-ES) 883.6 (M+Na)$^+$; [α]$^{20}_D$ +24.7 (c 1.6, CHCl$_3$).

The above ester (41 mg, 47 μmol) was dissolved in CH$_2$Cl$_2$ (2 ml)—H$_2$O (0.4 ml) and DDQ (32 mg, 0.14 mmol) was added at 0° C. and was followed same procedure for 43. Purification by flash column chromatography (EtOAc/Hexane 1:8) furnished the diol (25 mg, 84%) as a colorless oil: IR (CHCl$_3$) 3487, 2924, 2850, 1741, 1602, 1463, 1367, 1249, 838, 761 cm$^{-1}$; $^1$H NMR (300 MHz, CDCl$_3$) δ 6.59 (ddd, J=16.8, 10.8, 10.6 Hz, 1H), 6.04 (apparent t, J=11.0 Hz, 1H), 5.62 (t, J=10.1 Hz, 1H), 5.54–5.46 (m, 1H), 5.41–5.30 (m, 3H), 5.23 (d, J=17.9 Hz, 1H), 5.14 (d, J=10.2 Hz, 1H), 3.75–3.71 (m, 1H), 3.68 (s, 3H), 3.65–3.63 (m, 1H), 3.20 (t, J=5.8 Hz, 1H), 2.96–2.90 (m, 1H), 2.69–2.58 (m, 2H), 2.31 (t, J=7.6 Hz, 2H), 2.17–1.95 (m, 5H), 1.62–1.52 (m, 5H), 1.29 (br, 11H), 1.03 (d, J=6.9 Hz, 3H), 0.98 (d, J=6.7 Hz, 3H), 0.97 (d, J=6.7 Hz, 3H), 0.93 (s, 12H), 0.10 (s, 3H), 0.08 (s, 3H); $^{13}$C NMR (75 MHz, CDCl$_3$) 6174.3, 134.4, 133.7, 132.0, 131.4, 129.4, 128.8, 118.1, 114.3, 79.0, 78.7, 71.2, 51.4, 42.5, 35.8, 35.7, 35.5, 34.4, 34.1, 29.7, 29.3, 29.2, 29.1, 27.6, 26.1, 24.9, 24.3, 19.2, 18.3, 17.9, 15.0, 14.1, 9.5, −3.7, −3.9; LRMS (API-ES) 643.5 (M+Na)⁺, 471.4; [α]²⁰$_D$ +41.6 (c 0.74, CHCl₃).

To an above solution (25 mg, 40 μmol) in THF (2 mL) was added TBAF (1.0 M in THF, 0.12 mL, 0.12 mmol) and the mixture was stirred at room temperature for 2 h. The reaction mixture was diluted with EtOAc (10 mL) and was washed with water (10 mL). After drying over MgSO₄ and evaporation under vacuum, the crude was chromatographed on SiO₂ (EtOAc/hexane 1:3) to yield 8.5 mg (93%) of the ester 48 as a colorless oil: IR (CHCl₃) 3444, 2952, 2925, 2847, 1734, 1451, 1379, 1237, 1197, 1451, 967 cm⁻¹; ¹H NMR (300 MHz, CDCl₃) δ ☐☐☐. ddd, J=16.8, 10.7, 10.6 Hz, 1H), 6.20 (apparent t, J=10.7 Hz, 1H), 5.54–5.46 (m, 1H), 5.43–5.36 (m, 2H), 5.31–5.18 (m, 4H), 3.83 (dd, J=9.0, 3.9 Hz, 1H), 3.67 (s, 3H), 3.46 (dd, J=9.3, 2.0 Hz, 1H), 3.22 (apparent t, J=5.4 Hz, 1H), 2.85–2.78 (m, 1H), 2.72–2.59 (m, 2H), 2.31 (t, J=7.4 Hz, 3H), 2.20–1.95 (m, 3H), 1.74–1.59 (m, 6H), 1.29 (br, 12H), 1.01–0.93 (m, 12H); ¹³C NMR (75 MHz, CDCl₃) δ 174.3, 134.4, 133.7, 131.9, 131.3, 128.7, 118.9, 80.5, 79.1, 76.0, 51.4, 37.7, 36.4, 35.5, 35.1, 34.5, 34.1, 30.0, 29.3, 29.2, 29.1, 27.6, 24.9, 24.2, 22.7, 17.9, 16.7, 15.1, 4.5; LRMS (API-ES) 529 (M+Na)⁺, 507, 489, 471, 453; [α]²⁰$_D$ +27.3 (c 0.43, CHCl₃).

(12S,13S,14S,19R,20R,21R,22S)-13,19,21-Trihydroxy-12,14,20,22-tetramethylhexacosa-10,15,23,25-tetraenoic acid (49). To an above solution 48 (8.0 mg) in THF-H₂O (0.3 ml, 0.1 ml each) was added LiOH·H₂O (1.3 mg) and the solution was warmed to 60° C. After stirring 6 h, 1N HCl (1 ml) was added and reaction mixture was extracted with CH₂Cl₂ (10 ml×2). After drying over MgSO₄ and evaporation under vacuum, the crude was chromatographed on SiO₂ (EtOAc/hexane 1:3) to yield 6.3 mg (81%) of the 49 as a colorless oil: IR (CHCl₃) 3412, 2964, 2921, 2850, 2658, 1710, 1459, 1404, 1268, 971, 903 cm⁻¹; ¹H NMR (300 MHz, CDCl₃) δ 6.64 (ddd, J=16.7, 10.6, 10.0 Hz, 1H), 6.20 (apparent t, J=10.9 Hz, 1H), 5.54–5.46 (m, 1H), 5.42–5.36 (m, 2H), 5.32–5.18 (m, 4H), 3.88–3.84 (m, 1H), 3.48 (d, J=9.2 Hz, 1H), 3.23 (apparent t, J=5.7 Hz, 1H), 2.86–2.76 (m, 1H), 2.69–2.60 (m, 2H), 2.34 (t, J=7.4 Hz, 2H), 2.21–2.04 (m, 5H), 1.70–1.62 (m, 5H), 1.28 (br, 13H), 1.00 (d, J=6.8 Hz, 3H), 0.98 (d, J=6.9 Hz, 3H), 0.94 (d, J=6.7 Hz, 6H); ¹³C NMR (75 MHz, CDCl₃) δ 180.6, 134.4, 133.8, 132.1, 132.0, 132.0, 131.3, 128.8, 119.1, 80.7, 79.2, 76.2, 37.6, 35.5, 34.6, 29.8, 29.7, 29.5, 29.2, 29.1, 29.0, 27.6, 24.8, 24.2, 22.8, 18.1, 16.7, 15.4, 14.2, 4.5; LRMS (API-ES) 515.3 (M+Na)⁺, 493 (M+H)⁺, 475 (M+H-H₂O)⁺, 457 (M+H-2H₂O)⁺, 242; [α]²⁰$_D$ +33.0 (c 0.23, CHCl₃).

(4R,5R)-5-(4-Methoxybenzyloxy)-4-methyl-8-oxooct-2-enoic acid ethyl ester (51). To a cooled (0° C.) stirred suspension of NaH (2.27 g, 11.3 mmol, 60% dispersion in mineral oil) in THF (130 ml) was added dropwise a solution of triethyl phosphonoacetate (2.27 ml, 11.4 mmol) over 10 min period. The mixture was brought to room temperature with a water bath (30 min) and then cooled back to 0° C. and the aldehyde from 50 (3.43 g, 9.0 mmol) in THF (10 ml) was added. The resulting mixture was stirred for 1 h at 0° C. then pH7 phosphate buffer solution (30 ml) and diethyl ether (100 ml) were added. The mixture was allowed to warm to room temperature and the phase was separated. The organic phase was washed with sat'd NH₄Cl solution (30 ml) and brine (30 ml), dried with MgSO₄, filtered and concentrated to give oily crude product. Purification by flash chromatography (EtOAc/hexane 1:4) afforded pure ester (3.82 g, 94%): IR (CHCl₃) 2954, 2928, 2855, 1720, 1513, 1250, 1034, 835 cm⁻¹; ¹H NMR (300 MHz, CDCl₃) δ ☐9–7.25. m, 2H), 7.00 (dd, J=15.7, 7.5 Hz, 1H), 6.91–6.84 (m, 2H), 5.83 (d, J=15.7 Hz, 1H), 4.47 (dd, J=14.6, 11.1 Hz, 2H), 4.19 (q, J=7.1 Hz, 2H), 3.81 (s, 3H), 3.64–3.52 (m, 2H), 3.37–3.33 (m, 1H), 2.64 (dd, J=13.2, 6.5 Hz, 1H), 1.42–1.68 (m, 4H), 1.30 (t, J=7.1 Hz, 3H), 1.09 (d, J=6.7 Hz, 3H), 0.89 (s, 9H), 0.04 (s, 6H); ¹³C NMR (75 MHz, CDCl₃) δ 166.7, 159.3, 151.2, 130.8, 130.4, 129.5, 121.3, 113.9, 81.8, 71.6, 63.1, 60.3, 55.3, 39.8, 28.9, 27.7, 26.1, 18.5, 15.1, 14.4, −5.1; LRMS (API-ES) 489.1 (M+K)⁺, 435, 263, 204; [α]²⁰$_D$ +6.4 (c 0.43, CHCl₃).

To a solution of above TBS ether (0.324 g, 0.72 mmol) in THF (5 ml) was slowly added HF-pyridine in pyridine (8 ml, prepared by slow addition of 2.4 ml pyridine to 0.6 ml HF-pyridine complex followed by dilution with 5 ml THF). The mixture was stirred overnight at room temperature and quenched with sat'd NaHCO₃ (20 ml). The aqueous layer was separated and extracted with CH₂Cl₂ (3×10 ml). The combined organic layer was washed with sat'd CuSO₄ (3×20 ml), dried over MgSO₄, and concentrated. Flash column chromatography (EtOAc/hexane 1:3) afforded 0.203 g (84%) of the alcohol: IR (CHCl₃) 1715, 1612, 1514, 1249, 1180, 1035 cm⁻¹; ¹H NMR (300 MHz, CDCl₃) δ ☐☐7–7.24. m, 2H), 6.98 (dd, J=15.8, 7.5 Hz, 1H), 6.88–6.85 (m, 2H), 5.83 (d, J=15.8 Hz, 1H), 4.47 (dd, J=14.6, 11.1 Hz, 2H), 4.17 (q, J=7.1 Hz, 2H), 3.79 (s, 3H), 3.59–3.56 (m, 2H), 3.37–3.33 (m, 1H), 2.71–2.65 (m, 1H), 2.15 (br, 1H), 1.77–1.40 (m, 4H), 1.28 (t, J=7.1 Hz, 3H), 1.08 (d, J=6.8 Hz, 3H); ¹³C NMR (75 MHz, CDCl₃) δ 166.7, 159.3, 150.8, 130.4, 129.6, 121.4, 113.9, 81.9, 71.7, 62.8, 60.4, 55.3, 39.5, 28.9, 27.8, 15.2, 14.4; LRMS (API-ES) 375.1 (M+K)⁺, 359.1 (M+Na)⁺, 241, 225; [α]²⁰$_D$ +12.0 (c 0.15, CHCl₃).

The above alcohol (0.203 g, 0.61 mmol) in CH₂Cl₂ (6 mL) was treated with Dess-Martin periodinane (0.38 g, 0.90 mmol). After 2 h, the mixture was quenched with saturated NaHCO₃ (10 mL). The aqueous layer was extracted with ethyl ether (10 mL×2) and the combined extracts were dried over anhydrous MgSO₄. Filtration and concentration followed by short flash column chromatography (hexane/EtOAc 3:1) to remove the residue from Dess-Martin reagent provided 0.146 g (72%) of the crude aldehyde 51 as a colorless oil which was used for the next reaction without further purification: ¹H NMR (300 MHz, CDCl₃) δ 9.68 (s, 1H), 7.27–7.21 (m, 2H), 6.99 (dd, J=15.8, 7.3 Hz, 1H), 6.88–6.85 (m, 2H), 5.84 (d, J=15.8 Hz, 1H), 4.48 (d, J=11.0 Hz, 1H), 4.34 (d, J=11.0 Hz, 1H), 4.18 (q, J=7.1 Hz, 2H), 3.79 (s, 3H), 3.41–3.31 (m, 1H), 2.73–2.63 (m, 1H), 2.55–2.40 (m, 1H), 1.90–1.78 (m, 1H), 1.71–1.61 (m, 1H), 1.28 (t, J=7.1 Hz, 3H), 1.27–1.22 (m, 2H), 1.10 (d, J=6.8 Hz, 3H).

(4R,5R,10S,11R,12S,17R,18R,19R,20S)-19-(tert-Butyldimethylsilanyloxy)-5,11,17-tris-(4-methoxybenzyloxy)-4,10,12,18,20-pentamethyltetracosa-2,8,13,21,23-pentaenoic acid ethyl ester (52). NaHMDS (1.0 M in THF, 0.49 mL, 0.49 mmol) was slowly added to a solution of the salt 21 (0.35 g, 0.55 mmol) in dry THF (0.50 mL) at 0° C. The resulting red solution was stirred at room temperature for 20 min. The mixture was cooled to −78° C. and a solution of the aldehyde 51 (146 mg, 0.44 mmol) in THF (0.1 mL) was added dropwise. The mixture was stirred for 20 min at −78° C. and then warmed to room temperature. After 4 h at room temperature, the mixture was quenched with saturated NH₄Cl (2 mL) and extracted with ethyl ether (3×10 mL). The combined organic layers were dried over anhydrous MgSO₄, evaporated and the residue was flash column chromatographed (hexane/EtOAc 9:1) to yield (183 mg, 74%) as a colorless oil: IR (CHCl₃) 2962, 2850, 1716, 1614, 1515, 1249, 1179, 1035 cm⁻¹; ¹H NMR (300 MHz, CDCl₃)

δ 7.56–7.49. m, 2H), 7.41–7.36 (m, 2H), 7.12 (dd, J=15.8, 7.5 Hz, 1H), 7.00–6.97 (m, 4H), 5.95 (d, J=15.8 Hz, 1H), 5.56 (s, 1H), 5.52–5.39 (m, 2H), 4.53 (d, J=3.0 Hz, 2H), 4.33 (q, J=7.1 Hz, 2H), 4.22–4.14 (m, 2H), 3.93 (s, 3H), 3.91 (s, 3H), 3.69 (dd, J=9.6, 1.9 Hz, 1H), 3.46–3.40 (m, 1H), 2.88–2.80 (m, 1H), 2.75–2.67 (m, 1H), 2.36–2.14 (m, 2H), 1.84–1.81 (m, 1H), 1.67–1.55 (m, 2H), 1.43 (t, J=7.1 Hz, 3H), 1.32 (d, J=6.9 Hz, 3H), 1.15 (d, J=6.8 Hz, 3H), 1.03 (d, J=6.8 Hz, 3H); $^{13}$C NMR (75 MHz, CDCl$_3$) δ 166.8, 159.8, 159.3, 151.3, 134.0, 131.8, 130.9, 129.7, 129.5, 127.4, 121.1, 113.9, 113.5, 101.7, 83.9, 81.5, 74.0, 71.7, 60.3, 55.4, 39.7, 33.8, 31.5, 30.1, 23.9, 16.1, 15.0, 14.4, 11.2; LRMS (API-ES) 605.3 (M+K)$^+$, 589.3 (M+Na)$^+$, 567.3 (M+H)$^+$; [α]$^{20}_D$ +30.0 (c 0.01, CHCl$_3$).

Trimethylsilyl chloride (0.24 ml, 1.9 mmol) was added dropwise to a stirred mixture containing above acetal (0.177 g, 0.31 mmol), NaCNBH$_3$ (0.12 g, 1.9 mmol) and 4A molecular sieve in acetonitrile (6 ml) at 0° C. The reaction mixture was stirred for 1 h at 0° C. and filtered through Celite, poured into 1N HCl (10 ml). The aqueous phase was extracted by CH$_2$Cl$_2$ (2×20 ml), dried (MgSO$_4$), filtered and concentrated. The residue was purified by column chromatography on silica gel (EtOAc/hexane 1:3) to yield the alcohol (0.121 g, 68%) as a colorless oil: IR (CHCl$_3$) 3467, 2962, 2931, 2873, 1716, 1612, 1514, 1462, 1248, 1179, 1035 cm$^{-1}$; $^1$H NMR (300 MHz, CDCl$_3$) δ 7.26–7.24 (m, 4H), 6.98 (dd, J=15.7, 7.6 Hz, 1H), 6.91–6.85 (m, 4H), 5.83 (d, J=15.7 Hz, 1H), 5.48 (dd, J=10.8, 9.6 Hz, 1H), 5.41–5.33 (m, 1H), 4.58 (d, J=12.7 Hz, 1H), 4.46 (d, J=11.9 Hz, 3H), 4.19 (q, J=7.2 Hz, 2H), 3.81 (s, 3H), 3.79 (s, 3H), 3.63–3.49 (m, 2H), 3.39–3.29 (m, 2H), 2.78 (dd, J=15.7, 6.8 Hz, 1H), 2.61 (dd, J=13.1, 6.6 Hz, 1H), 2.23–2.17 (m, 1H), 2.09–1.94 (m, 3H), 1.58–1.44 (m, 2H), 1.29 (t, J=7.1 Hz, 3H), 1.06 (d, J=6.8 Hz, 3H), 0.96 (d, J=6.8 Hz, 3H), 0.94 (d, J=6.9 Hz, 3H); $^{13}$C NMR (75 MHz, CDCl$_3$) δ 166.8, 159.2, 151.1, 133.6, 131.1, 130.7, 129.5, 129.1, 128.7, 121.3, 114.0, 113.9, 113.8, 84.3, 81.6, 73.9, 71.6, 66.2, 60.4, 55.4, 39.7, 37.7, 34.8, 31.5, 23.8, 18.7, 15.1, 14.4, 11.5; LRMS (API-ES) 591.2 (M+Na)$^+$, 569.3 (M+H)$^+$, 551; [α]$^{20}_D$ +37.2 (c 0.39, CHCl$_3$).

The same procedure for 45 was used with above alcohol (0.088 g, 0.16 mmol) to yield 64 mg (42% for 2 steps) of the 52 by flash column chromatography (EtOAc/hexane 1:5): IR (CHCl$_3$) 2956, 2932, 2857, 1717, 1612, 1513, 1462, 1301, 1248, 1172, 1037, 835, 773 cm$^{-1}$; $^1$H NMR (300 MHz, CDCl$_3$) δ 7.29–7.23 (m, 6H), 6.98 (dd, J=15.9, 7.6 Hz, 1H), 6.89–6.85 (m, 6H), 6.40 (ddd, J=16.8, 10.6, 10.5 Hz, 1H), 5.96 (apparent t, J=10.9 Hz, 1H), 5.83 (d, J=15.8 Hz, 1H), 5.47 (apparent q, J=10.6 Hz, 1H), 5.36–5.24 (m, 4H), 5.15 (d, J=16.8 Hz, 1H), 5.05 (d, J=9.9 Hz, 1H), 4.58–4.32 (m, 6H), 4.20 (q, J=7.1 Hz, 2H), 3.81 (s, 6H), 3.80 (s, 3H), 3.58–3.57 (m, 1H), 3.30–3.28 (m, 2H), 3.06–3.04 (m, 1H), 2.71–2.65 (m, 2H), 2.62–2.56 (m, 2H), 2.19–2.17 (m, 2H), 2.06–1.88 (m, 4H), 1.76–1.42 (m, 6H), 1.30 (t, J=7.1 Hz, 3H), 1.07–0.97 (m, 12H), 0.92 (s, 9H), 0.06 (s, 6H); $^{13}$C NMR (75 MHz, CDCl$_3$) δ 166.7, 159.2, 159.1, 151.2, 134.8, 133.8, 132.9, 132.5, 131.4, 130.7, 129.5, 129.2, 128.9, 128.6, 121.2, 117.3, 113.8, 113.7, 88.0, 81.6, 78.9, 74.9, 71.6, 70.9, 60.3, 55.4, 40.0, 39.7, 36.5, 35.5, 35.4, 31.4, 26.3, 23.7, 20.8, 19.0, 18.8, 18.6, 17.2, 15.0, 14.4, 11.1, −3.2; LRMS (API-ES) 1034.2 (M+K)$^+$, 1017.6 (M+Na)$^+$, 995.7 (M+H)$^+$; [α]$^{20}_D$ +40.7 (c 4.09, CHCl$_3$).

(6R,7R,12S,13S,14S,19R,20R,21R,22S)-21-(tert-Butyldimethylsilanyloxy)-7,13,19-tris-(4-methoxybenzyloxy)-6,12,14,20,22-pentamethylhexacosa-2,4,10,15,23,25-hexaenoic acid methyl ester (53). To the above ester 52 (64 mg. 64 μmol) in CH$_2$Cl$_2$ (2 ml) was added DIBAL-H (0.16 ml, 0.16 mmol, 1.0 M solution in hexane) at −78° C. dropwise and then warmed up to 0° C. and stirred for 1 h. The reaction mixture was quenched by EtOAc (2 ml) and sat'd sodium potassium tartrate solution (20 mL) followed by vigorously stirring for 4 h. The aqueous phase was extracted with CH$_2$Cl$_2$ (3×10 mL) and the combined organic layers were washed with brine (10 mL). After drying over MgSO$_4$ and evaporation under vacuum, flash column chromatography (hexane/EtOAc 3:1) provided 47 mg of alcohol (77%) as a colorless oil: IR (CHCl$_3$) 3429, 2956, 2857, 2360, 1613, 1513, 1463, 1248, 1037, 835 cm$^{-1}$; $^1$H NMR (300 MHz, CDCl$_3$) δ 7.43–7.37 (m, 6H), 7.03–6.98 (m, 6H), 6.53 (ddd, J=16.8, 10.6, 10.5 Hz, 1H), 6.10 (apparent t, J=11.0 Hz, 1H), 5.81–5.77 (m, 2H), 5.64 (d, J=10.4 Hz, 1H), 5.57 (d, J=10.9 Hz, 1H), 5.18 (d, J=10.1 Hz, 1H), 4.72–4.45 (m, 6H), 4.21 (q, J=3.2 Hz, 2H), 3.94 (s, 6H), 3.93 (s, 31H), 3.71 (dd, J=5.6, 3.0 Hz, 1H), 3.41 (dd, J=10.5, 5.2 Hz, 1H), 3.33 (dd, J=11.1, 6.4 Hz, 1H), 3.19 (dd, J=12.1, 5.9 Hz, 1H), 2.36–2.19 (m, 2H), 2.12–2.02 (m, 3H), 1.87–1.59 (m, 5H), 1.16–1.13 (m, 9H), 1.07–1.05 (m, 6H), 1.04 (s, 9H), 0.19 (s, 6H); $^{13}$C NMR (75 MHz, CDCl$_3$) δ 159.3, 159.2, 159.1, 135.1, 134.8, 133.9, 132.7, 132.6, 131.5, 131.1, 129.7, 129.5, 129.3, 129.2, 128.8, 128.6, 117.4, 114.1, 113.8, 88.1, 82.5, 79.0, 74.9, 71.5, 70.9, 65.2, 64.0, 55.4, 40.0, 39.4, 36.6, 35.6, 35.4, 31.4, 29.9, 26.4, 23.9, 23.7, 19.1, 18.8, 18.7, 17.3, 16.1, 11.1, −3.1, −3.2; LRMS (API-ES) 991.6 (M+K)$^+$, 975.6 (M+Na)$^+$; [α]$^{20}_D$ +38.3 (c 1.05, CHCl$_3$).

The above alcohol (47 mg, 49 μmol) in CH$_2$Cl$_2$ (2 mL) was treated with Dess-Martin periodinane (31 mg, 73 μmol). After 2 h, the mixture was quenched with saturated NaHCO$_3$ (5 mL). The aqueous layer was extracted with ethyl ether (5 mL×2) and the combined extracts were dried over anhydrous MgSO$_4$. Filtration and concentration followed by short flash column chromatography filtration (hexane/EtOAc 3:1) to remove the residue from Dess-Martin reagent provided crude aldehyde as a colorless oil which was used for the next reaction without further purification. To a stirred solution of bis(2,2,2-trifluoroethyl)-(methoxycarbonylmethyl) phosphate (0.013 ml, 59 mmol), 18-crown-6 (0.065 g, 0.25 mmol) in THF (1 ml) cooled to −78° C. was added dropwise potassium bis(trimethylsilyl)amide (0.12 ml, 59 μmol, 0.5M solution in toluene). Thereafter the above aldehyde in THF (1 ml) was added and the solution was stirred for 6 h at −78° C. The reaction mixture was quenched by addition of a sat'd NH$_4$Cl solution (1 ml) and diluted with diethyl ether (10 ml). The layer was separated and organic phase was washed with brine (10 ml) and dried with MgSO$_4$, filtered, and concentrated. The residue was purified by flash chromatography (EtOAc/Hexane 1:5), yielding 40 mg of (E,Z)-doubly unsaturated ester 53 (85% for 2 steps): IR (CHCl$_3$) 2956, 2856, 1717, 1612, 1513, 1462, 1301, 1248, 1173, 1037, 820 cm$^{-1}$; $^1$H NMR (300 MHz, CDCl$_3$) δ 7.53 (dd, J=15.4, 11.3 Hz, 1H), 7.43–7.37 (m, 6H), 7.03–6.98 (m, 6H), 6.68 (dd, J=11.4, 11.3 Hz, 1H), 6.53 (ddd, J=17.0, 10.7, 10.4 Hz, 1H), 6.19 (dd, J=15.4, 7.6 Hz, 1H), 6.09 (apparent t, J=11.2 Hz, 1H), 5.73 (d, J=11.4 Hz, 1H), 5.64 (d, J=10.3 Hz, 1H), 5.56 (d, J=11.0 Hz, 1H), 5.45–5.41 (m, 3H), 5.28 (d, J=15.3 Hz, 1H), 5.18 (d, J=10.0 Hz, 1H), 4.71–4.45 (m, 6H), 3.94 (s, 6H), 3.93 (s, 3H), 3.87 (s, 3H), 3.70 (dd, J=6.1, 3.2 Hz, 1H), 3.44–3.38 (m, 1H), 3.19 (dd, J=6.9, 4.2 Hz, 1H), 2.85–2.77 (m, 3H), 2.34–2.31 (m, 2H), 2.08–2.04 (m, 3H), 1.84–1.55 (m, 5H), 1.20 (d, J=6.8 Hz, 3H), 1.14 (d, J=6.9 Hz, 3H), 1.12 (d, J=8.2 Hz, 3H), 1.07–1.01 (m, 15H), 0.16 (s, 6H); $^{13}$C NMR (75 MHz, CDCl$_3$) δ 166.9, 159.1, 158.9, 147.6, 145.6, 134.7, 133.7, 132.7, 132.4, 131.3, 130.9, 130.8, 129.5, 129.4, 129.0, 128.9, 128.4, 126.4, 117.2, 115.4, 113.7, 87.9, 82.1, 78.8, 74.7, 71.4, 70.8, 55.2, 53.4, 51.1, 40.0, 36.4, 35.4, 35.2, 31.4, 31.3, 29.7, 26.2, 23.7, 23.6, 18.9, 18.6, 18.5, 17.1, 15.4, 10.9, −3.3, −3.4; LRMS (API-ES) 1045.5 (M+K)+, 1029.5 (M+Na)+; [α]$^{20}_D$ +35.3 (c 0.96, CHCl$_3$).

(7R,8R,13S,14S,15S,20R,21R,22R,23S)-8,14,20-Trihydroxy-7,13,15,21-tetramethyl-22-(1-methylpenta-2,4-dienyl)-oxacyclodocosa-3,5,11,16-tetraen-2-one (54). To a stirred solution of protected alcohol 53 (33 mg, 33 μmol) in THF (1 ml) at 0° C. was added 2 ml of 3 N HCl (prepared by adding 25 ml of conc. HCl to 75 ml MeOH). After 6 h, the reaction mixture was diluted with EtOAc (5 ml) and H$_2$O (5 ml) and the organic phase was separated and aqueous phase was extracted with EtOAc (2×5 ml). The combined organic phase was washed with sat'd NaHCO$_3$ (10 ml), dried with MgSO$_4$, concentrated and the residue was purified by flash chromatography (EtOAc/Hexane 1:4) to yield 19 mg (21 mmol) of product (63%): IR (CHCl$_3$) 3491, 2958, 2869, 1716, 1612, 1513, 1456, 1248, 1036 cm$^{-1}$; $^1$H NMR (300 MHz, CDCl$_3$) δ 7.40 (dd, J=15.3, 11.5 Hz, 1H), 7.29–7.22 (m, 6H), 6.92–6.84 (m, 6H), 6.61 (ddd, J=17.7, 10.7, 10.4 Hz, 1H), 6.54 (dd, J=11.5, 11.4 Hz, 1H), 6.10 (apparent t, J=11.0 Hz, 1H), 6.06 (dd, J=15.1, 7.7 Hz, 1H), 5.59 (d, J=11.3 Hz, 1H), 5.49 (d, J=10.4 Hz, 1H), 5.41 (d, J=10.6 Hz, 1H), 5.37–5.30 (m, 3H), 5.21 (d, J=17.0 Hz, 1H), 5.11 (d, J=10.2 Hz, 1H), 4.58–4.34 (m, 6H), 3.81 (s, 3H), 3.80 (s, 3H), 3.79 (s, 3H), 3.73 (s, 3H), 3.47–3.44 (m, 2H), 3.31–3.25 (m 1H), 3.05 (dd, J=7.3, 4.0 Hz, 1H), 2.80–2.69 (m, 2H), 2.66–2.61 (m, 1H), 2.20–2.15 (m, 2H), 2.05–1.91 (m, 3H), 1.85–1.76 (m, 1H), 1.72–1.61 (m, 2H), 1.57–1.47 (m, 2H), 1.09 (d, J=6.8 Hz, 3H), 1.00 (apparent q, J=7.1 Hz, 9H), 0.91 (d, J=6.7 Hz, 3H); $^{13}$C NMR (75 MHz, CDCl$_3$) δ 167.1, 159.3, 159.1, 147.7, 145.7, 136.8, 134.1, 132.8, 132.5, 131.4, 132.8, 132.5, 131.4, 130.9, 130.4, 130.2, 129.6, 129.3, 128.3, 126.6, 118.0, 115.6, 114.0, 113.9, 88.1, 83.1, 82.2, 75.0, 71.5, 71.0, 55.4, 51.2, 40.1, 36.7, 36.3, 35.9, 35.4, 31.6, 30.6, 29.9, 23.9, 23.8, 19.0, 17.6, 15.6; LRMS (API-ES) 915.5 (M+Na)+; [α]$^{20}_D$ +41.1 (c 0.45, CHCl$_3$).

To the stirred solution of above ester (19 mg, 21 μmol) in EtOH (1 ml) was added 1N aqueous KOH solution (0.056 ml) and the mixture was refluxed gently until the ester disappeared (about 6 h) as determined by TLC. The ethanolic solution was concentrated and then diluted with EtOAc (2 ml). After the solution was acidified to pH3 with 1N HCl solution, organic phase was separated and aqueous phase was extracted with EtOAc (2×5 ml). The combined organic phase were dried with MgSO$_4$, concentrated and used as crude without further purification. The same procedure for 43 was used with above acid compound to yield 14 mg (79% for 2 steps) of the macrolactone product by flash column chromatography (EtOAc/hexane 1:3): IR (CHCl$_3$) 2961, 2869, 1708, 1612, 1513, 1462, 1248, 1174, 1076, 1036, 820, 755 cm$^{-1}$; $^1$H NMR (300 MHz, CDCl$_3$) δ 7.41–7.38 (m, 7H), 7.03–6.96 (m, 6H), 6.73–6.57 (m, 1H), 6.67 (apparent t, J=11.2 Hz, 1H), 6.31 (dd, J=15.8, 6.4 Hz, 1H), 6.12 (apparent t, J=11.0 Hz, 1H), 5.69 (d, J=11.1 Hz, 1H), 5.53–5.40 (m, 3H), 5.34–5.19 (m, 4H), 4.70–4.47 (m, 6H), 3.94 (s, 6H), 3.89 (s, 3H), 3.43–3.38 (m, 1H), 3.26–3.16 (m 2H), 3.08–3.03 (m, 1H), 2.87–2.86 (m, 1H), 2.78–2.73 (m, 2H), 2.22–2.19 (m, 2H), 2.07–2.05 (m, 3H), 1.93–1.55 (m, 5H), 1.23 (d, J=6.9 Hz, 3H), 1.19 (d, J=7.2 Hz, 9H), 1.07 (d, J=6.6 Hz, 3H); $^{13}$C NMR (75 MHz, CDCl$_3$) δ 166.3, 159.2, 158.9, 145.4, 143.6, 134.0, 133.0, 132.2, 131.4, 130.8, 130.7, 129.9, 129.53, 128.48, 129.43, 129.4, 129.3, 129.2, 129.0, 126.2, 117.7, 116.9, 113.8, 113.6, 88.0, 83.2, 75.2, 71.7, 71.2, 55.2, 39.4, 38.4, 37.0, 35.6, 34.3, 31.7, 25.4, 24.9, 19.7, 18.6, 17.2, 15.4, 10.0; LRMS (API-ES) 899.5 (M+K)+, 883.5 (M+Na)+; [α]$^{20}_D$ +40.4 (c 0.47, CHCl$_3$).

The same procedure for 43 was used with above lactone (14 mg, 16 μmol) to yield 3.7 mg (46%) of the product 54 by flash column chromatography (EtOAc/hexane 1:2): IR (CHCl$_3$) 3411, 2964, 2926, 2872, 1692, 1637, 1435, 1182, 999, 962 cm$^{-1}$; $^1$H NMR (600 MHz, CDCl$_3$) δ 7.27 (ddt, J=15.7, 11.2, 1.2 Hz, 1H), 6.61 (ddt, J=16.8, 1.1, 10.7 Hz, 1H), 6.53 (apparent t, J=11.3 Hz, 1H), 6.02 (dd, J=15.4, 6.7 Hz, 1H), 6.01 (apparent t, J=11.0 Hz, 1H), 5.56 (d, J=11.5 Hz, 1H), 5.43 (dd, J=10.8, 9.1 Hz, 1H), 5.39–5.36 (m, 1H), 5.33 (apparent t, J=10.6 Hz, 1H), 5.30–5.23 (m, 2H), 5.19 (dt, J=16.8, 0.9 Hz, 1H), 5.10 (d, J=10.1 Hz, 1H), 5.00 (dd, J=7.8, 3.2 Hz, 1H), 3.67 (ddd, J=11.7, 5.8, 4.6 Hz, 1H), 3.41 (ddd, J=8.9, 6.0, 2.4 Hz, 1H), 3.31 (dd, J=7.0, 5.0 Hz, 1H), 3.06–3.00 (m, 1H), 2.68–2.61 (m, 2H), 2.41 (dd, J=13.7, 6.8 Hz, 1H), 2.20–2.11 (m, 2H), 1.82 (dt, J=7.2, 3.2 Hz, 1H), 1.77–1.71 (m, 2H), 1.41–1.35 (m, 2H), 1.32–1.25 (m, 2H), 1.11 (d, J=6.9 Hz, 3H), 1.06 (d, J=6.9 Hz, 3H), 1.03 (d, J=7.0 Hz, 3H), 1.02 (d, J=7.0 Hz, 3H), 1.01 (d, J=6.7 Hz, 3H); $^{13}$C NMR (125 MHz, CDCl$_3$) δ 166.5, 145.8, 143.5, 133.8, 132.3, 132.1, 131.5, 130.0, 129.8, 129.7, 127.0, 117.9, 117.2, 79.3, 73.1, 72.7, 42.8, 40.4, 36.7, 35.0, 34.9, 34.6, 33.7, 24.7, 24.0, 18.7, 17.8, 17.3, 15.3, 9.9; HRMS (EI) calcd for C$_{31}$H$_{47}$O$_4$ 482.3396 (M−OH)+, found 482.3416; [α]$^{20}_D$ +19.2 (c 0.24, CHCl$_3$).

4(R)-Benzyl-3-[4-(2,2-dimethyl-[1,3(S)]dioxolan-4-yl)-3 (S)-hydroxy-2(R)-methyl-butyryl]-oxazolidin-2-one (56). Diisopropylethylamine (13 ml) was added to a solution of propionyloxazolidinone (13.1 g) in anhydrous CH$_2$Cl$_2$ (250 ml) at 0° C., followed by dropwise addition of nBu$_2$BOTf (1.0M in CH$_2$Cl$_2$, 68 ml). The solution was stirred for 1 h at 0° C. A solution of crude aldehyde from 55 (8.9 g) prepared before in anhydrous CH$_2$Cl$_2$ (10 ml) was added slowly at −78° C. After addition, the reaction mixture was warmed to 0° C. and stirred for 1 h then quenched with pH7 phosphate buffer (20 mL). A solution of hydrogen peroxide (30%, 40 mL) in MeOH (80 mL) was added at 0° C. and the mixture was allowed to stir for 1 h. The reaction mixture was extracted with CH$_2$Cl$_2$ (50 mL×2) and dried over MgSO$_4$ followed by flash chromatography (EtOAc/hexane 1:1) to yield 20.7 g of product (98%): IR (CHCl$_3$) 3434, 2956, 2929, 2858, 1724, 1472, 1463, 1257, 1097, 836, 775 cm$^{-1}$; $^1$H NMR (300 MHz, CDCl$_3$) δ 7.33. m, 3H), 7.22 (m 2H), 4.72 (ddd, J=10.5, 6.9, 3.2 Hz, 1 H), 4.35 (m, 1H), 4.23 (m, 3H), 4.12 (dd, J=8.5, 6.5 Hz, 1H), 3.82 (ddd, J=10.2, 7.0, 3.2 Hz, 1H), 3.61 (t, J=7.7 Hz, 1H), 3.25 (dd, J=13.4, 3.3 Hz, 1H), 2.82 (dd, J=13.4, 9.4 Hz, 1H), 1.80 (ddd, J=14.2, 9.7, 4.6 Hz, 1H), 1.68 (ddd, J=10.8, 7.8, 3.0 Hz, 1H), 1.43 (s, 3H), 1.38 (s, 3H), 1.30 (d, J=7.0 Hz, 3H); $^{13}$C NMR (75 MHz, CDCl$_3$) δ 176.9, 152.9, 134.9, 129.3, 128.8, 127.3, 108.6, 73.4, 69.5, 68.5, 66.0, 54.9, 42.4, 37.5, 26.8, 25.6, 14.1, 10.8; [α]$^{20}_D$ −28.1 (c 4.1, CHCl$_3$).

6-(2,2-Dimethyl-[1,3(S)]dioxolan-4-yl)-5(S)-hydroxy-4 (R)-methyl-hex-2-enoic acid ethyl ester (57). To a solution of RED-Al (4.6 ml) in THF (100 ml) at −78° C. was added aldol product 56 (5.39 g) in THF (10 ml) slowly over 10 min. The evolution of gas could be seen as the solution was stirred for 10–15 min at −78° C. The reaction was then warmed to −50° C. and stirred between −55 and −40° C. for 1 h. The reaction was quenched at −50° C. with 100 ml of EtOAc and 10 ml of MeOH and then poured into a mixture of sat'd Rochelle salt (30 ml) and Et$_2$O (60 ml) and stirred at −20° C. for 10 min. The aqueous layer froze as a gel. The ether layer was separated and the aqueous layer rinsed quickly with Et$_2$O (2×30 ml). The combined organic extracts were dried over MgSO₄ and concentrated in vacuo. The crude aldehyde was taken immediately on to the Wittig reaction. To a 200 ml of dry THF was added 3.26 ml of triethylphosphonoacetate, followed by 1.86 g of potassium tert-butoxide. The mixture was stirred at room temperature for 10 min before cooling to −78° C. The crude aldehyde was added in 20 ml of THF and stirred overnight while warming to room temperature. The mixture was poured into 30 ml of brine, extracted with Et₂O (3×40 ml), dried over MgSO₄ and concentrated in vacuo. Flash silica gel chromatography (hexane/EtOAc 3:2) provided 2.02 g (52% for 2 steps) of pure product as an colorless oil: ¹H NMR (300 MHz, CDCl₃) δ 6.88 (dd, J=15.8, 8.0 Hz, 1H), 5.83 (d, J=15.8 Hz, 1H), 4.28 (m, 1H), 4.14 (q, J=7.1 Hz, 1H), 4.03 (dd, J=8.1, 6.0 Hz, 1H), 3.76 (m, 1H), 3.53 (t, J=8.0 Hz, 1H), 2.48 (brs, 1H), 2.41 (m, 1H), 1.72~1.56 (m, 2H), 1.37 (s, 3H), 1.31 (s, 3H), 1.24 (t, J=7.1 Hz, 3H), 1.07 (d, J=6.8 Hz, 3H); ¹³C NMR (75 MHz, CDCl₃) δ 166.4, 150.3, 121.6, 108.6, 73.5, 71.3, 69.3, 60.2, 42.8, 37.2, 25.8, 25.5, 14.5, 14.1.

5(S),7(S),8-Tris-(tert-butyl-dimethyl-silanyloxy)-4(R)-methyl-oct-2-enoic acid ethyl ester (58). To a stirred solution of conjugated ester 57 (1.73 g) in MeOH (20 ml) was added Dowex HCR-W2 ion-exchange resin (2.0 g, activated by aqueous 1N HCl for 24 h then filtered, MeOH as eluent) and stirred for 24 h. The resin was filtered and filtrate was concentrated and dried for 2 h in vacuo. The triol was then used in next step without further purification. To a stirred solution of triol and 2,6-lutidine (3.3 mL, 28.6 mmol) in CH₂Cl₂ (30 mL) at 0° C. was added TBDMSOTf (5.1 mL, 22.2 mmol) and the reaction mixture was stirred for 1 h at 0° C. The reaction mixture was quenched by the addition of water (25 mL). The reaction mixture was extracted by CH₂Cl₂ and dried over MgSO₄ followed by the evaporation of the solvent under reduced pressure. The residue was purified by short column chromatography (hexane/EtOAc 9:1) whereupon the 58 (2.96 g, 81% for 2 steps) was obtained: ¹H NMR (300 MHz, CDCl₃) δ 7.04 (dd, J=15.9, 6.7 Hz, 1H), 5.75 (dd, J=15.9, 1.5 Hz, 1H), 4.16 (dq, J=1.3, 7.1 Hz, 2H), 3.84 (quint, J=3.6 Hz, 1H), 3.71 (m, 1 H), 3.49 (dd, J=10.1, 5.4 Hz, 1H), 3.36 (dd, J=10.1, 5.8 Hz, 1H), 2.48 (m, 1H), 1.59~1.40 (m, 2H), 1.25 (t, J=7.1 Hz, 3H), 0.99 (d, J=6.8 Hz, 3H), 0.85 (m, 27H), 0.056 (s, 3H), 0.049 (s, 3H), 0.04 (s, 3H), 0.02 (s, 3H), 0.01 (s, 6H); ¹³C NMR (75 MHz, CDCl₃) δ 166.6, 151.7, 120.8, 72.8, 71.4, 68.0, 60.0, 42.2, 39.5, 25.9, 25.7, 18.3, 18.1, 14.2, 13.3, −3.0, −3.6, −4.2, −4.5, −5.4.

5(S),7(S)-Bis-(tert-butyl-dimethyl-silanyloxy)-8-hydroxy-4(R)-methyl-oct-2-enoic acid ethyl ester (59) To a solution of TBS ether 58 (7.4 g, 12.9 mmol) in THF (10 ml) was slowly added HF-pyridine in pyridine (40 ml, prepared by slow addition of 12 ml pyridine to 3 ml HF-pyridine complex followed by dilution with 25 ml THF). The mixture was stirred overnight at room temperature and quenched with sat'd NaHCO₃ (100 ml). The aqueous layer was separated and extracted with Et₂O (3×50 ml). The combined organic layers were washed with sat'd CuSO₄ (3×50 ml), dried over MgSO₄, and concentrated. Flash column chromatography (EtOAc/Hexane 1:4) afforded 3.86 g (65%) of the alcohol 59: IR (CHCl₃) 3492, 2956, 2930, 2857, 1722, 1472, 1367, 1256, 1092, 1039, 836, 775 cm⁻¹; ¹H NMR (300 MHz, CDCl₃) δ 7.01. dd, J=15.9, 6.7 Hz, 1H), 5.75 (dd, J=15.9, 1.5 Hz, 1H), 4.15 (dq, J=1.2, 7.2 Hz, 2H), 3.75 (m, 1H), 3.56 (m, 1H), 3.40 (m, 1H), 2.44 (m, 1H), 1.85 (t, J=5.9 Hz, 1H), 1.61 (ddd, J=11.5, 6.4, 5.0 Hz, 1H), 1.50 (ddd, J=13.0, 7.2, 5.8 Hz, 1H), 1.25 (t, J=7.1 Hz, 3H), 0.99 (d, J=6.9 Hz, 3H), 0.86 (s, 9H), 0.85 (s, 9H), 0.60 (s, 6H), 0.34 (s, 3H), 0.02 (s, 3H); ¹³C NMR (75 MHz, CDCl₃) δ 166.5, 151.1, 121.1, 72.8, 71.0, 66.9, 60.1, 41.8, 38.7, 25.8, 18.0, 14.2, 13.3, −4.2, −4.3.

5(S),7(S)-Bis-(tert-butyl-dimethyl-silanyloxy)-4(R)-methyl-8-oxo-oct-2-enoic acid ethyl ester (60). The alcohol 59 (3.86 g, 8.34 mmol) in CH₂Cl₂ (20 mL) was treated with Dess-Martin periodinane (5.3 g, 12.5 mmol). After 1 h, the mixture was quenched with saturated NaHCO₃ (50 mL). The aqueous layer was extracted with ethyl ether (20 mL×2) and the combined extracts were dried over anhydrous MgSO₄. Filtration and concentration followed by short flash column chromatography (hexane/EtOAc 4:1) to remove the residue from Dess-Martin reagent provided the aldehyde as a colorless oil: ¹H NMR (300 MHz, CDCl₃) δ 9.53 (s, 1H), 7.02 dd, J=15.9, 6.6 Hz, 1H), 5.77 (dd, J=15.9, 1.4 Hz, 1H), 4.15 (dq, J=1.0, 7.2 Hz, 2H), 4.07 (ddd, J=6.4, 4.8, 1.4 Hz, 1H), 3.84 (ddd, J=8.6, 6. 8, 4.4 Hz, 1H), 2.52 (m, 1H), 1.66 (m, 2H), 1.25 (t, J=7.1 Hz, 3H), 0.99 (d, J=6.9 Hz, 3H), 0.89 (s, 9H), 0.86 (s, 9H), 0.07 (s, 3H), 0.05 (s, 3H), 0.03 (s, 6H).

5(S),7(S)-Bis-(tert-butyl-dimethyl-silanyloxy)-10(S)-[2-(4-methoxy-benzyl)-5(S)-methyl-[1,3(R)]dioxan-4-yl]-4(R)-methyl-undeca-2,8-dienoic acid ethyl ester (61). NaHMDS (1.0 M in THF, 12.3 mL, 12.3 mmol) was slowly added to a solution of the salt 21 (8.72 g, 13.7 mmol) in dry THF (13.7 mL) at 0° C. The resulting red solution was stirred at room temperature for 20 min. The mixture was cooled to −78° C. and a solution of the aldehyde 60 (5.03 g, 10.9 mmol) in THF (2.0 mL) was added dropwise. The mixture was stirred for 20 min at −78° C. and then warmed to room temperature. After 4 h at room temperature, the mixture was quenched with saturated NH₄Cl (20 mL) and extracted with ethyl ether (3×30 mL). The combined organic layers were dried over anhydrous MgSO₄, evaporated and the residue was flash column chromatographed (hexane/EtOAc 9:1) to yield 61 (5.65 g, 75%) as a colorless oil: IR (CHCl₃) 2957, 2929, 2856, 1720, 1650, 1617, 1518, 1463, 1370, 1250, 1158, 1073, 1032, 836, 774 cm⁻¹; ¹H NMR (300 MHz, CDCl₃) δ 7.34. m, 2H), 6.99 (dd, J=15.8, 6.9 Hz, 1H), 6.82 (m, 2H), 5.72 (dd, J=15.8, 1.5 Hz, 1H), 5.36 (s, 1H), 5.32 (dd, J=11.1, 8.6 Hz, 1H), 5.18 (t, J=10.8 Hz, 1H), 4.55 (ddd, J=12.6, 8.6, 4.1 Hz, 1H), 4.12 (m, 2H), 3.99 (d, J=7.2, 2.1 Hz, 1H), 3.91 (m, 1H), 3.77 (s, 3H), 3.52 (dd, J=9.3, 2.1 Hz, 1H), 2.64 (m, 1H), 2.37 (m, 1H), 1.64 (m, 1H), 1.46 (m, 2H), 1.22 (t, J=7.1 Hz, 3H), 1.15 (d, J=6.9 Hz, 3H), 0.93 (d, J=6.8 Hz, 6H), 0.86 (s, 18H), 0.06 (s, 3H), 0.05 (s, 3H), 0.04 (s, 3H), 0.02 (s, 3H); ¹³C NMR (75 MHz, CDCl₃) δ 166.5, 159.7, 151.9, 133.8, 132.7, 131.3, 120.8, 113.4, 101.7, 83.6, 73.8, 71.9, 66.4, 60.0, 55.1, 43.6, 42.9, 34.2, 29.8, 26.0, 25.9, 18.1, 15.6, 14.2, 13.5, 11.2, −3.0, −3.8, −4.1, −4.5; HRMS (ESI) calcd for C₃₆H₆₆O₇Si₂K 729.3984 (M+K)⁺, found 729.4013; [α]²⁰_D −8.7 (c 6.8, CHCl₃).

5(S),7(S)-Bis-(tert-butyl-dimethyl-silanyloxy)-10(S)-[2-(4-methoxy-benzyl)-5(S)-methyl-[1,3(R)]dioxan-4-yl]-4(R)-methyl-undeca-2,8-dien-1-ol (62). To the stirred solution of ester 61 (3.13 g, 4.53 μmol) in EtOH (20 ml), THF (2 ml) was added 1N aqueous KOH solution (45 ml) and the mixture was refluxed gently until the ester disappeared (about 6 h) as determined by TLC. The ethanolic solution was concentrated and then diluted with EtOAc (50 ml). After the solution was acidified to pH 3 with 1N HCl solution, organic phase was separated and aqueous phase was extracted with EtOAc (2×10 ml). The combined organic phase were dried with MgSO₄, concentrated and used as crude in next step without further purification. The carboxylic acid was treated with NEt₃ (1.5 ml) and ethyl chloroformate (0.67 ml) in dry THF (50 ml) at −10° C. After 15 min, the mixture was warmed to 0° C. and a solution of NaBH$_4$ (1.2 g) in H$_2$O (10 ml) were added. After 4 h, the reaction was quenched by addition of sat'd Rochelle salt solution and Et$_2$O. The layers were separated and the organic layer was washed with H$_2$O, sat'd NaHCO$_3$ solution and brine, dried with MgSO$_4$. Rotary evaporation and silica column chromatography (hexane/EtOAc 4:1) gave product 62 (1.79 g, 61%) as a colorless oil: IR (CHCl$_3$) 3433, 2957, 2929, 2856, 1617, 1518, 1462, 1388, 1250, 1074, 836, 773 cm$^{-1}$; $^1$H NMR (300 MHz, CDCl$_3$) δ 7.38 (m, 2H), 6.84 (m, 2H), 5.63 (dd, J=15.7, 6.2 Hz, 1H), 5.48 (dt, J=16.0, 5.6 Hz, 1H), 5.37 (t, J=10.6 Hz, 1H), 4.59 (m, 1H), 3.99 (m, 2H), 3.93 (m, 1H), 3.87 (m, 2H), 3.77 (s, 3H), 3.49 (dd, J=9.6, 2.0 Hz, 1H), 2.68 (m, 1H), 2.31 (m, 1H), 1.79 (brs, 1H), 1.64 (m, 1H), 1.44 (m, 2H), 1.15 (d, J=6.9 Hz, 3H), 0.92 (d, J=6.9 Hz, 3H), 0.88 (m, 21H), 0.09 (s, 3H), 0.06 (s, 3H), 0.05 (s, 6H); $^{13}$C NMR (75 MHz, CDCl$_3$) δ 159.6, 134.4, 134.3, 132.4, 131.5, 129.1, 127.4, 113.4, 101.5, 83.5, 73.8, 72.8, 66.5, 63.7, 55.2, 42.2, 34.1, 29.8, 26.1, 25.9, 18.14, 18.10, 15.5, 15.2, 11.3, −2.9, −4.1, −4.2; HRMS (ESI) calcd for C$_{36}$H$_{64}$O$_6$Si$_2$Na 671.4139 (M+Na)$^+$, found 671.4141; [α]$^{20}_D$ −14.0 (c 1.5, CHCl$_3$).

4-[4(S),6(S)-Bis-(tert-butyl-dimethyl-silanyloxy)-1 (S),7(R)-dimethyl-10-trityloxy-deca-2,8-dienyl]-2-(4-methoxy-benzyl)-5(S)-methyl-[1,3(R)]dioxane (63). To a solution of alcohol 62 (0.105 g) in pyridine (1.6 ml) was added trityl chloride (0.094 g) and DMAP (0.041 g). The mixture was then refluxed for 18 h, cooled to ambient temperature and added to a solution of sat'd CuSO$_4$ (20 ml). The mixture was extracted with Et$_2$O (2×20 ml), washed sat'd CuSO$_4$ (2×20 ml). The organic layer was separated, dried (MgSO$_4$), filtered, and concentrated in vacuo. Flash column chromatography (EtOAc/hexane 1:9) provided product 63 (0.142 g, 99%) as a pale yellow oil: IR (CHCl$_3$) 2956, 2926, 2855, 1616, 1517, 1462, 1378, 1249, 1073, 835, 773, 705 cm$^{-1}$; $^1$H NMR (300 MHz, CDCl$_3$) δ 7.63 (m, 6H), 7.51 (m, 2H), 7.40 (m, 9H), 6.93 (m, 2H), 5.91 (dd, J=15.7, 6.5 Hz, 1H), 5.66 (dt, J=15.5, 5.2 Hz, 1H), 5.55 (m, 1H), 5.53 (s, 1H), 5.39 (t, J=10.2 Hz, 1H), 4.78 (dt, J=3.1, 8.9 Hz, 1H), 4.10 (m, 3H), 3.80 (s, 3H), 3.70 (m, 3H), 2.85 (m, 1H), 2.45 (m, 1H), 1.78 (m, 1H), 1.65 (m, 2H), 1.31 (d, J=6.9 Hz, 3H), 1.08 (m, 24H), 0.28 (s, 3H), 0.27 (s, 3H), 0.25 (s, 6H); $^{13}$C NMR (75 MHz, CDCl$_3$) δ 159.5, 146.8, 144.3, 135.0, 134.1, 132.4, 131.3, 128.6, 127.8, 127.6, 127.3, 127.1, 126.7, 126.3, 113.6, 101.5, 86.6, 83.4, 73.8, 72.7, 66.6, 65.0, 55.0, 43.5, 42.8, 34.2, 29.9, 26.1, 25.9, 18.1, 15.7, 14.5, 11.3, −2.9, −3.8, −4.1, −4.3; HRMS (ESI) calcd for C$_{55}$H$_{78}$O$_6$Si$_2$K 929.4969 (M+K)$^+$, found 929.5008; [α]$^{20}_D$ −7.3 (c 1.1, CHCl$_3$).

7(S),9(S)-Bis-(tert-butyl-dimethyl-silanyloxy)-3-(4-methoxy-benzyloxy)-2(S)(S),10(R)-trimethyl-13-trityloxy-trideca-5,11-dien-1-ol (64). To the PMB acetal 63 (3.75 g. 4.21 μmol) in CH$_2$Cl$_2$ (20 ml) was added DIBAL-H (21 ml, 21 mmol, 1.0 M solution in hexane) at −78° C. dropwise and then warmed up to 0° C. and stirred for 1 h. The reaction mixture was quenched by EtOAc (10 ml) and sat'd sodium potassium tartrate solution (50 mL) followed by vigorously stirring for 4 h. The aqueous phase was extracted with CH$_2$Cl$_2$ (3×20 mL) and the combined organic layers were washed with brine (30 mL). After drying over MgSO$_4$ and evaporation under vacuum, flash column chromatography (hexane/EtOAc 4:1) provided 64 (2.78 g, 74%) as a colorless oil: IR (CHCl$_3$) 3434, 2956, 2928, 2856, 1612, 1514, 1471, 1249, 1073, 836, 774, 706 cm$^{-1}$; $^1$H NMR (300 MHz, CDCl$_3$) δ 7.48 (m, 6H), 7.29 (m, 1H), 6.84 (m, 2H), 5.84 (dd, J=15.7, 6.2 Hz, 1H), 5.57 (dt, J=15.7, 5.4 Hz, 1H), 5.44 (t, J=8.7 Hz, 2H), 4.63 (m, 1H), 4.53 (d, J=10.9 Hz, 1H), 4.46 (d, J=10.9 Hz, 1H), 3.94 (m, 1H), 3.80 (s, 3H), 3.57 (d, J=4.8 Hz, 2H), 3.48 (m, 1H), 3.31 (m, 2H), 2.80 (m, 1H), 2.42 (m, 1H), 1.84 (m, 2H), 1.55 (ddd, J=14.2, 10.1, 1.9 Hz, 1H), 1.40 (ddd, J=13.9, 8.6, 2.0 Hz, 1H), 1.07 (d, J=6.8 Hz, 3H), 0.97 (m, 12H), 0.93 (s, 9H), 0.87 (d, J=7.0 Hz, 3H), 0.16 (s, 3H), 0.15 (s, 3H), 0.11 (s, 3H), 0.10 (s, 3H); $^{13}$C NMR (75 MHz, CDCl$_3$) δ 159.0, 144.3, 134.0, 133.7, 131.5, 130.9, 129.3, 128.6, 127.9, 127.7, 127.2, 126.8, 126.5, 113.6, 86.7, 84.0, 73.9, 73.0, 66.2, 65.8, 65.1, 55.2, 42.3, 42.2, 38.0, 35.1, 26.0, 25.9, 18.5, 18.2, 18.1, 14.8, 12.0, −2.9, −4.0, −4.19, −4.23; HRMS (ESI) calcd for C$_{55}$H$_{80}$O$_6$Si$_2$K 931.5125 (M+K)$^+$, found 931.5152; [α]$^{20}_D$ −21.4 (c 0.52, CHCl$_3$).

9(S),11(S)-Bis-(tert-butyl-dimethyl-silanyloxy)-5(R)-(4-methoxy-benzyloxy)-4(S),6(S),12(R)-trimethyl-15-trityloxy-pentadeca-2,7,13-trienoic acid ethyl ester (65). The alcohol 64 (2.01 g, 2.25 μmol) in CH$_2$Cl$_2$ (20 mL) was treated with Dess-Martin periodinane (1.43 g, 3.4 μmol). After 1 h, the mixture was quenched with saturated NaHCO$_3$ (20 mL). The aqueous layer was extracted with ethyl ether (25 mL×2) and the combined extracts were dried over anhydrous MgSO$_4$. Filtration and concentration followed by short flash column chromatography filtration (hexane/EtOAc 3:1) to remove the residue from Dess-Martin reagent provided crude aldehyde as a colorless oil which was used for the next reaction without further purification. To a stirred solution of triethyl phosphonoacetate (0.51 ml, 2.60 □mol) in THF (20 ml) cooled to −78° C. was added dropwise potassium tert-butoxide (0.29 g, 2.5 □mol) and stirred for 30 min. Thereafter the above aldehyde in THF (5 ml) was added and the solution was stirred for 1 h at −78° C., then 2 h at 0° C. The reaction mixture was quenched by addition of a sat'd NH$_4$Cl solution (5 ml) and diluted with diethyl ether (20 ml). The layer was separated and organic phase was washed with brine (20 ml) and dried with MgSO$_4$, filtered, and concentrated. The residue was purified by flash chromatography (EtOAc/Hexane 1:9), yielding 2.01 g of unsaturated ester 65 (93% for 2 steps): IR (CHCl$_3$) 2956, 2929, 2856, 1718, 1650, 1612, 1514, 1448, 1250, 1180, 1074, 836, 774, 706 cm$^{-1}$; $^1$H NMR (300 MHz, CDCl$_3$) δ 7.55 (m, 6H), 7.34 (m, 11H), 7.09 (dd, J=15.8, 7.1 Hz, 1H), 6.89 (m, 2H), 5.89 (dd, J=15.7, 5.8 Hz, 1H), 5.78 (d, J=15.8 Hz, 1H), 5.66 (dt, J=6.0, 15.7 Hz, 1H), 5.45 (m, 2H), 4.66 (m, 1H), 4.51 (m, 2H), 4.23 (m, 2H), 3.99 (m, 1H), 3.83 (s, 3H), 3.66 (d, J=5.3 Hz, 2H), 3.29 (t, J=4.7 Hz, 1H), 2.79 (m, 1H), 2.65 (m, 1H), 2.49 (m, 1H), 1.60 (m, 1H), 1.48 (m, 1H), 1.33 (t, J=7.1 Hz, 3H), 1.12 (d, J=6.7 Hz, 3H), 1.11 (d, J=6.6 Hz, 3H), 1.06 (d, J=6.9 Hz, 3H), 1.01 (s, 9H), 1.00 (s, 9H), 0.20 (s, 3H), 0.19 (s, 3H), 0.17 (s, 3H), 0.15 (s, 3H); $^{13}$C NMR (75 MHz, CDCl$_3$) δ 166.5, 158.9, 152.2, 144.3, 134.3, 133.9, 131.0, 130.5, 129.3, 128.6, 127.6, 126.7, 126.4, 120.2, 113.5, 107.0, 86.6, 85.5, 73.4, 72.8, 66.3, 65.1, 59.9, 55.1, 42.2, 38.9, 35.2, 26.0, 25.9, 18.2, 18.1, 14.6, 14.2, 13.7, −3.0, −4.1, −4.2, −4.3; HRMS (ESI) calcd for C$_{59}$H$_{84}$O$_7$Si$_2$K 999.5393 (M+K)$^+$, found 999.5387; [α]$^{20}_D$ +4.6 (c 3.1, CHCl$_3$).

9(S),11(S)-Bis-(tert-butyl-dimethyl-silanyloxy)-5(R)-(4-methoxy-benzyloxy)-4(S),6(S),12(R)-trimethyl-15-trityloxy-pentadeca-7,13-dienoic acid ethyl ester (66). To a stirred solution of unsaturated ester 65 (2.02 g, 2.10 □mol) in MeOH (10 ml), THF (1 ml) at 0° C. was added 0.25 g of NiCl$_2$6H$_2$O then portionwise NaBH$_4$ (0.16 g). After 1 h, the reaction mixture was evaporated and filtered with Celite using Et$_2$O as an eluent (5 ml). The organic phase was concentrated and the residue was purified by flash chromatography (EtOAc/Hexane 1:9) to yield 1.96 g (2.04 μmol) of product 66 (97%) as a colorless oil: IR (CHCl$_3$) 2956, 2929, 2856, 1735, 1613, 1514, 1479, 1448, 1374, 1249, 1174, 1072, 836, 773, 706 cm$^{-1}$; $^1$H NMR (300 MHz, CDCl$_3$) δ 7.53 (m, 6H), 7.33 (m, 1H), 6.84 (m, 2H), 5.81 (dd, J=15.7, 6.1 Hz, 1H), 5.65 (m, 1H), 5.45 (m, 2H), 4.65 (m, 1H), 4.56 (d, J=10.9 Hz, 1H), 4.45 (d, J=10.9 Hz, 1H), 4.14 (q, J=7.1 Hz, 2H), 3.96 (m, 1H), 3.80 (s, 3H), 3.62 (m, 2H), 3.14 (m, 1H), 2.79 (m, 1H), 2.43 (m, 1H), 2.23 (m, 1H), 1.72 (m, 2H), 1.54 (m, 3H), 1.28 (t, J=7.1 Hz, 3H), 1.06 (d, J=6.7 Hz, 3H), 1.01 (d, J=6.9 Hz, 3H), 0.97 (s, 18H), 0.93 (d, J=6.4 Hz, 3H), 0.17 (s, 3H), 0.154 (s, 3H), 0.151 (s, 3H), 0.14 (s, 3H); $^{13}$C NMR (75 MHz, CDCl$_3$) δ 173.6, 158.8, 144.4, 134.6, 133.6, 132.1, 131.2, 129.1, 128.7, 127.7, 126.8, 126.4, 103.4, 86.6, 86.1, 73.8, 72.8, 66.5, 65.2, 60.0, 55.1, 42.8, 42.3, 35.4, 35.1, 32.3, 29.4, 26.0, 25.9, 18.4, 18.1, 14.6, 14.2, 13.9, −2.9, −4.0, −4.1; HRMS (ESI) calcd for C$_{59}$H$_{86}$O$_7$Si$_2$K 1001.5549 (M+K)$^+$, found 1001.5586; [α]$^{20}_D$ −9.8 (c 0.95, CHCl$_3$).

4(R)-Benzyl-3-[9(S),11(S)-bis-(tert-butyl-dimethyl-silanyloxy)-5(R)-(4-methoxy-benzyloxy)-4(R),6(S),12(S)-trimethyl-15-trityloxy-pentadeca-7,13-dienoyl]-oxazolidin-2-one (68). To the stirred solution of ester 66 (1.61 g, 1.670 mol) in EtOH (20 ml), THF (2 ml) was added 1N aqueous KOH solution (17 ml) and the mixture was refluxed gently until the ester disappeared (about 6 h) as determined by TLC. The ethanolic solution was concentrated and then diluted with EtOAc (20 ml). After the solution was acidified to pH3 with 1N HCl solution, organic phase was separated and aqueous phase was extracted with EtOAc (2×10 ml). The combined organic phase were dried with MgSO$_4$, concentrated and used as crude without further purification. A solution of the above acid and Et$_3$N (0.47 ml) in dry THF (17 ml) was cooled to −78° C., treated dropwise with pivaloyl chloride (0.25 ml), stirred in the cold for 1 h, and warmed to 0° C. prior to the addition of the (S)-oxazolidinone 4 (0.30 g) and LiCl (0.21 g). This reaction mixture was stirred overnight at room temperature and diluted with water (10 ml). The separated aqueous phase was extracted with ether (2×10 ml) and the combined organic phase were dried and evaporated and flash column chromatography (EtOAc/hexane 1:4) gave the product 68 (1.52 g, 83%) as a colorless oil: IR (CHCl$_3$) 2956, 2856, 1785, 1701, 1612, 1513, 1449, 1385, 1249, 1074, 910, 836, 774, 734, 706 cm$^{-1}$; $^1$H NMR (300 MHz, CDCl$_3$) δ 7.47 (m, 6H), 7.30 (m, 10H), 7.24 (m, 6H), 6.78 (m, 2H), 5.75 (dd, J=15.7, 6.2 Hz, 1H), 5.54 (dt, J=15.5, 5.5 Hz, 1H), 5.41 (m, 2H), 4.62 (m, 2H), 4.55 (d, J=11.0 Hz, 1H), 4.42 (d, J=11.1 Hz, 1H), 4.16 (m, 2H), 3.91 (m, 1H), 3.75 (s, 3H), 3.56 (m 2H), 3.30 (dd, J=13.4, 3.2 Hz, 1H), 3.15 (dd, J=6.7, 2.2 Hz, 1H), 2.85 (m, 2H), 2.77 (m, 2H), 2.37 (m, 1H), 1.78 (m, 2H), 1.61 (m, 3H), 1.44 (m, 3H), 1.01 (d, J=6.7 Hz, 3H), 0.96 (d, J=7.1 Hz, 3H), 0.92 (m, 21H), 0.12 (s, 3H), 0.10 (s, 3H), 0.09 (s, 6H); $^{13}$C NMR (75 MHz, CDCl$_3$) δ 173.1, 158.7, 153.2, 144.3, 135.3, 134.7, 133.6, 132.5, 131.2, 129.3, 129.1, 128.8, 128.6, 127.6, 127.2, 126.7, 126.2, 113.4, 86.5, 85.8, 73.7, 72.7, 66.4, 65.9, 65.1, 55.0, 42.8, 42.4, 37.8, 35.5, 34.9, 33.5, 28.7, 26.0, 25.9, 18.2, 18.1, 14.5, 13.9, −2.9, −4.0, −4.2; HRMS (ESI) calcd for C$_{67}$H$_{91}$NO$_8$Si$_2$K 1132.5920 (M+K)$^+$, found 1132.5874; [α]$^{20}_D$ +14.8 (c 0.61, CHCl$_3$).

4(R)-Benzyl-3-[9(S),11(S)-bis-(tert-butyl-dimethyl-silanyloxy)-5(R)-(4-methoxy-benzyloxy)-2(S),4(S),6(S),12(R)-tetramethyl-15-trityloxy-pentadeca-7,13-dienoyl]-oxazolidin-2-one (69). NaHMDS (1.0 M in THF, 1.68 ml) was added at −78° C. to a solution of 68 (1.67 g) in THF (4 ml). After 30 min, the reaction mixture was treated with MeI (0.29 ml) at −78° C., stirred for an additional 4 h, quenched with sat'd aqueous NH$_4$Cl, and extracted with ether (2×10 ml). The combined organic layers were dried (MgSO$_4$), concentrated and purified by flash column chromatography (EtOAc/hexane 1:9) to give product 69 (1.05 g, 62%) as a colorless oil: IR (CHCl$_3$) 2957, 2929, 2856, 1783, 1697, 1513, 1449, 1385, 1249, 1074, 836, 774, 705 cm$^{-1}$; $^1$H NMR (300 MHz, CDCl$_3$) δ 7.49 (m, 6H), 7.29 (m, 16H), 6.80 (m, 2H), 5.79 (dd, J=15.6, 6.2 Hz, 1H), 5.56 (dt, J=15.6, 5.7 Hz, 1H), 5.42 (m, 2H), 4.62 (m, 2H), 4.56 (d, J=11.3 Hz, 1H), 4.37 (d, J=11.1 Hz, 1H), 4.17 (m, 1H), 4.05 (m, 1H), 3.92 (m, 1H), 3.77 (s, 3H), 3.58 (d, J=5.2 Hz, 1H), 3.27 (m, 1H), 3.08 (dd, J=6.3, 2.5 Hz, 1H), 2.77 (m, 2H), 2.38 (m, 1H), 1.76 (m, 1H), 1.64 (m, 2H), 1.46 (m, 4H), 1.10 (d, J=6.7 Hz, 3H), 1.00 (d, J=6.3 Hz, 3H), 0.98 (d, J=6.7 Hz, 3H), 0.93 (m, 21H), 0.14 (s, 3H), 0.11 (s, 6H), 0.10 (s, 3H); $^{13}$C NMR (75 MHz, CDCl$_3$) δ 177.3, 158.7, 152.8, 144.4, 135.3, 134.9, 133.6, 132.3, 131.3, 129.4, 128.9, 128.8, 128.6, 127.6, 127.2, 126.7, 126.3, 113.5, 86.6, 86.5, 74.0, 72.8, 66.5, 65.8, 65.2, 43.0, 42.5, 37.8, 35.4, 35.3, 33.0, 26.3, 26.0, 25.9, 18.3, 18.1, 17.4, 14.5, 14.2, −2.9, −4.0, −4.1, −4.2; HRMS (ESI) calcd for C$_{68}$H$_{93}$NO$_8$Si$_2$K 1146.6077 (M+K)$^+$, found 1146.6079; [α]$^{20}_D$ +16.70 (c 1.1, CHCl$_3$).

9(S),11(S)-Bis-(tert-butyl-dimethyl-silanyloxy)-5(R)-(4-methoxy-benzyloxy)-2(S),4(S),6(S),12(R)-tetramethyl-15-trityloxy-pentadeca-7,13-dien-1-ol (70). To a stirred solution of 69 (0.41 g, 0.37 mmol) in THF (1.5 ml) at 0° C. was added MeOH (0.015 ml) and LiBH$_4$ (0.81 ml, 2.0 M soln in THF) dropwise. After stirring 2 h at 0° C., saturated sodium potassium tartrate (10 ml) was added dropwise. The reaction mixture was warmed to room temperature and extracted with CH$_2$Cl$_2$ (10 ml×2). The combined organic layer were washed with brine (10 ml) and dried over anhydrous MgSO$_4$, evaporated and the residue was chromatographed (hexane/EtOAc 4:1) to yield 70 (0.30 g, 87%) as a colorless oil: IR (CHCl$_3$) 3400, 2956, 2928, 2856, 1613, 1514, 1449, 1377, 1249, 1074, 836, 774, 706 cm$^{-1}$; $^1$H NMR (300 MHz, CDCl$_3$) δ 7.48 (m, 6H), 7.29 (m, 11H), 6.84 (m, 2H), 5.78 (dd, J=15.7, 6.0 Hz, 1H), 5.58 (dt, J=15.7, 5.2 Hz, 1H), 5.46 (m, 1H), 5.35 (m, 1H), 4.59 (t, J=9.5, Hz, 1H), 4.48 (q, J=10.9 Hz, 2H), 3.92 (m, 1H), 3.79 (s, 3H), 3.57 (d, J=5.5 Hz, 2H), 3.25 (m 2H), 3.03 (t, J=4.5 Hz, 1H), 2.75 (m 1H), 2.41 (m, 1H), 1.75 (m, 1H), 1.55 (m, 2H), 1.32 (m, 2H), 1.17 (m, 2H), 1.07 (d, J=6.7 Hz, 3H), 0.97 (d, J=6.8 Hz, 3H), 0.94 (s, 9H), 0.91 (m, 12H), 0.72 (d, J=6.6 Hz, 3H), 0.13 (s, 3H), 0.12 (s, 3H), 0.09 (s, 3H), 0.07 (s, 3H); $^{13}$C NMR (75 MHz, CDCl$_3$) δ 158.9, 144.4, 134.4, 133.4, 131.5, 131.4, 129.1, 128.7, 127.7, 126.8, 126.5, 113.6, 87.6, 86.8, 74.1, 73.0, 68.9, 66.5, 65.4, 55.2, 42.7, 42.4, 37.1, 35.0, 33.1, 26.0, 25.9, 18.9, 18.1, 15.8, 14.9, 14.7, −2.8, −4.0, −4.06, −4.10; HRMS (ESI) calcd for C$_{58}$H$_{86}$O$_6$Si$_2$K 973.6301 (M+K)$^+$, found 973.6264; [α]$^{20}_D$ −31.7 (c 1.3, CHCl$_3$).

{3(R)-[2-(4-Methoxy-phenyl)-5(S)-methyl-[1(S),3]dioxan-4-yl]-2-oxo-butyl}-phosphonic acid dimethyl ester (71). n-Butyllithium (4.5 ml, 1.6 M solution in hexane) was added dropwise to a stirred solution of dimethyl methanephosphonate (0.77 ml) in THF (7 ml) at −78° C. After 1 h, a solution of the known weinreb amide (Smith, A. B. et al. *J. Am. Chem. Soc.* 2000, 122, 8654–8664) (0.46 g) in THF (0.5 ml) was added. After 30 min, the reaction was then allowed to warm to 0° C. and quenched by pouring into brine (100 ml) and extracted with EtOAc (2×50 ml). The combined extracts were washed with brine (50 ml), dried over MgSO$_4$ and concentrated in vacuo. Flash silica gel column chromatography (EtOAc) gave the desired product 71 (0.47 g, 85%) as a colorless oil: $^1$H NMR (300 MHz, CDCl$_3$) δ 7.38 (m, 2H), 6.89 (m, 2H), 5.50 (s, 1H), 4.14 (dd, J=11.3, 4.7, Hz, 1H), 4.06 (dd, J=10.0, 2.7 Hz, 1H), 3.80 (s, 3H), 3.77 (s, 3H), 3.74 (s, 3H), 3.59 (t, J=11.1 Hz, 1H), 3.42 (d, J=14.5 Hz, 1H), 3.34 (d, J=14.5 Hz, 1H), 3.20 (d, J=14.5

Hz, 1H), 3.13 (d, J=14.5 Hz, 1H), 3.02 (dq, J=2.8, 7.0 Hz, 1H), 2.06 (m, 1H), 1.26 (d, J=7.0 Hz, 3H), 0.85 (d, J=6.7 Hz, 3H); $^{13}$C NMR (75 MHz, CDCl$_3$) δ 202.5, 159.5, 130.4, 126.9, 113.1, 100.5, 82.1, 72.4, 54.9, 52.6, 48.6, 39.3, 37.6, 30.6, 11.6, 8.7

13(S),15(S)-Bis-(tert-butyl-dimethyl-silanyloxy)-2-[2-(4-methoxy-benzyl)-5(S)-methyl-[1,3(S)]dioxan-4-yl]-9(R)-(4-methoxy-benzyloxy)-6(S),8(S),10(S),16(R)-tetramethyl-19-trityloxy-nonadeca-4,11,17-trien-3-one (72). The alcohol 70 (0.30 g, 0.32 μmol) in CH$_2$Cl$_2$ (10 mL) was treated with Dess-Martin periodinane (0.20 g, 0.47 μmol). After 1 h, the mixture was quenched with saturated NaHCO$_3$ (10 mL). The aqueous layer was extracted with ethyl ether (10 mL×2) and the combined extracts were dried over anhydrous MgSO$_4$. Filtration and concentration followed by short flash column chromatography filtration (hexane/EtOAc 4:1) to remove the residue from Dess-Martin reagent provided crude aldehyde as a colorless oil which was used for the next reaction without further purification. A mixture of ketophosphonate 71 (0.14 g) and Ba(OH)$_2$ (0.043 g, activated by heating to 100° C. for 1~2 h before use) in THF (2 ml) was stirred at room temperature for 30 min. A solution of the above aldehyde in wet THF (2 ml+2×1 ml washings, 40:1 THF/H$_2$O) was then added and stirred for overnight. The reaction mixture was diluted with Et$_2$O (10 ml) and washed with sat'd NaHCO$_3$ (10 ml) and brine (10 ml). The organic solution was dried (MgSO$_4$) and the solvent was evaporated in vacuo. The residue was chromatographed (hexane/EtOAc 4.5:1) to yield 72 (0.34 g, 90%) as a colorless oil: IR (CHCl$_3$) 2957, 2929, 2855, 1615, 1515, 1461, 1249, 1076, 1036, 835, 774 cm$^{-1}$; $^1$H NMR (300 MHz, CDCl$_3$) δ 7.47 (m, 6H), 7.38 (m, 2H), 7.28 (m, 12H), 6.89 (m, 2H), 6.78 (m, 2H), 6.22 (d, J=15.6 Hz, 1H), 5.74 (dd, J=15.7, 6.2 Hz, 1H), 5.57 (m, 1H), 5.45 (s, 1H), 5.38 (m, 2H), 4.60 (m, 1H), 4.52 (d, J=11.0 Hz, 1H), 4.33 (d, J=11.0 Hz, 1H), 4.12 (dd, J=11.2, 4.5 Hz, 1H), 3.90 (m, 2H), 3.81 (s, 3H), 3.76 (s, 3H), 3.55 (m, 3H), 3.04 (m, 1H), 2.92 (m, 1H), 2.75 (m, 1H), 2.36 (m, 1H), 2.25 (quint, J=7.2 Hz, 1H), 2.02 (m, 1H), 1.71 (m, 1H), 1.56~1.33 (m, 4H), 1.25 (d, J=6.9 Hz, 3H), 0.96 (d, J=7.8 Hz, 3H), 0.95 (d, J=7.1 Hz, 3H), 0.92 (m, 21H), 0.85 (d, J=7.3 Hz, 3H); $^{13}$C NMR (75 MHz, CDCl$_3$) δ 201.1, 159.7, 158.8, 153.1, 144.3, 134.6, 133.6, 132.4, 131.2, 131.0, 129.1, 128.6, 127.7, 127.2, 126.8, 126.3, 126.0, 113.5, 113.4, 100.7, 86.6, 85.7, 82.8, 73.8, 72.8, 66.4, 65.2, 55.2, 47.0, 42.8, 42.4, 40.4, 35.5, 34.2, 32.8, 32.2, 26.0, 25.9, 19.2, 18.4, 18.3, 18.1, 14.5, 14.4, 12.4, 10.7, −2.9, −4.0, −4.1; HRMS (ESI) calcd for C$_{74}$H$_{104}$O$_9$Si$_2$K 1231.6856 (M+K)$^+$, found 1231.6850; [α]$^{20}_D$ +22.8 (c 0.88, CHCl$_3$).

13(S),15(S)-Bis-(tert-butyl-dimethyl-silanyloxy)-2-[2-(4-methoxy-benzyl)-5(S)-methyl-[1,3(S)]dioxan-4-yl]-9(R)-(4-methoxy-benzyloxy)-6(S),8(S),10(S),16(R)-tetramethyl-19-trityloxy-nonadeca-11,17-trien-3-one (73). To a stirred solution of unsaturated ketone 72 (0.34 g, 0.29 mmol) in MeOH (4 ml), THF (0.5 ml) at 0° C. was added 0.034 g of NiCl$_2$.6H$_2$O then portionwise NaBH$_4$ (0.022 g). After 1 h, the reaction mixture was evaporated and filtered with Celite using Et$_2$O as a eluent (5 ml). The organic phase was concentrated and the residue was purified by flash chromatography (EtOAc/Hexane 1:4) to yield 0.31 g of product 73 (89%) as a colorless oil: IR (CHCl$_3$) 2956, 2929, 2855, 1713, 1614, 1515, 1461, 1249, 1075, 1036, 835, 774, 706 cm$^{-1}$; $^1$H NMR (300 MHz, CDCl$_3$) δ 7.47 (m, 6H), 7.29 (m, 13H), 6.87 (m, 2H), 6.80 (m, 2H), 5.75 (dd, J=15.7, 6.1 Hz, 1H), 5.55 (m, 1H), 5.45 (s, 1H), 5.38 (m, 2H), 4.60 (m, 1H), 4.48 (d, J=10.9 Hz, 1H), 4.36 (d, J=10.9 Hz, 1H), 4.13 (dd, J=11.2, 4.4 Hz, 1H), 3.93 (m, 1H), 3.79 (s, 3H), 3.76 (s, 3H), 3.55 (m, 2H), 2.99 (m, 2H), 2.70 (m, 2H), 2.45 (t, J=7.0 Hz, 1H), 2.36 (m, 1H), 2.02 (m, 1H), 1.75 (m, 1H), 1.63 (m, 1H), 1.49 (m, 2H), 1.37 (m, 3H), 1.23 (d, J=7.1 Hz, 3H), 1.02 (d, J=6.7 Hz, 3H), 0.95 (d, J=7.0 Hz, 3H), 0.91 (m, 211H), 0.81 (d, J=6.8 Hz, 3H), 0.80 (d, J=6.7 Hz, 3H), 0.12 (s, 3H), 0.09 (s, 6H), 0.08 (s, 3H); $^{13}$C NMR (75 MHz, CDCl$_3$) δ 211.9, 159.8, 158.8, 144.6, 144.4, 134.9, 133.4, 132.3, 131.8, 131.5, 131.0, 129.0, 128.9, 128.7, 127.7, 127.6, 127.2, 126.8, 126.7, 126.3, 113.5, 100.8, 87.4, 86.7, 83.1, 74.0, 72.9, 66.6, 65.2, 55.22, 55.18, 48.3, 43.1, 42.5, 41.6, 38.3, 35.5, 32.7, 31.5, 31.3, 29.6, 26.1, 26.0, 19.0, 18.5, 18.1, 14.5, 14.1, 12.1, 9.7, −2.9, −4.0, −4.1, −4.2; HRMS (ESI) calcd for C$_{74}$H$_{108}$O$_9$Si$_2$K 1233.7013 (M+K)$^+$, found 1233.7036; [α]$^{20}_D$ +3.0 (c 1.7, CHCl$_3$).

13(S),15(S)-Bis-(tert-butyl-dimethyl-silanyloxy)-2-[2-(4-methoxy-benzyl)-5(S)-methyl-[1,3(S)]dioxan-4-yl]-9(R)-(4-methoxy-benzyloxy)-6(S),8(S),10(S),16(R)-tetramethyl-19-trityloxy-nonadeca-11,17-dien-3-ol (74). To a solution of 73 (0.27 g) in MeOH (4 ml) was added NaBH$_4$ (0.013 g) at 0° C. After stirring for 2 h at 0° C., the reaction mixture was evaporated and water (5 ml) was added. The reaction mixture was extracted with ether (2×20 ml) and washed with brine (10 ml), dried over MgSO$_4$ and concentrated in vacuo. The residue was purified by flash chromatography (EtOAc/Hexane 1:4.5) to yield 0.19 g of major product 74 (71%) and 0.069 g (25%) of minor product as a colorless oil: (major isomer) IR (CHCl$_3$) 3533, 2956, 2929, 2855, 1614, 1515, 1462, 1250, 1072, 1036, 835, 774, 734 cm$^{-1}$; $^1$H NMR (300 MHz, CDCl$_3$) δ 7.51 (m, 6H), 7.43 (m, 2H), 7.30 (m, 1H), 6.92 (m, 2H), 6.84 (m, 2H), 5.78 (dd, J=15.6, 6.1 Hz, 1H), 5.61 (m, 1H), 5.57 (s, 1H), 5.43 (m, 2H), 4.65 (m, 1H), 4.55 (d, J=11.0 Hz, 1H), 4.45 (d, J=10.8 Hz, 1H), 4.18 (dd, J=11.2, 4.5 Hz, 1H), 3.95 (m, 1H), 3.84 (s, 3H), 3.82 (m, 1H), 3.79 (s, 3H), 3.74 (m, 1H), 3.59 (m, 2H), 3.06 (m, 2H), 2.78 (m, 1H), 2.41 (m, 1H), 2.19 (m, 1H), 1.81 (m, 2H), 1.56 (dd, J=13.8, 8.1 Hz, 3H), 1.44 (m, 3H), 1.34 (m, 3H), 1.08 (d, J=7.0 Hz, 6H), 0.99 (d, J=7.2 Hz, 3H), 0.96 (m, 18H), 0.90 (d, J=6.7 Hz, 3H), 0.82 (d, J=6.6 Hz, 6H), 0.16 (s, 3H), 0.14 (s, 6H), 0.13 (s, 3H); $^{13}$C NMR (75 MHz, CDCl$_3$) δ 160.0, 158.8, 144.6, 144.4, 134.9, 133.4, 132.3, 131.5, 130.7, 129.0, 128.9, 128.7, 127.7, 127.6, 127.2, 126.8, 126.7, 126.3, 113.7, 113.5, 89.0, 87.5, 86.7, 76.7, 74.0, 73.1, 72.8, 66.6, 65.2, 55.2, 55.1, 43.1, 42.5, 41.8, 37.4, 35.5, 34.4, 32.9, 32.4, 30.4, 30.1, 26.0, 25.9, 19.2, 18.5, 18.1, 14.5, 14.1, 11.9, 5.7, −2.9, −4.0, −4.1, −4.2; HRMS (ESI) calcd for C$_{74}$H$_{108}$O$_9$Si$_2$K 1235.7169 (M+K)$^+$, found 1235.7149; [α]$^{20}_D$ +3.5 (c 0.6, CHCl$_3$).

5,15(S),17(S)-Tris-(tert-butyl-dimethyl-silanyloxy)-11(R)-(4-methoxy-benzyloxy)-3(S)-[2-(4-methoxy-phenyl)-ethoxy]-2(S),4(R),8(S),10(S),12(S),18(R)-hexamethyl-21-trityloxy-heneicosa-13,19-dien-1-ol (76). To a stirred solution of 74 (0.19 g, 0.16 mmol) and 2,6-lutidine (0.037 mL, 0.32 mmol) in CH$_2$Cl$_2$ (16 mL) at 0° C. was added TBDMSOTf (0.055 mL, 0.24 mmol) and the reaction mixture was stirred for 2 h at ambient temperature. The reaction mixture was quenched by the addition of water (5 mL). The reaction mixture was extracted by CH$_2$Cl$_2$ and dried over MgSO$_4$ followed by the evaporation of the solution under reduced pressure. The residue was purified by short column chromatography (hexane/EtOAc 9:1). To a stirred solution of TBS protected acetal (0.20 g, 0.15 mmol) in anhydrous CH$_2$Cl$_2$ (3 mL), under an atmosphere of N$_2$ at 0° C. was added diisobutylaluminum hydride (1.0 M in THF, 1.5 mL, 1.5 mmol) dropwise, and the reaction mixture was stirred for additional 1 h at 0° C. The reaction mixture was quenched by the careful addition of aqueous sat'd potassium sodium tartrate solution (10 mL). The reaction mixture was stirred for 3 h at room temperature. The organic layer was separated, and the water layer was extracted by $CH_2Cl_2$ (20 mL). The combined organic layer was washed with brine and dried over $MgSO_4$ followed by the evaporation of the organic solution under reduced pressure. The residue was purified by column chromatography (EtOAc/hexane 1:4) whereupon the pure compound 76 (0.19 g, 91% for 2 steps) was obtained: IR ($CHCl_3$) 3466, 2955, 2928, 26, 1613, 1514, 1462, 1249, 1072, 1037, 835, 773 cm$^{-1}$; $^1$H NMR (300 MHz, $CDCl_3$) δ 7.52 (m, 6H), 7.30 (m, 13H), 6.94 (m, 2H), 6.85 (m, 2H), 5.79 (dd, J=15.7, 6.3 Hz, 1H), 5.59 (dt, J=15.7, 5.9 Hz, 1H), 5.44 (m, 2H), 4.67 (m, 1H), 4.60 (s, 2H), 4.57 (d, J=11.1 Hz, 1H), 4.44 (d, J=10.9 Hz, 1H), 3.97 (m, 1H), 3.91 (m, 1H), 3.85 (s, 3H), 3.79 (s, 3H), 3.68 (m, 2H), 3.60 (d, J=5.6 Hz, 1H), 3.52 (dd, J=6.6, 4.3 Hz, 1H), 3.07 (m, 2H), 2.97 (brs, 1H), 2.80 (dd, J=14.5, 6.7 Hz, 1H), 2.40 (m, 1H), 2.02 (m, 1H), 1.95 (ddd, J=9.6, 6.9, 4.0 Hz, 1H), 1.81 (m, 1H), 1.71 (m, 1H), 1.56 (m, 3H), 1.47 (m, 3H), 1.33 (m, 2H), 1.19 (d, J=7.0 Hz, 3H), 1.08 (d, J=6.7 Hz, 6H), 1.00 (s, 9H), 0.97 (m, 21H), 0.90 (d, J=6.7 Hz, 3H), 0.82 (d, J=6.4 Hz, 3H), 0.17 (s, 3H), 0.15 (s, 3H), 0.14 (s, 3H), 0.137 (s, 3H), 0.133 (s, 3H), 0.127 (s, 3H); $^{13}$C NMR (75 MHz, $CDCl_3$) δ 159.3, 158.8, 144.6, 144.4, 135.0, 133.6, 132.5, 131.4, 130.6, 129.2, 129.0, 128.9, 128.7, 127.7, 127.6, 126.8, 126.7, 126.3, 113.9, 113.5, 87.4, 86.7, 85.9, 75.3, 74.0, 73.6, 72.8, 66.6, 65.2, 65.1, 55.2, 55.1, 43.2, 42.5, 42.0, 41.5, 37.0, 35.6, 33.4, 32.9, 31.9, 30.1, 26.08, 26.05, 25.98, 19.4, 18.4, 18.1, 15.8, 14.4, 13.9, 10.0, −2.9, −3.7, −3.9, −4.1, −4.2, −4.4; HRMS (ESI) calcd for $C_{80}H_{124}O_9Si_3K$ 1351.8190 (M+K)$^+$, found 1351.8134; $[\alpha]^{20}_D$ −6.1 (c 0.48, $CHCl_3$).

7,17(S),19(S)-Tris-(tert-butyl-dimethyl-silanyloxy)-5(S),13(R)-bis-(4-methoxy-benzyloxy)-4(S),6(S),10(R),12(S),14(S),20(S)-hexamethyl-23-trityloxy-tetracosa-1,3,15,21-tetraen (77). The alcohol 76 (0.17 g, 0.13 μmol) in $CH_2Cl_2$ (5 ml) was treated with Dess-Martin periodinane (0.081 g, 0.2 μmol). After 1 h, the mixture was quenched with saturated $NaHCO_3$ (5 ml). The aqueous layer was extracted with ethyl ether (5 ml×2) and the combined extracts were dried over anhydrous $MgSO_4$. Filtration and concentration followed by short flash column chromatography filtration (hexane/EtOAc 4.5:1) to remove the residue from Dess-Martin reagent provided crude aldehyde as a colorless oil which was used for the next reaction without further purification. To a stirred solution of the above crude aldehyde and 1-bromoallyl trimethylsilane (160 mg, 0.65 mmol) in anhydrous THF (3 ml) under an atmosphere of $N_2$ at room temperature was added $CrCl_2$ (0.13 g, 1.1 mmol) and the mixture was stirred for additional 14 h at ambient temperature. The reaction mixture was diluted with hexane followed by filtration through celite. After the evaporation of the solvent under reduced pressure, the residue was purified by short silica gel column chromatography using EtOAc/hexane (1:9). The foregoing product in THF (3 ml) was cooled to 0° C. and NaH (95% w/w, 64 mg, 2.56 mmol) was added in one portion. The ice bath was removed after 15 min and the mixture was stirred for 2 h at ambient temperature. The reaction mixture was cooled to 0° C., quenched with $H_2O$ (5 ml), extracted with ethyl ether (5 ml×2). The combined organic layer was washed with brine and dried over $MgSO_4$ followed by the evaporation of the organic solution under reduced pressure. The residue was purified by column chromatography (hexane/EtOAc 9:1) whereupon the pure compound 77 (122 mg, 72% for 3 steps) was obtained: IR ($CHCl_3$) 2955, 2928, 2856, 1613, 1514, 1462, 1249, 1072, 1039, 835, 773, 705 cm$^{-1}$; $^1$H NMR (300 MHz, $CDCl_3$) δ 7.47 (m, 6H), 7.28 (m, 13H), 6.89 (m, 2H), 6.79 (m, 2H), 6.61 (ddd, J=16.8, 10.7, 10.6 Hz, 1H), 6.04 (t, J=10.8 Hz, 1H), 5.73 (dd, J=15.6, 6.3 Hz, 1H), 5.61 (t, J=10.4 Hz, 1H), 5.58 (m, 1H), 5.37 (m, 2H), 5.20 (d, J=16.8 Hz, 1H), 5.11 (d, J=10.1 Hz, 1H), 4.54 (m, 3H), 4.50 (d, J=11.0 Hz, 1H), 4.37 (d, J=10.8 Hz, 1H), 3.90 (m, 1H), 3.82 (s, 3H), 3.76 (s, 3H), 3.62 (m, 1H), 3.54 (d, J=5.3 Hz, 1H), 3.35 (dd, J=7.7, 3.1 Hz, 1H), 3.00 (m, 2H), 2.73 (m, 1H), 2.31 (m, 1H), 1.69 (m, 4H), 1.43 (m, 8H), 1.14 (d, J=6.8 Hz, 3H), 1.00 (d, J=7.1 Hz, 3H), 0.96 (s, 9H), 0.92 (s, 3H), 0.91 (s, 3H), 0.89 (m, 6H), 0.83 (d, J=6.6 Hz, 3H), 0.72 (d, J=6.4 Hz, 3H), 0.11 (s, 3H), 0.10 (s, 3H), 0.08 (s, 3H), 0.07 (s, 6H); $^{13}$C NMR (75 MHz, $CDCl_3$) δ 159.0, 158.8, 144.6, 144.4, 135.0, 134.6, 133.7, 133.4, 132.6, 132.4, 131.5, 131.4, 129.1, 129.0, 128.98, 128.94, 128.7, 127.7, 126.8, 126.3, 117.2, 113.7, 113.5, 87.3, 86.7, 84.3, 75.0, 74.0, 72.9, 72.8, 66.6, 65.2, 55.2, 55.1, 43.2, 42.6, 42.0, 40.6, 35.7, 35.3, 33.2, 32.8, 32.3, 30.1, 26.1, 26.0, 19.4, 18.8, 18.3, 18.2, 18.1, 14.4, 14.0, 13.9, −2.9, −3.6, −3.9, −4.1, −4.2, −4.4; $[\alpha]^{20}_D$ +2.5 (c 1.2, $CHCl_3$).

7(S),9(S),19-Tris-(tert-butyl-dimethyl-silanyloxy)-13(R),21(S)-bis-(4-methoxy-benzyloxy)-6(R),12(S),14(S),16(S),20(R),22(S)-hexamethyl-hexacosa-2,4,10,23,25-pentaenoic acid methyl ester (79). A solution of 77 (18.6 mg) in $CH_2Cl_2$ (0.2 ml) was cooled to −78° C. and B-chlorocatecholborane (0.25 M in $CH_2Cl_2$, 0.17 ml) was added. The solution was stirred at −78° C. for 1 h followed by treatment with sat'd aqueous $NaHCO_3$ (1 ml). The resulting reaction mixture was then diluted with $CH_2Cl_2$ (10 ml) and $H_2O$ (3 ml). The layers were separated and the aqueous layer was further extracted with $CH_2Cl_2$ (2×5 ml). The combined organic layers were washed with brine, dried over $MgSO_4$ and concentrated under vacuum. The residue was purified by flash chromatography (hexane/EtOAc 4;1) on silica gel to yield 78 (9.4 mg) as a colorless oil. The alcohol 78 (20 mg, 0.018 μmol) in $CH_2Cl_2$ (0.5 mL) was treated with Dess-Martin periodinane (12 mg, 0.028 mmol). After 1 h, the mixture was quenched with saturated $NaHCO_3$ (1 ml). The aqueous layer was extracted with ethyl ether (3 ml×2) and the combined extracts were dried over anhydrous $MgSO_4$. Filtration and concentration followed by short flash column chromatography filtration (hexane/EtOAc 4.5:1) to remove the residue from Dess-Martin reagent provided crude aldehyde as a colorless oil which was used for the next reaction without further purification. To a stirred solution of bis(2,2,2-trifluoroethyl)-(methoxycarbonylmethyl) phosphate (0.005 ml, 0.024 □mol), 18-crown-6 (0.024 g, 0.09 mmol) in THF (0.5 ml) cooled to −78° C. was added dropwise potassium bis(trimethylsilyl)amide (0.044 ml, 0.022 □mol, 0.5M solution in toluene). Thereafter the above aldehyde in THF (0.5 ml) was added and the solution was stirred for 6 h at −78° C. The reaction mixture was quenched by addition of a sat'd $NH_4Cl$ solution (1 ml) and diluted with diethyl ether (5 ml). The layers were separated and organic phase was washed with brine (5 ml) and dried with $MgSO_4$, filtered, and concentrated. The residue was purified by flash chromatography (EtOAc/Hexane 1:9) yielding 17 mg of (E,Z)-doubly unsaturated ester 79 (82% for 2 steps): IR ($CHCl_3$) 2956, 2929, 2856, 1720, 1613, 1514, 1462, 1249, 1173, 1075, 836, 773 cm$^{-1}$; $^1$H NMR (300 MHz, $CDCl_3$) δ 7.22 (m, 5H), 6.82 (m, 4H), 6.55 (ddd, J=16.8, 10.8, 10.8 Hz, 1H), 6.38 (t, J=11.4 Hz, 1H), 6.05 (dd, J=15.4, 6.2 Hz, 1H), 5.98 (t, J=11.0 Hz, 1H), 5.55 (t, J=10.5 Hz, 1H), 5.48 (d, J=11.5 Hz, 1H), 5.31 (m, 2H), 5.14 (d, J=16.8 Hz, 1H), 5.05 (d, J=10.1 Hz, 1H), 4.54 (m, 1H), 4.49 (m, 3H), 4.31 (d, J=10.9 Hz, 1H), 3.87 (m, 1H), 3.77 (s, 3H), 3.75 (s, 3H), 3.68 (s, 3H), 3.57 (m, 1H), 3.29 (dd, J=7.7, 3.1 Hz, 1H), 2.94 (m, 2H), 2.68 (m, 1H), 2.48 (m, 1H), 1.65 (m, 3H), 1.43–1.28 (m, 6H), 1.20 (m, 2H), 1.08 (d, J=6.8 Hz, 3H), 0.96 (d, J=6.9 Hz, 3H), 0.94 (d, J=6.1 Hz, 3H), 0.90 (s, 9H), 0.86 (m, 21H), 0.81 (d, J=6.7 Hz, 3H), 0.71 (d, J=6.4 Hz, 3H), 0.06 (s, 3H), 0.05 (s, 3H), 0.04 (s, 3H), 0.02 (s, 6H); $^{13}$C NMR (75 MHz, CDCl$_3$) δ 166.9, 159.0, 158.8, 147.7, 146.9, 145.8, 134.6, 133.5, 132.7, 132.5, 131.6, 131.4, 129.1, 128.9, 128.8, 128.7, 128.4, 127.9, 127.7, 127.3, 126.4, 117.2, 114.9, 113.7, 113.6, 87.6, 84.3, 77.2, 74.9, 74.2, 72.9, 72.7, 66.4, 55.3, 55.2, 50.9, 43.1, 42.5, 42.1, 40.6, 35.8, 35.3, 33.6, 33.2, 32.9, 18.14, 18.11, 14.6, 13.9, 9.3, −2.9, −3.6, −3.9, −4.1, −4.4; HRMS (ESI) calcd for C$_{67}$H$_{114}$O$_9$Si$_3$K 1185.7408 (M+K)$^+$, found 1185.7464; [α]$^{20}_D$ −12.6 (c 0.75, CHCl$_3$).

8(S),10(S),14(R),20-Tetrahydroxy-7(S),13(S),15(S),17(R),21(S)-pentamethyl-22(S)-(1 (S)-methyl-penta-2,4-dienyl)-oxa-cyclodocosa-3,5,11-trien-2-one (83). The ester 79 (8.5 mg, 7.4 μmol) was dissolved in CH$_2$Cl$_2$ (1 ml)-H$_2$O (0.05 ml) and DDQ (5.0 mg, 22 μmol) was added at 0° C. After 1 h of stirring at 0° C., the reaction mixture was quenched by adding sat'd NaHCO$_3$ (5 ml). The organic phase was washed by sat'd NaHCO$_3$ solution (3×10 ml) and brine, dried over MgSO$_4$ and concentrated. Purification by flash column chromatography (EtOAc/hexane 1:4.5) furnished diol (6.4 mg, 95%) as a colorless oil. To the stirred solution of the above diol (6.4 mg, 7.06 μmol) in EtOH (0.7 ml) was added 1N aqueous KOH solution (0.07 ml) and the mixture was refluxed gently until the ester disappeared (about 7 h) as determined by TLC. The ethanolic solution was concentrated and then diluted with ether (4 ml). After the solution was acidified to pH3 with 1N HCl solution, organic phase was separated and aqueous phase was extracted with EtOAc (2×2 ml). The combined organic phase were dried with MgSO$_4$, concentrated and used as crude without further purification. A solution of above dihydroxy acid in THF (0.5 ml) was treated at 0° C. with Et$_3$N (0.006 ml, 43 μmol) and 2,4,6-trichlorobenzoyl chloride (0.0055 ml, 35 μmol). The reaction mixture was stirred at 0° C. for 30 min and then added to a 4-DMAP (3.5 ml, 0.02 M solution in toluene) at 25° C. and stirred for overnight. The reaction mixture was concentrated, EtOAc (5 mL) was added and the crude was washed with 1N HCl (2×5 ml), dried over MgSO$_4$. Purification by flash column chromatography (EtOAc/hexane 1:9) furnished macrolactone (3.0 mg, 49% for 2 steps) as a colorless oil. To a stirred solution of the above macrolactone (2.7 mg, 3.1 μmol) in MeOH (0.5 ml) at 0° C. was added 0.5 ml of 3 N HCl (prepared by adding 25 ml of conc. HCl to 75 ml MeOH). After 2 h at room temperature, the reaction mixture was diluted with EtOAc (2 ml) and H$_2$O (2 ml) and the organic phase was separated and aqueous phase was extracted with EtOAc (2×2 ml). The combined organic phase was washed with sat'd NaHCO$_3$ (5 ml), dried with MgSO$_4$, concentrated and the residue was purified by flash chromatography (EtOAc/Hexane 1:1) to yield 83 (1.2 mg, 73%): IR (CHCl$_3$) 3400, 2960, 2926, 2854, 1693, 1635, 1599, 1461, 1378, 1277, 1183, 1075, 964 cm$^{-1}$; $^1$H NMR (500 MHz, CD$_3$OD) δ 7.34 (dd, J=15.3, 11.3 Hz, 1H), 6.64 (ddd, J=16.9, 10.5, 10.3 Hz, 1H), 6.57 (t, J=11.4 Hz, 1H), 5.96 (t, J=10.9 Hz, 1H), 5.95 (dd, J=15.3, 8.3 Hz, 1H), 5.48 (t, J=10.0 Hz, 1H), 5.47 (d, J=11.6 Hz, 1H), 5.38 (dd, J=11.1, 8.9 Hz, 1H), 5.27 (t, J=10.5 Hz, 1H), 5.16 (d, J=16.9 Hz, 1H), 5.08 (d, J=10.2 Hz, 1H), 5.02 (dd, J=8.0, 3.5 Hz, 1H), 4.65 (dt, J=3.1, 8.4 Hz, 1H), 3.72 (ddd, J=9.0, 6.3, 2.8 Hz, 1H), 3.25 (ddd, J=10.2, 7.4, 2.8 Hz, 1H), 3.16 (dd, J=5.4, 3.4 Hz, 1H), 3.06 (dd, J=16.3, 8.3 Hz, 1H), 2.72 (ddd, J=10.2, 6.7, 6.6 Hz, 1H), 2.36 (dd, J=14.7, 7.2 Hz, 1H), 1.86 (dt, J=6.6, 3.1 Hz, 1H), 1.81 (ddd, J=10.5, 6.8, 3.7 Hz, 1H), 1.69 (m, 2H), 1.58 (m, 1H), 1.47 (ddd, J=13.8, 9.5, 3.5 Hz, 1H), 1.37 (m, 1H), 1.25 (m, 1H), 1.17 (m, 1H), 1.13 (m, 1H), 1.09 (d, J=6.8 Hz, 3H), 1.03 (d, J=6.9 Hz, 6H), 0.98 (d, J=6.7 Hz, 3H), 0.87 (d, J=6.7 Hz, 3H), 0.76 (d, J=6.4 Hz, 3H); $^{13}$C NMR (125 MHz, CDCl$_3$) δ 166.3, 147.2, 145.3, 134.39, 134.37, 132.5, 132.3, 130.0, 127.6, 117.8, 116.5, 80.0, 75.4, 74.9, 72.0, 66.2, 43.2, 41.5, 40.7, 40.6, 35.6, 35.4, 35.0, 33.0, 31.2, 30.4, 20.4, 18.1, 17.3, 16.2, 12.4, 10.2; LRMS (ESI) calcd for C$_{32}$H$_{52}$O$_6$ 571.3 (M+K)$^+$, found 571.3; [α]$^{20}_D$ +32.6 (c 0.10, MeOH).

(Z)-(4R,5S,6S,7S)-tert-butyl-{6-(3, 4-dimethoxybenzyloxy)-4-[4-(4, 4, 5, 5, 6, 6, 7, 7, 8, 8, 9, 9, 10, 10, 11, 11, 11-heptadecafluoroundecyloxy)-benzyloxy]-5, 7-dimethylundec-8-enyloxy}dimethylsilane (85). A mixture solution of 84 (0.40 g, 0.39 mmol) in MeOH (8.0 ml) and CH$_2$Cl$_2$ (5.3 ml) was cooled to −78° C. and treated with a stream of ozone for 10 min. The reaction mixture was treated with dimethysulfide (2.0 ml) and pyridine (32 μl) and stirred for 3.0 h at ambient temperature. The reaction mixture was concentrated and diluted with Et$_2$O (80 ml). The organic layer was washed with saturated aqueous CuSO$_4$ (2×20 ml) and brine (20 ml), dried over MgSO$_4$, filtered and concentrated. At ambient temperature, a suspension of propyltriphenylphosphonium bromide (0.383 g 98% purity, 0.97 mmol) in THF (15.0 ml) was added NaN(TMS)$_2$ (1.0 M solution in THF, 0.98 ml) at ambient temperature. After stirring 1 h, this solution was cooled to −78° C. Then the crude residue in THF (2.0 ml) was introduced, and the resultant mixture was stirred for 3 h at −78° C. and was allowed to warm to ambient temperature for 12 h. The reaction mixture was quenched with saturated aqueous NaHCO$_3$ (20 ml) and extracted with Et$_2$O (2×40 ml). The combined extracts were washed with brine (20 ml), dried over MgSO$_4$, filtered and concentrated. Flash chromatography (10% AcOEt/hexane) afforded 85 (0.08 g, 26% yield): $^1$H-NMR (500 MHz, CDCl$_3$) δ 0.06 (s, 6H), 0.91 (s, 9H), 0.93 (t, J=7.6 Hz, 3H), 1.00 (d, J=6.8 Hz, 3H), 1.06 (d, J=6.8 Hz, 3H), 1.47 (m, 2H), 1.59 (m, 1H), 1.66 (m, 1 H), 1.83 (m, 1H), 1.94 (m, 2H), 2.11 (m, 2H), 2.33 (m, 2H), 2.66 (m, 1H), 3.35 (m, 1H), 3.60 (t, J=6.3 Hz, 2H), 3.88 (s, 6H), 4.04 (t, J=5.8 Hz, 2H), 4.38 (d, J=11.3 Hz, 1H), 4.48 (d, J=10.9 Hz, 1H), 4.53 (d, J=10.9 Hz, 1H), 4.59 (d, J=11.3 Hz, 1H), 5.35 (dt, J=7.0, 10.3 Hz, 1H), 5.42 (dd, J=10.3, 10.1 Hz, 1H), 6.82–7.02 (m, 4H), 7.21–7.28 (m, 2H); $^{13}$C NMR (125 MHz, CDCl$_3$) δ −5.2, 10.3, 14.5, 18.4, 18.9, 20.6, 20.9, 25.9, 26.9, 28.0 (t, J=22.5 Hz), 29.0, 34.9, 39.3, 55.8, 55.9, 63.2, 66.4, 70.8, 74.7, 79.4, 84.2, 110.5, 110.9, 114.3, 119.9, 106–122 (m), 129.6, 131.1, 131.3, 131.5, 131.6, 132.0, 148.4, 148.9, 158.2; IR (thin film/NaCl) cm$^{-1}$ 2933, 2858, 1729, 1612, 1515, 1465, 1242, 1153, 1032, 834; MS (EI) m/z 1060 (M$^+$), 1035, 1003, 909, 567; [α]$^{20}_D$ +2.37° (c 0.590, CHCl$_3$).

(4R,5S,6S,7S)-tert-butyl-{6-(3, 4-dimethoxybenzyloxy)-4-[4-(4, 4, 5, 5, 6, 6, 7, 7, 8, 8, 9, 9, 10, 10, 11, 11, 12, 12, 13, 13, 13-heneicosafluorotridecyloxy)benzyloxy]-5, 7-dimethyl-non-8-enyloxy}dimethylsilane (84). A solution of the alcohol (0.26 g, 0.57 mmol) and 1-bromomethyl-4-(4,4,5,5,6,6,7,7,8,8,9,9,10,10,11,11,12,12,13,13,13-heneicosafluorotridecyloxy)benzene (0.50 g, 0.66 mmol) in THF (6.0 ml) was cooled to −40° C. and $^t$BuOK (1.0 M solution in THF, 0.70 ml) was added. The reaction mixture was stirred for 3.0 h. Then $^t$BuOK (1.0 M solution in THF, 0.40 ml) was added again and the reaction solution was allowed to warm to ambient temperature for 9 h. The reaction mixture was quenched with saturated aqueous NaHCO$_3$ (20 ml) and extracted with Et$_2$O (2×40 ml). The combined extracts were washed with brine (20 ml), dried over MgSO$_4$, filtered and concentrated. Flash chromatography (10% AcOEt/hexane) afforded 84 (0.326 g, 50% yield): $^1$H-NMR (300 MHz, CDCl$_3$) δ 0.55 (s, 6H), 0.91 (s, 9H), 1.06 (apparent d, J=6.8 Hz, 3H), 1.49 (m, 2H), 1.64 (m, 2H), 1.93 (m, 1H), 2.07 (m, 2H), 2.21–2.48 (m, 3H), 3.38 (m, 2H), 3.61 (t, J=6.1 Hz, 2H), 3.85 (s, 3H), 3.87 (s, 3H), 4.00 (t, J=5.7 Hz, 2H), 4.39 (d, J=11.2 Hz, 1H), 4.47 (d, J=10.8 Hz, 1H), 4.49 (d, J=11.2 Hz, 1H), 4.56 (d, J=10.8 Hz, 1H), 5.00 (m, 2H), 5.92 (m, 1H), 6.79–6.91 (m, 4H), 7.27 (apparent d, J=8.4 Hz, 1H); $^{13}$C NMR (75 MHz, CDCl$_3$) δ 10.5, 14.0, 17.3, 18.3, 20.6, 22.7, 25.9, 26.9, 28.0 (t, J=22.2 Hz), 29.0, 38.5, 42.1, 55.7, 55.8, 63.1, 66.3, 70.9, 74.3, 79.9, 83.7, 110.9, 111.1, 114.3, 114.6, 119.9, 105–124 (m), 129.5, 131.6, 131.9, 141.2, 148.5, 148.9, 158.2; IR (thin film/NaCl) cm$^{-1}$ 2928, 2858, 1611, 1515, 1242, 1154; MS (EI) m/z 1132 (M$^+$), 1075, 981, 817, 667, 465; $[\alpha]_D^{20}$ +3.15° (c 1.11, CHCl$_3$).

(Z)-(4R,5S,6S,7S)-tert-Butyl-{6-(3, 4-dimethoxy-benzyloxy)-4-[4-(4, 4, 5, 5, 6, 6, 7, 7, 8, 8, 9, 9, 10, 10, 11, 11, 12, 12, 13, 13, 13-heneicosafluorotridecyloxy)benzyloxy]-9-iodo-5,7-dimethylnon-8-enyloxy}dimethylsilane (86). A mixture of 84 (0.326 g, 0.28 mmol) in MeOH (8.0 ml) and CH$_2$Cl$_2$ (6.0 ml) was cooled to −78° C. and treated with a stream of ozone for 5 min. The reaction mixture was treated with dimethylsulfide (1.5 ml) and pyridine (23 μl) and stirred for 3.0 h at ambient temperature. The reaction mixture was concentrated and diluted with Et$_2$O (80 ml). The organic layer was washed with saturated aqueous CuSO$_4$ (2×20 ml) and brine (20 ml), dried over MgSO$_4$, filtered and concentrated. At ambient temperature, a suspension of (iodomethyl) triphenylphosphonium iodide (0.213 g, 0.40 mmol) in THF (3.0 ml) was added NaN(TMS)$_2$ (1.0 M solution in THF, 0.40 ml). After stirring 0.5 h, this solution was cooled to −78° C. Then HMPA (0.13 ml) and the crude residue in THF (2.0 ml) were introduced, and the resultant mixture was stirred for 20 min at −78° C. and stirred at ambient temperature for 0.5 h. The reaction mixture was quenched with saturated aqueous NaHCO$_3$ (20 ml) and extracted with Et$_2$O (2×40 ml). The combined extracts were washed with brine (20 ml), dried over MgSO$_4$, filtered and concentrated. Flash chromatography (10% AcOEt/hexane) afforded (Z)-(4R,5S, 6S, 7S)-tert-butyl-{6-(3, 4-dimethoxy-benzyloxy)-4-[4-(4, 4, 5, 5, 6, 6, 7, 7, 8, 8, 9, 9, 10, 10, 11, 11, 12, 12, 13, 13, 13-heneicosafluorotridecyloxy)benzyloxy]-9-iodo-5,7-dimethylnon-8-enyloxy}dimethylsilane (0.119 g, 33% yield): $^1$H-NMR (300 MHz, CDCl$_3$) δ 0.04 (s, 6H), 0.89 (s, 9H), 1.03 (d, J=6.9 Hz, 3H), 1.04 (d, J=6.9 Hz, 3H), 1.23–1.77 (m, 5H), 2.04 (m, 2H), 2.23 (m, 2H), 2.70 (m, 1H), 3.44 (m, 2H), 3.59 (t, J=6.3 Hz, 2H), 3.86 (s, 3H), 3.87 (s, 3H), 4.03 (t, J=5.8 Hz, 2H), 4.40 (d, J=11.3 Hz, 1H), 4.53 (s, 2H), 4.57 (d, J=11.3 Hz, 1H), 6.15 (d, J=7.3 Hz, 1H), 6.28 (dd, J=7.3, 9.0 Hz, 1H), 6.80–6.89 (m, 4H), 7.22–7.30 (m, 2H); $^{13}$C NMR (75 MHz, CDCl$_3$) δ−5.2, 10.2, 14.2, 17.2, 18.4, 20.7, 22.8, 26.0, 27.3, 28.0 (t, J=22.1 Hz), 29.8, 31.7, 40.2, 42.9, 51.4, 55.9, 56.0, 63.3, 66.4, 71.1, 75.4, 78.9, 82.2, 84.1, 107–122 (m), 110.9, 111.2, 114.4, 120.1, 129.5, 131.6, 131.8, 143.2, 148.6, 148.9, 158.2; IR (thin film/NaCl) cm$^{-1}$ 2956, 2859, 1727, 1611, 1514, 1467, 1243, 1154, 856; MS (EI) m/z 1201 (M$^+$−C$_4$H$_9$), 1107, 667; $[\alpha]_D^{20}$ +4.04° (c 1.01, CHCl$_3$).

(Z)-(4R,5S,6S,7S)-tert-butyl-{6-(3,4-dimethoxybenzyloxy)-4-[4-(4,4,5,5,6,6,7,7,8, 8,9,9,10,10,11,11,12,12,13,13, 13-heneicosafluorotridecyloxy)benzyloxy]-5,7-dimethyl-9-phenyl-non-8-enyloxy}dimethylsilane (87). To a solution of (Z)-(4R,5S,6S,7S)-tert-butyl-{6-(3,4-dimethoxy-benzyloxy)-4-[4-(4, 4, 5, 5, 6, 6, 7, 7, 8, 8, 9, 9, 10, 10, 11, 11, 12, 12, 13, 13, 13-heneicosafluorotridecyloxy)benzyloxy]-9-iodo-5,7-dimethylnon-8-enyloxy}dimethylsilane (0.120 g, 0.09 mmol) and Pd(PPh$_3$)$_4$ (0.011 g, 0.01 mmol) in THF (1.0 ml) was added PhZnI (0.5 M solution in THF, 0.97 ml) at ambient temperature. After stirring for 24 h, the reaction mixture was quenched with saturated aqueous NaHCO$_3$ (20 ml) and extracted with Et$_2$O (2×40 ml). The combined extracts were washed with brine (20 ml), dried over MgSO$_4$, filtered and concentrated. Flash chromatography (10% AcOEt/hexane) afforded 87 (0.0726 g, 63% yield): $^1$H-NMR (300 MHz, CDCl$_3$) δ 0.09 (s, 6H), 0.95 (s, 9H), 1.07 (d, J=6.8 Hz, 3H), 1.19 (d, J=6.7 Hz, 3H), 1.27–1.59 (m, 4H), 1.85 (m, 1H), 2.13 (m, 21H), 2.35 (m, 2H), 3.11 (m, 2H), 3.39 (brt, J=5.2 Hz, 1H), 3.57 (t, J=6.2 Hz, 2H), 3.84 (s, 3H), 3.91 (s, 3H), 4.02 (d, J=11.3 Hz, 1H), 4.08 (t, J=5.8 Hz, 2H), 4.32 (d, J=11.3 Hz, 1H), 4.52 (d, J=10.6 Hz, 1H), 4.67 (d, J=10.6 Hz, 1H), 5.83, (dd, J=11.5, 11.5 Hz, 1H), 6.53 (d, J=11.5 Hz, 1H), 6.86–7.37 (m, 9H); $^{13}$C NMR (75 MHz, CDCl$_3$) δ−5.2, 10.2, 14.2, 18.4, 18.9, 20.7, 22.8, 26.1, 27.3, 27.8 (t, J=21.7 Hz), 28.9, 31.7, 35.6, 39.7, 55.8, 56.0, 63.3, 66.4, 71.2, 75.2, 79.9, 84.6, 107–122 (m), 110.9, 111.2, 114.3, 120.0, 126.7, 128.3, 128.7, 128.9, 129.3, 131.9, 135.3, 137.8, 148.5, 148.9, 158.1; IR (thin film/NaCl) cm$^{-1}$ 2926, 2857, 1727, 1515, 1464, 1242, 1154, 1031; MS (EI) m/z 1208 (M$^+$), 1151, 1066, 667; $[\alpha]_D^{20}$ +3.73° (c 0.805, CHCl$_3$).

[2R]-Butane-1,2,4-triol. To a dry 1 L two-necked flask equipped with a pressure-equalizing addition funnel, a magnetic stirring bar and a reflux condenser was added THF (200 mL), B(OMe)$_3$ (100 mL), and (R)-(+)-malic acid (40.0 g, 0.30 mol). To this solution was added dropwise BH$_3$—SMe$_2$ (100 mL, 1.0 mol) over 2 h in a water bath as instantaneous H$_2$ evolution occurred throughout the addition. After stirring for 20 h at rt, MeOH (200 mL) was added dropwise, and the resulting solution was filtered through a glass frit funnel charged with Celite to remove any solids. The clear, yellow filtrate was concentrated in vacuo to give a yellow oil. The residue was dissolved in MeOH (100 mL) and concentrated in vacuo. This was repeated 5 times giving 26.9 g of the triol (85%). The spectral data matched that of the known compound.

[2R]-2-(4-Methoxyphenyl)-[1,3]dioxan-4-yl]methanol (88). A solution of the triol (5.0 g, 47.1 mmol), p-anisaldehyde (9.62 g, 70.7 mmol), PPTS (0.12 g, 0.047 mmol) in benzene (100 mL) was refluxed for 10 h with the azeotropic removal of H$_2$O. NaHCO$_3$ (0.20 g, 2.4 mmol) was added to the solution and concentrated in vacuo. The crude mixture was purified by flash chromatography (20% to 50% EtOAc in hexanes) to give 88 (65%). $^1$H NMR (300 MHz, CDCl$_3$)– 7.41 (d, J=8.4 Hz, 2H), 6.90 (d, J=8.4 Hz, 2H), 5.49 (s, 1H), 4.28 (ddd, J=11.1, 5.1, 1.3 Hz, 1H), 4.00–3.95 (m, 2H), 3.79 (s, 3H), 3.67–3.64 (m, 2H), 2.04 (br s, 1H), 1.91 (dq, J=12.4, 5.1 Hz, 1H), 1.46–1.41 (m, 1H); $^{13}$C NMR (75 MHz, CDCl$_3$)–160.1, 132.0, 127.4, 113.6, 101.2, 76.6, 66.5, 65.6, 55.3, 26.9.

[2R]-tert-Butyl-[2-(4-methoxyphenyl)-[1,3]dioxan-4-ylmethoxy]diphenylsilane. A solution of alcohol 88 (8.13 g, 36.2 mmol), imidazole (3.9 g, 57.3 mmol), and TBDPSCl (10.2 mL, 39.7 mmol) in DMF (75 mL) was stirred overnight at room temperature under argon. A mixture of H$_2$O (250 mL) and EtOAc (150 mL) was added and the layers were separated. The aqueous layer was extracted with EtOAc (2×100 mL). The organic layers were combined and washed with H$_2$O (2×100 mL), brine (100 mL), dried over MgSO$_4$, filtered and concentrated in vacuo. The crude oil was purified by flash chromatography (20% EtOAc in hexanes) to yield 15.9 g (95%) of the silyl ether as a clear yellow oil. $^1$H NMR (300 MHz, CDCl$_3$) δ 7.69–7.66 (m, 4H), 7.41–7.34 (m, 8H), 6.86 (d, J=8.8 Hz, 2H), 5.46 (s, 1H), 4.28 (dd, J=11.0, 4.2 Hz, 1H), 4.02–3.96 (m, 2H), 3.86–3.83 (m, 1H), 3.79 (s, 3H), 3.67 (dd, J=10.2, 5.6 Hz, 1H), 1.84 (dq, J=12.2, 4.9 Hz, 1H), 1.65–1.61 (m, 1H), 1.05 (s, 9H);

$^{13}$C NMR (75 MHz, CDCl$_3$) δ 160.0, 135.7, 133.4, 130.0, 129.6, 128.2, 128.0, 113.4, 101.0, 77.5, 66.9, 66.0, 55.3, 28.1, 26.8, 19.3.

4-(tert-Butyldiphenylsilanyloxy)-3-(4-methoxybenzyloxy)-butan-1-ol. To a stirred solution of the acetal (5.0 g, 10.8 mmol) in toluene (20 mL) at −78° C. was added slowly via cannula DibalH in toluene (33.0 mL, 1M). The reaction mixture was maintained at −78° C. for 12 h and quenched by slow addition to a vigorously stirred saturated solution of Rochelle salt in H$_2$O (70 mL). The emulsion was stirred until two layers formed (1 h). The aqueous layer was extracted with CH$_2$Cl$_2$ (4×15 mL) and the organic layers were combined, dried over MgSO$_4$, filtered and concentrated in vacuo. The crude oil was purified by flash chromotaography (20% to 50% EtOAc in hexanes) providing 4.01 g (80%) of the corresponding alcohol as a clear, yellow oil. $^1$H NMR (300 MHz, CDCl$_3$) δ 7.69–7.66 (m, 4H), 7.43–7.38 (m, 6H), 7.20 (d, J=8.5 Hz, 2H), 6.86 (d, J=8.5 Hz, 2H), 4.60 (d, J=11.2 Hz, 1H), 4.41 (d, J=11.2 Hz, 1H), 3.79 (s, 3H), 3.77–3.66 (m, 5H), 1.82–1.79 (m, 2H), 1.05 (s, 9H); $^{13}$C NMR (75 MHz, CDCl$_3$) δ 159.3, 135.5, 133.2, 129.4, 129.0, 128.0, 127.6, 113.8, 78.3, 72.1, 66.4, 60.2, 55.2, 34.2, 26.8, 19.1.

4-(tert-Butyldiphenylsilanyloxy)-3-(4-methoxybenzyloxy)-butyraldehyde (89). DMSO (0.9 mL, 12.8 mmol) was added, dropwise, to a stirred solution of oxalyl chloride (0.5 mL, 6.0 mmol) in CH$_2$Cl$_2$ (8.0 mL) at −78° C. under argon. The reaction mixture was stirred for 5 min then a solution of the alcohol (2.04 g, 4.41 mmol) in CH$_2$Cl$_2$ (27.0 mL) was added dropwise. After 1 h at −78° C., Et$_3$N (3.15 mL, 22.4 mmol) was added slowly via syringe, the mixture was stirred for 5 min then warmed to room temperature. The reaction mixture was diluted with CH$_2$Cl$_2$ (30 mL), washed with ice cold 0.5 M HCl (50 mL) then H$_2$O (40 mL) and the layers were separated. The aqueous layers were combined and extracted with CH$_2$Cl$_2$ (2×40 mL) and the combined organic layers were dried over MgSO$_4$, filtered, and concentrated in vacuo. The intermediate aldehyde 89 was used in the following reaction without purification: $^1$H NMR (300 MHz, CDCl$_3$) δ 9.76 (s, 1H), 7.67–7.63 (m, 4H), 7.44–7.34 (m, 6H), 7.16 (d, J=8.5 Hz, 2H), 6.83 (d, J=8.5 Hz, 2H), 4.52 (d, J=11.1 Hz, 1H), 4.41 (d, J=11.1 Hz, 1H), 4.03–3.99 (m, 1H), 3.81 (s, 3H), 3.79–3.74 (m, 2H), 3.68–3.63 (m, 1H), 2.67 (dd, J=6.1, 1.9 Hz, 1H), 1.04 (s, 9H).

[3R,4R,6R]-7-(tert-Butyldiphenylsilanyloxy)-6-(4-methoxybenzyloxy)-3-methylhept-1-en-4-ol (90). A solution of (R,R)-diisopropyl tartrate (Z)-crotylboronate (15.0 mmol) was added to 4 Å powdered molecular sieves (0.170 g) in toluene (8.4 mL) under argon and the mixture was stirred for 20 min at room temperature. The mixture was cooled to −78° C. and a solution of the aldehyde 89 (2.0 g, 4.4 mmol) in toluene (5.0 mL) was added dropwise via cannula. The resulting mixture was maintained at −78° C. for 3 h and then treated with NaBH$_4$ (0.072 g, 1.75 mmol) in EtOH (2.0 mL) and warmed to 0° C. The reaction mixture was treated with 1N NaOH (30 mL) and stirred vigorously for 30 min, followed by separation of the organic layer. The aqueous layer was extracted with CH$_2$Cl$_2$ (5×55 mL) and the combined organic layers were dried over MgSO$_4$, filtered, and concentrated in vacuo. The crude oil was purified by flash chromatography (5% to 20% Et$_2$O in hexanes) providing 1.43 g (63% 2 seps) of alcohol, a clear oil: $[\alpha]^{20}_D$=+0.32 (c 1.8, CHCl$_3$); $^1$H NMR (300 MHz, CDCl$_3$) δ 7.67 (d, J=7.0 Hz, 2H), 7.45–7.35 (m, 6H), 7.20 (d, J=8.4 Hz, 2H), 6.84 (d, J=8.4 Hz, 2H), 5.73 (ddd, J=18.2, 11.0, 7.4 Hz, 1H0, 5.03 (dd, J=11.0, 1.7 Hz, 1H), 5.02 (dd, J=18.2, 1.7 Hz, 1H), 4.59 (d, J=11.3 Hz, 1H), 4.40 (d, J=11.3 Hz, 1H), 3.79 (s, 3H), 3.89–3.75 (m, 2H), 3.68–3.65 (m, 2H), 2.18 (sext, J=6.8 Hz, 1H), 1.84–1.55 (m, 2H), 1.05 (s, 9H), 1.01 (d, J=6.8 Hz, 3H); $^{13}$C NMR (75 MHz, CDCl$_3$) δ159.0, 140.6, 135.6, 133.5 (2C), 130.3, 131.0, 127.6, 129.6, 114.4, 113.6, 72.2, 83.1, 64.1, 71.3, 55.2, 40.8, 37.2, 26.8, 19.2, 14.4; IR (thin film) 3056, 2989, 2859, 1513, 1426, 1248, 1112, 1077 cm$^{-1}$; LRMS (EI) 517 (M–H), 435, 333, 303, 255, 241, 223, 199, 135, 121 m/z.

[2R,4R,5R]-[2,4-bis-(4-Methoxybenzyloxy)-5-methyl-hept-6-enyloxy]tert-butyldiphenyl silane. A mixture of NaH (1.8 g, 7.23 mmol) in THF (5 mL) was cooled to 0° C. then DMF (5 mL), the alcohol (1.25 g, 2.41 mmol) in THF (5 mL), and PMBBr (1.14 g, 6.03 mmol) were added. The reaction mixture was warmed to room temperature and stirred for 48 h. The resulting mixture was poured into a pH 7 phosphate buffer and diluted with ether (85 mL). The organic layer was separated and washed with pH 7 buffer (3×55 mL), dried over K$_2$CO$_3$, filtered and concentrated in vacuo. The resulting crude yellow oil was purified by flash chromatography (5% to 10% EtOAc in hexanes) providing 0.985 g (64%) of the PMB ether a clear, yellow tinted oil: $[\alpha]^{20}_D$=+0.31 (c 1.8, CHCl$_3$); $^1$H NMR (300 MHz, CDCl$_3$) δ 7.69–7.65 (m, 4H), 7.39–7.37 (m, 6H), 7.22–7.19 (m, 4H), 6.86–6.84 (m, 4H), 5.73 (ddd, J=17.8, 9.8, 7.0 Hz, 1H), 5.04–4.99 (m, 2H), 4.64 (d, J=11.2 Hz, 1H), 4.49 (d, J=11.1 Hz, 1H), 4.30 (d, J=11.2 Hz, 1H), 4.18 (d, J=11.1 Hz, 1H), 3.78 (s, 6H), 3.81–3.52 (m, 4H), 2.60–2.56 (m, 1H), 1.57–1.51 (m, 2H), 1.05 (s, 9H), 1.0 (d, J=6.9 Hz, 3H); $^{13}$C NMR (75 MHz, CDCl$_3$) δ 159.0, 140.6, 135.6, 133.5 (2C), 130.3, 131.0, 127.6, 129.6, 114.4, 113.6, 72.2, 83.1, 64.1, 75.4, 55.2, 40.8, 37.2, 26.8, 19.2, 14.4, −5.3; IR (thin film) 3055, 2985, 1422, 1280, 247 cm$^{-1}$; LRMS (EI) 581.34 (M–C$_4$H$_7$), 579.34, 522.34, 444, 326, 383, 323, 339, 301, 255, 137, 122 m/z.

[2R,3R,5R]-6-(tert-Butyldiphenylsilanyloxy)-3,5-bis-(4-methoxybenzyloxy)-2-methylhexanal. To a solution of MeOH (30 mL), CH$_2$Cl$_2$ (10 mL) and a few drops of pyridine was added the PMB ether (800 mg, 1.25 mmol) and the mixture was cooled to −78° C. Ozone was bubbled through the reaction mixture until a slight purple color was seen. Excess DMS (6.0 mL) was added to the solution and allowed to warm to RT. After 3 h, the mixture was concentrated in vacuo. The yellow residue was dissolved in hexanes (60 mL) and washed with H$_2$O (2×40 mL) and brine (20 mL). The organic layer was dried over MgSO$_4$, filtered and concentrated in vacuo to give the intermediate aldehyde (800 mg, 1.25 mmol) that was used in the following step without further purification: $^1$H NMR (300 MHz, CDCl$_3$) δ 9.70 (d, J=2.0, 1H), 7.69–7.65 (m, 4H), 7.39–7.37 (m, 6H), 7.22–7.19 (m, 4H), 6.86–6.84 (m, 4H), 4.64 (d, J=11.2 Hz, 1H), 4.49 (d, J=11.1 Hz, 1H), 4.30 (d, J=11.2 Hz, 1H), 4.18 (d, J=11.1 Hz, 1H), 3.78 (s, 6H), 3.81–3.52 (m, 4H), 2.60–2.56 (m, 1H), 1.57–1.51 (m, 2H), 1.05 (s, 9H), 1.0 (d, J=6.9 Hz, 3H).

[4R,5R,7R]-8-(tert-Butyldiphenylsilanyloxy)-5,7-bis-(4-methoxybenzyloxy)-4-methyloct-2-enoic acid ethyl ester (91). To a stirred suspension of NaH (36 g, 1.56 mmol) in toluene (10 mL) at 0° C. and under argon was added a solution of 2-(diethoxyphosphoryl)propionic acid ethyl ester (0.47 mL, 1.77 mmol) in toluene (0.40 mL) dropwise. The reaction mixture was warmed to rt for 30 min then recooled to 0° C. The intermediate aldehyde (0.5 g, 1.3 mmol) in THF (10 mL) was added dropwise and the reaction mixture was stirred at 0° C. for 2 h. The solution was quenched by addition of pH 7 buffer (5 mL) and diluted with Et$_2$O (12 mL). The emulsion was warmed to rt and the layers were separated. The organic layer was washed with a saturated solution of NH$_4$Cl (10 mL) and the aqueous layers were combined and extracted with Et$_2$O (3×20 ml). The organic layers were combined, dried over MgSO$_4$, filtered and concentrated in vacuo. The crude mixture was purified by flash chromatography (0% to 20% EtOAc in hexanes) to give 623 mg (70% 2 steps) of 91 a yellow oil: $^1$H NMR (300 MHz, CDCl$_3$) δ 7.69–7.65 (m, 4H), 7.39–7.37 (m, 4H), 7.21–7.18 (m, 4H), 6.85–6.83 (m, 4H), 6.98 (dd, J=15.7, 7.6 Hz, 1H), 5.82 (dd, J=15.7, 1.0 Hz, 1H), 4.64 (d, J=11.2 Hz, 1H), 4.50 (d, J=11.1 Hz, 1H), 4.36 (d, J=11.2 Hz, 1H), 4.20 (d, J=11.1 Hz, 1H), 3.78 (s, 6H), 3.81–3.52 (m, 4H), 2.60–2.56 (m, 1H), 1.57–1.51 (m, 2H), 1.05 (s, 9H), 1.0 (d, J=6.8 Hz, 3H); $^{13}$C NMR (75 MHz, CDCl$_3$) δ 166.3, 158.9, 150.5, 131.0, 130.0, 129.2, 129.1, 121.1, 113.5, 78.4, 75.9, 71.7, 71.2, 64.1, 59.9, 55.0, 38.9, 34.1, 25.7, 18.1, 14.4, 14.1, −5.5; IR (thin film) 3055, 2956, 2933, 2908, 2857, 1705, 1243, 1097 cm$^{-1}$; HRMS (EI) calcd for C$_{43}$H$_{54}$O$_7$Si 710.3628, found 371.3627.

[4R,5R,7R]-8-(tert-Butyldiphenylsilanyloxy)-5,7-bis-(4-methoxybenzyloxy)-4-methyloct-2-en-1-ol. To a stirred solution of ester 91 (600 mg, 0.84 mmol) in CH$_2$Cl$_2$ (6 mL) at −40° C. under argon was added slowly over 10 min via syringe DibalH in toluene (9 mL, 1M). After 30 min at 40° C., the reaction mixture was quenched by slow addition of MeOH (0.6 mL) and warmed to rt. The reaction mixture was poured into a vigorously stirred solution of saturated Rochelle salt in H$_2$O (8 mL) and EtOAc (12 mL) and stirred overnight. The aqueous layer was separated and extracted with EtOAc (3×5 mL), dried over MgSO$_4$, filtered and concentrated in vacuo. The crude mixture was purified by flash chromatography (20% EtOAc in hexanes) to produce 450 mg (80%) of the alcohol, a clear liquid: $^1$H NMR (300 MHz, CDCl$_3$) δ 7.70–7.66 (m, 4H), 7.39–7.35 (m, 6H), 7.21–7.18 (m, 4H), 6.85–6.82 (m, 4H), 5.68–5.65 (m, 2H), 4.64 (d, J=11.1 Hz, 1H), 4.51 (d, J=11.0 Hz, 1H), 4.46 (d, J=11.1 Hz, 1H), 4.24 (d, J=11.0 Hz, 1H), 4.10–4.06 (m, 2H), 3.78 (s, 6H), 3.81–3.52 (m, 4H), 2.60–2.56 (m, 1H), 1.57–1.51 (m, 2H), 1.05 (s, 9H), 1.03 (d, J=6.8 Hz, 3H); $^{13}$C NMR (75 MHz, CDCl$_3$) δ 159.0, 135.6, 135.1, 133.5 (2C), 131.1, 130.3, 130.0, 127.6, 129.4, 129.6, 83.1, 75.2, 72.4, 72.2, 64.4, 63.7, 55.2, 34.7, 26.8, 19.2, 15.4; IR (thin film) 3295, 3045, 2958, 2941, 2910, 2857, 1241, 1097 cm$^{-1}$; HRMS (EI) calcd for C$_{41}$H$_{52}$O$_6$Si 668.3599, found 668.3596.

[2R,3R,5R]-8-(tert-Butyldiphenylsilanyloxy)-5,7-bis-(4-methoxybenzyloxy)-4-methyl oct-2-enal. To a solution of the alcohol (400 mg, 0.59 mmol) in CH$_2$Cl$_2$ (2 mL) was added Dess-Martin periodane (330 mg, 0.78 mmol) and the reaction mixture was stirred for 30 min. The reaction mixture was diluted with Et$_2$O (10 mL) and poured into a stirring solution of saturated Na$_2$S$_2$O$_3$ (5 mL) and saturated NaHCO$_3$ (5 mL). The layers were separated and the organic layer was washed with saturated NaHCO$_3$ (3×5 mL), dried over MgSO$_4$, filtered and concentrated in vacuo to give the intermediate aldehyde which was used in the next reaction without further purification: $^1$H NMR (300 MHz, CDCl$_3$) δ 9.50 (d, 7.8 Hz, 1H), 7.69–7.64 (m, 4H), 7.39–7.37 (m, 7H), 7.20–7.14 (m, 4H), 6.84–6.79 (m, 4H), 6.10 (dd, J=7.8, 17.0 Hz, 1H), 4.64 (d, J=11.2 Hz, 1H), 4.49 (d, J=11.1 Hz, 1H), 4.30 (d, J=11.2 Hz, 1H), 4.18 (d, J=11.1 Hz, 1H), 3.78 (s, 6H), 3.81–3.52 (m, 4H), 2.60–2.56 (m, 1H), 1.57–1.51 (m, 2H), 1.05 (s, 9H), 1.00 (d, J=6.9 Hz, 3H).

[4R,5R,7R]-10-(tert-butyldiphenysilanyloxy)-7,9-bis(4-methoxybenzyloxy)-6-methyldeca-2,4-dienoicacid methyl ester. To a stirred solution of [bis-(2,2,2-trifluoroethoxy)phosphoryl]acetic acid methyl ester (210 mg, 0.65 mmol) in THF (12 mL) at −78° C. under argon was added dropwise KHMDS in toluene (1.4 mL, 0.5 M). The reaction mixture was warmed to −40° C. for 1 h then cooled to −78° C. and the intermediate aldehyde (400 mg, 0.59 mmol) in THF (0.5 mL) was added dropwise. After 3 h at −78° C., the solution was warmed to 0° C. and quenched by addition of a saturated solution of NH$_4$Cl (5 mL) and diluted with Et$_2$O (5 mL). The aqueous layer was separated and extracted with diethyl ether (5×3 mL). The combined organic phases were washed with brine (5 mL), dried over MgSO$_4$, filtered and concentrated in vacuo. The crude mixture was purified by flash chromatography (10% to 30% EtOAc in hexanes), yielding 220 mg (65% 2 steps) of conjugated ester, a clear oil: $^1$H NMR (300 MHz, CDCl$_3$) δ 7.69–7.65 (m, 4H), 7.39–7.37 (m, 7H), 7.20–7.16 (m, 4H), 6.85–6.79 (m, 4H), 6.64 (t, J=11.2 Hz, 1H), 6.22 (ddd, J=15.4, 6.8 Hz, 1H), 5.87 (d, J=11.2 Hz, 1H), 5.04–4.99 (m, 2H), 4.64 (d, J=11.2 Hz, 1H), 4.49 (d, J=11.1 Hz, 1H), 4.30 (d, J=11.2 Hz, 1H), 4.18 (d, J=11.1 Hz, 1H), 3.78 (s, 6H), 3.81–3.52 (m, 4H), 2.60–2.56 (m, 1H), 1.57–1.51 (m, 2H), 1.05 (s, 9H), 1.00 (d, J=6.9 Hz, 3H); $^{13}$C NMR (75 MHz, CDCl$_3$) δ 166.9, 147.3, 145.4, 135.6, 133.5 (2C), 130.3, 129.6, 126.7, 115.5, 113.5, 78.4, 75.9, 71.7, 71.8, 64.1, 55.0, 51.1, 39.7, 34.1, 26.8, 19.2, 14.1; IR (CH$_2$Cl$_2$) 3048, 2987, 2931, 2875, 2822, 1715, 15251, 1423, 1250, 1110 cm$^{-1}$; HRMS (EI) calcd for 722.3642, found 722.3640 m/z.

[6R,7S,9R]-10-Hydroxy-7,9-bis-(4-methoxybenzyloxy)-6-methyldeca-2,4-dienoic acid Methyl Ester (92). To a solution of the TBDPS ether (100 mg, 0.14 mmol) in THF 1 ml) was slowly added HF-pyridine in pyridine (1.5 ml, prepared by slow addition of 0.45 ml pyridine to 0.1 ml HF-pyridine complex followed by dilution with 0.94 ml THF) at 0° C. The mixture was warmed to room temperature and stirred overnight at room temperature. The reaction mixture was slowly quenched with saturated NaHCO$_3$ (5 mL) and the aqueous layer was separated and extracted with CH$_2$Cl$_2$ (5×2 mL). The combined organic layers were washed with saturated CuSO$_4$ (2 mL), dried over MgSO$_4$, filtered and concentrated in vacuo. The crude product was purified by flash chromatography (25% EtOAc in hexanes) affording 50 mg (75%) of alcohol 92: [α]$^{20}_D$=+8.56 (c 0.1, CHCl$_3$); $^1$H NMR (300 MHz, CDCl$_3$) δ 7.53 (dd, J=15.0, 11.4 Hz, 1H), 7.35–7.30 (m, 4H), 6.97–6.93 (m, 6H), 6.65 (dd, J=11.3, 1.3 Hz, 1H), 6.23 (dd, J=15.0, 6.9 Hz, 1H), 5.69 (d, J=11.3 Hz, 1H), 4.64 (d, J=10.9 Hz, 1H), 4.59 (d, J=11.2 Hz, 1H), 4.44 (d, J=11.2 Hz, 1H), 4.34 (d, J=10.9 Hz, 1H), 3.88 (s, 3H), 3.82 (s, 3H), 2.77–2.73 (m, 2H), 3.67–3.64 (m, 1H), 3.54 (dd, J=3.6, 11.5 Hz, 1H), 2.95–2.89 (m, 1H), 1.90–1.81 (m, 2H), 1.19 (d, J=6.7 Hz, 3H); $^{13}$C NMR (75 MHz, CDCl$_3$) δ 166.9, 159.0, 147.3, 145.4, 130.1, 130.3, 129.7, 126.7, 115.5, 113.6, 75.9, 78.5, 71.1, 63.9, 55.0, 51.0, 38.4, 33.7, 14.1; IR (thin film) 3315, 3055, 2986, 2858, 1710, 1513, 1423, 1247, 1105 cm$^{-1}$; LRMS (EI) 484, 469, 349, 425, 223, 121 m/z; HRMS (EI) calcd for C$_{28}$H$_{36}$O$_7$ 484.2582, found 484.2579.

(R,R)-diisopropyl tartrate (Z)-crotylboronate. An oven-dried 1 L three-neck round bottom flask equipped with a magnetic stir bar and a −100° C. thermometer was charged with 206 mL of anhydrous THF and KOtBu (28.2 g, 250 mmol). This mixture was flushed with Ar and cooled to −78° C., then cis-2-butene (23 mL, 250 mmol), condensed from a gas lecture bottle into a rubber-stoppered round bottom flask immersed in a −78° C. dry ice-acetone bath, was poured into the reaction mixture. n-BuLi (100 mL, 2.5 M in hexane) was then added dropwise via cannula over 1.5 h. After completion of the addition, the cooling bath was removed and the reaction mixture was allowed to warm to −20 to −25° C. for 30 min before being recooled to −78° C. Triisopropylborate (57.8 mL, 250 mmol) was added dropwise via cannula to the (Z)-crotylpotassium solution over 2 h. After addition, the reaction mixture was maintained at −78° C. for 30 min and then rapidly poured into a 2 L separatory funnel containing 470 mL of 1 N HCl saturated with NaCl. The aqueous layer was adjusted to pH 1 by using 1 N HCl (100–150 mL), and then a solution of (R,R)-diisopropyl tartrate (52.8 g, 250 mmol) in 88 mL of $Et_2O$ was added. The phases were separated, and the aqueous layer was extracted with additional $Et_2O$ (4×120 mL). The combined extracts were dried over $MgSO_4$ for 1 h then vacuum filtered through a fritted glass funnel under Ar blanket into an oven-dried round-bottom flask. The filtrate was concentrated in vacuo, and pumped to constant weight at under vacuum. Anhydrous toluene (170 mL) was added to the flask make a 1M solution.

[4S,3S,2R]-4-Benzyl-3-(3-hydroxy-2,4-dimethylpent-4-enoyl)oxazolidin-2-one (93). Oxazolidinone 4 (10.0 g, 43.1 mmol) was treated with $MgCl_2$ (0.20 g, 2.2 mmol), $NaSbF_6$ (1.7 g, 6.5 mmol), $Et_3N$ (6.03 mL, 86.2 mmol), methacrolein (2.67 mL, 25.9 mmol) and TMSCl (3.92 mL, 32.3 mmol) in EtOAc (50 mL) and allowed to stir under Ar at rt for 24 h. The yellow-green slurry was filtered through a plug of silica gel with $Et_2O$ (1 L). GC analysis of the solution gave the isomeric composition of the TMS ether in a 16:1 ratio with its diastereomers. The ether was concentrated in vacuo, and MeOH (86 mL) and TFA (1 mL) was added. The reaction mixture was stirred for 30 min and concentrated to give a yellow which was purified by flash chromatography (10% acetone in hexanes) to yield 5.02 g of alcohol 93 (78% 2 steps). Data matches known literature.[32] $[\alpha]^{20}_D$=+0.06 (c 0.1, $CHCl_3$); $^1H$ NMR (300 MHz, $CDCl_3$) δ 7.39–7.31 (m, 5H), 5.08 (s, 1H), 5.02 (s, 1H), 4.77–4.75 (m, 1H), 4.27–4.22 (m, 4H), 3.35 (dd, J=13.5, 3.2 Hz, 1H), 2.83 (dd, J=13.5, 9.5 Hz, 1H), 2.75 (br s, 1H), 1.86 s (3H), 1.19 (d, J=6.7 Hz, 3H); $^{13}C$ NMR (75 MHz, $CDCl_3$) δ 175.6, 152.9, 145.0, 135.7, 129.3, 128.9, 127.1, 114.5, 80.1, 65.6, 55.5, 41.9, 38.4, 16.1, 14.7; IR (thin film) 3300, 3057, 2931, 2857, 1781, 1702, 1422, 1384, 1271, 1209, 1079 $cm^{-1}$; HRMS (EI) calcd for $C_{17}H_{21}NO_4$ 303.1582, found 303.1581.

[4R,2S,3R]-4-Benzyl-3-[3-(tert-butyldimethylsilanyloxy)-2,4-dimethylpent-4-enoyl]oxazolidin-2-one. To a stirred solution of alcohol 93 (20.24 g, 66.72 mmol) in $CH_2Cl_2$ (170 mL) at 0° C. under argon was added 2,6-lutidine (9.3 mL, 79.85 mmol) and TBSOTf (16.1 mL, 73.4 mmol). After 3 h at 0° C. the reaction mixture was quenched with MeOH (34 mL) then concentrated to dryness. The residue was taken up in $Et_2O$ (225 mL) and washed with a saturated solution of $NH_4Cl$ (2×50 mL). The aqueous layers were combined and extracted with $Et_2O$ (2×20 mL) and the combined organic layers were dried over $MgSO_4$ and concentrated in vacuo. Flash chromatography of the crude mixture (10% to 20% EtOAc in hexanes) gave 26.5 g (95%) of the silyl ether as a clear oil: $[\alpha]^{20}_D$=+0.07 (c 0.15, $CHCl_3$); $^1H$ NMR (300 MHz, $CDCl_3$) δ 7.40–7.29 (m, 5H), 5.00 (s, 1H), 4.98 (s, 1H), 4.72 (dq, J=7.0, 3.2 Hz, 1H), 4.51 (d, J=9.6 Hz, 1H), 4.21–4.18 (m 3H), 3.49 (dd, J=13.3, 3.2 Hz, 1H), 2.64 (dd, J=13.3, 10.2 Hz, 1H), 1.80 (s, 3H), 1.03 (d, J=7.0 Hz, 3H), 0.9 (s, 9H), 0.11 (s, 3H), 0.09 (s, 3H); $^{13}C$ NMR (75 MHz, $CDCl_3$) δ 175.9, 153.1, 145.0, 135.7, 129.3, 128.9, 127.2, 114.6, 79.4, 65.8, 55.5, 41.9, 38.4, 25.8, 18.1, 16.1, 14.7, −4.7, −5.1; IR (thin film) 3047, 2938, 2854, 1779, 1702, 1429, 1380, 1271, 1210, 1082 $cm^{-1}$; LRMS (EI) 417, 402, 360, 290, 234, 185, 117; HRMS (EI) calcd for $C_{23}H_{35}NO_4Si$ 417.2335, found 417.2345.

[4S,2S,3R]-4-Benzyl-3-[3-(tert-butyldimethylsilanyloxy)-5-hydroxy-2,4-dimethylpentanoyl]oxazolidin-2-one (94). A stirred solution of 9-BBN in THF (29 mL, 0.5 M) was treated with the alkene (5.0 g, 11.97 mmol) in THF (29 mL). The reaction mixture was stirred at rt for 24 h, then treated sequentially with 1:1 EtOH-THF (29 mL), pH 7 buffer (29 mL) and 30% aq. $H_2O_2$ (14.5 mL) and stirred for 12 h at rt. The mixture was extracted with diethyl ether (3×20 mL). The combined organic layers were washed with $H_2O$ (15 mL) and saturated aqueous NaCl (15 mL) then dried over $MgSO_4$, filtered and concentrated in vacuo. Purification of the mixture by flash chromatography (20% EtOAc in hexanes) gave 94 as a clear oil (3.91 g, 75%): $[\alpha]^{20}_D$=+0.24 (c 0.05, $CHCl_3$); $^1H$ NMR (300 MHz, $CDCl_3$) δ 7.33–7.23 (m, 5H), 4.69–4.60 (m, 1H), 4.21 (dd, J=6.8, 3.8 Hz, 1H), 4.17–4.04 (m, 3H), 3.77–3.60 (m 2H), 3.44 (dd, J=13.1, 3.2 Hz, 1H), 2.60 (dd, J=13.1, 10.7 Hz, 1H), 2.50 (br s, 1H), 2.02–1.85 (m, 1H), 1.23 (d, J=6.9 Hz, 3H), 1.00 (d, J=7.0 Hz, 3H), 0.9 (s, 9H), 0.14 (s, 3H), 0.09 (s, 3H); $^{13}C$ NMR (75 MHz, $CDCl_3$) δ 174.7, 153.1, 135.4, 129.3, 129.0, 127.3, 66.1, 65.4, 55.8, 43.9, 38.3, 37.0, 26.7, 26.0, 18.2, 16.4, 12.4, −4.2, −4.8; IR (thin film) 3538, 2927, 1780, 1700, 1273, 1201 $cm^{-1}$; HRMS (EI) calcd for $C_{23}H_{37}NO_5Si$ 435.2461, found 435.2460.

(4S)-[2R,3R,4R]-Benzyl-3-[3,5-bis(tert-butyldimethylsilanyloxy)-2,4-dimethylpentanoyl]oxazolidin-2-one. To a stirred solution of alcohol 94 (2.6 g, 5.97 mmol) in $CH_2Cl_2$ (15 mL) at 0° C. under argon was added 2,6-lutidine (0.83 mL, 7.14 mmol) and TBSOTf (1.44 mL, 6.57 mmol). After 3 h at 0° C. the reaction mixture was quenched with MeOH (3 mL) then concentrated to dryness. The residue was taken up in $Et_2O$ (20 mL) and washed with a saturated solution of $NH_4Cl$ (2×5 mL). The aqueous layers were combined and extracted with $Et_2O$ (2×5 mL) and the combined organic layers were dried over $MgSO_4$ and concentrated in vacuo. Flash chromatography of the crude mixture (10% to 20% EtOAc in hexanes) gave 3.01 g (95%) of the silyl ether as a clear oil: $[\alpha]^{20}_D$=+0.24 (c 0.05, $CHCl_3$); $^1H$ NMR (300 MHz, $CDCl_3$) δ 7.33–7.22 (m, 5H), 4.69–4.61 (m, 1H), 4.24 (dd, J=3.7, 7.0 Hz, 1H), 4.13–4.11 (m, 3H), 3.76 (dd, J=6.0, 10.3 Hz, 1H), 3.48–3.42 (m, 2H), 2.60 (dd, J=10.3, 13.1 Hz, 1H), 2.01–1.87 (m, 1H), 1.17 (d, J=7.0 Hz, 3H), 0.976 (d, J=7.0 Hz, 3H), 0.90 (s, 9H), 0.88 (s, 9H), 0.11 (s, 3H), 0.08 (s, 3H), 0.05 (s, 6H); $^{13}C$ NMR (75 MHz, $CDCl_3$) δ 175.5, 153.1, 135.7, 129.3, 129.0, 127.3, 74.4, 66.0, 64.9, 55.7, 43.2, 39.9, 38.5, 26.1, 26.0, 18.3, 14.4, 13.5, −4.0, −4.6, −5.4 (2C); IR (thin film) 3057, 2952, 2860, 1781, 1699, 1382, 1259, 1100 $cm^{-1}$; LRMS (EI) 492 (M−$C_4H_9$), 377, 374, 199, 177, 115; HRMS (EI) calcd for $C_{25}H_{42}NO_5Si_2$ 492.3306, found 492.3301.

[2R,3R,4R]-3,5-bis(tert-Butyldimethylsilanyloxy)-2,4-dimethylpentan-1-ol (95). To a stirred solution of silyl ether (5 g, 9.09 mmol) in THF (50 mL) at 0° C. were added MeOH (1.14 mL, 27.3 mmol) and $LiBH_4$ in THF (14 mL, 2M) under argon. The solution was stirred at 0° C. for 30 min and then quenched by the addition of a saturated solution of Rochelle salt in $H_2O$ (60 mL) and stirred for 10 min at 0° C. The mixture was poured into $CH_2Cl_2$ (100 mL) and stirred vigorously until 2 layers appeared (2 h). The aqueous layer was separated extracted with of $CH_2Cl_2$ (40 mL). The combined organic layers were washed with brine (40 mL), dried ($MgSO_4$), filtered and concentrated in vacuo. Flash chromatography (30% EtOAc in hexanes) gave 2.32 g (65%) of alcohol 95 as a colorless oil: $[\alpha]^{20}_D$=+10.0 (c 1.2, $CHCl_3$); $^1H$ NMR (300 MHz, $CDCl_3$) δ 3.67 (t, J=5.2 Hz, 1H), 3.55–3.50 (m, 3H), 3.39 (dd, J=10.0, 6.5 Hz, 1H), 2.98 (br s, 1H), 1.87–1.77 (m, 2H), 0.92 (d, J=7.0 Hz, 3H), 0.86 (d, J=7.0 Hz, 3H), 0.83 (s, 9H), 0.81 (s, 9H), 0.03 (s, 3H), 0.01 (s, 3H), −0.03 (s, 6H); $^{13}C$ NMR (75 MHz, $CDCl_3$) δ 800.2, 66.0, 65.2, 39.7, 38.8, 25.9, 25.6, 18.3, 18.0, 14.9, 14.7, −5.4, −5.3, −4.1; IR (thin film) 3330, 2930, 2858, 1471, 1250, 1023 cm$^{-1}$; HRMS (EI) calcd for $C_{19}H_{44}O_3Si_2$ 376.2859, found 376.2858.

[2R,3R,4R]-3,5-bis-(tert-Butyldimethylsilanyloxy)-2,4-dimethylpentanal (96). Following the procedure for 4-(tert-butyldiphenylsilanyloxy)-3-(4-methoxybenzyloxy)-butyraldehyde 89, 96 can be prepared in a similar manner.

(2R)-3-(tert-Butyldimethylsilanyloxy)-2-methylpropionic acid methyl ester. A solution of alcohol (10.0 g, 84.6 mmol), imidazole (9.2 g, 133.9 mmol), and TBSCl (19.1 g, 126.9 mmol) in DMF (150 mL) was stirred overnight at room temperature under argon. A mixture of $H_2O$ (500 mL) and EtOAc (300 mL) was added and the layers were separated. The aqueous layer was extracted with EtOAc (2×200 mL). The organic layers were combined and washed with $H_2O$ (2×200 mL), brine (200 mL), dried over $MgSO_4$, filtered and concentrated in vacuo. The crude oil was purified by flash chromatography (20% EtOAc in hexanes) to yield 17.7 g (90%) of the silyl ether as a clear yellow oil: The spectral data matched that of the known compound. $^1$H NMR (300 MHz, CDCl$_3$) δ 3.62 (dd, J=6.7, 7.0 Hz, 1H), 3.50 (dd, J=6.7, 7.0 Hz, 1H), 3.50 (m, 3), 2.48 (sext, J=7.0 Hz, 1H), 0.97 (d, J=7.0 Hz, 3H), 0.71 (s, 9H), −0.1 (s, 6H); $^{13}$C NMR (75 MHz, CDCl$_3$) δ 175.4, 65.2, 51.5, 42.5, 25.7, 18.2, 13.4, −5.5.

[2R]-3-(tert-Butyldimethylsilanyloxy)-2-methylpropan-1-ol. To a stirred solution of silyl ether (5.0 g, 21.5 mmol) in $CH_2Cl_2$ (125 mL) at −40° C. under argon was added slowly over 1.5 h via cannula DibalH in toluene (100 mL, 1M). After 30 min at −40° C., the reaction mixture was quenched by slow addition of MeOH (15 mL) and warmed to RT. The reaction mixture was poured into a vigorously stirred solution of saturated Rochelle salt (200 mL) and EtOAc (300 mL) and stirred overnight. The aqueous layer was separated and extracted with EtOAc (3×50 mL), dried (MgSO$_4$) and concentrated in vacuo. The crude mixture was purified by flash chromatography (20% EtOAc in hexanes) to produce 3.46 g (79%) of the alcohol, a clear liquid. The spectral data matched that of the known compound: $^1$H NMR (300 MHz, CDCl$_3$) δ 3.73 (dd, J=4.5, 9.8, Hz, 1H), 3.57 (m, 3H), 2.80 (br s, 1H), 1.99–1.86 (m, 1H), 0.89 (s, 9H), 0.82 (d, J=7.0 Hz, 3H), 0.06 (d, 6H); $^{13}$C NMR (75 MHz, CDCl$_3$) δ 68.8, 68.4, 37.0, 25.8, 18.1, 13.0, −5.6.

[2R]-3-(tert-Butyldimethylsilanyloxy)-2-methyl propionaldehyde (ent-17). DMSO (3.0 mL, 42.6 mmol) was added, dropwise, to a stirred solution of oxalyl chloride (1.5 mL, 19.9 mmol) in $CH_2Cl_2$ (80 mL) at −78° C. under argon. The reaction mixture was stirred for 5 min then a solution of alcohol (3.0 g, 14.7 mmol) in $CH_2Cl_2$ (25 mL) was added dropwise. After 1 h at −78° C., Et$_3$N (10.5 mL, 74.7 mmol) was added slowly via syringe, the mixture was stirred for 5 min then warmed to room temperature. The reaction mixture was diluted with $CH_2Cl_2$ (25 mL), washed with ice cold 0.5 M HCl (50 mL) then $H_2O$ (30 mL) and the layers were separated. The aqueous layers were combined and extracted with $CH_2Cl_2$ (2×30 mL) and the combined organic layers were dried over MgSO$_4$, filtered, and concentrated in vacuo. The intermediate aldehyde ent-17 was used in the following reaction without purification: $^1$H NMR (300 MHz, CDCl$_3$) δ 9.75 (δ, 1.5 Hζ, 1H), 3.86–3.82 (m, 2H), 2.53–2.50 (m, 1H), 1.10 (d, J=7.0 Hz, 3H), 0.88 (s, 9H), 0.05 (s, 6H).

[3S,4S,5S]-2,4-dimethyl-1-[(tert-butyldimethylsilyl)oxy]-hexene-5-en-3-ol (97). A solution of (R,R)-diisopropyl tartrate (E)-crotylboronate (22.1 mmol) was added to 4 Å powdered molecular sieves (0.025 g) in toluene (1 mL) under argon and the mixture was stirred for 20 min at room temperature. The mixture was cooled to −78° C. and a solution of the aldehyde ent-17 (3.0 g, 14.7 mmol) in toluene (8 mL) was added dropwise via syringe. The resulting mixture was maintained at −78° C. for 3 h and then treated with NaBH$_4$ (0.106 g, 2.6 mmol) in EtOH (4 mL) and warmed to 0° C. The reaction mixture was treated with 1N NaOH (40 mL) and stirred vigorously for 30 min, followed by separation of the organic layer. The aqueous layer was extracted with $CH_2Cl_2$ (5×80 mL) and the combined organic layers were dried over MgSO$_4$, filtered, and concentrated in vacuo. The crude oil was purified by flash chromatography (5% to 25% Et$_2$O in hexanes) providing 2.87 g (65%) of 97, a clear, yellow tinted oil: $^1$H NMR (300 MHz, CDCl$_3$) δ 5.91 (ddd, J=8.8, 12.0, 15.8 Hz, 1H), 5.05 (dd, J=1.8, 12.0 Hz, 1H), 5.04 (dd, J=1.8, 15.8 Hz, 1H), 3.81 (s, 1H), 3.73 (dd, J=4.2, 9.8 Hz, 1H), 3.60 (dd, J=8.2, 9.8 Hz 1H), 3.37 (dd, J=3.0, 4.8 Hz, 1H), 2.39–2.29 (m, 1H), 1.83–1.70 (m, 1H), 1.09 (d, J=6.9 Hz, 3H), 0.89 (s, 9H), 0.81 (d, J=6.9 Hz, 3H), 0.06 (s, 6H); $^{13}$C NMR (75 MHz, CDCl$_3$) δ 139.9, 114.9, 80.2, 68.7, 41.2, 37.5, 25.8 [2C], 18.1, 17.7, 13.4, −5.6, −5.7.

[2S,3S,4S]-tert-Butyl-[3-(4-methoxybenzyloxy)-2,4-dimethylhex-5-enyloxy]dimethylsilane. A mixture of NaH (2.9 g, 11.6 mmol) in THF (5 mL) was cooled to 0° C. then DMF (5 mL), alcohol 97 (1.0 g, 3.87 mmol) in THF (5 mL), and PMBBr (1.8 g, 9.7 mmol) were added. The reaction mixture was warmed to room temperature and stirred for 48 h. The resulting mixture was poured into a pH 7 phosphate buffer and diluted with ether (90 mL). The organic layer was separated and washed with pH 7 buffer (3×60 mL), dried over $K_2CO_3$, filtered and concentrated in vacuo. The resulting crude yellow oil was purified by flash chromatography (5% to 10% EtOAc in hexanes) providing 1.39 g (75%) of the PMB ether as a clear, yellow tinted oil: $[α]^{20}_D$=+0.06 (c 1.3, CHCl$_3$); $^1$H NMR (300 MHz, CDCl$_3$) δ 7.31 (d, J=8.6 Hz, 2H), 6.90 (d, J=8.6 Hz, 2H), 5.93 (ddd, J=15.6, 12.0, 8.3 Hz, 1H), 5.05 (d, J=12 Hz, 1H), 5.04 (d, J=15.6 1H), 3.89 (s, 3H), 3.29 (dd, J=4.6, 2.9 Hz, 1H), 2.51–2.49 (m, 1H), 1.91–1.86 (m, 1H), 1.01 (d, J=6.9 Hz, 3H), 0.08 (s, 6H); $^{13}$C NMR (75 MHz, CDCl$_3$) δ 158.9, 142.1, 131.2, 129.2, 114.0, 113.6, 82.8, 74.1, 65.7, 55.7, 38.4, 37.3, 25.9, 18.2, 15.6, 11.2, −5.2; IR (thin film) 3057, 2957, 2857, 1612, 1513, 1246, 1085 cm$^{-1}$; LRMS (EI) 323 (M−C$_4$H$_7$), 321, 271, 255, 186, 122 m/z.

[2S,3S,4S]-5-(tert-Butyldimethylsilanyloxy)-3-(4-methoxybenzyloxy)-2,4-dimethyl pentanal (98). Following the procedure for [2R,3R,5R]-6-(tert-Butyldiphenylsilanyloxy)-3,5-bis-(4-methoxybenzyloxy)-2-methylhexanal, 98 can be prepared in a similar manner.

(R,R)-Diisopropyl tartrate (E)-crotylboronate. An oven-dried 1 L three-neck round bottom flask equipped with a magnetic stir bar and a −100° C. thermometer was charged with 206 mL of anhydrous THF and KOtBu (28.2 g, 250 mmol). This mixture was flushed with Ar and cooled to −78° C., then trans-2-butene (23 mL, 250 mmol), condensed from a gas lecture bottle into a rubber-stoppered round bottom flask immersed in a −78° C. dry ice-acetone bath, was poured into the reaction mixture. n-BuLi (100 mL, 2.5 M in hexane) was then added dropwise via cannula over 1.5 h. After completion of the addition, the cooling bath was removed and the reaction mixture was allowed to warm to an internal temperature of −50° C. for 15 min then immediately recooled to −78° C. Triisopropylborate (57.8 mL, 250 mmol) was added drop-wise via cannula to the (E)-crotylpotassium solution over 2 h. After addition, the reaction mixture was maintained at −78° C. for 30 min and then rapidly poured into a 2 L separatory funnel containing 470 mL of 1 N HCl saturated with NaCl. The aqueous layer was adjusted to pH 1 by using 1 N HCl (100–150 mL), and then a solution of (R,R)-diisopropyl tartrate (52.8 g, 250 mmol) in 88 mL of Et$_2$O was added. The phases were separated, and the aqueous layer was extracted with additional Et$_2$O (4×120 mL). The combined extracts were dried over MgSO$_4$ for 1 h then vacuum filtered through a fritted glass funnel under Ar blanket into an oven-dried round-bottom flask. The filtrate was concentrated in vacuo, and pumped to constant weight at under vacuum. Anhydrous toluene (170 mL) was added to the flask make a 1M solution.

Biology

General. Tubulin without microtubule-associated proteins was prepared from fresh bovine brains.[32] The normoisotopic and tritiated forms of paclitaxel and normoisotopic docetaxel were provided by the Drug Synthesis and Chemistry Branch, National Cancer Institute. (+)-Discodermolide was from Novartis Pharmaceutical Corporation. Ca$^{2+}$- and Mg$^{2+}$-free RPMI-1640 culture medium were from GIBCO/BRL-Life Technologies. Fetal bovine serum (FBS) was from Hyclone. Cell lines were obtained from American Type Culture Collection (Manassas, Va.).

Tubulin Polymerization.[32] Tubulin assembly was followed in a Beckman-Coulter 7400 spectrophotometer, equipped with an electronic Peltier temperature controller, reading absorbance (turbidity) at 350 nm. Reaction mixtures (0.25 mL final volume) contained tubulin (final concentration 10 µM; 1 mg/mL), monosodium glutamate (0.8 M from a stock solution adjusted to pH 6.6 with HCl), DMSO (final volume 4% v/v), and differing concentrations of test agent where indicated. Reaction mixtures without test agent were cooled to 0° C. and added to cuvettes held at 0.25–0.5° C. in the spectrophotometer. Test agent in DMSO was then rapidly mixed in the reaction mixture. Each run contained one positive control (paclitaxel, 10 µM final concentration) and one negative control (DMSO only). Baselines were established at 0.25–2.5° C. and temperature was rapidly raised to 30° C. (in approximately 1 min) and held there for 20 min. The temperature was then rapidly lowered back to 0.25–2.5° C.

Cell Growth Inhibition[34] Cells were plated (500–2000 cells/well depending on the cell line) in 96-well microplates, allowed to attach and grow for 48 h, then treated with vehicle (4% DMSO, a concentration that allowed doubling times of 24 h or less) or test agent (50, 10, 2, 0.4 and 0.08 µM for the new agents; 0.001, 0.005, 0.010, 0.020 and 0.100 µM for paclitaxel and discodermolide) for the given times. One plate consisted of cells from each line used for a time zero cell number determination. The other plates in a given determination contained eight wells of control cells, eight wells of medium and each agent concentration tested in quadruplicate. Cell numbers were obtained spectrophotometrically (absorbance at 490 nm minus that at 630 nm) in a Dynamax plate reader after treatment with 3-(4,5-dimethylthiazol-2-yl)-5-(3-carboxymethoxyphenyl)-2-(4-sulfophenyl)-2H-tetrazolium (MTS) using phenazine methanesulfonate as the electron acceptor. After initial screening with the above 5-fold dilutions, fifty percent growth inhibitory concentration (GI$_{50}$) values were determined for each agent by repeating the screen using 2-fold dilutions (five concentrations) centered on the initial estimated GI$_{50}$ concentration, again in quadruplicate.

Paclitaxel binding site inhibition assay. [34] A stock solution of [$^3$H]paclitaxel (26.8 µM, 16.2 Ci/mmol), obtained from the NCI, was prepared in 37% (v/v) DMSO. The test agents were prepared in 25% (v/v) DMSO-0.75 M monosodium glutamate (prepared from a 2M stock solution adjusted to pH 6.6 with HCl). The radiolabeled paclitaxel and test agents, as indicated in terms of final concentrations, were mixed in equal volumes and warmed to 37° C. A reaction mixture (50 µL) containing 0.75 M monosodium glutamate, 4.0 µM tubulin, and 40 µM ddGTP (a non-hydrolyzable analog of GTP) was prepared and incubated at 37° C. for 30 min to preform microtubules. An equivalent volume of drug mixture with [$^3$H]paclitaxel was added to preformed polymer and incubated for 30 min at 37° C. Bound [$^3$H]paclitaxel was separated from free drug by centrifugation of the reaction mixtures at 14000 rpm for 20 min at room temperature. Non-specific binding was determined by addition of a 12-fold excess of docetaxel. Radioactive counts from the supernatant (50 µL) were determined by scintillation spectrometry. Bound [$^3$H]paclitaxel was calculated from the following: total paclitaxel added to each reaction mixture minus the paclitaxel present in the supernatant (free drug). The % bound values were normalized to the control values with no inhibitor added.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A compound of the following structure

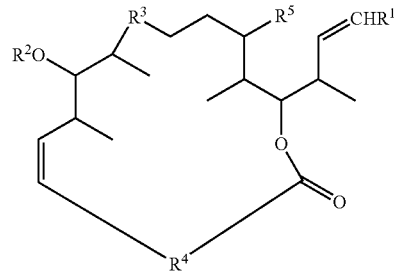

wherein R$^1$ is H, an alkyl group, an aryl group, an alkenyl group, an alkynyl group, or a halogen atom;

R$^2$ is H, an alkyl group, a benzyl group, a trityl group, —SiR$^a$R$^b$R$^c$, CH$_2$OR$^d$, or COR$^e$;

R$^a$, R$^b$ and R$^c$ are independently an alkyl group or an aryl group;

R$^d$ is an alkyl group, an aryl group, an alkoxylalkyl group, —R$^i$SiR$^a$R$^b$R$^c$ or a benzyl group, wherein R$^i$ is an alkylene group;

R$^e$ is an alkyl group, an allyl group, a benzyl group, an aryl group, an alkoxy group, or —NR$^g$R$^h$, wherein R$^g$ and R$^h$ are independently H, an alkyl group or an aryl group;

R$^3$ is (CH$_2$)$_n$ where n is and integer in the range of 0 to 5, —CH$_2$CH(CH$_3$)—, —CH=CH—, —CH=C(CH$_3$)—, or —C≡C—;

$R^4$ is $(CH_2)_p$ where p is an integer in the range of 4 to 12, —$(CHR^{k1})_{y1}(CHR^{k2})_{y2}(CHR^{k3})_{y3}(CHR^{k4})_{y4}(CHR^{k5})_{y5}C(R^{s1})=C(R^{s2})C(R^{s3})=C(R^{s4})$—, —$(CHR^{k1})_{y1}(CHR^{k2})_{y2}(CHR^{k3})_{y3}(CHR^{k4})_{y4}(CHR^{k5})_{y5}CH(R^{s1})CH(R^{s2})C(R^{s3})=C(R^{s4})$—, —$(CHR^{k1})_{y1}(CHR^{k2})_{y2}(CHR^{k3})_{y3}(CHR^{k4})_{y4}(CHR^{k5})_{y5}C(R^{s1})=C(R^{s2})CH(R^{s3})CH(R^{s4})$—, —$(CHR^{k1})_{y1}(CHR^{k2})_{y2}(CHR^{k3})_{y3}(CHR^{k4})_{y4}(CHR^{k5})_{y5}CH(R^{s1})CH(R^{s2})CH(R^{s3})CH(R^{s4})$—, wherein y1 and y2 are 1 and y3, y4 and y5 are independently 0 or 1, $R^{k1}$, $R^{k2}$, $R^{k3}$, $R^{k4}$ and $R^{k5}$ are independently H, $CH_3$, or $OR^{2a}$, and $R^{s1}$, $R^{s2}$, $R^{s3}$, and $R^{s4}$ are independently H or $CH_3$, wherein $R^{2a}$ is H, an alkyl group, an aryl group, a benzyl group, a trityl group, —$SiR^aR^bR^c$, $CH_2OR^d$, or $COR^e$; and $R^5$ is H or $OR^{2b}$, wherein $R^{2b}$ is H, an alkyl group, an aryl group, a benzyl group, a trityl group, —$SiR^aR^bR^c$, $CH_2OR^d$, or $COR^e$; provided that the compound is not dictyostatin 1.

2. The compound of claim 1 with the following stereo-structure, or its enantiomer

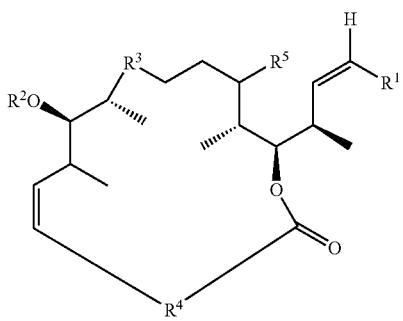

wherein $R^1$ is alkenyl; $R^2$ is H; $R^3$ is —$CH_2CH(CH_3)$ or —$CH=C(CH_3)$; and $R^4$ is —$(CHR^{k1})_{y1}(CHR^{k2})_{y2}(CHR^{k3})_{y3}(CHR^{k4})_{y4}(CHR^{k5})_{y5}C(R^{s1})=C(R^{s2})C(R^{s3})=C(R^{s4})$— wherein y1–y4 are 1, y5 is 0, $R^{k1}$ and $R^{k3}$ are OH, $R^{k2}$ is H, $R^{k4}$ is $CH_3$, $R^{s1}$, $R^{s2}$, $R^{s3}$ and $R^{s4}$ are H, and $R^5$ is OH.

3. The compound of claim 2 wherein $R^1$ is —$CH=CH_2$ and $R^4$ is

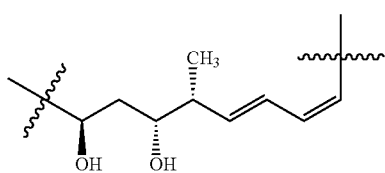

4. The compound of claim 2 wherein $R^1$ is —$CH=CH_2$ and $R^4$ is:

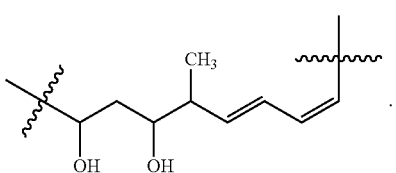

5. A process for conversion of a first compound with the formula

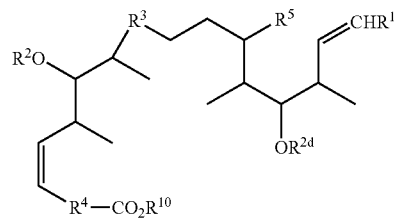

wherein $R^1$ is H, an alkyl group, an aryl group, an alkenyl group, an alkynyl group, or a halogen atom;

$R^2$ is H, an alkyl group, a benzyl group, a trityl group, —$SiR^aR^bR^c$, $CH_2OR^d$, or $COR^e$;

$R^{2d}$ is H $R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$, wherein $R^g$ and $R^h$ are independently H, an alkyl group or an aryl group;

$R^3$ is $(CH_2)_n$ where n is and integer in the range of 0 to 5, —$CH_2CH(CH_3)$—, —$CH=CH$—, —$CH=C(CH_3)$—, or —$C\equiv C$—;

$R^4$ is $(CH_2)_p$ where p is an integer in the range of 4 to 12, —$(CHR^{k1})_{y1}(CHR^{k2})_{y2}(CHR^{k3})_{y3}(CHR^{k4})_{y4}(CHR^{k5})_{y5}C(R^{s1})=C(R^{s2})C(R^{s3})=C(R^{s4})$—, —$(CHR^{k1})_{y1}(CHR^{k2})_{y2}(CHR^{k3})_{y3}(CHR^{k4})_{y4}(CHR^{k5})_{y5}C(R^{s1})=C(R^{s2})CH(R^{s3})CH(R^{s4})$—, —$(CHR^{k1})_{y1}(CHR^{k2})_{y2}(CHR^{k3})_{y3}(CHR^{k4})_{y4}(CHR^{k5})_{y5}CH(R^{s1})CH(R^{s2})CH(R^{s3})CH(R^{s4})$—, wherein y1 and y2 are 1 and y3, y4 and y5 are independently 0 or 1, $R^{k1}$, $R^{k2}$, $R^{k3}$, $R^{k4}$ and $R^{k5}$ are independently H, $CH_3$, or $OR^{2a}$, and $R^{s1}$, $R^{s2}$, $R^{s3}$, $R^{s4}$ are independently H or $CH_3$, wherein $R^{2a}$ is H, an alkyl group, an aryl group, a benzyl group, a trityl group, —$SiR^aR^bR^c$, $CH_2OR^d$, or $COR^e$;

$R^5$ is H or $OR^{2b}$, wherein $R^{2b}$ is H, an alkyl group, an aryl group, a benzyl group, a trityl group, —$SiR^aR^bR^c$, $CH_2OR^d$, or $COR^e$; and $R^{10}$ is H;

to a second compound with the formula

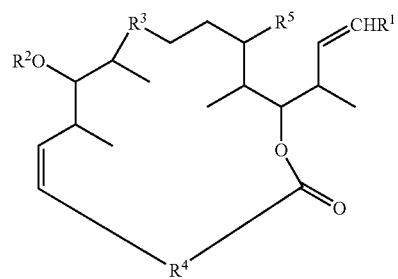

comprising the step of reacting the first compound under conditions suitable to effect macrolactonization.

6. The process of claim 5 for conversion of a compound with the following stereostructure or its enantiomer

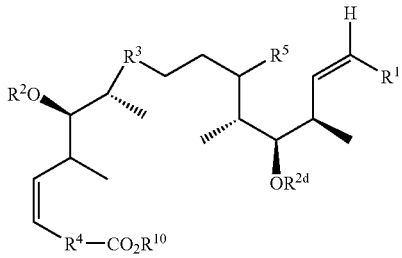

wherein $R^1$ is H, an alkyl group, an alkenyl group, an alkynyl group, or a halogen atom;

$R^2$ is H, an alkyl group, a benzyl group, a trityl group, —$SiR^aR^bR^c$, $CH_2OR^d$, or $COR^e$;

$R^{2d}$ is H $R^a$, $R^b$ and $R^c$ are independently an alkyl group or an aryl group;

$R^d$ is an alkyl group, an aryl group, an alkoxylalkyl group, —$R^iSiR^aR^bR^c$ or a benzyl group, wherein $R^i$ is an alkylene group;

$R^e$ is an alkyl group, an allyl group, a benzyl group, an aryl group, an alkoxy group, or —$NR^gR^h$ wherein $R^g$ and $R^h$ are independently H, an alkyl group or an aryl group;

$R^3$ is $(CH_2)_n$ where n is and integer in the range of 0 to 5, —$CH_2CH(CH_3)$—, —CH=CH—, —CH=C$(CH_3)$—, or —C≡C—;

$R^4$ is $(CH_2)_p$ where p is an integer in the range of 4 to 12, —$(CHR^{k1})_{y1}(CHR^{k2})_{y2}(CHR^{k3})_{y3}(CHR^{k4})_{y4}(CHR^{k5})_{y5}C(R^{s1})$=$C(R^{s2})C(R^{s3})$=$C(R^{s4})$—, —$(CHR^{k1})_{y1}(CHR^{k2})_{y2}(CHR^{k3})_{y3}(CHR^{k4})_{y4}(CHR^{k5})_{y5}CH(R^{s1})CH(R^{s2})C(R^{s3})$=$C(R^{s4})$—, —$(CHR^{k1})_{y1}(CHR^{k2})_{y2}(CHR^{k3})_{y3}(CHR^{k4})_{y4}(CHR^{k5})_{y5}C(R^{s1})$=$C(R^{s2})CH(R^{s3})CH(R^{s4})$—, —$(CHR^{k1})_{y1}(CHR^{k2})_{y2}(CHR^{k3})_{y3}(CHR^{k4})_{y4}(CHR^{k5})_{y5}CH(R^{s1})CH(R^{s2})CH(R^{s3})CH(R^{s4})$—, wherein y1 and y2 are 1 and y3, y4 and y5 are independently 0 or 1, $R^{k1}$, $R^{k2}$, $R^{k3}$, $R^{k4}$ and $R^{k5}$ are independently H, —$CH_3$, or $OR^{2a}$, and $R^{s1}$, $R^{s2}$, $R^{s3}$, $R^{s4}$ are independently H or $CH_3$, wherein $R^{2a}$ is H, an alkyl group, an aryl group, a benzyl group, a trityl group, —$SiR^aR^bR^c$, $CH_2OR^d$, or $COR^e$; and $R^5$ is H or $OR^{2b}$, wherein $R^{2b}$ is H, an alkyl group, an aryl group, a benzyl group, a trityl group, —$SiR^aR^bR^c$, $CH_2OR^d$, or $COR^e$; and $R^{10}$ is H to a second compound with the formula

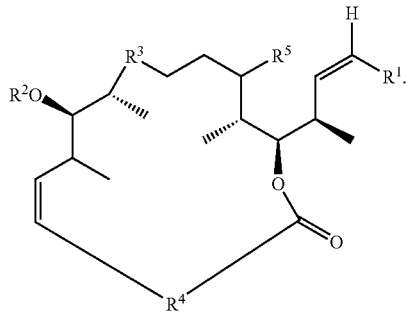

7. The process of claim 6 wherein $R^1$ is alkenyl; $R^3$ is $CH_2CH(CH_3)$ or CH=C$(CH_3)$; and $R^4$ is —$(CHR^{k1})_{y1}(CHR^{k2})_{y2}(CHR^{k3})_{y3}(CHR^{k4})_{y4}(CHR^{k5})_{y5}C(R^{s1})$=$C(R^{s2})C(R^{s3})$=$C(R^{s4})$— wherein y1–y4 are 1, y5 is 0, $R^{k1}$ and $R^{k3}$ are $R^{2a}$, $R^{k2}$ is H, $R^{k4}$ is $CH_3$, $R^{s1}$–$R^{s4}$ are H, and $R^5$ is $OR^{2b}$.

8. The process of claim 6 wherein $R^1$ is CH=$CH_2$ and $R^4$ is

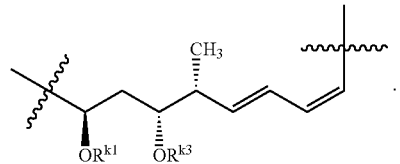

9. The process of claim 5 wherein the first compound is reacted with 2,4,6-trichlorobenzoylchloride.

10. The process of claim 6 wherein the first compound is reacted with 2,4,6-trichlorobenzoylchloride.

* * * * *